US012721856B2

(12) United States Patent
Elder et al.

(10) Patent No.: US 12,721,856 B2
(45) Date of Patent: Sep. 1, 2026

(54) PSILOCYBIN COMPOSITIONS, METHODS OF MAKING AND METHODS OF USING THE SAME

(71) Applicant: Compass Pathfinder Limited, Altrincham (GB)

(72) Inventors: David Philip Elder, Hertfordshire (GB); Nigel Richardson, Stevenage (GB)

(73) Assignee: Compass Pathfinder Limited, Altrincham (GB)

( * ) Notice: Subject to any disclaimer, the term of this patent is extended or adjusted under 35 U.S.C. 154(b) by 381 days.

(21) Appl. No.: 18/285,109

(22) PCT Filed: Mar. 30, 2022

(86) PCT No.: PCT/EP2022/058483

§ 371 (c)(1),
(2) Date: Sep. 29, 2023

(87) PCT Pub. No.: WO2022/207746

PCT Pub. Date: Oct. 6, 2022

(65) Prior Publication Data

US 2024/0197758 A1 Jun. 20, 2024

Related U.S. Application Data

(60) Provisional application No. 63/168,055, filed on Mar. 30, 2021.

(51) Int. Cl.

*A61K 31/661* (2006.01)
*A61K 9/20* (2006.01)
*A61K 9/48* (2006.01)

(52) U.S. Cl.

CPC .......... *A61K 31/661* (2013.01); *A61K 9/2059* (2013.01); *A61K 9/4833* (2013.01); *A61K 9/4866* (2013.01)

(58) Field of Classification Search

CPC .................................................... A61K 31/661
See application file for complete search history.

(56) References Cited

U.S. PATENT DOCUMENTS

| | | | |
|---|---|---|---|
| 3,075,992 | A | 1/1963 | Albert et al. |
| 3,183,172 | A | 5/1965 | Roger et al. |
| 3,192,111 | A | 6/1965 | Albert et al. |
| 4,499,096 | A | 2/1985 | Lotsof |
| 4,587,243 | A | 5/1986 | Lotsof |
| 4,721,612 | A | 1/1988 | Janoff et al. |
| 5,145,677 | A | 9/1992 | Von Eichborn et al. |
| 5,264,443 | A | 11/1993 | Jarreau et al. |
| 5,468,486 | A | 11/1995 | Reddick et al. |
| 5,482,706 | A | 1/1996 | Igari et al. |
| 5,545,617 | A | 8/1996 | Dartt et al. |
| 5,573,776 | A | 11/1996 | Harrison et al. |
| 5,626,863 | A | 5/1997 | Hubbell et al. |
| 5,629,307 | A | 5/1997 | Olney |
| 5,643,586 | A | 7/1997 | Perricone |
| 5,696,125 | A | 12/1997 | Altura et al. |
| 5,725,871 | A | 3/1998 | Illum |
| 5,736,161 | A | 4/1998 | Garces et al. |
| 5,785,989 | A | 7/1998 | Stanley et al. |
| 5,804,592 | A | 9/1998 | Volicer |
| 5,827,819 | A | 10/1998 | Yatvin et al. |
| 5,871,710 | A | 2/1999 | Bogdanov et al. |
| 5,874,477 | A | 2/1999 | McConnell et al. |
| 5,879,690 | A | 3/1999 | Perricone |
| 5,902,815 | A | 5/1999 | Olney et al. |
| 5,914,129 | A | 6/1999 | Mauskop |
| 5,922,341 | A | 7/1999 | Smith et al. |
| 5,925,634 | A | 7/1999 | Olney |
| 5,935,925 | A | 8/1999 | Weinshank et al. |
| 5,942,241 | A | 8/1999 | Chasin et al. |
| 5,942,503 | A | 8/1999 | Jung et al. |
| 5,958,919 | A | 9/1999 | Olney et al. |
| 6,037,346 | A | 3/2000 | Doherty, Jr. et al. |
| 6,121,264 | A | 9/2000 | Sakamoto et al. |
| 6,126,924 | A | 10/2000 | Scales-Medeiros et al. |
| 6,204,245 | B1 | 3/2001 | Siegel et al. |
| 6,217,904 | B1 | 4/2001 | Midha et al. |
| 6,228,864 | B1 | 5/2001 | Smith et al. |
| 6,294,550 | B1 | 9/2001 | Place et al. |
| 6,323,236 | B2 | 11/2001 | McElroy |
| 6,348,456 | B1 | 2/2002 | Mash et al. |
| 6,380,176 | B2 | 4/2002 | Takahashi et al. |
| 6,383,471 | B1 | 5/2002 | Chen et al. |
| 6,444,665 | B1 | 9/2002 | Helton et al. |
| 6,479,074 | B2 | 11/2002 | Murdock et al. |
| 6,489,341 | B1 | 12/2002 | Jerussi |
| 6,495,154 | B1 | 12/2002 | Tam et al. |
| 6,495,498 | B2 | 12/2002 | Niemiec et al. |
| 6,500,459 | B1 | 12/2002 | Chhabra et al. |
| 6,541,043 | B2 | 4/2003 | Lang |
| 6,544,998 | B2 | 4/2003 | Mylari |
| 6,592,901 | B2 | 7/2003 | Durig et al. |
| 6,604,698 | B2 | 8/2003 | Verhoff et al. |
| 6,635,279 | B2 | 10/2003 | Kolter et al. |
| 6,693,135 | B2 | 2/2004 | Yeager et al. |

(Continued)

FOREIGN PATENT DOCUMENTS

| | | | |
|---|---|---|---|
| AU | 2016208412 | A1 | 8/2016 |
| AU | 2018203524 | A1 | 6/2018 |

(Continued)

OTHER PUBLICATIONS

Anonymous: "Record History I ver. 1: Aug. 8, 2019 | NCT04052568 ClinicalTrials.gov Effects of Psilocybin in Anorexia Nervosa", Aug. 8, 2019, pp. 1-13, Retrieved from the Internet: URL:https://clinicaltrials.gov/study/NCT04052568?tab=history&a=1#version-content-panel.

(Continued)

*Primary Examiner* — Rei Tsang Shiao
(74) *Attorney, Agent, or Firm* — COOLEY LLP

(57) ABSTRACT

The present disclosure provides pharmaceutical compositions comprising a therapeutically effective amount of psilocybin and one or more pharmaceutically acceptable excipients. Methods of making such compositions and use thereof in treating depressive disorders are also disclosed.

22 Claims, 22 Drawing Sheets

(56) References Cited

U.S. PATENT DOCUMENTS 6,720,348 B2 4/2004 Mylari
6,814,976 B1 11/2004 Hille et al.
6,893,662 B2 5/2005 Dittmar et al.
6,913,768 B2 7/2005 Couch et al.
6,962,717 B1 11/2005 Huber et al.
6,977,070 B2 12/2005 Dugger, III
6,979,447 B2 12/2005 Jameson et al.
7,045,543 B2 5/2006 Yatvin et al.
7,084,156 B2 8/2006 DeVita et al.
7,186,293 B2 3/2007 Cunningham
7,220,737 B1 5/2007 Mash
7,229,784 B2 6/2007 Holtzman et al.
7,241,797 B2 7/2007 Horseman
7,294,649 B2 11/2007 Hui et al.
7,384,651 B2 6/2008 Hille et al.
7,517,900 B2 4/2009 Pendri et al.
7,638,651 B2 12/2009 Gant et al.
7,666,877 B2 2/2010 Baenteli et al.
7,670,627 B2 3/2010 Shefer et al.
7,671,030 B2 3/2010 Mickle et al.
7,678,770 B2 3/2010 Mickle et al.
7,754,710 B2 7/2010 Mash
7,772,222 B2 8/2010 Mickle
7,799,337 B2 9/2010 Levin
7,833,546 B2 11/2010 Petereit et al.
7,838,034 B2 11/2010 Kugelmann et al.
7,981,441 B2 7/2011 Pantelidis et al.
8,008,285 B2 8/2011 Roberts et al.
8,067,028 B2 11/2011 Bennett
8,101,661 B2 1/2012 Mickle
8,263,561 B2 9/2012 Saeed
8,318,210 B2 11/2012 Tengler et al.
8,318,813 B2 11/2012 Sanfilippo
8,329,663 B2 12/2012 Griffin
8,362,007 B1 1/2013 Mash et al.
8,445,016 B2 5/2013 Santerre et al.
8,512,751 B2 8/2013 Rariy et al.
8,574,604 B2 11/2013 Esfand et al.
8,617,607 B2 12/2013 Moses et al.
8,673,351 B2 3/2014 Andrysek et al.
8,742,096 B2 6/2014 Moriarty et al.
8,747,832 B2 6/2014 Uhrich et al.
8,754,119 B2 6/2014 Scheller et al.
8,784,835 B2 7/2014 Austin
8,785,500 B2 7/2014 Charney et al.
8,846,100 B2 9/2014 Shojaei et al.
8,852,638 B2 10/2014 Luk et al.
8,859,579 B2 10/2014 Sewell
8,859,622 B1 10/2014 Bristol et al.
8,906,413 B2 12/2014 Chang et al.
8,906,847 B2 12/2014 Cleemann et al.
8,921,393 B2 12/2014 Weiner et al.
8,962,697 B2 2/2015 Laronde et al.
8,980,308 B2 3/2015 Horstmann et al.
8,980,880 B1 3/2015 King et al.
9,737,759 B2 8/2017 Mrowka et al.
9,878,138 B2 1/2018 Altschul et al.
10,058,253 B2 8/2018 Parton et al.
10,058,584 B2 8/2018 Young et al.
10,064,856 B2 9/2018 Bosse et al.
10,085,994 B2 10/2018 Lozinsky et al.
10,148,534 B2 12/2018 Lazarescu et al.
10,183,001 B1 1/2019 King et al.
10,231,651 B2 3/2019 Deng et al.
10,254,298 B1 4/2019 Koh
10,519,175 B2 * 12/2019 Londesbrough ........ A61P 25/00
10,596,378 B2 3/2020 Rustick
10,729,706 B2 8/2020 Kucuksen et al.
10,738,268 B2 8/2020 Leo
10,947,257 B2 3/2021 Londesbrough et al.
10,954,259 B1 3/2021 Londesbrough et al.
11,149,044 B2 10/2021 Londesbrough et al.
11,180,517 B2 11/2021 Londesbrough et al.
11,447,510 B2 9/2022 Londesbrough et al.
11,505,564 B2 11/2022 Londesbrough et al.
11,564,935 B2 1/2023 Londesbrough et al.
11,629,159 B2 4/2023 Londesbrough et al.
11,738,035 B2 8/2023 Londesbrough et al.
11,851,451 B2 12/2023 Londesbrough et al.
11,865,126 B2 1/2024 Londesbrough et al.
11,939,346 B2 3/2024 Londesbrough et al.
12,377,112 B2 8/2025 Londesbrough et al.
12,433,904 B2 10/2025 Londesbrough et al.
12,447,164 B2 * 10/2025 Londesbrough ........ A61P 25/24
12,459,965 B2 11/2025 Londesbrough et al.
2001/0004644 A1 6/2001 Levin
2002/0015730 A1 2/2002 Hoffmann et al.
2002/0019421 A1 2/2002 Biberman
2002/0044962 A1 4/2002 Cherukuri et al.
2002/0137785 A1 9/2002 Kindness et al.
2003/0013689 A1 1/2003 Helton et al.
2003/0049308 A1 3/2003 Theobald et al.
2003/0051728 A1 3/2003 Lloyd et al.
2003/0082225 A1 5/2003 Mason
2003/0096831 A1 5/2003 Stone et al.
2003/0099711 A1 5/2003 Meadows et al.
2003/0114512 A1 6/2003 Collier, Jr. et al.
2003/0119884 A1 6/2003 Epstein et al.
2003/0135202 A1 7/2003 Harper et al.
2003/0144220 A1 7/2003 Obach
2003/0153552 A1 8/2003 Mash et al.
2003/0171435 A1 9/2003 Pouletty et al.
2003/0180357 A1 9/2003 Martino et al.
2003/0203912 A1 10/2003 May et al.
2003/0224057 A1 12/2003 Martin-Letellier et al.
2003/0235617 A1 12/2003 Martino et al.
2004/0006043 A1 1/2004 Margalit et al.
2004/0023952 A1 2/2004 Leventhal
2004/0024038 A1 2/2004 Ebert et al.
2004/0029860 A1 2/2004 Gil-Ad et al.
2004/0077540 A1 4/2004 Quay
2004/0132780 A1 7/2004 Allen et al.
2004/0186155 A1 9/2004 Dayno et al.
2004/0214215 A1 10/2004 Yu et al.
2004/0224942 A1 11/2004 Weiner et al.
2005/0009815 A1 1/2005 DeVita et al.
2005/0014786 A1 1/2005 Sun et al.
2005/0026842 A1 2/2005 Simon
2005/0070501 A1 3/2005 Neurath et al.
2005/0096396 A1 5/2005 Davis et al.
2005/0106220 A1 5/2005 Inagawa et al.
2005/0148673 A1 7/2005 Harbut et al.
2005/0176790 A1 8/2005 Bartholomaus et al.
2005/0203011 A1 9/2005 Ron
2005/0209218 A1 9/2005 Meyerson et al.
2005/0215521 A1 9/2005 Lalji et al.
2005/0215571 A1 9/2005 Romano
2005/0222270 A1 10/2005 Olney et al.
2005/0233010 A1 10/2005 Satow
2005/0245460 A1 11/2005 Meyerson et al.
2005/0245617 A1 11/2005 Meyerson et al.
2005/0255091 A1 11/2005 Loomis
2005/0260258 A1 11/2005 Ficht et al.
2005/0261278 A1 11/2005 Weiner et al.
2005/0265955 A1 12/2005 Raman et al.
2005/0288375 A1 12/2005 Hobden et al.
2006/0019963 A1 1/2006 Barnette et al.
2006/0025387 A1 2/2006 Hochman
2006/0030625 A1 2/2006 Hart et al.
2006/0034872 A1 2/2006 Woolf
2006/0045865 A1 3/2006 Jacob et al.
2006/0051408 A1 3/2006 Parente Duena et al.
2006/0067937 A1 3/2006 Karumanchi et al.
2006/0093679 A1 5/2006 Mayer et al.
2006/0110327 A1 5/2006 Emigh et al.
2006/0135403 A1 6/2006 Gervais et al.
2006/0183744 A1 8/2006 Rohrer et al.
2006/0229293 A1 10/2006 Lotsof
2006/0240014 A1 10/2006 Sukhatme
2006/0240043 A1 10/2006 Meyerson et al.
2006/0241172 A1 10/2006 Zhou et al.
2006/0264508 A1 11/2006 Stone
2006/0270592 A1 11/2006 Ousler, III et al.
2007/0053954 A1 3/2007 Rowe et al.

(56) References Cited

U.S. PATENT DOCUMENTS

| | | | |
|---|---|---|---|
| 2007/0059367 | A1 | 3/2007 | Cherukuri |
| 2007/0065463 | A1 | 3/2007 | Aung-Din |
| 2007/0066996 | A1 | 3/2007 | Katzman et al. |
| 2007/0092586 | A1 | 4/2007 | Cutler |
| 2007/0099977 | A1 | 5/2007 | Nudelman et al. |
| 2007/0100000 | A1 | 5/2007 | Epstein et al. |
| 2007/0190130 | A1 | 8/2007 | Mark et al. |
| 2007/0190142 | A1 | 8/2007 | Breitenbach et al. |
| 2007/0203216 | A1 | 8/2007 | Ebert et al. |
| 2007/0207222 | A1 | 9/2007 | Yu et al. |
| 2007/0213394 | A1 | 9/2007 | Beguin et al. |
| 2008/0015181 | A1 | 1/2008 | Roberts et al. |
| 2008/0026014 | A1 | 1/2008 | Michel |
| 2008/0026189 | A1 | 1/2008 | Lin et al. |
| 2008/0066741 | A1 | 3/2008 | LeMAHIEU et al. |
| 2008/0075789 | A1 | 3/2008 | Vawter et al. |
| 2008/0103127 | A1 | 5/2008 | Haas |
| 2008/0103165 | A1 | 5/2008 | Barlow et al. |
| 2008/0103179 | A1 | 5/2008 | Tam et al. |
| 2008/0103199 | A1 | 5/2008 | Haas |
| 2008/0193540 | A1 | 8/2008 | Soula et al. |
| 2008/0207600 | A1 | 8/2008 | Goldstein et al. |
| 2008/0226715 | A1 | 9/2008 | Cha et al. |
| 2008/0233201 | A1 | 9/2008 | Royere et al. |
| 2008/0241255 | A1 | 10/2008 | Rose et al. |
| 2008/0255096 | A1 | 10/2008 | Knipper-Breer et al. |
| 2008/0260844 | A1 | 10/2008 | Soula et al. |
| 2009/0036468 | A1 | 2/2009 | Samoriski et al. |
| 2009/0041838 | A1 | 2/2009 | Guimberteau et al. |
| 2009/0069308 | A1 | 3/2009 | Deregnaucourt et al. |
| 2009/0105222 | A1 | 4/2009 | Kranzler et al. |
| 2009/0143435 | A1 | 6/2009 | Ebert et al. |
| 2009/0156581 | A1 | 6/2009 | Dillon et al. |
| 2009/0169566 | A1 | 7/2009 | Rawlin et al. |
| 2009/0176792 | A1 | 7/2009 | Gant et al. |
| 2009/0186099 | A1 | 7/2009 | Dugger, III |
| 2009/0198145 | A1 | 8/2009 | Chow |
| 2009/0232898 | A1 | 9/2009 | Pettersson et al. |
| 2009/0252786 | A1 | 10/2009 | Hanz |
| 2009/0259039 | A1 | 10/2009 | Bristol et al. |
| 2009/0285916 | A1 | 11/2009 | Haritou |
| 2009/0291137 | A1 | 11/2009 | Guimberteau et al. |
| 2009/0298814 | A1 | 12/2009 | Nudelman et al. |
| 2010/0016280 | A1 | 1/2010 | Nichols et al. |
| 2010/0098722 | A1 | 4/2010 | Bachmann et al. |
| 2010/0152108 | A1 | 6/2010 | Hung et al. |
| 2010/0166889 | A1 | 7/2010 | Sanfilippo |
| 2010/0179221 | A1 | 7/2010 | Nagel et al. |
| 2010/0189818 | A1 | 7/2010 | Tsai |
| 2010/0216964 | A1 | 8/2010 | Zech et al. |
| 2010/0255094 | A1 | 10/2010 | Jackson et al. |
| 2010/0266701 | A1 | 10/2010 | Guimberteau et al. |
| 2010/0303903 | A1 | 12/2010 | Hackett |
| 2011/0038915 | A1 | 2/2011 | Gonzalez |
| 2011/0053859 | A1 | 3/2011 | Deadwyler et al. |
| 2011/0077239 | A1 | 3/2011 | Knipper et al. |
| 2011/0091508 | A1 | 4/2011 | Esfand et al. |
| 2011/0111029 | A1 | 5/2011 | Schmitz et al. |
| 2011/0118189 | A1 | 5/2011 | Farr et al. |
| 2011/0144209 | A1 | 6/2011 | Zachar |
| 2011/0207718 | A1 | 8/2011 | Bird |
| 2011/0217289 | A1 | 9/2011 | Kolter et al. |
| 2011/0245261 | A1 | 10/2011 | Lagarde et al. |
| 2011/0274634 | A1 | 11/2011 | Rieth et al. |
| 2011/0306596 | A1 | 12/2011 | Rao et al. |
| 2012/0058125 | A1 | 3/2012 | Strittmatter et al. |
| 2012/0059066 | A1 | 3/2012 | Bartholomaus et al. |
| 2012/0108510 | A1 | 5/2012 | Young et al. |
| 2012/0129834 | A1 | 5/2012 | Hughes et al. |
| 2012/0135960 | A2 | 5/2012 | Mouthon et al. |
| 2012/0159656 | A1 | 6/2012 | Gerber et al. |
| 2012/0282255 | A1 | 11/2012 | Plucinski |
| 2012/0302590 | A1 | 11/2012 | Bhide et al. |
| 2012/0302592 | A1 | 11/2012 | Johnson et al. |
| 2013/0045979 | A1 | 2/2013 | Sanfilippo |
| 2013/0116215 | A1 | 5/2013 | Coma et al. |
| 2013/0276799 | A1 | 10/2013 | Davidson et al. |
| 2013/0281401 | A1 | 10/2013 | Turner |
| 2013/0295170 | A1 | 11/2013 | Dordunoo |
| 2014/0093577 | A1 | 4/2014 | Tengler et al. |
| 2014/0099336 | A1 | 4/2014 | Woiwode et al. |
| 2014/0100282 | A1 | 4/2014 | Wong |
| 2014/0148491 | A1 | 5/2014 | Valia et al. |
| 2014/0178480 | A1 | 6/2014 | King et al. |
| 2014/0187655 | A1 | 7/2014 | Mash et al. |
| 2014/0220150 | A1 | 8/2014 | Stamets |
| 2014/0255522 | A1 | 9/2014 | Lozinsky et al. |
| 2014/0288056 | A1 | 9/2014 | Friedhoff |
| 2014/0294923 | A1 | 10/2014 | Cartt et al. |
| 2014/0315837 | A1 | 10/2014 | Mash et al. |
| 2014/0356428 | A1 | 12/2014 | Barnscheid et al. |
| 2014/0364367 | A1 | 12/2014 | Cotter |
| 2015/0011644 | A1 | 1/2015 | Leech |
| 2015/0094466 | A1 | 4/2015 | Moriarty |
| 2015/0099741 | A1 | 4/2015 | Li et al. |
| 2015/0118301 | A1 | 4/2015 | Haswani et al. |
| 2015/0118327 | A1 | 4/2015 | Sewell |
| 2015/0196533 | A1 | 7/2015 | Mao et al. |
| 2015/0216799 | A1 | 8/2015 | Farber |
| 2015/0231300 | A1 | 8/2015 | Lozinsky et al. |
| 2015/0258114 | A1 | 9/2015 | Friedhoff |
| 2016/0051476 | A1 | 2/2016 | Pilgaonkar et al. |
| 2016/0331725 | A1 | 11/2016 | Gillessen et al. |
| 2016/0338945 | A1 | 11/2016 | Knight |
| 2016/0340334 | A1 | 11/2016 | Knight |
| 2017/0086727 | A1 | 3/2017 | Dagum |
| 2017/0258382 | A1 | 9/2017 | Dagum |
| 2017/0258383 | A1 | 9/2017 | Dagum |
| 2017/0276676 | A1 | 9/2017 | Slotman |
| 2017/0287348 | A1 | 10/2017 | Mosher et al. |
| 2017/0348303 | A1 | 12/2017 | Bosse et al. |
| 2018/0021326 | A1 | 1/2018 | Stamets |
| 2018/0036303 | A1 | 2/2018 | Raz |
| 2018/0104490 | A1 | 4/2018 | Rustick |
| 2018/0147142 | A1 | 5/2018 | Knight |
| 2018/0221396 | A1 | 8/2018 | Chadeayne |
| 2018/0343812 | A1 | 12/2018 | Leo |
| 2018/0344743 | A1 | 12/2018 | Lozinsky et al. |
| 2018/0353434 | A1 | 12/2018 | Hatanaka et al. |
| 2018/0354995 | A1 | 12/2018 | Gudkov et al. |
| 2019/0105313 | A1 | 4/2019 | Stamets |
| 2019/0119310 | A1 * | 4/2019 | Londesbrough ....... A61K 47/38 |
| 2019/0142851 | A1 | 5/2019 | Chadeayne |
| 2019/0187163 | A1 | 6/2019 | Koh |
| 2019/0192498 | A1 | 6/2019 | Stamets |
| 2019/0246591 | A1 | 8/2019 | Leo |
| 2020/0078368 | A1 | 3/2020 | Lehmann et al. |
| 2020/0093416 | A1 | 3/2020 | Rogers et al. |
| 2020/0101041 | A1 | 4/2020 | Kleidon |
| 2020/0147038 | A1 | 5/2020 | Russ et al. |
| 2020/0215297 | A1 | 7/2020 | Rabin et al. |
| 2020/0375967 | A1 | 12/2020 | Stamets |
| 2021/0015738 | A1 † | 1/2021 | LaRosa |
| 2021/0015833 | A1 | 1/2021 | LaRosa et al. |
| 2021/0069170 | A1 † | 3/2021 | Stamets |
| 2021/0267966 | A1 | 9/2021 | Petcavich |
| 2022/0088041 | A1 | 3/2022 | Londesbrough et al. |
| 2022/0169668 | A1 | 6/2022 | Londesbrough et al. |
| 2022/0402949 | A1 | 12/2022 | Londesbrough et al. |
| 2023/0000883 | A1 | 1/2023 | Londesbrough et al. |
| 2023/0023092 | A1 | 1/2023 | Londesbrough et al. |
| 2023/0119714 | A1 | 4/2023 | Londesbrough et al. |
| 2023/0124137 | A1 | 4/2023 | Londesbrough et al. |
| 2023/0250115 | A1 | 8/2023 | Londesbrough et al. |
| 2023/0277568 | A1 | 9/2023 | Bridges et al. |
| 2024/0199660 | A1 | 6/2024 | Londesbrough et al. |
| 2024/0252521 | A1 | 8/2024 | Londesbrough et al. |
| 2024/0360162 | A1 | 10/2024 | Londesbrough et al. |
| 2025/0000881 | A1 | 1/2025 | Mill |
| 2025/0122232 | A1 | 4/2025 | Londesbrough et al. |
| 2025/0302851 | A1 | 10/2025 | Londesbrough et al. |
| 2025/0304607 | A1 | 10/2025 | Londesbrough et al. |
| 2025/0319095 | A1 | 10/2025 | Hickey |
| 2025/0352514 | A1 | 11/2025 | Morphy et al. |

(56) References Cited

U.S. PATENT DOCUMENTS

| | | | |
|---|---|---|---|
| 2025/0361251 | A1 | 11/2025 | Londesbrough et al. |
| 2025/0367223 | A1 | 12/2025 | Londesbrough et al. |
| 2025/0368665 | A1 | 12/2025 | Londesbrough et al. |

FOREIGN PATENT DOCUMENTS

| | | | |
|---|---|---|---|
| CA | 672478 | A | 10/1963 |
| CA | 2338326 | A1 | 2/2000 |
| CA | 2416650 | A1 | 1/2002 |
| CA | 2422730 | A1 | 3/2002 |
| CA | 2492823 | A1 | 3/2003 |
| CA | 2492826 | A1 | 3/2003 |
| CA | 2487849 | A1 | 1/2004 |
| CA | 2489410 | A1 | 1/2004 |
| CA | 2498938 | A1 | 4/2004 |
| CA | 2517675 | A1 | 10/2004 |
| CA | 2541090 | A1 | 5/2005 |
| CA | 2594451 | A1 | 6/2007 |
| CA | 3050679 | A1 | 7/2018 |
| CN | 103535561 | A | 1/2014 |
| CN | 103549133 | A | 2/2014 |
| CN | 103751943 | A | 4/2014 |
| CN | 103773056 | A | 5/2014 |
| CN | 107252080 | A | 10/2017 |
| CN | 108619214 | A | 10/2018 |
| EP | 0152379 | A2 | 8/1985 |
| EP | 0218479 | A2 | 4/1987 |
| EP | 0493380 | B1 | 10/1997 |
| EP | 0628042 | B1 | 8/2001 |
| EP | 0554352 | B1 | 3/2003 |
| EP | 0932416 | B1 | 6/2005 |
| EP | 1944017 | A2 | 7/2008 |
| EP | 2106799 | A1 | 10/2009 |
| EP | 1774968 | B1 | 12/2011 |
| EP | 1861427 | B1 | 8/2012 |
| EP | 2142185 | B1 | 8/2012 |
| EP | 2525226 | A1 | 11/2012 |
| EP | 2649989 | A1 | 10/2013 |
| EP | 2053919 | B1 | 12/2013 |
| EP | 2183227 | B1 | 9/2014 |
| EP | 2023900 | B1 | 12/2014 |
| EP | 2818177 | A1 | 12/2014 |
| EP | 2481740 | B1 | 11/2015 |
| EP | 3151906 | B1 | 12/2019 |
| ES | 2693502 | T3 | 12/2018 |
| FI | 20176142 | A1 | 6/2019 |
| FI | 20185254 | A1 | 9/2019 |
| GB | 911946 | A | 12/1962 |
| GB | 912714 | A | 12/1962 |
| HR | P20050421 | A2 | 12/2005 |
| IE | 24138 | L | 8/1959 |
| JP | S5576859 | A | 6/1980 |
| JP | S5728046 | A | 2/1982 |
| JP | 4174016 | B2 | 10/2008 |
| JP | 2013233437 | A | 11/2013 |
| MX | 2014005372 | A | 7/2014 |
| TW | 201605856 | A | 2/2016 |
| WO | WO-9728798 | A1 | 8/1997 |
| WO | WO-9728799 | A1 | 8/1997 |
| WO | WO-9728800 | A1 | 8/1997 |
| WO | WO-9729121 | A1 | 8/1997 |
| WO | WO-9747285 | A1 | 12/1997 |
| WO | WO-9850027 | A1 | 11/1998 |
| WO | WO-9859234 | A1 | 12/1998 |
| WO | WO-9903458 | A1 | 1/1999 |
| WO | WO-9909828 | A1 | 3/1999 |
| WO | WO-9948501 | A1 | 9/1999 |
| WO | WO-9966909 | A2 | 12/1999 |
| WO | WO-0003679 | A2 | 1/2000 |
| WO | WO-0003701 | A1 | 1/2000 |
| WO | WO-0003746 | A2 | 1/2000 |
| WO | WO-0006139 | A2 | 2/2000 |
| WO | WO-0056403 | A1 | 9/2000 |
| WO | WO-0113935 | A2 | 3/2001 |
| WO | WO-0126642 | A2 | 4/2001 |
| WO | WO-0152832 | A1 | 7/2001 |
| WO | WO-0167890 | A2 | 9/2001 |
| WO | WO-0172839 | A2 | 10/2001 |
| WO | WO-0182915 | A2 | 11/2001 |
| WO | WO-0205851 | A2 | 1/2002 |
| WO | WO-0224865 | A2 | 3/2002 |
| WO | WO-03016903 | A2 | 2/2003 |
| WO | WO-03024480 | A2 | 3/2003 |
| WO | WO-03024481 | A2 | 3/2003 |
| WO | WO-03026564 | A2 | 4/2003 |
| WO | WO-03041645 | A2 | 5/2003 |
| WO | WO-03045353 | A1 | 6/2003 |
| WO | WO-03047551 | A1 | 6/2003 |
| WO | WO-03066030 | A2 | 8/2003 |
| WO | WO-2004000275 | A1 | 12/2003 |
| WO | WO-2004007538 | A2 | 1/2004 |
| WO | WO-2004009116 | A2 | 1/2004 |
| WO | WO-2004014429 | A1 | 2/2004 |
| WO | WO-2004025268 | A2 | 3/2004 |
| WO | WO-2004032900 | A1 | 4/2004 |
| WO | WO-2004071431 | A2 | 8/2004 |
| WO | WO-2004084940 | A1 | 10/2004 |
| WO | WO-2004111185 | A2 | 12/2004 |
| WO | WO-2005039502 | A2 | 5/2005 |
| WO | WO-2005039546 | A2 | 5/2005 |
| WO | WO-2005058319 | A1 | 6/2005 |
| WO | WO-2005067930 | A2 | 7/2005 |
| WO | WO-2005102390 | A2 | 11/2005 |
| WO | WO-2006006858 | A1 | 1/2006 |
| WO | WO-2006047032 | A2 | 5/2006 |
| WO | WO-2006079999 | A2 | 8/2006 |
| WO | WO-2006121552 | A2 | 11/2006 |
| WO | WO-2006127418 | A1 | 11/2006 |
| WO | WO-2007050697 | A2 | 5/2007 |
| WO | WO-2007066240 | A2 | 6/2007 |
| WO | WO-2007067519 | A2 | 6/2007 |
| WO | WO-2007085898 | A2 | 8/2007 |
| WO | WO-2007092043 | A2 | 8/2007 |
| WO | WO-2007101884 | A1 | 9/2007 |
| WO | WO-2008009125 | A1 | 1/2008 |
| WO | WO-2008010223 | A2 | 1/2008 |
| WO | WO-2008023261 | A1 | 2/2008 |
| WO | WO-2008026046 | A1 | 3/2008 |
| WO | WO-2008038291 | A1 | 4/2008 |
| WO | WO-2008039179 | A1 | 4/2008 |
| WO | WO-2008119097 | A1 | 10/2008 |
| WO | WO-2008122990 | A1 | 10/2008 |
| WO | WO-2008130638 | A2 | 10/2008 |
| WO | WO-2009018338 | A2 | 2/2009 |
| WO | WO-2009021055 | A1 | 2/2009 |
| WO | WO-2009050354 | A1 | 4/2009 |
| WO | WO-2009055001 | A2 | 4/2009 |
| WO | WO-2009061436 | A1 | 5/2009 |
| WO | WO-2009079765 | A1 | 7/2009 |
| WO | WO-2009091605 | A2 | 7/2009 |
| WO | WO-2009097596 | A1 | 8/2009 |
| WO | WO-2009102805 | A1 | 8/2009 |
| WO | WO-2009109428 | A2 | 9/2009 |
| WO | WO-2009118179 | A1 | 10/2009 |
| WO | WO-2009118763 | A1 | 10/2009 |
| WO | WO-2009149252 | A1 | 12/2009 |
| WO | WO-2010099522 | A1 | 9/2010 |
| WO | WO-2010123577 | A2 | 10/2010 |
| WO | WO-2010124089 | A2 | 10/2010 |
| WO | WO-2011027060 | A2 | 3/2011 |
| WO | WO-2011028875 | A1 | 3/2011 |
| WO | WO-2011045443 | A1 | 4/2011 |
| WO | WO-2011045769 | A2 | 4/2011 |
| WO | WO-2011048494 | A2 | 4/2011 |
| WO | WO-2011072398 | A1 | 6/2011 |
| WO | WO-2011097269 | A1 | 8/2011 |
| WO | WO-2011109809 | A2 | 9/2011 |
| WO | WO-2011116189 | A1 | 9/2011 |
| WO | WO-2011138142 | A1 | 11/2011 |
| WO | WO-2011143254 | A2 | 11/2011 |
| WO | WO-2011158964 | A1 | 12/2011 |
| WO | WO-2012012764 | A1 | 1/2012 |
| WO | WO-2012019989 | A2 | 2/2012 |
| WO | WO-2012022928 | A2 | 2/2012 |

(56) References Cited

FOREIGN PATENT DOCUMENTS

| | | | |
|---|---|---|---|
| WO | WO-2012031125 | A2 | 3/2012 |
| WO | WO-2012039660 | A1 | 3/2012 |
| WO | WO-2012045118 | A1 | 4/2012 |
| WO | WO-2012054815 | A1 | 4/2012 |
| WO | WO-2012063257 | A2 | 5/2012 |
| WO | WO-2012066537 | A2 | 5/2012 |
| WO | WO-2012074588 | A2 | 6/2012 |
| WO | WO-2012077110 | A2 | 6/2012 |
| WO | WO-2012085919 | A2 | 6/2012 |
| WO | WO-2012110537 | A1 | 8/2012 |
| WO | WO-2012134436 | A1 | 10/2012 |
| WO | WO-2012137971 | A1 | 10/2012 |
| WO | WO-2012158892 | A2 | 11/2012 |
| WO | WO-2012177962 | A1 | 12/2012 |
| WO | WO-2013004999 | A1 | 1/2013 |
| WO | WO-2013040471 | A2 | 3/2013 |
| WO | WO-2013068949 | A1 | 5/2013 |
| WO | WO-2013083710 | A1 | 6/2013 |
| WO | WO-2013085849 | A2 | 6/2013 |
| WO | WO-2013085850 | A2 | 6/2013 |
| WO | WO-2013085922 | A1 | 6/2013 |
| WO | WO-2013091900 | A1 | 6/2013 |
| WO | WO-2013097947 | A1 | 7/2013 |
| WO | WO-2013112163 | A1 | 8/2013 |
| WO | WO-2013112757 | A1 | 8/2013 |
| WO | WO-2013169355 | A1 | 11/2013 |
| WO | WO-2014015993 | A1 | 1/2014 |
| WO | WO-2014031958 | A1 | 2/2014 |
| WO | WO-2014035473 | A1 | 3/2014 |
| WO | WO-2014064703 | A1 | 5/2014 |
| WO | WO-2014078857 | A1 | 5/2014 |
| WO | WO-2014093277 | A1 | 6/2014 |
| WO | WO-2014098877 | A1 | 6/2014 |
| WO | WO-2014117089 | A1 | 7/2014 |
| WO | WO-2014140925 | A2 | 9/2014 |
| WO | WO-2014143085 | A1 | 9/2014 |
| WO | WO-2014145126 | A2 | 9/2014 |
| WO | WO-2014146082 | A1 | 9/2014 |
| WO | WO-2014153099 | A2 | 9/2014 |
| WO | WO-2014176556 | A1 | 10/2014 |
| WO | WO-2014186623 | A2 | 11/2014 |
| WO | WO-2014190440 | A1 | 12/2014 |
| WO | WO-2014195872 | A1 | 12/2014 |
| WO | WO-2015004245 | A1 | 1/2015 |
| WO | WO-2015006315 | A1 | 1/2015 |
| WO | WO-2015034846 | A1 | 3/2015 |
| WO | WO-2015061125 | A1 | 4/2015 |
| WO | WO-2015065546 | A2 | 5/2015 |
| WO | WO-2015066344 | A1 | 5/2015 |
| WO | WO-2015112168 | A2 | 7/2015 |
| WO | WO-2015134405 | A1 | 9/2015 |
| WO | WO-2015187289 | A1 | 12/2015 |
| WO | WO-2016161138 | A1 | 10/2016 |
| WO | WO-2016176177 | A1 | 11/2016 |
| WO | WO-2016178053 | A1 | 11/2016 |
| WO | WO-2017023679 | A1 | 2/2017 |
| WO | WO-2018035477 | A1 | 2/2018 |
| WO | WO-2018135943 | A1 | 7/2018 |
| WO | WO-2018141063 | A1 | 8/2018 |
| WO | WO-2018145219 | A1 | 8/2018 |
| WO | WO-2018148605 | A1 | 8/2018 |
| WO | WO-2018184206 | A1 | 10/2018 |
| WO | WO-2018195455 | A1 | 10/2018 |
| WO | WO-2018223044 | A1 | 12/2018 |
| WO | WO-2019073379 | A1 | 4/2019 |
| WO | WO-2019079742 | A1 | 4/2019 |
| WO | WO-2019081764 | A1 | 5/2019 |
| WO | WO-2019099745 | A1 | 5/2019 |
| WO | WO-2019109124 | A1 | 6/2019 |
| WO | WO-2019122525 | A1 | 6/2019 |
| WO | WO-2019144140 | A1 | 7/2019 |
| WO | WO-2019161050 | A1 | 8/2019 |
| WO | WO-2019173797 | A1 | 9/2019 |
| WO | WO-2019180309 | A1 | 9/2019 |
| WO | WO-2019213551 | A1 | 11/2019 |
| WO | WO-2019246532 | A1 | 12/2019 |
| WO | WO-2020024060 | A1 | 2/2020 |
| WO | WO-2020041329 | A1 | 2/2020 |
| WO | WO-2020053196 | A1 | 3/2020 |
| WO | WO-2020142259 | A1 | 7/2020 |
| WO | WO-2020157569 | A1 | 8/2020 |
| WO | WO-2020169850 | A1 | 8/2020 |
| WO | WO-2020212948 | A1 | 10/2020 |
| WO | WO-2020212951 | A1 | 10/2020 |
| WO | WO-2020212952 | A1 | 10/2020 |
| WO | WO-2022207746 | A1 | 10/2022 |

OTHER PUBLICATIONS

De Heer et al., The Association of Depression and Anxiety with Pain: A Study from NESDA. PLOS ONE 9(10): e106907 pp. 1-11 (2014).

Dodick D W, et al., "Assessing Clinically Meaningful Treatment Effects in Controlled Trials: Chronic Migraine As an example," The Journal of pain, Feb. 2015; 16(2):164-75.

Jacobs H, et al., "Medical Comorbidities in Pediatric Headache," Seminars in Pediatric Neurology, 23(1):60-7, 2016, Epub Feb. 3, 2016.

Leonard, "What is the link between anxiety and ADHD?," https://www.medicalnewstoday.com/articles/315303 May 15, 2017 , 19 pages.

Magnuson K M, et al., "Characterization of depression in children with autism spectrum disorders," Journal of developmental and Behavioral Pediatrics, May 2011;32(4):332-40.

Meinzer M C, et al., "ADHD and the Development of Depression: Commentary on the Prevalence, Proposed Mechanisms, and Promising Interventions," Current developmental disorders reports, Mar. 2017;4(1):1-4, Epub Feb. 27, 2017.

Sheng et al, "The Link between Depression and Chronic Pain: Neural Mechanisms in the Brain," Neural Plast. 2:9724371, pp. 1-10 (2017); Epub 2017 Jun. 19, 2017.

Verroust Vincent et al., "Psilocybin in the treatment of anorexia nervosa: The English transition of a French 1959 case study", Annales Medico-Psychologiques, Elsevier, Amsterdam, NL 179(8):777-781 (Sep. 28, 2021).

White S W, et al., "Anxiety in Children and Adolescents with Autism Spectrum Disorders," Clinical psychology review, 29(3):216-29, 2009, Epub Jan. 25, 2009.

Chen et al., "Attention-deficit hyperactivity disorder comorbidity and antidepressant resistance among patients with major depression: A nationwide longitudinal study". Eur Neuropsychopharmacol. Nov. 2016;26(11): 1760-1767.

Nutt, "5HT2a Receptors—a New Target for Depression?" European Psychiatry, vol. 30, Supplement 1, Mar. 28-31, 2015, p. 35, 1 page total.

Vollenweider et al. The neurobiology of psychedelic drugs: implications for the treatment of mood disorders. Nat Rev Neurosci 11:642-651 (2010).

Whelan, A & Johnson, M, "Lysergic Acid Diethylamide and Psilocybin for the Management of Patients with Persistent Pain: a Potential Role?," Pain Management 8:217-229 (2018).

Aaron, M. (2017) "Open Your Mind: Merging Psychedelic Therapy with Sex Therapy" Psychology Today [online]. Retrieved from: https://www.psychologytoday.com/us/blog/standard-deviations/201710/open-your-mind-merging-psychedelic-therapy-sex-therapy, retrieved Oct. 24, 2017, 4 pages.

Abramovitch, A. et al. (Jul./Aug. 2015). Comorbidity Between Attention Deficit/Hyperactivity Disorder and Obsessive-Compulsive Disorder Across the Lifespan: A Systematic and Critical Review. Harvard Review of Psychiatry, 23(4):245-262.

Adams, K.S. et al., (2014). Melatonin agonists in the management of sleep disorders: A focus on ramelteon and tasimelteon. Ment Health Clin, 4:59-64. https://doi.org/10.9740/mhc.n190087.

Adams, T.G. et al. (Apr. 2017). Intranasal ketamine and cognitive-behavioral therapy for treatment-refractory obsessive-compulsive disorder. Journal of Clinical Psychopharmacology, 37(2):269-271. HHS Public Access Author Manuscript; available in PMC Apr. 1, 2018, 4 pages.

(56) References Cited

OTHER PUBLICATIONS

Adelow, C. et al. (Jan. 2012). Hospitalization for psychiatric disorders before and after onset of unprovoked seizures/epilepsy. Neurology, 78(6), 396-401. https://doi.org/10.1212/WVNL.0b013e318245f461.

Advokat, C. et al., (May 2013). Attention-deficit hyperactivity disorder (ADHD) stimulant medications as cognitive enhancers. Front Neurosci, 7:Article 92, 8 pages.

Agh, T. et al. (Jan. 2015). Epidemiology, health-related quality of life and economic burden of binge eating disorder: a systematic literature review. Eating and Weight Disorders, 20:1-12.

Agin-Liebes, G.I. et al. (2020). Long-term follow-up of psilocybin-assisted psychotherapy for psychiatric and existential distress in patients with life-threatening cancer. J Psychopharmacol [online]; retrieved from: https://doi.org/10.1177/0269881119897615, 12 pages.

Aguglia, A., Signorelli, M. S., Albert, U., & Maina, G. (Mar. 2018). The impact of general medical conditions in obsessive-compulsive disorder. Psychiatry Investigation, 15(3):246-253. https://doi.org/10.30773/pi.2017.06.17.2.

Alayadhi, L.Y. et al. (Dec. 2016). High-resolution SNP genotyping platform identified recurrent and novel CNVs in autism multiplex families. Neuroscience, 339:561-570.

Albelda, N., & Joel, D. (Jun. 2012). Current animal models of obsessive compulsive disorder: An update. Neuroscience, 211:83-106. https://doi.org/10.1016/j.neuroscience.2011.08.070.

Alcaro, A., and J. Panksepp (Oct. 2011). The SEEKING mind: Primal neuro- affective substrates for appetitive incentive states and their pathological dynamics in addictions and depression. Neurosci Biobehav Rev, 35:1805-1820. https://doi.org/10.1016/j.neubiorev.2011.03.002.

Alderson, R.M. et al. (May 2013) Attention-deficit/hyperactivity disorder (ADHD) and working memory in adults: A meta-analytic review. Neuropsychology, 27(3):287-302.

Allam, J.S., Collop, N., 2018. Central Sleep Apnea Syndrome (Idiopathic CSA, Cheyne-Stokes Respiration, CSA due to a drug or substance, High-altitude Periodic breathing, CSA due to a medical condition other than Cheyne-Stokes). Pulmonology Advisor (2018): pp. 1-14. Retrieved from: https://www.pulmonologyadvisor.com/home/decision-support-in-medicine/pulmonary-medicine/central-sleep-apnea-syndrome-idiopathic-csa-cheyne-stokes-respiration-csa-due-to-a-drug-or-substance-high-altitude-periodic-breathing-csa-due-to-a-medical-condition-ot (accessed Jul. 30, 2020).

Allen, G. and E. Courchesne (Jan. 1, 2001). Attention function and dysfunction in autism. Frontiers In Bioscience, 6:d105-119.

Alonso, P., Lopez-Sola, C., Real, E., Segalas, C., & Menchon, J. M. (Aug. 2015). Animal models of obsessive-compulsive disorder: Utility and limitations. In Neuropsychiatric Disease and Treatment, 11:1939-1955. https://doi.org/10.2147/NDT.S62785.

Alvarez, A.J. et al. (2009) "Polymorph Screening: Comparing a Semi-Automated Approach with a High Throughput Method" Crystal Growth and Design, 9:4181-4188.

Alzheimer's Association (2019). Alzheimer's Disease Facts and Figures. Alzheimers Dement, 15(3):321-387, with Appendices, 90 total pages.

Alzheimer's Association (2019). FDA-approved treatments for Alzheimer's. TS-0087. 5 pages.

American Parkinson Disease Association. (2019). Medications for Parkinson's. Retrieved from https://www.apdaparkinson.org/what-is-parkinsons/treatment-medication/medication/; retrieved on Jul. 30, 2020, 18 pages.

American Psychiatric Association (2013) Binge-eating disorder. In: Diagnostic and Statistical Manual of Mental Disorders. 5th ed. Arlington, VA: American Psychiatric Association; p. 350-353.

American Psychiatric Association (2013). Diagnostic and statistical manual of mental disorders (5th ed.). American Journal of Psychiatry. https://doi.org/10.1176/appi.books.9780890425596.744053, 970 pages.

American Psychiatric Association (2013). Sleep-Wake Disorders. In: Diagnostic and Statistical Manual of Mental Disorders. 5th Edition. [online]. Retrieved from: https://doi.org/10.1176/appi.books.9780890425596.dsm12, 2 pages.

Amiri, S. et al. (Jan. 2008) Modafinil as a treatment for Attention-Deficit/Hyperactivity Disorder in children and adolescents: A double blind, randomized clinical trial. Prog Neuro-Psychopharmacol Biol Psychiatry. 32(1):145-149.

Amodeo, D.A. et al. (Feb. 2012). Differences in BTBR T+ tf/J and C57BL/6J mice on probabilistic reversal learning and stereotyped behaviors. Behavioural Brain Research, 227(1):64-72. NIH Public Access Author Manuscript, available Mar. 1, 2012, 19 pages.

Andermann, F. (Jul. 1987). Migraine-epilepsy relationships. Epilepsy Research, 1(4):213-226. https://doi.org/10.1016/0920-1211(87)90028-3.

Andersson et al., "Psychoactive substances as a last resort-a qualitative study of self-treatment of migraine and cluster headaches", Harm Reduction Journal, Dec. 2017, 10 pages.

Andres-Pepina, S. et al. (2019). Long-term outcome and psychiatric comorbidity of adolescent-onset anorexia nervosa. Clinical Child Psychology and Psychiatry [online]. Retrieved from: https://doi.org/10.1177/1359104519827629, 12 pages.

Angst, J., Gamma, A., Endrass, J., Goodwin, R., Ajdacic, V., Eich, D., & Rossler, W. (Jun. 2004). Obsessive-compulsive severity spectrum in the community: Prevalence, comorbidity, and course. European Archives of Psychiatry and Clinical Neuroscience, 254(3):156-164. https://doi.org/10.1007/s00406-004-0459-4.

Anonymous: "COMPASS Pathways announces positive outcome of 25mg COMP360 psilocybin therapy as adjunct to SRI antidepressants in open-label treatment-resistant depression study", Dec. 13, 2021 (Dec. 13, 2021), 7 pages.

Anonymous: "Psilocybin in Depression Resistant to Standard Treatments—Full Text View—ClinicalTrials.gov", Jul. 13, 2021 (Jul. 13, 2021), XPO93024023, Retrieved from the Internet: URL:https://clinicaltrials.gov/ct2/show/NCT04959253?term=depression&cond=psilocyb in&draw=2&rank=11 [retrieved on Feb. 15, 2023], 5 pages.

Anwar, M.A. et al. (2013). Negative regulatory approaches to the attenuation of Toll-like receptor signaling. Experimental & Molecular Medicine, 45(2):e11, 14 pages. https://doi.org/10.1038/emm.2013.28.

Ara, A. et al. (2016). Sleep disturbances and substance use disorders: A bi-directional relationship. Psychiatr Ann, 46(7):408-412.

Arcelus, J., Mitchell, A. J., Wales, J., & Nielsen, S. (Jul. 2011). Mortality rates in patients with anorexia nervosa and other eating disorders. A meta-analysis of 36 studies. Archives of General Psychiatry, 68(7):724-731. https://doi.org/10.1001/archgenpsychiatry.2011.74.

Armstrong, M.J. and M.S. Okun (2020). Diagnosis and Treatment of Parkinson Disease. A Review. JAMA, 323(6):548-560.

Arzt, E. et al. (1991). Serotonin inhibition of tumor necrosis factor-α synthesis by human monocytes. Life Sciences, 48(26):2557-2562.

Asnis, G.M. et al. (2016). Pharmacotherapy treatment options for insomnia: A primer for clinicians. Int J Mol Sci, 17:50, 11 pages. https://doi.org/10.3390/ijms17010050.

Attia, E., Kaplan, A. S., Walsh, B. T., Gershkovich, M., Yilmaz, Z., Musante, D., & Wang, Y. (Oct. 2011). Olanzapine versus placebo for out-patients with anorexia nervosa. Psychological Medicine, 41(10):2177-2182. https://doi.org/10.1017/S0033291711000390.

Auger, R.R. et al. (Jun. 2005). Risks of high-dose stimulants in the treatment of disorders of excessive somnolence: A case-control study. Sleep, 28(6):667-672.

Avidan, A.Y. (2012). Comorbidities of central nervous system hypersomnia. Sleep Med Clin, 7:291-302.

Ayaz, G. et al. (Feb. 2017). Evaluation of 5-HT7 Receptor Trafficking on In Vivo and In Vitro Model of Lipopolysaccharide (LPS)-Induced Inflammatory Cell Injury in Rats and LPS-Treated A549 Cells. Biochemical Genetics, 55(1):34-47.

Babu, C.S. et al. (Oct. 2009). Co-morbidities in people living with epilepsy: Hospital based case-control study from a resource-poor setting. Epilepsy Research, 86(2-3):146-152.

(56) References Cited

OTHER PUBLICATIONS

Baglioni, C. et al. (Sep. 2016). Sleep and mental disorders: A meta-analysis of polysomnographic research. Psychol Bull, 142:969-990. HHS Public Access Author Manuscript, available Sep. 1, 2017, 56 pages.
Bahi Camile: II Antidepressants and Psychedelics—What Do We Know and What Could Be the Risks?, MIND Foundation, (Sep. 11, 2020), Retrieved from the Internet: URL:https://mind-foundation.org/psychedelicantidepressant-interactions/[retrieved on Jan. 20, 2022], 12 pages.
Bai, D. et al. (Jul. 17, 2019). Association of Genetic and Environmental Factors With Autism in a 5-Country Cohort. JAMA Psychiatry, 76(10):1035-1043.
Baio, J. (Mar. 30, 2012). Prevalence of autism spectrum disorders-Autism and developmental disabilities monitoring network, 14 sites, United States, 2008. Morbidity and Mortality Weekly Report (MMWR), 61(3):1-24.
Baker, L.A. et al. (2006) Behavioral Genetics: the Science of Antisocial Behavior. Law Contemp Probl, 69(1-2):7-46. NIH Public Access Author Manuscript, 37 pages.
Bandeen-Roche, K. et al. (Dec. 2009). Measuring Systemic Inflammatory Regulation in Older Adults: Evidence and Utility. Rejuvenation Research, 12(6):403-410.
Bandelow, B. and S. Michaelis (2015). Epidemiology of anxiety disorders in the 21st century. Dialogues Clin Neurosci, 17:327-335.
Banks, W.A. et al. (Sep. 1994). Penetration of interleukin-6 across the murine blood-brain barrier. Neuroscience Letters, 179(1-2):53-56.
Barnes, D.T. (Dec. 1970). The uses and abuses of L.S.D. and other hallucinogenic drugs. The Australian and New Zealand Journal of Psychiatry, 4(4):170-173.
Barnes, P. J. (Jun. 2006). How corticosteroids control inflammation: Quintiles Prize Lecture 2005. British Journal of Pharmacology, 148(3):245-254.
Barnes, T.R.E. (May 1989) A Rating Scale for Drug-Induced Akathisia. Br J Psychiatry, 154:672-676.
Baron-Cohen, S. et al. (May 2000) The amygdala theory of autism. Neurosci Biobehav Rev, 24(3):355-364.
Barrett, F.S. et al. (Nov. 2015) Validation of the revised Mystical Experience Questionnaire in experimental sessions with psilocybin. Journal of Psychopharmacology. 29:1182-1190. HHS Public Access Author Manuscript, 20 pages.
Barrett, F.S. et al. (Dec. 2016) The Challenging Experience Questionnaire: Characterization of challenging experiences with psilocybin mushrooms. Journal of Psychopharmacology, 30(12):1279-1295. HHS Public Access Author Manuscript, 42 pages.
Barrett, F.S. et al. (Nov. 2018) Serotonin 2A Receptor Signaling Underlies LSD-Induced Alteration of the Neural Response to Dynamic Changes in Music. Cerebral Cortex, 28:3939-3950.
Basetti and Aldrich, "Idiopathic hypersomnia. A series of 42 patients," Brain, (Aug. 1997) 120(8): 1423-1435.
Bateman, R.J. et al. (Aug. 30, 2012). Clinical and biomarker changes in dominantly inherited Alzheimer's disease. The New England Journal of Medicine, 367(9):795-804.
Bech, P. et al. (Jun. 1978) The mania rating scale: scale construction and inter-observer agreement. Neuropharmacology. 17(6):430-431.
Becker Anna M. et al: "Acute Effects of Psilocybin After Escitalopram or Placebo Pretreatment in a Randomized, Double-Blind, Placebo-Controlled, Crossover Study in Healthy Subjects", Clinical Pharmacology and Therapeutics, vol. 111, No. 4, Nov. 22, 2021 (Nov. 22, 2021), pp. 886-895.
Becker, D. and Grilo, C. (2015). Comorbidity of mood and substance use disorders in patients with binge-eating disorder: Associations with personality disorder and eating disorder pathology. Journal of Psychosomatic Research, 79(2), pp. 159-164.
Becker, P.M. (Dec. 2006). Insomnia: Prevalence, Impact, Pathogenesis, Differential Diagnosis, and Evaluation. Psychiatr Clin North Am, 26:855-870.
Bell, R.F. and E.A. Kalso (2018) Ketamine for pain management. Pain Reports, 3:e674, 8 pages.
Belli, H. et al. (Oct. 2012). Dissociative symptoms and dissociative disorder comorbidity in patients with obsessive-compulsive disorder. Comprehensive Psychiatry, 53(7):975-980.
Bello, N. and Yeomans, B. (2018). Safety of pharmacotherapy options for bulimia nervosa and binge eating disorder. Expert Opinion on Drug Safety, 17(1), pp. 17-23.
Belzeaux, R. et al. (Feb. 2018). Focusing on the Opioid System for Addiction Biomarker Discovery. Trends in Molecular Medicine, 24(2), pp. 206-220.
Benzon, H.T. et al. (2013) Preface. Practical Management of Pain, 5th Edition. Philadelphia, PA: Elsevier Mosby; 13 total pages.
Berg, A.T. (Jan. 2011). Epilepsy, cognition, and behavior: The clinical picture. Epilepsia, 52(Suppl 1):7-12. NIH Public Access Author Manuscript, available Jan. 1, 2012, 8 pages.
Berg, A.T. et al. (Aug. 2008). Residual cognitive effects of uncomplicated idiopathic and cryptogenic epilepsy. Epilepsy & Behavior, 13(4):614-619.
Berg, D. et al. (Nov. 12, 2015). MDS research criteria for prodromal Parkinson's disease. Movement Disorders, 30(12):1600-1609.
Berlin, H.A. et al. (May 2011). Double-blind, placebo-controlled trial of topiramate augmentation in treatment-resistant obsessive-compulsive disorder. Journal of Clinical Psychiatry, 72(5):716-721. https://doi.org/10.4088/JCP.09m05266gre.
Berthold-Losleben, M. & H. Himmerich (Sep. 2008). The TNF-alpha System: Functional Aspects in Depression, Narcolepsy and Psychopharmacology. Current Neuropharmacology, 6(3):193-202.
Besnard, J. et al. (Dec. 13, 2012) Automated design of ligands to polypharmacological profiles. Nature, 492(7428):215-220. https://doi.org/10.1038/nature11691.
Bhidayasiri, R. & P. Martinez-Martin (Feb. 2017). Clinical Assessments in Parkinson's Disease: Scales and Monitoring. 132:129-182.
Billiard, M. & Bentley, A. (Jun. 2004). Is insomnia best categorized as a symptom or a disease? Sleep Med. 5(Suppl 1):S35-S40. https://doi.org/10.1016/S1389-9457(04)90006-8.
Billiard, M. (Jun. 2008). Narcolepsy: Current treatment options and future approaches. Neuropsychiatr Dis Treat, 4(3):557-566.
Binukumar, B.K. et al. (Sep. 2015). Peptide TFP5/TP5 derived from Cdk5 activator P35 provides neuroprotection in the MPTP model of Parkinson's disease. Molecular Biology of the Cell, 26(24):4478-4491. https://doi.org/10.1091/mbc.E15-06-0415.
Bird, A.D., et al., (Jun. 4, 2019). Dissecting Sholl Analysis into Its Functional Components. Cell Reports, 27(10):3081-3096.
Bison, S. et al. (2009). Differential behavioral, physiological, and hormonal sensitivity to LPS challenge in rats. International Journal of Interferon, Cytokine and Mediator Research, 1:1-13. https://doi.org/10.2147/IJICMR.S4273.
Black, D.W. (Jul. 2015) The Natural History of Antisocial Personality Disorder. The Canadian Journal of Psychiatry. 60(7):309-314.
Blair, J.B. et al. (Nov. 2000) Effect of Ring Fluorination on the Pharmacology of Hallucinogenic Tryptamines. J Med Chem, 43(24):4701-4710. https://doi.org/10.1021/jm000339w.
Blasio, A. et al. (Jul. 2014). Opioid system in the medial prefrontal cortex mediates binge-like eating. Addiction Biology, 19(4), pp. 652-662.
Blum, A. (May 2014). HMG-COA reductase inhibitors (statins), inflammation, and endothelial progenitor cells-New mechanistic insights of atherosclerosis. BioFactors, 40(3), 295-302. https://doi.org/10.1002/biof.1157.
Bogenschutz et al. (Mar. 2015) Psilocybin-assisted treatment for alcohol dependence: A proof-of-concept study. J Psychopharmacol, 29:289-299.
Bonnet, M.H. et al. (Feb. 1990). The effect of triazolam on arousal and respiration in central sleep apnea patients. Sleep, 13:31-41.
Borovcanin, M.M. et al. (Nov. 6, 2017). Interleukin-6 in Schizophrenia—Is There a Therapeutic Relevance?Frontiers in Psychiatry, 8:Article 221, 10 pages. https://doi.org/10.3389/fpsyt.2017.00221.
Bortolato, B. et al. (2015). The Involvement of TNF-alpha in Cognitive Dysfunction Associated with Major Depressive Disorder: An Opportunity for Domain Specific Treatments. Current Neuropharmacology, 13(5):558-576.
Bosanac, P. et al. (Mar. 2005). Serotonergic and dopaminergic systems in anorexia nervosa: a role for atypical antipsychotics? Australian and New Zealand Journal of Psychiatry, 39(3):146-153.

(56) References Cited

OTHER PUBLICATIONS

Bossers, K. et al. (Jan. 2009). Analysis of gene expression in Parkinson's disease: possible involvement of neurotrophic support and axon guidance in dopaminergic cell death. Brain Pathology, 19(1):91-107.
Boszormenyi, Z. (1961) Psilocybin and diethyltryptamine: Two tryptamine hallucinogens. In: Rothlin E (ed) neuropsychopharmacology, vol. II. Elsevier, Amsterdam, pp. 226-229.
Braak, H. et al. (Apr. 2003). Staging of brain pathology related to sporadic Parkinson's disease. Neurobiology of Aging, 24(2):197-211.
Bradley, T.D. and Phillipson, E.A. (1992). Central sleep apnea. Clin. Chest Med, 13(3):493-505 (abstract).
Bradley, T.D. et al. (Aug. 1986). Clinical and physiologic heterogeneity of the central sleep apnea syndrome. Am. Rev. Respir. Dis., 134:217-221.
Braga, R.J. et al. (Nov. 2013). Anxiety comorbidity in schizophrenia. Psychiatry Res, 210:1-7.
Brakoulias, V. et al. (Jul. 2017). Comorbidity, age of onset and suicidality in obsessive-compulsive disorder (OCD): An international collaboration. Comprehensive Psychiatry, 76:79-86.
Brandt, C. & Mula, M. (Jun. 2016). Anxiety disorders in people with epilepsy. Epilepsy Behav., 59:87-91. https://doi.org/10.1016/j.yebeh.2016.03.020.
Brandt, R.B. et al. (Feb. 2020) Pharmacotherapy for Cluster Headache. CNS Drugs, 34:171-184, doi.org/10.1007/s40263-019-00696-2.
Brasure, M. et al. (2015). Management of Insomnia Disorder. Comparative Effectiveness Review No. 159. (Prepared by the Minnesota Evidence-based Practice Center under Contract No. 290-2012-00016-I). AHRQ Publication No. 15(16)-EHC027-EF. Rockville, MD: Agency for Healthcare Research and Quality. Dec. 2015 [online]. Retrieved from: www.effectivehealthcare.ahrq.gov/reports/final.cfm, 288 pages.
Bratland-Sanda, S. et al. (Apr. 2019). Defining compulsive exercise in eating disorders: Acknowledging the exercise paradox and exercise obsessions. Journal of Eating Disorders, 7(1):8, https://doi.org/10.1186/s40337-019-0238-2, 3 pages.
Brawman-Mintzer, O. et al. (Aug. 1993). Psychiatric comorbidity in patients with generalized anxiety disorder. Am. J. Psychiatry, 150:1216-1218.
Brockmeyer, T. et al. (Sep. 2017) Advances in the treatment of anorexia nervosa: A review of established and emerging interventions. Psychological Medicine, 48(8):1228-1256. Cambridge University Press. https://doi.org/10.1017/S0033291717002604.
Brown, C. M., & Stokes, M.A. (Apr. 2020). Intersection of Eating Disorders and the Female Profile of Autism. Child and Adolescent Psychiatric Clinics of North America, 29:409-417.
Brown, R.T. et al. (Dec. 2017). Pharmacokinetics of Escalating Doses of Oral Psilocybin in Healthy Adults. Clinical Pharmacokinetics, 56(12):1543-1554. https://doi.org/10.1007/s40262-017-0540-6.
Brown, T.A. et al. (Nov. 2001). Current and Lifetime Comorbidity of the DSM-IV Anxiety and Mood Disorders in a Large Clinical Sample. J. Abnorm. Psychol., 110:585-599.
Brownley, K. et al. (Sep. 2016). Binge-Eating Disorder in Adults. Annals of Internal Medicine, 165(6):409-420.
Bruce, S.E. et al. (Jun. 2005). Influence of psychiatric comorbidity on recovery and recurrence in generalized anxiety disorder, social phobia, and panic disorder: A 12-year prospective study. Am. J. Psychiatry, 162:1179-1187. NIH Public Access Author Manuscript, available in PMC Feb. 6, 2012, 16 pages.
Buescher, A.V. S. et al. (Aug. 2014). Costs of autism spectrum disorders in the United Kingdom and the United States. JAMA Pediatrics, 168(8):721-728.
Bulik, C.M. et al. (Aug. 1997). Eating disorders and antecedent anxiety disorders: a controlled study. Acta Psychiatr. Scand. 96, 101-107. https://doi.org/10.1111/j.1600-0447.1997.tb09913.x.
Burgess, E. et al. (Oct. 2016). Effects of transcranial direct current stimulation (tDCS) on binge-eating disorder. International Journal of Eating Disorders, 49(10), pp. 930-936.
Burt, D.R. et al. (Jul. 1976). Binding interactions of lysergic acid diethylamide and related agents with dopamine receptors in the brain. Molecular Pharmacology, 12(4):631-638.
Buscemi, N. et al. (Jun. 2005). Manifestations and management of chronic insomnia in adults: summary. In: AHRQ Evidence Report Summaries. Rockville (MD): Agency for Healthcare Research and Quality (US); 1998-2005. 125. https://doi.org/10.1037/e439752005-001, 11 pages.
Buxbaum, J.D., & Hof, P.R. (2013). Introduction. In The Neuroscience of Autism Spectrum Disorders. Elsevier, 7 pages. https://doi.org/10.1016/C2011-0-04170-4.
Buysse, D.J. et al. (May 1989). The Pittsburgh Sleep Quality Index: A New Instrument for Psychiatric Practice and Research. Psychiatry Res, 28:193-213.
Cabarkapa S. et al. (Aug. 1, 20193) Co-morbid obsessive-compulsive disorder and attention deficit hyperactivity disorder: Neurobiological commonalities and treatment implications. Front Psychiatry, 10:Article 557, 4 pages.
Cahill, C.M., & Rogers, J.T. (Sep. 19, 2008). Interleukin (IL) 1β Induction of IL-6 Is Mediated by a Novel Phosphatidylinositol 3-Kinase-dependent AKT/IκB Kinase α Pathway Targeting Activator Protein-1. Journal of Biological Chemistry, 283(38):25900-25912.
Caira, M. R., "Crystalline Polymorphism of Organic Compounds", Topics in Current Chemistry (Jan. 1, 1998); 198:163-208.
Callahan, P. M., & Appel, J.B. (Sep. 1988). Differences in the stimulus properties of 3,4-methylenedioxyamphetamine and 3,4-methylenedioxymethamphetamine in animals trained to discriminate hallucinogens from saline. J Pharmacol Exp Ther, 246(3):866-870.
Calvin, A.D. et al. (Apr. 2010). Advanced heart failure and nocturnal hypoxaemia due to central sleep apnoea are associated with increased serum erythropoietin. Eur. J. Heart Fail., 12:354-359. https://doi.org/10.1093/eurjhf/hfq005.
Campolongo, M. et al. (Jun. 2018) Sociability deficits after prenatal exposure to valproic acid are rescued by early social enrichment. Molecular Autism, 9:36, https://doi.org/10.1186/s13229-018-0221-9, 17 pages.
Canellas, F. et al. (Sep. 2014). Dual cases of type 1 narcolepsy with schizophrenia and other psychotic disorders. J. Clin. Sleep Med., 10(9):1011-1018. https://doi.org/10.5664/jcsm.4040.
Carhart-Harris et al., "Psilocybin for treatment-resistant depression: fMRI-measured brain mechanisms," Scientific Reports, Oct. 2017, 7:13187, 11 pages.
Carhart-Harris, R. et al. (Mar. 2012). Implications for psychedelic-assisted psychotherapy: functional magnetic resonance imaging study with psilocybin. British Journal of Psychiatry, 200(3):238-244.
Carhart-Harris, R.L. et al. (May 17, 2016) "Psilocybin with psychological support for treatment-resistant depression: an open-label feasibility study" Lancet Psychiatry, 3:619-627.
Carhart-Harris, R.L. et al. (Feb. 2018) "Psilocybin with psychological support for treatment-resistant depression: six-month follow-up" Psychopharmacology, 235:399-408.
Carlsson, T. et al. (Jun. 2011). Systemic administration of neuregulin-1β1 protects dopaminergic neurons in a mouse model of Parkinson's disease. Journal of Neurochemistry, 117(6), 1066-1074. https://doi.org/10.1111/j.1471-4159.2011.07284.x.
Carosi, J. M., & Sargeant, T. J. (Aug. 2019). Rapamycin and Alzheimer disease: a double-edged sword? Autophagy, 15(8):1460-1462. https://doi.org/10.1080/15548627.2019.1615823.
Carter, O.L. (Oct. 2005) Using psilocybin to investigate the relationship between attention, working memory, and the serotonin 1A and 2A receptors. J Cogn Neurosci., 17(10):1497-1508.
Cashman, J.N. (1996). The mechanisms of action of NSAIDs in analgesia. Drugs, 52(SUPPL. 5):13-23. https://doi.org/10.2165/00003495-199600525-00004.
Cassano, G.B et al. (Sep. 2002). Psychopharmacology of anxiety disorders. Dialogues Clin. Neurosci., 4(3):271-285.
Cavalli, E et al. (Dec. 2019). The neuropathic pain: An overview of the current treatment and future therapeutic approaches. Intl J Immunopathol Pharmacol, 33:1-10; DOI: 10.1177/2058738419838383.

(56) References Cited

OTHER PUBLICATIONS

Chang, A et al. (Jun. 3, 2020). Capsaicin. StatPearls. NCBI Bookshelf [online]. Retrieved from: https://www.ncbi.nlm.nih.gov/books/NBK459168/?report=printable; retrieved on Jul. 30, 2020, 4 pages.
Chang, S et al. (Oct. 2015). Disease monitoring in inflammatory bowel disease. World Journal of Gastroenterology, 21(40):11246-11259.
Chang, T .- T. and Yen, Y .- C. (2010). Cytokines and Major Psychiatric Disorders. Taiwanese Journal of Psychiatry, 24(4):257-268.
Chang, Y.C et al. (May 2017). Behavioral phenotyping for autism spectrum disorders in mice. Current Protocols in Toxicology. 72:11. 22.1-11.22.21, doi: 10.1002/cptx. 19.
Charles, P et al. (Aug. 1999). Regulation of Cytokines, Cytokine Inhibitors, and Acute-Phase Proteins Following Anti-TNF-a Therapy in Rheumatoid Arthritis. The Journal of Immunology, 163(3): 1521-1528. http://www.jimmunol.org/content/163/3/1521.
Chelminski, P.R. et al. (Jan. 2005) A primary care, multi-disciplinary disease management program for opioid-treated patients with chronic non-cancer pain and a high burden of psychiatric comorbidity. BMC Health Serv Res, 5:3, doi:10.1186/1472-6963-5-3, 13 pages.
Cheng, Z. et al. (Jan. 2019). Ethnic differences in eating disorder prevalence, risk factors, and predictive effects of risk factors among young women. Eating Behaviors, 32, pp. 23-30.
Chieffi, S. et al. (May 2017). Orexin system: The key for a healthy life. Front. Physiol., 8:357, doi: 10.3389/fphys.2017.00357, 9 pages.
Choi, G.B. et al. (Feb. 2016). The maternal interleukin-17a pathway in mice promotes autism-like phenotypes in offspring. Science, 351(6276):933-939.
Chrem, Mendez, P. et al. (2019). Biomarkers for Alzheimer's disease. Where we stand and where we are headed. Medicina (Buenos Aires), 79:546-551.
Citrome, L. (Aug. 2019). Binge eating disorder revisited: what's new, what's different, what's next. CNS Spectrums, 24, pp. 4-12.
Citrome, L. (Dec. 2014). Suvorexant for insomnia: A systematic review of the efficacy and safety profile for this newly approved hypnotic—What is the number needed to treat, number needed to harm and likelihood to be helped or harmed? Int. J. Clin. Pract., 68(12):1429-1441. https://doi.org/10.1111/ijcp.12568.
Ciz, M. et al. (Dec. 2007). Serotonin modulates the oxidative burst of human phagocytes via various mechanisms. Platelets, 18(8):583-590. https://doi.org/10.1080/09537100701471865.
Clark, B. (1968). Some early observations on the use of psilocybin in psychiatric patients. Brit. J. Soc. Psychiatry, 2:21-25.
Clemmensen, C. et al. (May 2012). The microtubule-associated protein 1A (MAP1A) is an early molecular target of soluble Aβ-peptide. Cellular and Molecular Neurobiology, 32(4):561-566.
Clinicaltrials.gov, "Effects of Psilocybin in Major Depressive Disorder", NCT03181529, First posted Jun. 8, 2017, pp. 1-6.
Clinicaltrials.gov, "Effects of SERT Inhibition on the Subjective Response to Psilocybin in Healthy Subjects", Study NCT03912974, Submitted Feb. 28, 2020. Retrieved from the Internet: URL:https://www.clinicaltrials.gov/ct2/history/NCT03912974?V_4=View#StudyPageTop [retrieved on Jan. 21, 2022]; 7 printed pages.
Cloez-Tayarani, I. et al. (Feb. 2003). Differential effect of serotonin on cytokine production in lipopolysaccharide-stimulated human peripheral blood mononuclear cells: Involvement of 5-hydroxytryptamineza receptors. International Immunology, 15(2), 233-240. https://doi.org/10.1093/intimm/dxg027.
Coley, A.A., & Gao, W.J. (Jul. 2019). PSD-95 deficiency disrupts PFC-associated function and behavior during neurodevelopment. Scientific Reports, 9:9486, https://doi.org/10.1038/s41598-019-45971-w, 13 pages.
Collins, K.L. et al. (Jun. 2018). A review of current theories and treatments for phantom limb pain. J Clin Invest, 128(6):2168-2176. https://doi.org/10.1172/JCI94003.
Colloca, L. et al. (Feb. 2017) Neuropathic pain. Nat Rev Dis Primers, 3:17002, doi:10.1038/nrdp.2017.2, 45 pages.
Connolly, J. et al. (Sep. 2015). ADHD & Pharmacotherapy: Past, Present and Future. Ther Innoc Regul Sci., 49(5):632-642. HHS Public Access, available in PMC Sep. 1, 2016, 19 pages.
Cooper, C.M. et al. (May 2015) Tianeptine in an experimental medicine model of antidepressant action. Journal of Psychopharmacology, 29(5):582-590.
Co-pending U.S. Appl. No. 18/032,320, inventor Hickey; Molly Tabitha, filed Apr. 17, 2023.
Coric, V. et al. (Sep. 2005). Riluzole augmentation in treatment-resistant obsessive-compulsive disorder: An open-label trial. Biological Psychiatry, 58(5):424-428. https://doi.org/10.1016/j.biopsych.2005.04.043.
Cornillie, F. et al. (Apr. 2001) Infliximab induces potent anti-inflammatory and local immunomodulatory activity but no systemic immune suppression in patients with Crohn's disease. Alimentary Pharmacology and Therapeutics, 15(4), 463-473. https://doi.org/10.1046/j.1365-2036.2001.00956.x.
Cossrow, N. et al. (Aug. 2016). Estimating the Prevalence of Binge Eating Disorder in a Community Sample From the United States: Comparing DSM-IV-TR and DSM-5 Criteria. The Journal of Clinical Psychiatry, 77(8), pp. e968-e974.
Costa-Mattioli, M., & Monteggia, L.M. (Nov. 2013). mTOR complexes in neurodevelopmental and neuropsychiatric disorders. Nature Neuroscience, 16(11):1537-1543.
Cowie, M.R. et al. (Sep. 2015) Adaptive servo-ventilation for central sleep apnea in systolic heart failure. N. Engl. J. Med., 373:1095-1105. doi.org/10.1056/NEJMoa1506459.
Croall, I.D. et al. (Jun. 2020). Cognitive Deficit and White Matter Changes in Persons with Celiac Disease: a Population-Based Study. Gastroenterology. 158:2112-2122.
Crow, S.J. et al. (Dec. 2009). Increased mortality in bulimia nervosa and other eating disorders. American Journal of Psychiatry, 166(12):1342-1346.
Crowson, C. S. et al. (Aug. 2009). Which Measure of Inflammation to Use? A Comparison of Erythrocyte Sedimentation Rate and C-Reactive Protein Measurements from Randomized Clinical Trials of Golimumab in Rheumatoid Arthritis. The Journal of Rheumatology, 36(8):1606-1610. https://doi.org/10.3899/jrheum.081188.
Cruccu, G. (Dec. 2017) A Review of Neuropathic Pain: From Guidelines to Clinical Practice. Pain Ther, 6(Suppl 1):S35-S42.
Cryan, J.F. & Sweeney, F.F. (Oct. 2011). The age of anxiety: Role of animal models of anxiolytic action in drug discovery. British Journal of Pharmacology, 164:1129-1161.
Csicsvari, J. et al. (Jan. 2003). Mechanisms of gamma oscillations in the hippocampus of the behaving rat. Neuron, 37:311-322.
Culbert, K.M. et al. (Nov. 2015). Research Review: What we have learned about the causes of eating disorders—A synthesis of sociocultural, psychological, and biological research. Journal of Child Psychology and Psychiatry, 56:11, pp. 1141-1164. https://doi.org/10.1111/jcpp.12441.
Curatolo, P. et al. (Dec. 2010) The neurobiological basis of ADHD. Ital J Pediatr, 36:79, http://www.ijponline.net/content/36/1/79, 7 pages.
Cuthbert, P.C. et al. (Mar. 2007). Synapse-associated protein 102/dlgh3 couples the NMDA receptor to specific plasticity pathways and learning strategies. Journal of Neuroscience, 27(10):2673-2682. https://doi.org/10.1523/JNEUROSCI.4457-06.2007.
Da Silveira, D.X. et al. (Jun. 2005). Ayahuasca in adolescence: A preliminary psychiatric assessment. Journal of Psychoactive Drugs, 37:2, 129-133. https://doi.org/10.1080/02791072.2005.10399792.
Dahan, A. et al. (Oct. 2014) Comorbidities and the Complexities of Chronic Pain. Anesthesiology, 121(4):675-677.
Dalic, L., & Cook, M. (Oct. 2016). Managing drug-resistant epilepsy: challenges and solutions. Neuropsychiatric Disease and Treatment, vol. 12, p. 2605-2616. https://doi.org/10.2147/NDT.S84852.
Damaslo, A., "Alzheimer's Disease and Related Dementias," Cecil Textbook of Medicine, Eds. J. Claude Bennett, MD and Fred Plum, 20th edition (1996), vol. 2, pp. 1992-1996.
Dansie, E.J. & Turk, D.C. (Jul. 2013) Assessment of patients with chronic pain. Br J Anaesth. 111(1):19-25.

(56) References Cited

OTHER PUBLICATIONS

Darveaux, J., & Busse, W. W. (Apr. 2015). Biologics in Asthma—The Next Step Toward Personalized Treatment. J Allergy Clin Immunol Pract, 3(2), 152-160. https://doi.org/10.1016/j.jaip.2014.09.014.
Dash, S. (2019). The impact of genetic and cultural factors on anorexia and bulimia. Life Research, 2(2), 71-79. https://doi.org/10.12032/life2019-0425-004.
Dauer, W., & Przedborski, S. (Sep. 2003). Parkinson's Disease: Mechanisms and Models. Neuron, 39(6), 889-909. https://doi.org/10.1016/S0896-6273(03)00568-3.
Dauvilliers, Y. & Barateau, L. (Aug. 2017). Narcolepsy and Other Central Hypersomnias. Continyyn (Minneap Minn), 23(4):989-1004. https://doi.org/10.1212/CON.0000000000000492.
Dauvilliers, Y. et al. (Feb. 2007). Narcolepsy with cataplexy. Lancet 369, 499-511. https://doi.org/10.1016/S0140-6736(07)60237-2.
Dauvilliers, Y. et al.(Jun. 2009). Psychological health in central hypersomnias: The French Harmony study. J. Neurol. Neurosurg. Psychiatry, 80, 636-641. https://doi.org/10.1136/jnnp.2008.161588.
Davila Gonzalez, I. et al. (Apr. 2019). Benralizumab: A New Approach for the Treatment of Severe Eosinophilic Asthma. Journal of Investigational Allergology and Clinical Immunology, 29(2), 84-93. https://doi.org/10.18176/jiaci.0385.
Davis, C. (Dec. 2015). The epidemiology and genetics of binge eating disorder (BED). CNS Spectrums, 20(6), pp. 522-529.
Davis, H., & Attia, E. (Nov. 2017). Pharmacotherapy of eating disorders. Current Opinion in Psychiatry, 30(6), 452-457. https://doi.org/10.1097/YCO.0000000000000358.
De Veen, B.T.H et al. (Feb. 2017) "Psilocybin for treating substance use disorders?" Exp Rev Neurotherapeutics, 17(2):203-212; DOI: 10.1080/14737175.2016.1220834.
Deacon, R.M.J. & Rawlins, J.N.P. (2006) T-maze alternation in the rodent. Nat Protoc, 1(1):7-12. Available from: http://www.ncbi.nlm.nih.gov/pubmed/17406205.
Debacker, W.A. et al. (Jan. 1995). Central apnea index decreases after prolonged treatment with acetazolamide. Am. J. Respir. Crit. Care Med., 151:87-91, https://doi.org/10.1164/ajrccm.151.1.7812578.
Debotton, N. and A. Dahan (Jan. 2017) Applications of Polymers as Pharmaceutical Excipients in Solid Oral Dosage Forms. Med Res Rev, 37(1):52-97.
Decaluwe, V. and Braet, C. (2003). Prevalence of binge-eating disorder in obese children and adolescents seeking weight-loss treatment. International Journal of Obesity, 27(3), pp. 404-409.
Dejong, H. et al. (Nov. 2013). Quality of life in anorexia nervosa, bulimia nervosa and eating disorder not-otherwise-specified. Journal of Eating Disorders, 1:43, http://www.jeatdisord.com/content/1/1/43, 8 pages.
Delisi, M. et al. (Jul. 2019) The etiology of antisocial personality disorder: The differential roles of adverse childhood experiences and childhood psychopathology. Compr Psychiatry, 92:1-6.
Dell'Osso, B. et al. (Feb. 2018). Prevalence of suicide attempt and clinical characteristics of suicide attempters with obsessive-compulsive disorder: A report from the International College of Obsessive-Compulsive Spectrum Disorders (ICOCS). CNS Spectrums, 23(1), 59-66. https://doi.org/10.1017/S1092852917000177.
Depboylu, C. et al. (May 2015). Systemically administered neuregulin-1β1 rescues nigral dopaminergic neurons via the ErbB4 receptor tyrosine kinase in MPTP mouse models of Parkinson's disease. Journal of Neurochemistry, 133(4), 590-597. https://doi.org/10.1111/jnc.13026.
Di Lodovico, L., & Gorwood, P. (Feb. 2020). The relationship between moderate to vigorous physical activity and cognitive rigidity in anorexia nervosa. Psychiatry Research, 284:112703, https://doi.org/10.1016/j.psychres.2019.112703, 9 pages.
Dijkstra, P.U. et al. (Dec. 2002) Phantom pain and risk factors: A multivariate analysis. J Pain Symptom Manage. 24(6):578-585.
Diniz, J.B. et al. (Mar. 2010) "Quetiapine versus clomipramine in the augmentation of selective serotonin reuptake inhibitors for the treatment of obsessive-compulsive disorder: A randomized, open-label trial" Journal of Psychopharmacology, 24(3):297-307.
Dold, M. et al. (Feb. 2015) "Second-Generation Antipsychotic Drugs in Anorexia Nervosa: A Meta-Analysis of Randomized Controlled Trials" Psychotherapy and Psychosomatics, 84(2):110-116. https://doi.org/10.1159/000369978.
Dold, M. et al. (May 2015). Antipsychotic Augmentation of Serotonin Reuptake Inhibitors in Treatment-Resistant Obsessive-Compulsive Disorder: An Update Meta-Analysis of Double-Blind, Randomized, Placebo-Controlled Trials. The International Journal of Neuropsychopharmacology, 1-11, https://doi.org/10.1093/ijnp/pyv047.
Dotterer, H.L. et al. (Apr. 2017) Amygdala reactivity predicts adolescent antisocial behavior but not callous-unemotional traits. Dev Cogn Neurosci, 24:84-92.
Drakatos, P. et al.(Jul. 2017). Safety and efficacy of long-term use of sodium oxybate for narcolepsy with cataplexy in routine clinical practice. Sleep Med, 35:80-84. https://doi.org/10.1016/j.sleep.2017.03.028.
Droogleever Fortuyn, H.A. et al. (Aug. 2011). Narcolepsy and psychiatry: An evolving association of increasing interest. Sleep Med. 12, 714-719. https://doi.org/10.1016/j.sleep.2011.01.013.
Drover, D.R., 2004. Comparative pharmacokinetics and pharmacodynamics of short-acting hypnosedatives: Zaleplon, zolpidem and zopiclone. Clin. Pharmacokinet. 423(4):227-238. https://doi.org/10.2165/00003088-200443040-00002.
drugs.com (2014) Venlafaxine. Drugs.com, Web Archives [online]. Retrieved from: https://web.archive.org/web/20140502180823/https://www.drugs.com/venlafaxine.html; on May 2, 2014; 5 pages.
Dunning, C.J.R. et al. (May 2016). Multisite tyrosine phosphorylation of the N-terminus of Mint1/X11α by Src kinase regulates the trafficking of amyloid precursor protein. Journal of Neurochemistry, 137(4), 518-527. https://doi.org/10.1111/jnc.13571.
Durk, T. et al. (May 2005). 5-Hydroxytryptamine modulates cytokine and chemokine production in LPS-primed human monocytes via stimulation of different 5-HTR subtypes. International Immunology, 17(5), 599-606. https://doi.org/10.1093/intimm/dxh242.
Earle, W. J. (2014) "DSM-5" The Philosophical Forum [online]. Retrieved from: https://doi.org/10.1111/phil.12034; pp. 179-196.
Eckert, D.J. et al. (Feb. 2007). Central sleep apnea: Pathophysiology and treatment. Chest, 131:595-607. NIH Public Access Author Manuscript, available Apr. 3, 2008, 22 pages.
Edfawy, M. et al. (Mar. 2019). Abnormal mGluR-mediated synaptic plasticity and autism-like behaviours in Gprasp2 mutant mice. Nature Communications. 10:1431, https://doi.org/10.1038/s41467-019-09382-9, 15 pages.
Edwards, A. (Jun. 2010) Book Review: Handbook of Depression (2nd ed.). Gotlib, I.H., Hammen, C.L. (Eds.), The Guilford Press: New York, 2009. Psychology Medicine, 40:1051-1052.
Eijk, S. et al. (Jul. 2018). Autism Spectrum Disorder in an Unselected Cohort of Children with Neurofibromatosis Type 1 (NF1). Journal of Autism and Developmental Disorders, 15:2278-2285. https://doi.org/10.1007/s10803-018-3478-0.
Ekbom, K. et al. (Mar. 2002) Age at onset and sex ratio in cluster headache: Observations over three decades. Cephalalgia, 22(2):94-100.
Elbassuoni, E. A., & Ahmed, R. F. (Dec. 2019). Mechanism of the neuroprotective effect of GLP-1 in a rat model of Parkinson's with pre-existing diabetes. Neurochemistry International, 131, 104583. https://doi.org/10.1016/j.neuint.2019.104583, 8 pages.
El-Emshaty, H. M., Nasif, W. A., & Mohamed, I. E. (Dec. 2015). Serum Cytokine of IL-10 and IL-12 in Chronic Liver Disease: The Immune and Inflammatory Response. Disease Markers, https://doi.org/10.1155/2015/707254, 7 pages.
El-Gabalawy, H., Guenther, L. C., & Bernstein, C. N. (May 2010). Epidemiology of Immune-Mediated Inflammatory Diseases: Incidence, Prevalence, Natural History, and Comorbidities. The Journal of Rheumatology Supplement, 85, 2-10. https://doi.org/10.3899/jrheum.091461.
Epstein Jn, Loren Rea. (Oct. 2013) Changes in the definition of ADHD in DSM-5: Subtle but important. Neuropsychiatry, 3(5):455-8.

(56) References Cited

OTHER PUBLICATIONS

Erdur, L. et al. (Feb. 2012). Somatic comorbidity in anorexia nervosa: First results of a 21-year follow-up study on female inpatients. BioPsychoSocial Medicine, 6:4, https://doi.org/10.1186/1751-0759-6-4, 6 pages.

Erskine, H. and Whiteford, H.(Nov. 2018). Epidemiology of binge eating disorder. Current Opinion in Psychiatry, 31(6), pp. 462-470.

Essau, C.A. et al. (Jul. 2014). Anxiety disorders in adolescents and psychosocial outcomes at age 30. J. Affect. Disord. 163, 125-132. https://doi.org/10.1016/j.jad.2013.12.033. NIH Public Access Author Manuscript, 19 pages.

Evans, M.M. et al. (Jun. 2016) Ego-dissolution and psychedelics: Validation of the Ego-Dissolution Inventory (EDI). Front Human Neurosci, 10:269, doi: 10.3389/fnhum.2016.00269, 13 pages.

Everitt, H. et al. (May 2018). Antidepressants for insomnia in adults (Review). Cochrane Database Syst. Rev., Issue 5, Art. No. CD010753, https://doi.org/10.1002/14651858.CD010753.pub2, 117 pages.

Fadiman, J. & Korb, S. (Mar. 2019) Might Microdosing Psychedelics Be Safe and Beneficial? An Initial Exploration. J Psychoactive Drugs, 51(2):118-22. Available from: https://doi.org/10.1080/02791072.2019.1593561.

Fan, L.Y. et al. (Oct. 2018) Visual processing as a potential endophenotype in youths with attention-deficit/hyperactivity disorder: A sibling study design using the counting Stroop functional MRI. Hum Brain Mapp, 39(10):3827-35. Available from: http://www.ncbi.nlm.nih.gov/pubmed/29749060.

Fayaz, A. et al. (2016) Prevalence of chronic pain in the UK: a systematic review and meta-analysis of population studies. BMJ Open [Internet]. 6:e010364, doi:10.1136/bmjopen-2015-010364, 12 pages.

FDA mulls drug to slow late-stage Alzheimer's [online], [retrieved on Sep. 23, 2003]. Retrieved from the internet, http;//www.cnn/com/2003/HEALTH/conditions/09/24/alzheimers.drug.ap/index.html. pp. 1-3.

Feinstein, A.R. (Dec. 1970). The pre-therapeutic classification of co-morbidity in chronic disease. Journal of Chronic Diseases, 23(7), 455-468. https://doi.org/10.1016/0021-9681(70)90054-8.

Fekadu et al., "Standardisation framework for the Maudsley staging method for treatment resistance in depression," BMC Psychiatry (Apr. 11, 2018) 18:100, 13 pages.

Ferguson, S.A. et al. (Feb. 2010). Melatonin agonists and insomnia. Expert Rev. Neurother., 10(2):305-318. https://doi.org/10.1586/ern.10.1.

Fernandez, B. A., & Scherer, S.W. (Dec. 2017). Syndromic autism spectrum disorders: Moving from a clinically defined to a molecularly defined approach. Dialogues in Clinical Neuroscience, 19:353-371.

Feyder, M. et al. (Dec. 2010). Association of mouse Dlg4 (PSD-95) gene deletion and human DLG4 gene variation with phenotypes relevant to autism spectrum disorders and Williams' syndrome. American Journal of Psychiatry, 167:1508-1517. https://doi.org/10.1176/appi.ajp.2010.10040484.

Fiebich, B.L. et al. (2004). Antiinflammatory effects of 5-HT3 receptor antagonists in lipopolysaccharide-stimulated primary human monocytes. Scandinavian Journal of Rheumatology. 33:28-32. https://doi.org/15515409.

Fisher, G. (1970). The psycholytic treatment of a childhood schizophrenic girl. International Journal of Social Psychiatry. 16(2):112-130. https://doi.org/10.1177/002076407001600204.

Fisher, K.A. & Hany, M. (Jun. 24, 2020) Antisocial Personality Disorder. StatPearls [Internet]. NCBI Bookshelf. Retrieved from: http://www.ncbi.nlm.nih.gov/pubmed/31536279, 6 printed pages.

Fisher, R.S. et al. (Apr. 2005). Epileptic Seizures and Epilepsy: Definitions Proposed by the International League Against Epilepsy (ILAE) and the International Bureau for Epilepsy (IBE). Epilepsia, 46(4), 470-472. https://doi.org/10.1111/j.0013-9580.2005.66104.x.

Flament, M.F. et al. (Mar. 2012) Evidence-based pharmacotherapy of eating disorders. The International Journal of Neuropsychopharmacology, 15(02), 189-207. https://doi.org/10.1017/S1461145711000381.

Flanagan, T.W. et al. (Nov. 2019). 5-HT2 receptor activation alleviates airway inflammation and structural remodeling in a chronic mouse asthma model. Life Sciences, 236:116790, https://doi.org/10.1016/j.lfs.2019.116790, 9 pages.

FMC Product Overview (2017) Avicel® SMCC HD 50 Silicified Microcrystalline cellulose NF. Product Specifications, 2 pages.

FMC Product Overview (2017) Avicel® SMCC HD 90 Silicified Microcrystalline cellulose NF. Product Specifications, 2 pages.

Folen, V. (Apr. 1975) X-ray powder diffraction data for some drugs, excipients, and adulterants in illicit samples. Journal of Forensic Science. 1975, 20, 348-372.

Fond, G. et al. (Dec. 2014). Anxiety and depression comorbidities in irritable bowel syndrome (IBS): a systematic review and meta-analysis. Eur. Arch. Psychiatry Clin. Neurosci. 264, 651-660. https://doi.org/10.1007/s00406-014-0502-z.

Fornasari, D. (Dec. 2017) Pharmacotherapy for Neuropathic Pain: A Review. Pain Ther, 6(Suppl 1):S25-S33.

Fortuyn, H.A.D. et al. (Feb. 2010). Anxiety and mood disorders in narcolepsy: a case-control study. Gen. Hosp. Psychiatry, 32:49-56. https://doi.org/10.1016/j.genhosppsych.2009.08.007.

Fortuyn, H.A.D. et al. (Mar. 2008). High Prevalence of Eating Disorders in Narcolepsy with Cataplexy: A Case-Control Study. Sleep 31, 335-341. https://doi.org/10.1093/sleep/31.3.335.

*Freedom To Operate, Inc.* v. *Compass Pathways Limited.* Case PGR2022-00012, U.S. Pat. No. 10,947,257. and *Freedom To Operate, Inc.* v. *Compass Pathways Limited.* Case PGR2022-00018, U.S. Pat. No. 10,954,259; Order that the requests for POP review are denied and original panel maintains authority over all matters, including considering the submitted rehearing requests, dated Feb. 10, 2023, 3 pages.

*Freedom To Operate, Inc.* v. *Compass Pathways Limited.* Case PGR2022-00012, U.S. Pat. No. 10,947,257. and *Freedom To Operate, Inc.* v. *Compass Pathways Limited.* Case PGR2022-00018, U.S. Pat. No. 10,954,259; Paper No. 21, Order Denying Petitioners Request on Rehearing, dated May 23, 2023, 9 pages.

*Freedom To Operate, Inc.* v. *Compass Pathways Limited.* Case PGR2022-00012, U.S. Pat. No. 10,947,257. Exhibit 1006: Declaration of Sven Lidin, Ph.D. (PTAB Dec. 15, 2021), 68 pages.

*Freedom To Operate, Inc.* v. *Compass Pathways Limited.* Case PGR2022-00012, U.S. Pat. No. 10,947,257. Exhibit 1007: Curriculum Vitae—Sven Lidin, Ph.D. (PTAB Dec. 15, 2021), 2 pages.

*Freedom To Operate, Inc.* v. *Compass Pathways Limited.* Case PGR2022-00012, U.S. Pat. No. 10,947,257. Exhibit 1008: Declaration of James A. Kaduk, Ph.D. (PTAB Dec. 15, 2021), 25 pages.

*Freedom To Operate, Inc.* v. *Compass Pathways Limited.* Case PGR2022-00012, U.S. Pat. No. 10,947,257. Exhibit 1009: Curriculum Vitae—James A. Kaduk, Ph.D. (PTAB Dec. 15, 2021), 3 pages.

*Freedom To Operate, Inc.* v. *Compass Pathways Limited.* Case PGR2022-00012, U.S. Pat. No. 10,947,257. Exhibit 1010: Declaration of Raj Suryanarayanan, Ph.D. (PTAB Dec. 15, 2021), 23 pages.

*Freedom To Operate, Inc.* v. *Compass Pathways Limited.* Case PGR2022-00012, U.S. Pat. No. 10,947,257. Exhibit 1011: Curriculum Vitae—Raj Suryanarayanan, Ph.D. (PTAB Dec. 15, 2021), 53 pages.

*Freedom To Operate, Inc.* v. *Compass Pathways Limited.* Case PGR2022-00012, U.S. Pat. No. 10,947,257. Exhibit 1012: Declaration of Charles L. Raison, M.D. (Ptab Dec. 15, 2021), 6 pages.

*Freedom To Operate, Inc.* v. *Compass Pathways Limited.* Case PGR2022-00012, U.S. Pat. No. 10,947,257. Exhibit 1013: Hancock, B.C. and G. Zografi. Characteristics and Significance of the Amorphous State In Pharmaceutical Systems. Journal of Pharmaceutical Sciences, vol. 86, No. 1. (PTAB Dec. 15, 2021), 12 pages.

*Freedom To Operate, Inc.* v. *Compass Pathways Limited.* Case PGR2022-00012, U.S. Pat. No. 10,947,257. Exhibit 1014: Arlin, J.B et al. Experimental Crystal Structure Determination, pp. 1-3, 2021 (PTAB Dec. 15, 2021).

*Freedom To Operate, Inc.* v. *Compass Pathways Limited.* Case PGR2022-00012, U.S. Pat. No. 10,947,257. Exhibit 1015: Bernstein J. Polymorphism in Molecular Crystals, International Union Of Crystallography, Oxford, 2002 (PTAB Dec. 15, 2021), 429 pages.

*Freedom To Operate, Inc.* v. *Compass Pathways Limited.* Case PGR2022-00012, U.S. Pat. No. 10,947,257. Exhibit 1016: Boratto,

(56) References Cited

OTHER PUBLICATIONS

M. H. Semiconducting and Insulating Oxides Applied to Electronic Devices. Thesis Ph.D. UNESP, School of Science, Bauru, 2018. (PTAB Dec. 15, 2021), 117 pages.

*Freedom To Operate, Inc.* v. *Compass Pathways Limited.* Case PGR2022-00012, U.S. Pat. No. 10,947,257. Exhibit 1017: D.E. Nichols, Synthesis of High Purity Psilocybin: Lot 10415-25, Nov. 1, 2009. (PTAB Dec. 15, 2021), 43 pages.

*Freedom To Operate, Inc.* v. *Compass Pathways Limited.* Case PGR2022-00012, U.S. Pat. No. 10,947,257. Exhibit 1018: Jun. 6, 2012 Letter from D. Nichols to R. Griffiths. (PTAB Dec. 15, 2021), 7 pages.

*Freedom To Operate, Inc.* v. *Compass Pathways Limited.* Case PGR2022-00012, U.S. Pat. No. 10,947,257. Exhibit 1019: Apr. 15, 2014 Letter from C. Kim to E. Elder. (PTAB Dec. 15, 2021), 4 pages.

*Freedom To Operate, Inc.* v. *Compass Pathways Limited.* Case PGR2022-00012, U.S. Pat. No. 10,947,257. Exhibit 1020: Declaration of Brett D. Bobzien. (PTAB Dec. 15, 2021), 5 pages.

*Freedom To Operate, Inc.* v. *Compass Pathways Limited.* Case PGR2022-00012, U.S. Pat. No. 10,947,257. Exhibit 1021: Triclinic Labs Report, Characterization of Psilocybin, Dec. 2, 2021. (PTAB Dec. 15, 2021), 11 pages.

*Freedom To Operate, Inc.* v. *Compass Pathways Limited.* Case PGR2022-00012, U.S. Pat. No. 10,947,257. Exhibit 1023: USP35-(941) Physical Tests/X-Ray Powder Diffraction. (PTAB Dec. 15, 2021), 7 pages.

*Freedom To Operate, Inc.* v. *Compass Pathways Limited.* Case PGR2022-00012, U.S. Pat. No. 10,947,257. Exhibit 1024: Ottoboni S et al. Understanding API Static Drying with Hot Gas Flow: Design and Test of a Drying Rig Prototype and Drying Modeling Development. Org. Process Res. Dev. 2020, 24, 2505-2520. (PTAB Dec. 15, 2021).

*Freedom To Operate, Inc.* v. *Compass Pathways Limited.* Case PGR2022-00012, U.S. Pat. No. 10,947,257. Exhibit 1025: Airaksinen S et al. Comparison of the effects of two drying methods on polymorphism of theophylline. International Journal of Pharmaceutics 276 (2004) 129-141. (PTAB Dec. 15, 2021).

*Freedom To Operate, Inc.* v. *Compass Pathways Limited.* Case PGR2022-00012, U.S. Pat. No. 10,947,257. Exhibit 1026: Lim, H.L et al., Understanding and preventing agglomeration in a filter drying process. Powder Technology, 300 (2016) 146-156. (PTAB Dec. 15, 2021).

*Freedom To Operate, Inc.* v. *Compass Pathways Limited.* Case PGR2022-00012, U.S. Pat. No. 10,947,257. Exhibit 1028: Curriculum Vitae-Charles L. Raison, M.D. (Ptab Dec. 15, 2021), 59 pages.

*Freedom To Operate, Inc.* v. *Compass Pathways Limited.* Case PGR2022-00012, U.S. Pat. No. 10,947,257. Exhibit 1029: Excerpt from Diagnostic and Statistical Manual of Mental Disorders, Fifth Edition, DSM-5. Am. Psychiatric Assn., 2013; pp. 160-168. (PTAB Dec. 15, 2021).

*Freedom To Operate, Inc.* v. *Compass Pathways Limited.* Case PGR2022-00012, U.S. Pat. No. 10,947,257. Exhibit 1030: Declaration of Roland R. Griffiths, Ph.D. (PTAB Dec. 15, 2021), 6 pages.

*Freedom To Operate, Inc.* v. *Compass Pathways Limited.* Case PGR2022-00012, U.S. Pat. No. 10,947,257. Exhibit 1031: Excerpt from A. Dictionary of Chemistry, 6th Edition. John Daintith (Ed.) Oxford University Press; p. 428 (PTAB Dec. 15, 2021).

*Freedom To Operate, Inc.* v. *Compass Pathways Limited.* Case PGR2022-00012, U.S. Pat. No. 10,947,257. Exhibit 1032: *Astrazeneca AB* v. *Reddy's Laboratories, Inc.*, Civil Action No. 11-2317 (May 1, 2013). 2013 U.S. Dist. LEXIS 62149; Dec. 13, 2021. (PTAB Dec. 15, 2021), 17 pages.

*Freedom To Operate, Inc.* v. *Compass Pathways Limited.* Case PGR2022-00012, U.S. Pat. No. 10,947,257. Exhibit 1033: Baker R.W et al. Molecular Structures of Hallucinogenic Substances: Lysergic Acid Diethylamide, Psilocybin, and 2,4,5-Trimethoxyamphetamine. Molecular Pharmacology, 9, 1973, 23-32. (PTAB Dec. 15, 2021).

*Freedom To Operate, Inc.* v. *Compass Pathways Limited.* Case PGR2022-00012, U.S. Pat. No. 10,947,257. Exhibit 1034: Petcher, T.J. and Weber, H.P. Crystal Structures of the Teonanacatl Hallucinogens. J. Chem Soc. Perkins Trans., 2, 8, 946-948, 1974.

*Freedom To Operate, Inc.* v. *Compass Pathways Limited.* Case PGR2022-00012, U.S. Pat. No. 10,947,257. Exhibit 1035: Kuhnert-Brandstätter, M. and Heindl, W. Polymorphe Modifikationen und Solvate von Psilocin und Psilocybin. Arch. Pharm, 1976, 309, 625-631 (German, English abstract on p. 626) (PTAB Dec. 15, 2021).

*Freedom To Operate, Inc.* v. *Compass Pathways Limited.* Case PGR2022-00012, U.S. Pat. No. 10,947,257. Exhibit 1036: Hofmann, A. et al. (1959) Psylocybin and Psilocin, zwei psychotrope Wirkstoffe aus mexikanischen Rauschpilzen. Helvetica Chimica Acta, vol. XLII (v), 1557-1572. (PTAB Dec. 15, 2021).

*Freedom To Operate, Inc.* v. *Compass Pathways Limited.* Case PGR2022-00012, U.S. Pat. No. 10,947,257. Exhibit 1041: Sherwood A.M. et al. An Improved, Practical, and Scalable Five-Step Synthesis of Psilocybin. Synthesis 2020, 52, 688-694 (PTAB Dec. 15, 2021).

*Freedom To Operate, Inc.* v. *Compass Pathways Limited.* Case PGR2022-00012, U.S. Pat. No. 10,947,257. Exhibit 1042: dos Santos, R.G et al. Antidepressive, anxiolytic, and antiaddictive effects of ayahuasca, psilocybin and lysergic acid diethylamide (LSD): a systematic review of clinical trials published in the last 25 years. Ther Adv Psychopharmacol, 2016, vol. 6(3), 193-213. (PTAB Dec. 15, 2021).

*Freedom To Operate, Inc.* v. *Compass Pathways Limited.* Case PGR2022-00012, U.S. Pat. No. 10,947,257. Exhibit 1043: Hill, R.J. Expanded Use of the Rietveld Method in Studies of Phase Abundance in Multiphase Mixtures. Powder Diffraction, Jun. 1991, vol. 6, No. 2, pp. 74-77. (PTAB Dec. 15, 2021).

*Freedom To Operate, Inc.* v. *Compass Pathways Limited.* Case PGR2022-00012, U.S. Pat. No. 10,947,257. Exhibit 1044: Groom, C.R et al. The Cambridge Structural Database. Acta Cryst. (2016). B72, 171-179. (PTAB Dec. 15, 2021).

*Freedom To Operate, Inc.* v. *Compass Pathways Limited.* Case PGR2022-00012, U.S. Pat. No. 10,947,257. Exhibit 1045: Lee, P.L. et al. A twelve-analyzer detector system for high-resolution powder diffraction. J Synchrotron Rad. (2008). 15, 427-432. (PTAB Dec. 15, 2021).

*Freedom To Operate, Inc.* v. *Compass Pathways Limited.* Case PGR2022-00012, U.S. Pat. No. 10,947,257. Exhibit 1046: Wang, J. et al. A dedicated powder diffraction beamline at the Advanced Photon Source: Commissioning and early operational results. Review of Scientific Instruments, 79, 085105 (2008). (PTAB Dec. 15, 2021), 8 pages.

*Freedom To Operate, Inc.* v. *Compass Pathways Limited.* Case PGR2022-00012, U.S. Pat. No. 10,947,257. Exhibit 1047: Antao, S.M. et al. State-of-the-Art High- Resolution Powder X-Ray Diffraction (HRPXRD) Illustrated With Rietveld Structure Refinement of Quartz, Sodalite, Tremolite, and Meionite. The Canadian Mineralogist, vol. 46, pp. 1501-1509 (2008). (PTAB Dec. 15, 2021).

*Freedom To Operate, Inc.* v. *Compass Pathways Limited.* Case PGR2022-00012, U.S. Pat. No. 10,947,257. Exhibit 1048: Toby B.H. and Von Dreele, B. Gsas-II: The genesis of a modern open-source all purpose crystallography software package. J Appl Cryst, (2013) 46, 544-549. (PTAB Dec. 15, 2021).

*Freedom To Operate, Inc.* v. *Compass Pathways Limited.* Case PGR2022-00012, U.S. Pat. No. 10,947,257. Exhibit 1049: Sykes, R.A. et al. New software for statistical analysis of Cambridge Structural Database data. J Appl Cryst, (2011) vol. 44, pp. 882-886. (PTAB Dec. 15, 2021).

*Freedom To Operate, Inc.* v. *Compass Pathways Limited.* Case PGR2022-00012, U.S. Pat. No. 10,947,257. Exhibit 1050: Bruno, I.J et al. Retrieval of Crystallographically-Derived Molecular Geometry Information, J Chem Inf Comput Sci (2004) vol. 44, pp. 2133-2144. (PTAB Dec. 15, 2021).

*Freedom To Operate, Inc.* v. *Compass Pathways Limited.* Case PGR2022-00012, U.S. Pat. No. 10,947,257. Exhibit 1051: Kresse, G. and Furthmüller, J. Efficiency of ab- initio total energy calcula-

(56) References Cited

OTHER PUBLICATIONS tions for metals and semiconductors using a plane-wave basis set. Computational Materials Science (1996) vol. 6, pp. 15-50. (PTAB Dec. 15, 2021).
*Freedom To Operate, Inc.* v. *Compass Pathways Limited.* Case PGR2022-00012, U.S. Pat. No. 10,947,257. Exhibit 1052: Dovesi, R et al. Quantum-mechanical condensed matter simulations with CRYSTAL. WIREs Comput Mol Sci (2018) e1360, pp. 1-36. (PTAB Dec. 15, 2021).
*Freedom To Operate, Inc.* v. *Compass Pathways Limited.* Case PGR2022-00012, U.S. Pat. No. 10,947,257. Exhibit 1053: Gatti, C et al. Crystal field effects on the topological properties of the electron density in molecular crystals: The case of urea. J Chem Phys (1994) vol. 101, 10686. (PTAB Dec. 15, 2021), 12 pages.
*Freedom To Operate, Inc.* v. *Compass Pathways Limited.* Case PGR2022-00012, U.S. Pat. No. 10,947,257. Exhibit 1054: Peintinger, M.F. et al. Consistent Gaussian Basis Sets of Triple-Zeta Valence with Polarization Quality for Solid-State Calculations. Journal of Computational Chemistry (2012) 1-9. (PTAB Dec. 15, 2021).
*Freedom To Operate, Inc.* v. *Compass Pathways Limited.* Case PGR2022-00012, U.S. Pat. No. 10,947,257. Exhibit 1055: Louer, D. and Boultif, A. Some further considerations in powder diffraction pattern indexing with the dichotomy method. Powder Diffraction, 29(S2), S7-S12, Dec. 2014. (PTAB Dec. 15, 2021).
*Freedom To Operate, Inc.* v. *Compass Pathways Limited.* Case PGR2022-00012, U.S. Pat. No. 10,947,257. Exhibit 1056: Kourkoumelis, K. Powdl: a Reusable .net Component for Interconverting Powder Diffraction Data. Recent Developments. Powder Diffr., vol. 28, No. 2, Jun. 2013, pp. 137-148. (PTAB Dec. 15, 2021).
*Freedom To Operate, Inc.* v. *Compass Pathways Limited.* Case PGR2022-00012, U.S. Pat. No. 10,947,257. Exhibit 1057: Curriculum Vitae—Roland R. Griffiths. (PTAB Dec. 15, 2021), 64 pages.
*Freedom To Operate, Inc.* v. *Compass Pathways Limited.* Case PGR2022-00012, U.S. Pat. No. 10,947,257. Exhibit 1058: Zeeh Pharmaceutical Experiment Station, University of Wisconsin—Madison School of Pharmacy. Certificate of Analysis for Lot No. 10415-25. (PTAB Dec. 15, 2021), 1 page.
*Freedom To Operate, Inc.* v. *Compass Pathways Limited.* Case PGR2022-00012, U.S. Pat. No. 10,947,257. Exhibit 1059: Barrett, F.S et al. Double-blind comparison of the two hallucinogens psilocybin and dextromethorphan: Effects on cognition. Psychopharmacology (Berl), Oct. 2018; 235(10): 2915-2927. HHS Public Access Author Manuscript. (PTAB Dec. 15, 2021).
*Freedom To Operate, Inc.* v. *Compass Pathways Limited.* Case PGR2022-00012, U.S. Pat. No. 10,947,257. Exhibit 1060: Non-Final Office Action, Aug. 13, 2020 (PTAB Dec. 15, 2021), 9 pages.
*Freedom To Operate, Inc.* v. *Compass Pathways Limited.* Case PGR2022-00012, U.S. Pat. No. 10,947,257. Exhibit 1061: Applicant-Initiated Interview Summary, filed Oct. 14, 2020 (PTAB Dec. 15, 2021), 3 pages.
*Freedom To Operate, Inc.* v. *Compass Pathways Limited.* Case PGR2022-00012, U.S. Pat. No. 10,947,257. Exhibit 1062: Amendment/Response to Non-Final Office Action, filed Nov. 13, 2020 (PTAB Dec. 15, 2021), 8 pages.
*Freedom To Operate, Inc.* v. *Compass Pathways Limited.* Case PGR2022-00012, U.S. Pat. No. 10,947,257. Exhibit 1063: Lakshmana Prabhu, S. and Suriyaprakash, T.N.K. Impurities and Its Importance In Pharmacy. Int Journal of Pharmaceutical Sciences Review and Research, vol. 3, Issue 2, July - Aug. 2010, Article 012, pp. 66-71. (PTAB Dec. 15, 2021).
*Freedom To Operate, Inc.* v. *Compass Pathways Limited.* Case PGR2022-00012, U.S. Pat. No. 10,947,257. Exhibit 1064: ICH Topic Q 3 A (R2) Impurities In New Drug Substances, 2006. (PTAB Dec. 15, 2021), 15 pages.
*Freedom To Operate, Inc.* v. *Compass Pathways Limited.* Case PGR2022-00012, U.S. Pat. No. 10,947,257. Exhibit 1065: Excerpts of Handbook of Pharma Excipients, Sixth Edition. Rowe, R.C. et al. (Eds.) London, UK: Pharmaceutical Press, 2011; pp. 129-133, 139-141 (PTAB Dec. 15, 2021).
*Freedom To Operate, Inc.* v. *Compass Pathways Limited.* Case PGR2022-00012, U.S. Pat. No. 10,947,257. Exhibit 1066: Martin's Physical Pharmacy and Pharmaceutical Sciences, Sixth Edition. P.J. Sinko (Ed.) Lippincott Williams & Wilkins, 2011; p. 564 (PTAB Dec. 15, 2021).
*Freedom To Operate, Inc.* v. *Compass Pathways Limited.* Case PGR2022-00012, U.S. Pat. No. 10,947,257. Exhibit 1067: Supplemental Amendment, filed Nov. 19, 2020 (PTAB Dec. 15, 2021), 7 pages.
*Freedom To Operate, Inc.* v. *Compass Pathways Limited.* Case PGR2022-00012, U.S. Pat. No. 10,947,257. Exhibit 1068: The Manufacturing Process. Solid Dose Experts Techceuticals, vol. 15. (2015). (PTAB Dec. 15, 2021), 12 pages.
*Freedom To Operate, Inc.* v. *Compass Pathways Limited.* Case PGR2022-00012, U.S. Pat. No. 10,947,257. Exhibit 1069: Documentation of shipment of sample from Johns Hopkins University Batch to Triclinic Labs, Jul. 21, 2021. (PTAB Dec. 15, 2021), 3 pages.
*Freedom To Operate, Inc.* v. *Compass Pathways Limited.* Case PGR2022-00012, U.S. Pat. No. 10,947,257. Exhibit 1070: Usp 24|NF 19. The Official Compendia of Standards, U.S. Pharmacopeia, 2000; pp. 738-739, 865-866. (PTAB Dec. 15, 2021).
*Freedom To Operate, Inc.* v. *Compass Pathways Limited.* Case PGR2022-00012, U.S. Pat. No. 10,947,257. Exhibit 1071: Sixsmith, D. The effect of compression on some physical properties of microcrystalline cellulose powders. J Pharm Pharmac, 1977, 29, 33-36. (PTAB Dec. 15, 2021).
*Freedom To Operate, Inc.* v. *Compass Pathways Limited.* Case PGR2022-00012, U.S. Pat. No. 10,947,257. Exhibit 1072: Curriculum Vitae—Brett D. Bobzien. (PTAB Dec. 15, 2021), 2 pages.
*Freedom To Operate, Inc.* v. *Compass Pathways Limited.* Case PGR2022-00012, U.S. Pat. No. 10,947,257. Exhibit 1073: Documentation of shipment of sample from Johns Hopkins University Batch to Triclinic Labs, Jul. 21, 2021. (PTAB Dec. 15, 2021), 3 pages.
*Freedom To Operate, Inc.* v. *Compass Pathways Limited.* Case PGR2022-00012, U.S. Pat. No. 10,947,257. Exhibit 1074: Altomare, A. et al. Expo2013: A kit of tools for phasing crystal structures from powder data. Journal of Applied Crystallography (2013) 46, 1231-1235. (PTAB Dec. 15, 2021).
*Freedom To Operate, Inc.* v. *Compass Pathways Limited.* Case PGR2022-00012, U.S. Pat. No. 10,947,257. Exhibit 1078: Petzoldt, C. et al. An example of how to handle amorphous fractions in API during early pharmaceutical development: SAR114137—A successful approach. European Journal of Pharmaceutics and Biopharmaceutics, 86 (2014) 337-350. (PTAB Dec. 15, 2021).
*Freedom To Operate, Inc.* v. *Compass Pathways Limited.* Case PGR2022-00012, U.S. Pat. No. 10,947,257. Exhibit 1079: Siven, M. et al. Challenge of paediatric compounding to solid dosage forms sachets and hard capsules—Finnish perspective. Journal of Pharmacy and Pharmacol (2017) vol. 69, pp. 593-602 (PTAB Dec. 15, 2021).
*Freedom To Operate, Inc.* v. *Compass Pathways Limited.* Case PGR2022-00012, U.S. Pat. No. 10,947,257. Exhibit 1080: Tobyn, M. et al. (1998) Physicochemical comparison between microcrystalline cellulose and silicified microcrystalline cellulose. International Journal of Pharmaceutics, 169 (1998) 183-194. (PTAB Dec. 15, 2021).
*Freedom To Operate, Inc.* v. *Compass Pathways Limited.* Case PGR2022-00012, U.S. Pat. No. 10,947,257. Exhibit 1081: Packing Slip, Johns Hopkins BPRU Pharmacy to Triclinic Laboratories, Inc., Jul. 21, 2021. (PTAB Dec. 15, 2021), 2 pages.
*Freedom To Operate, Inc.* v. *Compass Pathways Limited.* Case PGR2022-00012, U.S. Pat. No. 10,947,257. Exhibit 1082: Triclinic Labs Inc., Standard Operating Procedure. Controlled Substances, No. G026.10 (Ptab Dec. 15, 2021), 11 pages.
*Freedom To Operate, Inc.* v. *Compass Pathways Limited.* Case PGR2022-00012, U.S. Pat. No. 10,947,257. Exhibit 1085: Sherwood, A.M. et al. Psilocybin: crystal structure solutions enable phase analysis of prior art and recently patented examples. Acta Cryst. (2022) C78, pp. 1-20. (PTAB Dec. 15, 2021).

(56) References Cited

OTHER PUBLICATIONS

*Freedom To Operate, Inc.* v. *Compass Pathways Limited.* Case PGR2022-00012, U.S. Pat. No. 10,947,257. Paper No. 18: Decision Denying Institution of Post-Grant Review (PTAB Jun. 22, 2022); 25 pages.
*Freedom To Operate, Inc.* v. *Compass Pathways Limited.* Case PGR2022-00012, U.S. Pat. No. 10,947,257. Paper No. 2: Petition for Post-Grant Review (PTAB Dec. 15, 2021), 68 pages.
*Freedom To Operate, Inc.* v. *Compass Pathways Limited.* Case PGR2022-00012, U.S. Pat. No. 10,947,257: Petitioner's Request for Rehearing Under 37 C.F.R. § 42.71 (PTAB Jul. 22, 2022); 17 pages.
*Freedom To Operate, Inc.* v. *Compass Pathways Limited.* Case PGR2022-00018, U.S. Pat. No. 10,954,259. Exhibit 1106: Declaration of Sven Lidin, Ph.D. (PTAB Dec. 22, 2021), 69 pages.
*Freedom To Operate, Inc.* v. *Compass Pathways Limited.* Case PGR2022-00018, U.S. Pat. No. 10,954,259. Exhibit 1108: Declaration of James A. Kaduk, Ph.D. (PTAB Dec. 22, 2021), 25 pages.
*Freedom To Operate, Inc.* v. *Compass Pathways Limited.* Case PGR2022-00018, U.S. Pat. No. 10,954,259. Exhibit 1110: Declaration of Raj Suryanarayanan, Ph.D. (PTAB Dec. 22, 2021), 23 pages.
*Freedom To Operate, Inc.* v. *Compass Pathways Limited.* Case PGR2022-00018, U.S. Pat. No. 10,954,259. Exhibit 1112: Declaration of Charles L. Raison, M.D. (PTAB Dec. 22, 2021), 6 pages.
*Freedom To Operate, Inc.* v. *Compass Pathways Limited.* Case PGR2022-00018, U.S. Pat. No. 10,954,259. Exhibit 1113: Roy, J. An Introduction to Pharmaceutical Sciences, Biohealthcare, UK (2011) (PTAB Dec. 22, 2021), 37 pages.
*Freedom To Operate, Inc.* v. *Compass Pathways Limited.* Case PGR2022-00018, U.S. Pat. No. 10,954,259. Exhibit 1120: Declaration of Brett D. Bobzien. (PTAB Dec. 22, 2021), 5 pages.
*Freedom To Operate, Inc.* v. *Compass Pathways Limited.* Case PGR2022-00018, U.S. Pat. No. 10,954,259. Exhibit 1130: Declaration of Roland R. Griffiths, Ph.D. (PTAB Dec. 22, 2021), 6 pages.
*Freedom To Operate, Inc.* v. *Compass Pathways Limited.* Case PGR2022-00018, U.S. Pat. No. 10,954,259. Exhibit 1160: Claims of '739 Application as Filed and Preliminary Amendment filed Dec. 9, 2020. (PTAB Dec. 22, 2021), 10 pages.
*Freedom To Operate, Inc.* v. *Compass Pathways Limited.* Case PGR2022-00018, U.S. Pat. No. 10,954,259. Exhibit 1161: Terminal Disclaimer. (PTAB Dec. 22, 2021), 3 pages.
*Freedom To Operate, Inc.* v. *Compass Pathways Limited.* Case PGR2022-00018, U.S. Pat. No. 10,954,259. Paper No. 16: Decision Denying Institution of Post-Grant Review (PTAB Jun. 22, 2022); 25 pages.
*Freedom To Operate, Inc.* v. *Compass Pathways Limited.* Case PGR2022-00018, U.S. Pat. No. 10,954,259. Paper No. 2: Petition for Post-Grant Review (PTAB Dec. 22, 2021), 67 pages.
*Freedom To Operate, Inc.* v. *Compass Pathways Limited.* Case PGR2022-00018, U.S. Pat. No. 10,954,259: Petitioner's Request for Rehearing Under 37 C.F.R. § 42.71 (PTAB Jul. 22, 2022); 17 pages.
Freudenberg, F., Alttoa, A., & Reif, A. (Jan. 2015). Neuronal nitric oxide synthase (Nos. 1) and its adaptor, Nos. 1AP, as a genetic risk factors for psychiatric disorders. Genes, Brain and Behavior, 14(1), 46-63. https://doi.org/10.1111/gbb.12193.
Fuchs, X. et al. (Jun. 2018) Psychological factors associated with phantom limb pain: A review of recent findings. Pain Res Manag, 2018:5080123, http://doi.org/10.1155/2018/5080123, 12 pages.
Funk, C. D., & Fitzgerald, G. A. (Nov. 2007). COX-2 Inhibitors and Cardiovascular Risk. Journal of Cardiovascular Pharmacology, 50(5), 470-479. https://doi.org/10.1097/FJC.0b013e318157f72d.
Galbiati, A. et al. (Feb. 2019). The risk of neurodegeneration in REM sleep behavior disorder: A systematic review and meta-analysis of longitudinal studies. Sleep Medicine Reviews, 43, 37-46. https://doi.org/10.1016/j.smrv.2018.09.008.
Galimberti, D. et al. (Sep. 2008). Association of a NOS1 promoter repeat with Alzheimer's disease. Neurobiology of Aging, 29(9), 1359-1365. https://doi.org/10.1016/j.neurobiolaging.2007.03.003.
Galmiche, M. et al. (May 2019). Prevalence of eating disorders over the 2000-2018 period: a systematic literature review. The American Journal of Clinical Nutrition, 109(5), pp. 1402-1413.
Gamez, W. et al. (Mar. 2014) The Brief Experiential Avoidance Questionnaire: Development and Initial Validation. Psychological Assessment. 26:35-45.
Gan, W., Mohamad, N. and Law, L. (2018). Factors Associated with Binge Eating Behavior among Malaysian Adolescents. Nutrients, 10:66, doi:10.3390/nu10010066, 12 pages.
Gandal, M. J. et al. (Feb. 2018). Shared molecular neuropathology across major psychiatric disorders parallels polygenic overlap. Science, 359:693-697. https://doi.org/10.1126/science.aad6469.
Gandy, M. et al. (Jan. 2013). Rates of DSM-IV mood, anxiety disorders, and suicidality in Australian adult epilepsy outpatients: A comparison of well-controlled versus refractory epilepsy. Epilepsy Behav. 26, 29-35. https://doi.org/10.1016/j.yebeh.2012.10.023.
Ganesan, H. et al. (Jun. 2019). mTOR signalling pathway—A root cause for idiopathic autism? BMB Reports, 52(7):424-433.
Garcia-Rayado, G., Navarro, M., & Lanas, A. (Oct. 2018). NSAID induced gastrointestinal damage and designing GI-sparing NSAIDs. Expert Review of Clinical Pharmacology, 11(10), 1031-1043. https://doi.org/10.1080/17512433.2018.1516143.
Garcia-Romeu, A., Griffiths, R. and Johnson, M. (2015). Psilocybin-Occasioned Mystical Experiences in the Treatment of Tobacco Addiction. Current Drug Abuse Reviews, 7(3), pp. 157-164.
Gasior, M. et al.(Jun. 2017). A Phase 3, Multicenter, Open-Label, 12-Month Extension Safety and Tolerability Trial of Lisdexamfetamine Dimesylate in Adults With Binge Eating Disorder. Journal of Clinical Psychopharmacology, 37(3), pp. 315-322.
Gau, S.S.-F. & Huang, W.L. (Jan. 2014) Rapid visual information processing as a cognitive endophenotype of attention deficit hyperactivity disorder. Psychol Med, 44(2):435-446.
Gaul, C. et al. (Aug. 2011) Cluster Headache—Clinical Features and Therapeutic Options. Deutsches Arzteblatt International, 108(33):543-549.
GBD 2016 Parkinson's Disease Collaborators. (2018). Global, regional, and national burden of Parkinson's disease, 1990-2016: a systematic analysis for the Global Burden of Disease Study 2016. The Lancet. Neurology, 17(11), 939-953. https://doi.org/10.1016/S1474-4422(18)30295-3.
Gessner, P.K. et al. (Oct. 1960) The relationship between the metabolic fate and pharmacological actions of serotonin, bufotenine and psilocybin. J. Pharmacol. Exp. Ther., 130:126-133.
Ghanizadeh, A. (May 2015 ) A systematic review of reboxetine for treating patients with attention deficit hyperactivity disorder. Nord J Psychiatry. 69(4):241-8.
Gibb, A. & Deeks, E.D.(Jan. 2014). Vortioxetine: First global approval. Drugs 74:135-145, https://doi.org/10.1007/s40265-013-0161-9, 11 pages.
Gilon Mann, T. et al. (Jul. 2018). Different attention bias patterns in anorexia nervosa restricting and binge/purge types. European Eating Disorders Review, 26(4):293-301. https://doi.org/10.1002/erv.2593.
Giovinazzo, S. et al. (Apr. 2019). Anorexia nervosa and heart disease: a systematic review. Eating and Weight Disorders—Studies on Anorexia, Bulimia and Obesity, vol. 24, Issue 2, pp. 199-207. https://doi.org/10.1007/s40519-018-0567-1.
Glaesmer, H. et al. (May 2012) Psychometric properties and population-based norms of the Life Orientation Test Revised (LOT-R). British Journal of Health Psychology, 17:432-445.
Glashouwer, K. A., Van Der Veer, R. M. L., Adipatria, F., De Jong, P. J., & Vocks, S. (Dec. 2019). The role of body image disturbance in the onset, maintenance, and relapse of anorexia nervosa: A systematic review. Clinical Psychology Review, 74:101771; DOI:10.1016/j.cpr.2019.101771, 21 pages.
Glenn, A.L. et al. (Dec. 2013) Antisocial personality disorder: A current review. Current Psychiatry Reports, 15:427, DOI: 10.1007/s11920-013-0427-7, 9 pages.
Global Burden of Disease Study Aug. 2013 Collaborators. (2015). Global, regional, and national incidence, prevalence, and years lived with disability for 301 acute and chronic diseases and injuries in 188 countries, 1990-2013: a systematic analysis for the Global Burden

(56) References Cited

OTHER PUBLICATIONS of Disease Study 2013. Lancet (London, England), 386(9995), 743-800. https://doi.org/10.1016/S0140-6736(15)60692-4.
Golden, E.C. & Lipford, M.C. (Dec. 2018). Narcolepsy: Diagnosis and management. Cleveland Clin. J. Med., 85(12):959-969. https://doi.org/10.3949/ccjm.85a.17086.
Goldstein-Piekarski, A.N. et al. (Jun. 2016). A trans-diagnostic review of anxiety disorder comorbidity and the impact of multiple exclusion criteria on studying clinical outcomes in anxiety disorders. Transl. Psychiatry, 6:e847, doi.org/10.1038/tp.2016.108, 9 pages.
Golyala, A., & Kwan, P. (Jan. 2017). Drug development for refractory epilepsy: The past 25 years and beyond. Seizure, 44, 147-156. https://doi.org/10.1016/j.seizure.2016.11.022.
Golzari, S.E.J. et al. Lidocaine and pain management in the emergency department: A review article. Anesthesiol Pain Med. (Feb. 2014);4(1):1-6.
Gong, D. et al. (Jun. 2012). TGFB signaling plays a critical role in promoting alternative macrophage activation. BMC Immunology, 13:31, https://doi.org/10.1186/1471-2172-13-31, 10 pages.
Gonzalez-Maeso J. et al. (Mar. 2, 20084) "Identification of a serotonin/glutamate receptor complex implicated in psychosis" Nature, 452(7183):93-7. Available from: http://www.nature.com/articles/nature06612.
Gonzalez-Maeso, J. et al. (Feb. 2007) "Hallucinogens Recruit Specific Cortical 5-$HT_{2a}$ Receptor-Mediated Signaling Pathways to Affect Behavior" Neuron, 53(3):439-452.
Gooriah, R. et al. (Nov. 2015) Evidence-based treatments for cluster headache. Ther Clin Risk Manag, 11:1687-1696. Available from: http://dx.doi.org/10.2147/TCRM.S94193.
Gorla, K., & Mathews, M. (Jun. 2005). Pharmacological treatment of eating disorders. Psychiatry, 2(6), 43-48. http://www.ncbi.nlm.nih.gov/pubmed/21152155.
Gotvaldova et al., "Stability of psilocybin and its four analogs in the biomass of the psychotropic mushroom Psilocybe cubensis," Drug Test Anal. Feb. 2021; 13(2):439-446. Epub Nov. 4, 2020.
Gouzoulis-Mayfrank, E. et al.(2002). Effects of the hallucinogen psilocybin on covert orienting of visual attention in humans. Neuropsychobiology, 45(4):205-212. Available from: http://www.ncbi.nlm.nih.gov/pubmed/12097810.
Grant, A.M. et al. (2002) The Self-Reflection and Insight Scale: A New Measure of Private Self-Consciousness. Social Behavior and Personality, 30(8), 821-836.
Grant, J. et al. (Jul. 2019). A double-blind, placebo-controlled study of vortioxetine in the treatment of binge-eating disorder. International Journal of Eating Disorders, 52(7), pp. 786-794.
Greenan, C. et al.(Feb. 1, 20203) "Preparation and Characterization of Novel Crystalline Solvates and Polymorphs of Psilocybin and Identification of Solid Forms Suitable for Clinical Development" Preprint [online]. Retrieved from ResearchGate: https://www.researchgate.net/publication/339238710, 29 printed pages.
Greten, F.R. et al. (Sep. 2007). NF-κB Is a Negative Regulator of IL-1β Secretion as Revealed by Genetic and Pharmacological Inhibition of IKKβ. Cell, 130(5), 918-931. https://doi.org/10.1016/j.cell.2007.07.009.
Greyson, B., The Near-Death Experience Scale, The Journal of Nervous and Mental Disease, 171:369-375 (1983).
Grieco, M et al. (Oct. 2019). Glucagon-Like Peptide-1: A Focus on Neurodegenerative Diseases. Frontiers in Neuroscience, 13, Article 1112, 7 pages. https://doi.org/10.3389/fnins.2019.01112.
Grieshaber, A. F., Moore, K. A., & Levine, B. (May 2001). The detection of psilocin in human urine. Journal of Forensic Sciences, 46(3), 627-630. http://www.ncbi.nlm.nih.gov/pubmed/11373000.
Griffin, C.E. et al. (2013). Benzodiazepine pharmacology and central nervous system-mediated effects. Ochsner J. 13, 214-223.
Griffiths, K. (Jul. 2019). Understanding the neural mechanisms of lisdexamfetamine dimesylate (LDX) pharmacotherapy in Binge Eating Disorder (BED): a study protocol. Journal of Eating Disorders, 7:23, https://doi.org/10.1186/s40337-019-0253-3, 10 pages.
Griffiths, K.R. et al. (2017). "Sustained attention and heart rate variability in children and adolescents with ADHD." Biol Psychol [Internet]. 124:11-20. Available from: http://www.ncbi.nlm.nih.gov/pubmed/28099875.
Griffiths, R.R. (Dec. 2011) Psilocybin occasioned mystical-type experiences: Immediate and persisting dose-related effects. Psychopharmacol, 218(4):649-665. NIH Public Access Author Manuscript, 27 pages.
Griffiths, R.R. et al. (Aug. 2006) Psilocybin can occasion mystical-type experiences having substantial and sustained meaning and spiritual significance. Psychopharmacol (Berl), 187(3):268-283.
Griffiths, R.R. et al. (Dec. 2016) Psilocybin produces substantial and sustained decreases in depression and anxiety in patients with life-threatening cancer: A randomized double-blind trial. Journal of Psychopharmacology, 30(12):1181-1197.
Griffiths, S. (Oct. 2019). "The Vulnerability Experiences Quotient (VEQ): A Study of Vulnerability, Mental Health and Life Satisfaction in Autistic Adults." Autism Research. (10):1516-28. https://doi.org/10.1002/aur.2162.
Grilo, C. et al. (Dec. 2012). 12-month follow-up of fluoxetine and cognitive behavioral therapy for binge eating disorder. Journal of Consulting and Clinical Psychology, 80(6), pp. 1108-1113.
Grilo, C., Reas, D. and Mitchell, J. (2016). Combining Pharmacological and Psychological Treatments for Binge Eating Disorder: Current Status, Limitations, and Future Directions. Current Psychiatry Reports, 18:55, doi:10.1007/s11920-016-0696-z, 11 pages.
Grob, C.S. et al. (Jan. 2011) Pilot Study of Psilocybin Treatment for Anxiety in Patients with Advanced-Stage Cancer. Arch Gen Psychiatry, 68(1):71-78.
Grob, C.S. et al. (2013) Chapter 17: Use of the Classic Hallucinogen Psilocybin for Treatment of Existential Distress Associated with Cancer. In B.I. Carr and J. Steel (Eds.) Psychological Aspsects of Cancer. Springer Science + Business Media; p. 291-308.
Guerdjikova, A. et al. (Apr. 2016). Novel pharmacologic treatment in acute binge eating disorder—role of lisdexamfetamine. Neuropsychiatric Disease and Treatment, 12:833-841.
Guerreiro, R. et al. (Oct. 2015). "The age factor in Alzheimer's disease." Genome Medicine, 7:106, https://doi.org/10.1186/s13073-015-0232-5, 3 pages.
Guo, M. et al. (2003) "Potential Application of Silicified Microcrystalline Cellulose in Direct-Fill Formulations for Automatic Capsule-Filling Machines," Pharmaceutical Development and Technology, vol. 8, No. 1, pp. 47-59.
Gupta, S. P. et al. (Jul. 2016). "Association of Polymorphism of Neuronal Nitric Oxide Synthase Gene with Risk to Parkinson's Disease." Molecular Neurobiology, 53(5), 3309-3314. https://doi.org/10.1007/s12035-015-9274-3.
Guze, S.B. (1995) Diagnostic and Statistical Manual of Mental Disorders, 4th ed. (DSM-IV). Am. J. Psychiatry, 152, 1228. https://doi.org/10.1176/ajp.152.8.1228.
Hajihosseini, A. et al. (Apr. 2012). "The role of beta-gamma oscillations in unexpected rewards processing." Neuroimage. 60(3):1678-85. https://doi.org/10.1016/j.neuroimage.2012.01.125.
Halberstadt, A. L. et al. (Jan. 2011). "Multiple receptors contribute to the behavioral effects of indoleamine hallucinogens." Neuropharmacology, 61(3):364-381, https://doi.org/10.1016/j.neuropharm.2011.01.017.
Halberstadt et al., "Correlation between the potency of hallucinogens in the mouse head-twitch response assay and their behavioral and subjective effects in other species," Neuropharmacology. May 1, 2020;167:107933, pp. 1-35. doi: 10.1016/j.neuropharm.2019.107933. Epub Jan. 7, 2020.
Hall N. et al. (2018). "Phantom limb pain: a review of pharmacological management." Br J Pain [Internet]. 12(4):202-7. Available from: https://doi.org/10.1177/2049463717747307.
Halpern, J.H. (Oct. 2003) Hallucinogens: An Update. Current Psychiatry Reports, 5:347-354.
Hama, Y. et al. (2015). "Level of plasma neuregulin-1 SMDF is reduced in patients with idiopathic Parkinson's disease." Neuroscience Letters, 587, 17-21. https://doi.org/10.1016/j.neulet.2014.12.024.
Hamadjida, A. et al. (Jun. 2020). "The highly selective mGlu2 receptor positive allosteric modulator LY-487,379 alleviates I-DOPA-

(56) References Cited

OTHER PUBLICATIONS induced dyskinesia in the 6-OHDA-lesioned rat model of Parkinson's disease." The European Journal of Neuroscience. 51(12): 2412-2422. https://doi.org/10.1111/ejn.14679.
Hamilton, M., "A rating scale for depression", Journal of Neurology, Neurosurgery, and Psychiatry (1960); 23(1): 56-62.
Hanes, K.R. (Apr. 1996). "Serotonin, Psilocybin, and Body Dysmorphic Disorder." Journal of Clinical Psychopharmacology, 16(2), pp. 188-189.
Hanyu-Deutmeyer, A.A. et al. (2020) Phantom Limb Pain. StatPearls. StatPearls Publishing. [online]. Available from NCBI Bookshelf: http://www.ncbi.nlm.nih.gov/pubmed/28846343, 6 pages.
Haroon, E. et al. (May 2018). Antidepressant treatment resistance is associated with increased inflammatory markers in patients with major depressive disorder. Psychoneuroendocrinology, 95:43-49. https://doi.org/10.1016/j.psyneuen.2018.05.026.
Hasler, F. et al. (Jun. 1997). "Determination of psilocin and 4-hydroxyindole-3-acetic acid in plasma by HPLC-ECD and pharmacokinetic profiles of oral and intravenous psilocybin in man." Pharmaceutica Acta Helvetiae, 72(3), 175-184. https://doi.org/10.1016/S0031-6865(97)00014-9.
Hasler, F. et al. (Mar. 2004) Acute psychological and physiological effects of psilocybin in healthy humans: A double-blind, placebo-controlled dose-effect study. Psychopharmacology, 172(2):145-156.
Hasler, F. et al. (Sep. 2002). "Renal excretion profiles of psilocin following oral administration of psilocybin: A controlled study in man." Journal of Pharmaceutical and Biomedical Analysis, 30(2), 331-339. https://doi.org/10.1016/S0731-7085(02)00278-9.
Heal, D. et al. (Jun. 2017). Dopamine and u-opioid receptor dysregulation in the brains of binge-eating female rats—possible relevance in the psychopathology and treatment of binge-eating disorder. Journal of Psychopharmacology, 31(6), pp. 770-783.
Hebert, L.E. et al. (May 2013). "Alzheimer disease in the United States (2010-2050) estimated using the 2010 census." Neurology, 80(19), 1778-1783. https://doi.org/10.1212/WNL.0b013e31828726f5.
Heim, R. et al. (Mar. 3, 1958) "Mycologie—Determinisme de la formation des carpophores et des sclerotes dans la culture du Psilocybe mexicana Heim, Agaric hallucinogene du Mexique, et mise en evidence de la psilocybine et de la psilocine [Mycology-Determinism in the formation of carpophores and sclerotia in the cultivation of Psilocybe mexicana Heim, an hallucinogenic Agaric of Mexico, and isolation of psilocybin and psilocyn]" Comptes Rendus Hebdomadaires des Seances de L'Academie des Sciences [Weekly Reports of the Sessions of the Academy of Sciences], 246(9):1346-1351.
Herr, N. et al. (Jul. 2017). "The Effects of Serotonin in Immune Cells." Frontiers in Cardiovascular Medicine, 4, Article 48, 11 pages. https://doi.org/10.3389/fcvm.2017.00048.
Herring, W.J. et al. (Dec. 2012). "Orexin receptor antagonism for treatment of insomnia: A randomized clinical trial of suvorexant." Neurology 79, 2265-2274. https://doi.org/10.1212/WNL.0b013e31827688ee.
Hibicke, M. et al. (Apr. 1, 2019). "Psychedelics Improve the Mental Health of Rats." FASEB J., 33(S1):666.1; https://doi.org/10.1096/fasebj.2019.33.1_supplement.666.1, 3 pages.
Hilbert, A. et al. (Jan. 2019). Meta-analysis of the efficacy of psychological and medical treatments for binge-eating disorder. Journal of Consulting and Clinical Psychology, 87(1), pp. 91-105.
Hill, L.S. et al. (May 2010) SCOFF, the development of an eating disorder screening questionnaire. International Journal of Eating Disorders, 43(4):344-351. https://doi.org/10.1002/eat.20679.
Himmerich, H. et al. (Apr. 2019). "Psychiatric comorbidity as a risk factor for mortality in people with anorexia nervosa." European Archives of Psychiatry and Clinical Neuroscience, 269(3), 351-359. https://doi.org/10.1007/s00406-018-0937-8.
Hoek, H. et al. (Dec. 2003). "Review of the Prevalence and Incidence of Eating Disorders." International Journal of Eating Disorders, vol. 34, Issue 4, pp. 383-396. https://doi.org/10.1002/eat.10222.
Hofmann, A. et al. (Mar. 15, 1958) "Psilocybin, ein psychotroper Wirkstoff aus dem mexikanischen Rauschpilz Psilocybe mexicana Heim [Psilocybin, a psychotropic substance from Mexican magic mushrooms Psilocybe mexicana Heim]" Experientia, 14(3):107-109, with English translation (3 pages).
Hofmann, A. et al. (1959) "Psilocybin und Psilocin, zwei psychotrope Wirkstoffe aus mexikanischen Rauschpilzen [Psilocybin and Psilocin, two psychotropic active substances from Mexican magic mushrooms" Helvetica Chimica Acta, Volumen XLII, Issue v, No. 168, pp. 1557-1572, with English translation (17 pages).
Hofmann, A. et al. (Nov. 1958) "Konstitutionsaufklärung und Synthese von Psilocybin [Constitutional elucidation and synthesis of psilocybin]" Experientia, 14(11):397-399, with English translation (3 pages).
Holtkamp, K. et al. (May 2005). "A retrospective study of SSRI treatment in adolescent anorexia nervosa: Insufficient evidence for efficacy." Journal of Psychiatric Research, 39(3), 303-310. https://doi.org/10.1016/j.jpsychires.2004.08.001.
Hood, S.D. et al. (Feb. 2014). "Benzodiazepine dependence and its treatment with low dose flumazenil." Br. J. Clin. Pharmacol. 77, 285-294. https://doi.org/10.1111/bcp.12023.
Howell, M. J. et al. (Jun. 2015). "Rapid Eye Movement Sleep Behavior Disorder and Neurodegenerative Disease." JAMA Neurology, 72(6), 707-712. https://doi.org/10.1001/jamaneurol.2014.4563.
Hoyer, D. et al. (1985). "Molecular pharmacology of 5-HT1 and 5-HT2 recognition sites in rat and pig brain membranes: Radioligand binding studies with [3H]5-HT, [3H]8-OH-DPAT, (-)[125I]iodocyanopindolol, [3H]mesulergine and [3H]Ketanserin." Eur J Pharmacol. 118(1-2): 13-23.
Hsu, E. et al. (Feb. 2013). "Postamputation pain: Epidemiology, mechanisms, and treatment." J Pain Res, 6:121-136. http://dx.doi.org/10.2147/JPR.S32299.
Huang, H. et al. (Oct. 2016). "Genetic association of NOS1 exon18, NOS1 exon29, ABCB1 1236C/T, and ABCB1 3435C/T polymorphisms with the risk of Parkinson's disease: A meta-analysis." Medicine, 95(40), e4982, pp. 1-9. https://doi.org/10.1097/MD.0000000000004982.
Hudson, C.C. et al. (Jan. 2019). "Prevalence of Depressive Disorders in Individuals with Autism Spectrum Disorder: a Meta-Analysis." Journal of Abnormal Child Psychology. 47(1):165-75. https://doi.org/10.1007/s10802-018-0402-1.
Hudson, J.I. et al. (Feb. 2007). "The Prevalence and Correlates of Eating Disorders in the National Comorbidity Survey Replication." Biological Psychiatry, 61(3), 348-358. https://doi.org/10.1016/j.biopsych.2006.03.040.
Hudson, J.I. et al. (May 1992). "Polysomnographic Characteristics of Young Manic Patients: Comparison with Unipolar Depressed Patients and Normal Control Subjects." Arch. Gen. Psychiatry 49, 378-383. https://doi.org/10.1001/archpsyc.1992.01820050042006.
Huecker, M. et al. (2020). Bupropion. StatPearls. NCBI Bookshelf [online]. Retrieved from: https://www.ncbi.nlm.nih.gov/books/NBK470212/; retrieved on Jul. 30, 2020, 4 pages.
Huedo-Medina, T.B. et al. (Dec. 2012). "Effectiveness of non-benzodiazepine hypnotics in treatment of adult insomnia: Meta-analysis of data submitted to the Food and Drug Administration." BMJ, 345:e8343,. https://doi.org/10.1136/bmj.e8343, 13 pages.
Huff et al. (2020) Neuroanatomy, Cranial Nerve 5 (Trigeminal). StatPearls. StatPearls Publishing; Available from NCBI Bookshelf: http://www.ncbi.nlm.nih.gov/pubmed/29489263, pp. 1-8.
Hughes, J.R. (Jul. 2008). "Gamma, fast, and ultrafast waves of the brain: Their relationships with epilepsy and behavior." Epilepsy Behav. 13(1):25-31. https://doi.org/10.1016/j.yebeh.2008.01.011.
Hussman, J.P. et al. (Jan. 2011). "A noise-reduction GWAS analysis implicates altered regulation of neurite outgrowth and guidance in autism." Molecular Autism. 2, 1, pp. 1-16. https://doi.org/10.1186/2040-2392-2-1.
Hutson, P., Balodis, I. and Potenza, M. (Feb. 2018). Binge-eating disorder: Clinical and therapeutic Advances. Pharmacology & Therapeutics, 182:15-27.
Hutten, N.R.P.W. et al. (2019). "Self-Rated Effectiveness of Microdosing With Psychedelics for Mental and Physical Health Problems Among Microdosers." Front Psychiatry [Internet]. 10:672, pp. 1-9. Available from: http://www.ncbi.nlm.nih.gov/pubmed/31572246.

(56) References Cited

OTHER PUBLICATIONS

Huysmans, S. et al. (2019). "Melatonin and sleep disorders: Overview of literature and testing in psychiatric practice." Tijdschr. Psychiatr. 61, 854-861.
Hvolby, A. (Aug. 2014). "Associations of sleep disturbance with ADHD: implications for treatment." ADHD Atten. Deficit Hyperact. Disord. 7(1):1-8. https://doi.org/10.1007/s12402-014-0151-0.
Hwang, J.Y. et al. (2008) The development of the Santa Clara brief compassion scale: An abbreviation of Sprecher and Fehr's compassionate love scale. Pastoral Psychology, 56(4):421-428.
ICH (Jun. 2017) Q3C—Tables and List Guidance for Industry. U.S. Department of Health and Human Services, Food and Drug Administration, Center for Drug Evaluation and Research (CDER), Center for Biologics Evaluation and Research (CBER) Revision 3, 10 pages.
Infliximab Side Effects. (2019). Drugs.Com [online]. Retrieved from: https://www.drugs.com/sfx/infliximab-side-effects.html, 11 pages.
Institute for Quality and Efficiency in Health Care (IQWIG) (Oct. 2017). Treatment options for generalized anxiety disorder [online]. InformedHealth.org. Retrieved from: https://www.ncbi.nlm.nih.gov/books/NBK279594/?report=printable; retrieved on Jul. 30, 2020, 3 pages.
Institute for Quality and Efficiency in Health Care (IQWIG) (2018, Feb). What is an inflammation? [online]. Retrieved from: https://www.ncbi.nlm.nih.gov/books/NBK279298/; retrieved on Jul. 30, 2020, 1 page.
International Search Report and Written Opinion for International Application No. PCT/US2022/052368 dated Mar. 30, 2023, 14 Pages.
International Search Report and Written Opinion for PCT/IB2018/057811 mailed on Mar. 11, 2019, 10 pages.
International Search Report and Written Opinion for PCT/US2022/048713 dated Feb. 24, 2023, 17 pages.
International Search Report and Written Opinion issued in International Patent Application No. PCT/EP2021/079287, mailed Feb. 3, 2022, with Notification of Transmittal; 17 pages.
International Search Report and Written Opinion issued in International Patent Application No. PCT/EP2022/058483, mailed Aug. 4, 2022, with Notification of Transmittal; 17 pages.
International Search Report and Written Opinion issued in International Patent Application No. PCT/IB2020/053684, mailed Aug. 26, 2020, with Notification of Transmittal; 24 total pages.
International Search Report and Written Opinion issued in International Patent Application No. PCT/IB2020/053687, mailed Aug. 26, 2020, with Notification of Transmittal; 22 total pages.
International Search Report and Written Opinion issued in International Patent Application No. PCT/IB2020/053688, mailed Aug. 26, 2020, with Notification of Transmittal; 30 total pages.
Isaacson, R.S. et al. (Dec. 2018). "The clinical practice of risk reduction for Alzheimer's disease: A precision medicine approach." Alzheimer's & Dementia : The Journal of the Alzheimer's Association, 14(12), 1663-1673. https://doi.org/10.1016/j.jalz.2018.08.004.
Isooka, N. et al. (Jan. 2020) "Dopaminergic neuroprotective effects of rotigotine via 5-HT1A receptors: Possibly involvement of metallothionein expression in astrocytes." Neurochemistry International, 132:104608, https://doi.org/10.1016/j.neuint.2019.104608, 13 pages.
Ivarsson, M. et al. (Oct. 2005). "Antidepressants and REM sleep in Wistar-Kyoto and Sprague-Dawley rats" Eur. J. Pharmacol., 522(1-3):63-71. https://doi.org/10.1016/j.ejphar.2005.08.050.
Jack, C. R. et al. (Apr. 2018). "NIA-AA Research Framework: Toward a biological definition of Alzheimer's disease." Alzheimer's & Dementia : The Journal of the Alzheimer's Association, 14(4), 535-562. https://doi.org/10.1016/j.jalz.2018.02.018.
Jaeger, J. and Domingo, S.Z. (2016) The Digit Symbol Substitution Test (DSST): Psychometric properties and clinical utility in major depressive disorder. Poster presented at the 29th ECNP Congress, Sep. 17-20, 2016, Vienna, Austria. Retrieved from ResearchGate [online], http://www.researchgate.net/publication/309602300.
Jafarian, S. et al. (2008). "High-altitude sleep disturbance: Results of the Groningen Sleep Quality Questionnaire survey." Sleep Med. 9, 446-449. https://doi.org/10.1016/j.sleep.2007.06.017.
Jagielska et al. (Apr. 2017). "Outcome, comorbidity and prognosis in anorexia nervosa." Psychiatr. Pol, 51(2), 205-218. https://doi.org/10.12740/PP/64580.
Jagmag, S.A. et al. (Jan. 2016). "Evaluation of Models of Parkinson's Disease." Frontiers in Neuroscience, 9: 503, pp. 1-13. https://doi.org/10.3389/fnins.2015.00503.
Jankovic, J. (Apr. 2008). "Parkinson's disease: clinical features and diagnosis." Journal of Neurology, Neurosurgery & Psychiatry, 79(4), 368-376. https://doi.org/10.1136/jnnp.2007.131045.
Jansen, C. et al. (Nov. 2018). "Interictal psychiatric comorbidities of drug- resistant focal epilepsy: Prevalence and influence of the localization of the epilepsy." Epilepsy Behav. 94, 288-296. https://doi.org/10.1016/j.yebeh.2018.06.046.
Javaheri, S. et al. (Aug. 1996). "Effect of theophylline on sleep-disordered breathing in heart failure." N. Engl. J. Med. 335, 562-567. https://doi.org/10.1056/NEJM199608223350805.
Javaheri, S. (Oct. 2005). "Acetazolamide improves central sleep apnea in heart failure: a double-blind, prospective study." Am. J. Respir. Crit. Care Med. 173, 234-237.
Jayakumar, A.R. & Norenberg, M.D. (2016). Glutamine Synthetase: Role in Neurological Disorders. The Glutamate/GABA-Glutamine Cycle. A. Schousboe, R. Sonnewald (eds.), Springer International Publishing. Advances in Neurobiology, vol. 13, https://doi.org/10.1007/978-3-319-45096-4_13; pp. 327-350.
Jennings, K. M. et al. (Dec. 2017). "Eating Disorder Examination-Questionnaire (EDE-Q): Norms for Clinical Sample of Female Adolescents with Anorexia Nervosa." Archives of Psychiatric Nursing, 31(6), 578-581. https://doi.org/10.1016/j.apnu.2017.08.002.
Jiang, H.-R. et al. (Nov. 2002). "Secretion of interleukin-10 or interleukin-12 by LPS-activated dendritic cells is critically dependent on time of stimulus relative to initiation of purified DC culture" Journal of Leukocyte Biology, 72(5):978-985.
Jiao, J.-J. et al. (2017). "GLP-1/GIP/Gcg receptor Triagonist improves the cognitive behaviors in triple-transgenic mice of Alzheimer's disease." Sheng Li Xue Bao : [Acta Physiologica Sinica], 69(2), 135-145. Retrieved from http://www.ncbi.nlm.nih.gov/pubmed/28435972.
Jin, L. et al. (May 2019). "Antidepressants for the treatment of narcolepsy: A prospective study of 148 patients in northern China." J. Clin. Neurosci. 63, 27-31. https://doi.org/10.1016/j.jocn.2019.02.014.
Johanson, M. et al. (Feb. 2020) A Systematic Literature Review of Neuroimaging of Psychopathic Traits. Front Psychiatry. 10:1027, doi: 10.3389/fpsyt.2019.01027, 20 pages.
John, O. P., & Srivastava, S. (1999). The Big-Five trait taxonomy: History, measurement, and theoretical perspectives. In L. A. Pervin & O. P. John (Eds.), Handbook of personality: Theory and Research (vol. 2, pp. 102-138). New York: Guilford Press.
Johns, M. (1991). "New Method for Measuring Daytime Sleepiness: The Epworth Sleepiness Scale." Sleep. 14(6):540-5 [online]. Retrieved from:https://academic.oup.com/sleep/article/14/6/540/2742871 (accessed Mar. 26, 2020).
Johnson et al., "Pilot Study of the 5-HT2AR Agonist Psilocybin in the Treatment of Tobacco Addiction," Journal of Psychopharmacology 2014, vol. 28(11) 983-992.
Johnson et al., "Potential Therapeutic Effects of Psilocybin," Neurotherapeutics (Jul. 2017) 14:734-7 40 (published Jun. 5, 2017).
Johnson, M.W. (Aug. 2008) Human hallucinogen research: guidelines for safety. J Psychopharmacol, 22(6):603-620.
Johnson, M.W. et al. (Jan. 2017) Long-term follow-up of psilocybin-facilitated smoking cessation. Am J Drug Alcohol Abuse. 2017;43(1):55-60. doi: 10.3109/00952990.2016.1170135 [published correction appears in Am J Drug Alcohol Abuse. Jan. 2017;43(1):127]. HHS Public Access Author Manuscript, 10 pages.
Johnstad, P.G. (Feb. 2018). "Powerful substances in tiny amounts: An interview study of psychedelic microdosing" Nord Stud Alcohol Drugs, 35(1):39-51.
Jones, S.A.V., et al., "Psychedelics as a Treatment for Alzheimer's Disease Dementia," Frontiers in Synaptic Neuroscience, Aug. 21, 2020, vol. 12, pp. 34.

(56) References Cited

OTHER PUBLICATIONS

Jyonouchi, H. (2013). "Immunological abnormalities in autism spectrum disorders." Advances in Neuroimmune Biology. vol. 4, No. 3, pp. 141-159. https://doi.org/10.3233/NIB-130061.
Kaelen, M. et al. (Aug. 2015) LSD enhances emotional response to music. Psychopharmacology, 232(19):3607-3614.
Kaelen, M. et al. (Feb. 2018) "The hidden therapist: evidence for a central role of music in psychedelic therapy" Psycopharmacology, 235:505-519.
Kaladjian, A. et al. (2014). "Troubles affectifs et comorbidites anxieuses." Encephale 40, S18-S22. https://doi.org/10.1016/S0013-7006(14)70126-5.
Kalliolias, G. D. et al. (Jan. 2016). "TNF biology, pathogenic mechanisms and emerging therapeutic strategies." Nature Reviews Rheumatology, 12(1), 49-62. https://doi.org/10.1038/nrrheum.2015.169.
Kandel, S.A. and Mandiga P. (2020) Cluster Headache. StatPearls. StatPearls Publishing [Internet]. Available from NCI Bookshelf: http://www.ncbi.nlm.nih.gov/pubmed/31334961, 6 pages.
Kandil, E. et al. (Jan. 2017). "Lidocaine Infusion: A Promising Therapeutic Approach for Chronic Pain." J Anesth Clin Res. 08(01): 697, pp. 1-29.
Kandratavicius, L. et al. (Sep. 2014). Animal models of epilepsy: use and limitations. Neuropsychiatric Disease and Treatment, 1693. https://doi.org/10.2147/NDT.S50371, pp. 1-13.
Kang, D. W. et al. (Apr. 2019). "Long-term benefit of Microbiota Transfer Therapy on autism symptoms and gut microbiota." Scientific Reports. 9(1): 1-9. https://doi.org/10.1038/s41598-019-42183-0.
Kang Y. et al. (Oct. 2017). "Self-report pain assessment tools for cognitively intact older adults: Integrative review." International journal of older people nursing. 13(2):e12170, pp. 1-29.
Kanner, A.M. (May 2011). "Anxiety disorders in epilepsy: The forgotten psychiatric comorbidity." Epilepsy Curr. 11(3):90-91. https://doi.org/10.5698/1535-7511-11.3.90.
Kantojarvi, K. et al. (Jun. 2011). "Fine mapping of Xq11.1-q21.33 and mutation screening of RPS6KA6, ZNF711, ACSL4, DLG3, and IL1RAPL2 for autism spectrum disorders (ASD)." Autism Research. 4(3):228-33. https://doi.org/10.1002/aur.187.
Kargbo, R.B. et al. (Jul. 2020) "Direct Phosphorylation of Psilocin Enables Optimized cGMP Kilogram-Scale Manufacture of Psilocybin" ACS Omega, 5:16959-16966.
Karimi, P. et al. (Feb. 2017). Environmental factors influencing the risk of autism. J Res Med Sci. 22:27, https://doi.org/10.4103/1735-1995.200272, 12 pages.
Kasper LJ et al. (Jul. 2012). "Moderators of working memory deficits in children with attention-deficit/hyperactivity disorder (ADHD): A meta-analytic review." Clinical Psychology Review. vol. 32, p. 605-17.
Kasper, S. et al. (Mar. 2009). "Efficacy of pregabalin and venlafaxine-XR in generalized anxiety disorder: Results of a double-blind, placebo-controlled 8-week trial." Int. Clin. Psychopharmacol. 24, 87-96. https://doi.org/10.1097/YIC.0b013e32831d7980.
Katzman, M.A. et al. (Aug. 2017). "Adult ADHD and comorbid disorders: Clinical implications of a dimensional approach." BMC Psychiatry. 17(1):1-15.
Kaur A. et al. (Dec. 2018). "Phantom limb pain: A literature review." Chinese Journal of Tramatology, 21(6):366-8. https://doi.org/10.1016/j.cjtee.2018.04.006.
Kaur, H. et al. (2018). Chronic Insomnia. StatPearls. NLM Bookshelf [online]. Retrieved from: https://www.ncbi.nih.gov/books/NBK526136/?report=reader; retrieved on Jul. 30, 2002; 5 pages.
Keezer, M. R. et al. (Nov. 2015). "Comorbidities of epilepsy: current concepts and future perspectives." The Lancet Neurology, 15(1), 106-115. https://doi.org/10.1016/S1474-4422(15)00225-2.
Kelly, W.E. et al. (2019). "A brief self-report measure for frequent distressing nightmares: The Nightmare Experience Scale (NExS)." Dreaming 29, 180-195. https://doi.org/10.1037/drm0000106.
Kelton, M.C. et al. (Jun.-Aug. 2000). The effects of nicotine on Parkinson's disease. Brain and Cognition, 43(1-3):274-282 (abstract). Retrieved from http://www.ncbi.nlm.nih.gov/pubmed/10857708, 1 page.
Kessler, R. et al. (Apr. 2016). The neurobiological basis of binge-eating disorder. Neuroscience & Biobehavioral Reviews, 63, pp. 223-238.
Kessler, R.C. et al. (Jan. 2013). The prevalence and correlates of binge eating disorder in the World Health Organization World Mental Health Surveys. Biological Psychiatry, 73(9):904-914.
Khajehpour, H. et al. (Dec. 2019). "Disrupted resting-state brain functional network in methamphetamine abusers: A brain source space study by EEG." Plos One 14, e0226249, pp. 1-20. https://doi.org/10.1371/journal.pone.0226249.
Khalifa, N. et al. (Aug. 2010) Pharmacological interventions for antisocial personality disorder. Cochrane Database Syst Rev. (8):CD007667, doi: 10.1002/14651858.CD007667.pub2. Europe PMC Funders Group Author Manuscript, 83 pages.
Khemka, S. et al. (Jul. 2017). "Dissecting the function of hippocampal oscillations in a human anxiety model." J. Neurosci. 37, 6869-6876.
Khurshid KA. (Apr. 2018). "Comorbid insomnia and psychiatric disorders: an update." Innovations in Clinical Neuroscience. 15(3-4):28.
Kim, J.W. et al. (Aug. 2014). "Subchronic treatment of donepezil rescues impaired social, hyperactive, and stereotypic behavior in valproic acid-induced animal model of autism." PLoS One. 9(8):e104927, pp. 2-23.
Kim, Y. E., & Jeon, B. S. (2014). Clinical Implication of REM Sleep Behavior Disorder in Parkinson's Disease. Journal of Parkinson's Disease, 4(2), 237-244. https://doi.org/10.3233/JPD-130293.
Kinnaird, E. et al. (Jun. 2019). Same behaviours, different reasons: what do patients with co-occurring anorexia and autism want from treatment? International Review of Psychiatry, 31(4), 308-317. https://doi.org/10.1080/09540261.2018.1531831.
Kirsh, K.L. (Mar. 2010). "Differentiating and Managing Common Psychiatric Comorbidities Seen in Chronic Pain Patients." J Pain Palliat Care Pharmacother, 24(1):39-47. Available from: https://www.tandfonline.com/action/journalInformation?journalCode=ippc20.
Kishi, T. et al. (Jun. 2012). Are Antipsychotics Effective for Anorexia Nervosa? Are Antipsychotics Effective for the Treatment of Anorexia Nervosa? Results From a Systematic Review and Meta-Analysis. J Clin Psychiatry, 73(6), 757-766. https://doi.org/10.4088/JCP.12r07691.
Kishi, T. et al. (Aug. 2015). "Suvorexant for primary insomnia: A systematic review and meta-analysis of randomized placebo-controlled trials." PLoS One. 10(8):e0136910, pp. 1-11. https://doi.org/10.1371/journal.pone.0136910.
Klinkenberg I et al. (Apr. 2010). "The validity of scopolamine as a pharmacological model for cognitive impairment: A review of animal behavioral studies." Neuroscience and Biobehavioral Reviews. vol. 34, p. 1307-50.
Knotkova, H. et al. (2012). "Current and future options for the management of phantom-limb pain." J Pain Res [Internet]. 5:39-49. Available from: http://dx.doi.org/10.2147/JPR.S16733.
Knyazev, G.G. et al. (Oct. 2005). "Uncertainty, anxiety, and brain oscillations." Neurosci. Lett. 387, 121-125. https://doi.org/10.1016/j.neulet.2005.06.016.
*Kohn & Associates PLLC* v. *Compass Pathways Limited*, Case PGR2020-00030, U.S. Pat. No. 10,519,175, Exhibit 1005: The United States Pharmacopeial Convention (USP). Characterization of Crystalline and Partially Crystalline Solids By X-Ray Powder Diffraction (XRPD). The United States Pharmacopeia. 35th Revision: The National Formulary. 30th ed (USP 35). 2011 (Official from May 1, 2012); pp. 427-433 (Exhibit E) (PTAB Feb. 21, 2020).
*Kohn & Associates PLLC* v. *Compass Pathways Limited*, Case PGR2020-00030, U.S. Pat. No. 10,519,175, Exhibit 1008: Declaration of Poncho Meisenheimer and Alex Sherwood (Exhibit H), (PTAB Feb. 21, 2020), pp. 1-4.
*Kohn & Associates PLLC* v. *Compass Pathways Limited*, Case PGR2020-00030, U.S. Pat. No. 10,519,175, Exhibit 1016: Abstracts

(56) References Cited

OTHER PUBLICATIONS of articles resulting from search of psilocybin treating depression and treatment resistant depression (Exhibit P) (PTAB Feb. 21, 2020), pp. 1-8.
*Kohn & Associates PLLC* v. *Compass Pathways Limited*, Case PGR2020-00030, U.S. Pat. No. 10,519,175, Exhibit 1017: Declaration of Jordan Sloshower, MD (Exhibit Q) (PTAB Feb. 21, 2020), 1 Page.
*Kohn & Associates PLLC* v. *Compass Pathways Limited*, Case PGR2020-00030, U.S. Pat. No. 10,519,175, Exhibit 1018: Declaration of Charles L. Raison, MD (Exhibit R) (PTAB Feb. 21, 2020), pp. 1-2.
*Kohn & Associates PLLC* v. *Compass Pathways Limited*, Case PGR2020-00030, U.S. Pat. No. 10,519,175, Exhibit 2004: Email Correspondence Between Petitioner and Patent Owner, dated Mar. 19-Apr. 1, 2020 (PTAB May 26, 2020), pp. 1-5.
*Kohn & Associates PLLC* v. *Compass Pathways Limited*, Case PGR2020-00030, U.S. Pat. No. 10,519,175, Exhibit 2005: Delaware Division of Corporations Details for Freedom to Operate, Inc., dated Apr. 1, 2020 (PTAB May 26, 2020), 1 Page.
*Kohn & Associates PLLC* v. *Compass Pathways Limited*, Case PGR2020-00030, U.S. Pat. No. 10,519,175, Exhibit 2006: A. Harrison, "Challenges to a Company's Psilocybin Patent Highlight Contrasting Business Strategies for Developers of Psychedelic Therapies," https://www.lucid.news/challenges-to-a-companyspsilocybin-patent-highlight-contrasting-business-strategies-fordevelopers-of-psychedelic-therapies/ (Apr. 7, 2020) (PTAB May 26, 2020), pp. 1-11.
*Kohn & Associates PLLC* v. *Compass Pathways Limited*, Case PGR2020-00030, U.S. Pat. No. 10,519,175, Exhibit 2007: Biography of Alexander Sherwood, Ph.D. (PTAB May 26, 2020), pp. 1-4.
*Kohn & Associates PLLC* v. *Compass Pathways Limited*, Case PGR2020-00030, U.S. Pat. No. 10,519,175, Exhibit 2008: Biography of Poncho Meisenheimer, Ph.D. (PTAB May 26, 2020), pp. 1-4.
*Kohn & Associates PLLC* v. *Compass Pathways Limited*, Case PGR2020-00030, U.S. Pat. No. 10,519,175, Exhibit 2009: Biography of Chuck Raison, M.D. (PTAB May 26, 2020), pp. 1-4.
*Kohn & Associates PLLC* v. *Compass Pathways Limited*, Case PGR2020-00030, U.S. Pat. No. 10,519,175, Exhibit 2010: Biography of Jordon Sloshower, M.D., MSc (PTAB May 26, 2020), pp. 1-4.
*Kohn & Associates PLLC* v. *Compass Pathways Limited*, Case PGR2020-00030, U.S. Pat. No. 10,519,175, Exhibit 2011: Biography of Bill Linton (PTAB May 26, 2020), pp. 1-3.
*Kohn & Associates PLLC* v. *Compass Pathways Limited*, Case PGR2020-00030, U.S. Pat. No. 10,519,175, Paper 1: Petition for Post Grant Review of U.S. Pat. No. 10,519,175 under 35 U.S.C. 321 (PTAB Feb. 21, 2020), pp. 1-30.
*Kohn & Associates PLLC* v. *Compass Pathways Limited*, Case PGR2020-00030, U.S. Pat. No. 10,519,175, Paper 11: Patent Owner's Exhibit List (PTAB Mar. 13, 2020), pp. 1-4.
*Kohn & Associates PLLC* v. *Compass Pathways Limited*, Case PGR2020-00030, U.S. Pat. No. 10,519,175, Paper 12: Notice Accepting Corrected Petition (PTAB Mar. 17, 2020), pp. 1-3.
*Kohn & Associates PLLC* v. *Compass Pathways Limited*, Case PGR2020-00030, US Patent 10,519, 175, Paper 13: Corrected Petition for Post Grant Review of US Patent No. 10,519, 175 Under 35 U.S.C. 321 (PTAB Mar. 20, 2020), pp. 1-48.
*Kohn & Associates PLLC* v. *Compass Pathways Limited*, Case PGR2020-00030, U.S. Pat. No. 10,519,175, Paper 15: Patent Owner's Preliminary Response (PTAB May 26, 2020), pp. 1-24.
*Kohn & Associates PLLC* v. *Compass Pathways Limited*, Case PGR2020-00030, U.S. Pat. No. 10,519,175, Paper 17: Reply to Patent Owner's Preliminary Response (PTAB Jul. 7, 2020), pp. 1-11.
*Kohn & Associates PLLC* v. *Compass Pathways Limited*, Case PGR2020-00030, U.S. Pat. No. 10,519, 175, Paper 2: Petition for Post Grant Review of U.S. Pat. No. 10,519,175 Under 35 U.S.C. 321 Petitioner's List of Exhibits (PTAB Feb. 21, 2020), pp. 1-30.
*Kohn & Associates PLLC* v. *Compass Pathways Limited*, Case PGR2020-00030, U.S. Pat. No. 10,519,175, Paper 23: Patent Owner's Sur-Reply to Petitioner's Reply (PTAB Jul. 22, 2020), 12 pages.
*Kohn & Associates PLLC* v. *Compass Pathways Limited*, Case PGR2020-00030, U.S. Pat. No. 10,519,175, Paper 25: Decision Denying Institution of Post-Grant Review PTAB Aug. 20, 2020), 16 pages.
*Kohn & Associates PLLC* v. *Compass Pathways Limited*, Case PGR2020-00030, U.S. Pat. No. 10,519,175, Paper 5: Notice of Filing Date Accorded to Petition and Time for Filing Patent Owner Preliminary Response (PTAB Feb. 26, 2020), pp. 1-5.
*Kohn & Associates PLLC* v. *Compass Pathways Limited*, Case PGR2020-00030, U.S. Pat. No. 10,519,175, Paper 6: Corrected Petition for Post Grant Review of U.S. Pat. No. 10,519,175 Under 35 U.S.C. 321 (PTAB Mar. 6, 2020), pp. 1-33.
*Kohn & Associates PLLC* v. *Compass Pathways Limited*, Case PGR2020-00030, U.S. Pat. No. 10,519,175, Paper 8: Patent Owner's Mandatory Notices (PTAB Mar. 13, 2020), pp. 1-5.
*Kohn & Associates PLLC* v. *Compass Pathways Limited*, Case PGR2020-00030, U.S. Pat. No. 10,519,175, Exhibit 2017: Clinical Trials.gov, "A Study of Psilocybin for Major Depressive Disorder (MDD)" Identifier: NCT03866174, Apr. 22, 2020, 12 pages (PTAB Jul. 22, 2020).
*Kohn & Associates PLLC* v. *Compass Pathways Limited*, Case PGR2020-00030, U.S. Pat. No. 10,519, 175, Exhibit 2018: Sloshower, J. (May 6, 2020) "Psychedelics in the Treatment of Mood and Substance Use Disorders" Presentation, 31 pages (PTAB Jul. 22, 2020).
Kolar, D. et al. (Apr. 2008) Treatment of adults with attention-deficit/hyperactivity disorder. Neuropsychiatric Dis Treat, 4(2):389-403.
Kolarik, J. (1967). Eeg-Veranderungen nach Psilocybin bei Epilepsien. Acta Univ. Palackianae Olomucensis, 47:253-263. (English Summary on p. 262).
Kolden, G.G. et al. (Sep. 2000) The Therapeutic Realizations Scale-Revised (TRS-R): Psychometric Characteristics and Relationship to Treatment Process and Outcome. Journal of Clinical Psychology. 56(9):1207-1220.
Kolla, B. et al. (2017). "The prevalence of hypersomnolence, its correlates and associated role impairment in the National Comorbidity Survey Replication (NCS-R)." Sleep. 40(suppl_1), pp. A239-A239. https://doi.org/10.1093/sleepj/zsx050.645.
Kometer, M. et al. (Jun. 2013). "Activation of Serotonin 2A Receptors Underlies the Psilocybin-Induced Effects on Oscillations, N170 Visual-Evoked Potentials, and Visual Hallucinations." Journal of Neuroscience, 33(25), 10544-10551. https://doi.org/10.1523/JNEUROSCI.3007-12.2013.
Korecka, J.A. et al. (Sep. 2017). "Repulsive Guidance Molecule a (RGMa) Induces Neuropathological and Behavioral Changes That Closely Resemble Parkinson's Disease." The Journal of Neuroscience : The Official Journal of the Society for Neuroscience, 37(39), 9361-9379. https://doi.org/10.1523/JNEUROSCI.0084-17.2017.
Kornum, B.R. et al. (Feb. 2017). "Narcolepsy." Nat. Rev. Dis. Prim. 3(1):1-9. https://doi.org/10.1038/nrdp.2016.100.
Kothare, S.V. et al. (Apr. 2008) "Zonisamide: review of pharmacology, clinical efficacy, tolerability, and safety." Expert Opinion on Drug Metabolism & Toxicology, 4(4), 493-506. https://doi.org/10.1517/17425255.4.4.493.
Kotov, S.B. Bellman, and D.B. Watson (2004) Multidimensional Iowa Suggestibility Scale (MISS) Brief Manual. [online] Retrieved from: https://renaissance.stonybrookmedicine.edu/sites/default/files/MISSBriefManual.pdf, 16 pages.
Kouli, A. et al. (Dec. 2018). Parkinson's Disease: Etiology, Neuropathology, and Pathogenesis. In Parkinson's Disease: Pathogenesis and Clinical Aspects. Thomas B. Stoker & Julia C. Greenland (Eds.) Codon Publications, pp. 3-26. Retrieved from http://www.ncbi.nlm.nih.gov/pubmed/30702842.
Kountza, M. et al. (Nov. 2018). "La comorbidité psychiatrique de l'anorexie mentale : une étude comparative chez une population de patients anorexiques français et grecs." L'Encéphale, 44(5), 429-434. https://doi.org/10.1016/j.encep.2017.07.005. English abstract on p. 429.

(56) References Cited

OTHER PUBLICATIONS

Kryzhanovskii, G.N. et al. (1992). [The antiepileptic effects of sodium valproate and the calcium antagonist riodipine when used jointly in a model of generalized korazol-induced epileptic activity]. Biulleten' Eksperimental'noi Biologii i Meditsiny, 114(10), 376-378 [Abstract]. Retrieved from http://www.ncbi.nlm.nih.gov/pubmed/1288691, 1 page.
Krzyszkowiak, W. et al. (Aug. 2019) "Treatment of obsessive-compulsive disorders (OCD) and obsessive-compulsive-related disorders (OCRD)" Psychiatr Pol, 53(4):825-843; DOI: https://doi.org/10.12740/PP/105130.
Kubera, M. et al. (Apr. 2005). Effects of serotonin and serotonergic agonists and antagonists on the production of tumor necrosis factor a and interleukin-6. Psychiatry Research, 134(3), 251-258. https://doi.org/10.1016/j.psychres.2004.01.014.
Kuhnert, M. et al. (Aug. 1976) "Polymorphe Modifikationen und Solvate von Psilocin und Psilocybin [Polymorphic Modifications and Solvates of Psilocin and Psilocybin]" Archiv der Pharmazie, 309:625-631, with English translation from Google Translate (14 total pages).
Kurrasch-Orbaugh, D.M. et al. (Jan. 2003). Serotonin 5-Hydroxytryptamineza Receptor-Coupled Phospholipase C and Phospholipase $A_2$ Signaling Pathways Have Different Receptor Reserves. J Pharmacol Exp Ther., 304(1), 229-237.
Kwan, P., & Brodie, M. J. (Jan. 2001). Neuropsychological effects of epilepsy and antiepileptic drugs. The Lancet, 357(9251), 216-222. https://doi.org/10.1016/S0140-6736(00)03600-X.
Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.
Lader, M., 2015. Generalized Anxiety Disorder BT—Encyclopedia of Psychopharmacology, in: Stolerman, I.P., Price, L.H. (Eds.). Springer Berlin Heidelberg, pp. 699-702. https://doi.org/10.1007/978-3-642-36172-2_317.
Lahdenpaa et al., "Direct compression with silicified and non-silicified microcrystalline cellulose: study of some properties of powders and tablets," S.T.P. Pharma Sciences, 2001; 11(2):129-135. Supplied by the British Library Oct. 12, 2019, 8 pages.
Lahey, B.B. et al. (Jun. 2005) Predicting Future Antisocial Personality Disorder in Males From a Clinical Assessment in Childhood. J Consult Clin Psychol, 73(3):389-399.
Lahmame, A. et al. (Oct. 1997). "Are Wistar-Kyoto rats a genetic animal model of depression resistant to antidepressants?" Eur. J. Pharmacol. 337(2-3):115-23. https://doi.org/10.1016/S0014-2999(97)01276-4.
Lai, M.C. et al. (Oct. 2019). "Prevalence of co-occurring mental health diagnoses in the autism population: a systematic review and meta-analysis." The Lancet Psychiatry. 6(10):819-29. https://doi.org/10.1016/S2215-0366(19)30289-5.
Landau, A.M. et al. (Sep. 2005). "Defective Fas expression exacerbates neurotoxicity in a model of Parkinson's disease." The Journal of Experimental Medicine, 202(5), 575-581. https://doi.org/10.1084/jem.20050163.
Larrosa, O. et al. (May 2001). "Stimulant and Anticataplectic Effects of Reboxetine in Patients with Narcolepsy: A Pilot Study." Sleep. 24(3):282-5.
Layzer, R., "Section 5—Degenerative Diseases of the Nervous System," Cecil Textbook of Medicine, , Eds. J. Claude Bennett, Md and Fred Plum, 20th edition (1996), vol. 2, pp. 2050-2057.
Lecavalier, L. (Nov. 2006). "Behavioral and emotional problems in young people with pervasive developmental disorders: Relative prevalence, effects of subject characteristics, and empirical classification." Journal of Autism and Developmental Disorders. 36(8):1101-14. https://doi.org/10.1007/s10803-006-0147-5.
Lecendreux, M. et al. (Aug. 2015). Attention-Deficit/Hyperactivity Disorder (ADHD) Symptoms in Pediatric Narcolepsy: A Cross-Sectional Study. Sleep 38, 1285-1295. https://doi.org/10.5665/sleep.4910.
Leclerc, S. et al. (Jun. 2015). "Pharmacological therapies for autism spectrum disorder: A review." Pharmacy and Therapeutics. 40(6):389-397.
Ledonne, A., & Mercuri, N. B. (Dec. 2019). On the modulatory roles of neuregulins/ErbB signaling on synaptic plasticity. International Journal of Molecular Sciences, 21:275, 23 pages. https://doi.org/10.3390/ijms21010275.
Lee, P. H. et al. (Dec. 2019). "Genomic Relationships, Novel Loci, and Pleiotropic Mechanisms across Eight Psychiatric Disorders." Cell. 179(1469-1482):e11. https://doi.org/10.1016/j.cell.2019.11.020.
Lee, R.M. and Robbins, S.B. (1995) Measuring belongingness: the social connectedness and the social assurance scales Journal of Counseling Psychology. 42:232-241.
Lee, T. J. et al. (Mar. 2017). "Repeated adolescent activity-based anorexia influences central estrogen signaling and adulthood anxiety-like behaviors in rats." Physiology and Behavior, 171, 199-206. https://doi.org/10.1016/j.physbeh.2016.12.039.
Lee, Y.C. et al. (Dec. 2010). "A review of SSRIs and SNRIs in neuropathic pain." Expert Opin Pharmacother. 11(17):2813-25.
Leigh, J. P. et al. (Dec. 2015). "Brief Report: Forecasting the Economic Burden of Autism in 2015 and 2025 in the United States." Journal of Autism and Developmental Disorders. 45(12):4135-9. https://doi.org/10.1007/s10803-015-2521-7.
Leonard, H.L., & Rapoport, J.L. (Sep. 1987) "Letter to the Editor: Relief of obsessive-compulsive symptoms by LSD and psilocin" American Journal of Psychiatry, 144(9): 1239-1240.
Leroux, E. and Ducros, A. (2008) Cluster headache. Orphanet J Rare Dis, 3:20, doi: 10.1186/1750-1172-3-20, 11 pages.
Levin, E. D., & Rezvani, A. H. (Mar. 2000). Development of nicotinic drug therapy for cognitive disorders. European Journal of Pharmacology, 393(1-3), 141-146. https://doi.org/10.1016/s0014-2999(99)00885-7.
Leysen, J.E. et al. (1982). [$^3$H]Ketanserin (R 41 468), a selective $^3$H-ligand for serotonin$_2$ receptor binding sites. Binding properties, brain distribution, and functional role. Molecular Pharmacology, 21(2), 301-314.
Li, T. et al. (Nov. 2016). A scored human protein-protein interaction network to catalyze genomic interpretation. Nature Methods, 14(1), 61-64. https://doi.org/10.1038/nmeth.4083.
Li, Y. et al. (Aug. 2011) "Quantification of polymorphic impurity in an enantiotropic polymorph system using differential scanning calorimetry, X-ray powder diffraction and Raman spectroscopy" Intl J Pharma, 415:110-118.
Liang, H. et al. (2019). Mammalian Target of Rapamycin at the Crossroad Between Alzheimer's Disease and Diabetes. In Diabetes Mellitus. A Risk Factor for Alzheimer's Disease. Advances in Experimental Medicine and Biology, 1128, 185-225. https://doi.org/10.1007/978-981-13-3540-2_10.
Limakatso K. et al. (2019). "The prevalence of phantom limb pain and associated risk factors in people with amputations: A systematic review protocol." Syst Rev. 8:17, 5 pages. https://doi.org/10.1186/s13643-018-0938-8.
Lindenblatt, H. et al. (May 1998). "Quantitation of psilocin in human plasma by high-performance liquid chromatography and electrochemical detection: Comparison of liquid—liquid extraction with automated on-line solid-phase extraction." J Chromatogr B Biomed Appl. 709(2):255-63.
Liu, L. et al. (Jul. 2018). "Deficiency of Sustained Attention in ADHD and Its Potential Genetic Contributor MAOA" J Atten Disord, 22(9):878-885.
Liu, P.-P. et al. (Aug. 2019). "History and progress of hypotheses and clinical trials for Alzheimer's disease." Signal Transduction and Targeted Therapy, 4:29, https://doi.org/10.1038/s41392-019-0063-8, 22 pages.
Lopez-Castejon, G. et al. (Aug. 2011). "Understanding the mechanism of IL-1B secretion." Cytokine & Growth Factor Reviews, 22(4), 189-195. https://doi.org/10.1016/j.cytogfr.2011.10.001.
Loth, E. et al. (Jan. 2018). "Facial expression recognition as a candidate marker for autism spectrum disorder: how frequent and severe are deficits?" Molecular Autism, 9:7, https://doi.org/10.1186/s13229-018-0187-7, 11 pages.

(56) References Cited

OTHER PUBLICATIONS

Lu, T.-T., Wan, C., Yang, W., & Cai, Z. (2019). Role of Cdk5 in Amyloid-beta Pathology of Alzheimer's Disease. Current Alzheimer Research, 16(13), 1206-1215. https://doi.org/10.2174/1567205016666191210094435.

Lucchina, L. et al. ( Oct. 2013). "Altered Peripheral and Central Inflammatory Responses in a Mouse Model of Autism." Autism Research. 7(2):273-89. https://doi.org/10.1002/aur.1338.

Lucza, T. et al. (May 2015). "Screening Mild and Major Neurocognitive Disorders in Parkinson's Disease." Behavioural Neurology, 2015, Article ID 983606, 10 pages. https://doi.org/10.1155/2015/983606.

Lugli, S.M. et al. (Feb. 1997). "Tumor Necrosis Factor a Enhances the Expression of the Interleukin (IL)-4 Receptor a-Chain on Endothelial Cells Increasing IL-4 or IL-13-induced Stat6 Activation." Journal of Biological Chemistry, 272(9), 5487-5494. https://doi.org/10.1074/jbc.272.9.5487.

Lynch ME et al. (2006). "The pharmacotherapy of chronic pain: A review." Pain Res Manag. 11(1):11-38.

Lyons, T. and R.L. Carhart-Harris (Jul. 2018) Increased nature relatedness and decreased authoritarian political views after psilocybin for treatment-resistant depression. Journal of Psychopharmacology, 32(7):811-819.

Mabunga, D.F.N. et al. (Dec. 2015). "Exploring the Validity of Valproic Acid Animal Model of Autism." Experimental Neurobiology. 24(4):285-300. https://doi.org/10.5607/en.2015.24.4.285.

Macy, A.S. et al. (Jan. 2013) "Quality of life in obsessive compulsive disorder" CNS Spectrums, 18(1):21-33.

Mahapatra et al., "Role of psilocybin in the treatment of depression," Ther Adv Psychopharmacol, Jan. 2017; 7(1): 54-56.

Mahfoud, Y. et al. (Sep. 2009). Sleep disorders in substance abusers: How common are they? Psychiatry, 6(9):38-42.

Mahone EM et al. (2017). "Attention-Deficit/Hyperactivity Disorder: A Historical Neuropsychological Perspective." J Int Neuropsychol Soc [Internet]. 23:916-29. Available from: http://www.rmtcnet.com/resources/Phenylbutazone_Review-Dr._Lawrence_R._Soma.pdf.

Maiano, C. et al. (Jul. 2019). Psychometric Properties of the Body Checking Questionnaire (BCQ) and of the Body Checking Cognitions Scale (BCCS): A Bifactor- Exploratory Structural Equation Modeling Approach. Assessment, 1-15, https://doi.org/10.1177/1073191119858411.

Maimoun, L. et al. (Jun. 2018). Effects of the two types of anorexia nervosa (binge eating/purging and restrictive) on bone metabolism in female patients. Clinical Endocrinology, 88(6):863-872. https://doi.org/10.1111/cen.13610.

Maina, G. et al. (Jan. 2003) "Antipsychotic augmentation for treatment resistant obsessive-compulsive disorder: What if antipsychotic is discontinued?" International Clinical Psychopharmacology, 18(1):23-28; DOI: 10.1097/01.yic.0000047784.24295.2b.

Manavalan, A. et al. (Sep. 2013). Brain site-specific proteome changes in aging-related dementia. Experimental & Molecular Medicine. 45:e39, 17 pages. https://doi.org/10.1038/emm.2013.76.

Marras, C. et al. (Jul. 2018). Prevalence of Parkinson's disease across North America. npjParkinson's Disease. 4:21, https://doi.org/10.1038/s41531-018-0058-0, 7 pages.

Martin, W., Vaupel, D., Nozaki, M. and Bright, L. (1978). The identification of LSD-like hallucinogens using the chronic spinal dog. Drug and Alcohol Dependence, 3(2), pp. 113-123.

Martins, G.R. et al. (Feb. 2016). Proinflammatory and Anti-Inflammatory Cytokines Mediated by NF-78 B Factor as Prognostic Markers in Mammary Tumors. Mediators of Inflammation, 2016:1-10. https://doi.org/10.1155/2016/9512743.

Martinussen R. et al. (Apr. 2005). A meta-analysis of working memory impairments in children with attention-deficit/hyperactivity disorder. J Am Acad Child Adolesc Psychiatry, 44(4):377-84.

Marvanova, M. & Gramith, K. (Apr. 2018). Role of antidepressants in the treatment of adults with anorexia nervosa. Ment Health Clin [Internet] 8(3):127-37. DOI: 10.9740/mhc.2018.05.127.

Mason, N.L. et al. (Jun. 2019). Sub-Acute Effects of Psilocybin on Empathy, Creative Thinking, and Subjective Well-Being. Journal of Psychoactive Drugs, https://doi.org/10.1080/02791072.2019.1580804, 13 pages.

Mathes, B.M. et al. (Apr. 2019). Epidemiological and Clinical Gender Differences in OCD. In Current Psychiatry Reports (vol. 21, Issue 5, pp. 1-7). Curr Psychiatry Rep, 21:36, 7 pages, https://doi.org/10.1007/s11920-019-1015-2.

Matheson, E. & Hainer, B.L. (Jul. 2017) Insomnia: Pharmacologic Therapy—American Family Physician. Am Fam Physician, 96(1):29-35.

Matsushima, Y. et al. (Aug. 2009). Effects of Psilocybe argentipes on Marble-Burying Behavior in Mice. Bioscience Biotechnology and Biochemistry, 73(8):1866-1868. https://doi.org/10.1271/bbb.90095.

Mattingly, G. et al. (May 2012). Attention deficit hyperactivity disorder subtypes and symptom response in adults treated with lisdexamfetamine dimesylate. Innov Clin Neurosci, 9(5-6):22-30.

Maxwell, C.R. et al. (Feb. 2015). Atypical Laterality of Resting Gamma Oscillations in Autism Spectrum Disorders, 45(2):292-297, doi:10.1007/s10803-013-1842-7.

Mayhew A. & Argaez, C. (Jan. 2018). Intravenous lidocaine for chronic pain: a review of the clinical effectiveness and guidelines. Ottawa: CADTH; Jan. 2018 (CADTH rapid response report: summary with critical appraisal), 22 pages.

Mazza M, Marano G, Janiri L. (Aug. 2016) An update on pharmacotherapy for personality disorders. Expert Opinion on Pharmacotherapy. 17:(15):1977-1979.

McCarberg, B. & Billington, R. (Jun. 2006). Consequences of neuropathic pain: Quality-of-life issues and associated costs. Am J Manag Care, 12(Suppl. 9):S263-8.

McCuen-Wurst, C. et al. (Jan. 2018). Disordered eating and obesity: associations between binge-eating disorder, night-eating syndrome, and weight-related comorbidities. Annals of the New York Academy of Sciences, 1411(1), pp. 96-105.

McCullough et al., "The Grateful Disposition: A Conceptual and Empirical Topography," Journal of Personality and Social Psychology, 82:112-127 (2002).

McElroy, S. et al. (Feb. 2013). A placebo-controlled pilot study of the novel opioid receptor antagonist ALKS-33 in binge eating disorder. International Journal of Eating Disorders, 46(3), pp. 239-245.

McElroy, S. et al. (Mar. 2015). Efficacy and Safety of Lisdexamfetamine for Treatment of Adults With Moderate to Severe Binge-Eating Disorder. JAMA Psychiatry, 72(3), p. 235-246.

McElroy, S. et al. (May 2012). Pharmacological management of binge eating disorder: current and emerging treatment options. Therapeutics and Clinical Risk Management, 8:219-241.

McGuire-Snieckus, R. et al. (Nov. 2006) A new scale to assess the therapeutic relationship in community mental health care: STAR. Psychological Medicine. 37:85-95.

Medical News Today, M. (2020). What to know about Parkinson's dementia. Retrieved from https://www.medicalnewstoday.com/articles/314486, 14 pages.

Medzhitov, R. (Jul. 2008). Origin and physiological roles of inflammation. Nature, 454(7203):428-435. https://doi.org/10.1038/nature07201.

Mei, L., & Nave, K.-A. (2014). Neuregulin-ERBB signaling in the nervous system and neuropsychiatric diseases. In Neuron, 83:27-49, https://doi.org/10.1016/j.neuron.2014.06.007.

Meier, S.M. et al. (Mar. 2016). Mortality among persons with obsessive-compulsive disorder in Denmark. JAMA Psychiatry, 73(3):268-274. https://doi.org/10.1001/jamapsychiatry.2015.3105.

Meldrum, B.S. & Naquet, R. (Sep. 1970). Effects of psilocybin, dimethyltryptamine and various lysergic acid derivatives on photically-induced epilepsy in the baboon (Papio papio). British Journal of Pharmacology, 40(1):144P-145P. Retrieved from http://www.ncbi.nlm.nih.gov/pubmed/4992165.

Mertens, L.J., et al., "Therapeutic mechanisms of psilocybin: Changes in amygdala and prefrontal functional connectivity during emotional processing after psilocybin for treatment-resistant depression," Journal of Psychopharmacology, Feb. 2020, vol. 34 (2), pp. 167-180.

(56) References Cited

OTHER PUBLICATIONS

Meyer, A.-C. et al. (Sep. 2009). Global disparities in the epilepsy treatment gap: a systematic review. Bulletin of the World Health Organization, 88(4):260-266. https://doi.org/10.2471/BLT.09.064147.
Miller, A.H., & Raison, C. L. (Jan. 2016). Role of inflammation in depression from evolutionary imperative to modern treatment target. Nat Rev Immunol, 16(1):22-34. https://doi.org/10.1038/nri.2015.5.
Mills, S.E.E et al. (Aug. 2019). Chronic pain: a review of its epidemiology and associated factors in population-based studies. Br J Anaesth. 123(2):273-83.
Milos, G. et al. (Apr. 2002). Comorbidity of obsessive-compulsive disorders and duration of eating disorders. International Journal of Eating Disorders, 31(3):284-289. https://doi.org/10.1002/eat.10013.
Min, S.S. et al. (Nov. 2011). Neuregulin-1 prevents amyloid β-induced impairment of long-term potentiation in hippocampal slices via ErbB4. Neuroscience Letters, 505(1):6-9. https://doi.org/10.1016/j.neulet.2011.05.246.
Minen, M.T. et al. (Jan. 2016). Migraine and its psychiatric comorbidities. J. Neurol. Neurosurg. Psychiatry, 87:741-749. https://doi.org/10.1136/jnnp-2015-312233.
Miniati, M. et al. (Apr. 2016). Psychopharmacological options for adult patients with anorexia nervosa. CNS Spectrums, 21:134-142. https://doi.org/10.1017/S1092852914000790.
Mitsuyama, F. et al. (Sep. 2009). Amyloid beta: a putative intra-spinal microtubule-depolymerizer to induce synapse-loss or dentritic spine shortening in Alzheimer's disease. Italian Journal of Anatomy and Embryology, 114(2-3), 109-120. [Abstract]. Retrieved from http://www.ncbi.nlm.nih.gov/pubmed/20198823, 1 page.
Molero, P. et al. (May 2018). Antidepressant Efficacy and Tolerability of Ketamine and Esketamine: A Critical Review. CNS Drugs 32:411-420). https://doi.org/10.1007/s40263-018-0519-3.
Montejo, A.L. et al. (2008) Psychometric Properties of the Psychotropic-Related Sexual Dysfunction Questionnaire (PRSexDQ-SALSEX) in Patients with Schizophrenia and Other Psychotic Disorders. Journal of Sex Marital Therapy. 34(3):227-39.
Montigny, C. (Jun. 1989). Cholecystokinin Tetrapeptide Induces Panic-like Attacks in Healthy Volunteers: Preliminary Findings. Archives of General Psychiatry, 46:511-517. https://doi.org/10.1001/archpsyc.1989.01810060031006.
Moran, P. et al. (Sep. 2003) Standardised Assessment of Personality—Abbreviated Scale (SAPAS): preliminary validation of a brief screen for personality disorder. The British Journal of Psychiatry, 183(3):228-232.
Moreno, F. A., & Delgado, P. L. (Jul. 1997). Hallucinogen-induced relief of obsessions and compulsions. American Journal of Psychiatry, vol. 154, Issue 7, pp. 1037-1038. https://doi.org/10.1176/ajp.154.7.1037b.
Moreno, F.A. et al. (Nov. 2006). Safety, tolerability, and efficacy of psilocybin in 9 patients with obsessive-compulsive disorder. Journal of Clinical Psychiatry, 67(11), 1735-1740. https://doi.org/10.4088/JCP.v67n1110.
Morgan, C. et al. (Feb. 2017). Tripping up addiction: the use of psychedelic drugs in the treatment of problematic drug and alcohol use. Current Opinion in Behavioral Sciences, 13, pp. 71-76.
Morilak, D.A. et al. (Oct. 2005). Role of brain norepinephrine in the behavioral response to stress. Prog. Neuro-Psychopharmacology Biol. Psychiatry, 29:1214-1224. https://doi.org/10.1016/j.pnpbp.2005.08.007.
Moscovich, M. et al. (Aug. 2017). Death certificate data and causes of death in patients with parkinsonism. Parkinsonism & Related Disorders, 41:99-103. https://doi.org/10.1016/j.parkreldis.2017.05.022.
Moser, P.C. et al. (Jul. 7, 1988) "The effect of benzodiazepines on the 5-HT agonist-induced head-twitch response in mice", Eur J. Pharmacol, 151(2): 223-231.
Mukherjee, S. et al. (Jul. 2009). Lipopolysaccharide-driven Th2 Cytokine Production in Macrophages Is Regulated by Both MyD88 and TRAM. Journal of Biological Chemistry, 284(43):29391-29398. https://doi.org/10.1074/jbc.M109.005272.
Mula, M. et al. (Dec. 2006). Psychopharmacology of topiramate: From epilepsy to bipolar disorder. Neuropsychiatric Disease and Treatment, 2(4):475-488. https://doi.org/10.2147/nedt.2006.2.4.475.
Mulvey, M.R. (Oct. 2017) Neuropathic pain in cancer: systematic review, performance of screening tools and analysis of symptom profiles. British Journal of Anaesthesia, 119(4):765-774.
Municio, C. et al. (May 2018). Methotrexate limits inflammation through an A20-dependent cross-tolerance mechanism. Annals of the Rheumatic Diseases, 77(5):752-759. https://doi.org/10.1136/annrheumdis-2017-212537.
Murphy-Beiner, A. & Soar, K. (Apr. 2020). Ayahuasca's 'after-glow': improved mindfulness and cognitive flexibility in ayahuasca drinkers. Psychopharmacology, published online, https://doi.org/10.1007/s00213-019-05445-3, 9 pages.
Murrough, J.W. et al. (Sep. 2015). Emerging drugs for the treatment of anxiety. Expert Opin. Emerg. Drugs, 20(3):393-406. https://doi.org/10.1517/14728214.2015.1049996.
Nam, H. et al. (Apr. 2014). Learned helplessness and social avoidance in the Wistar-Kyoto rat. Front. Behav. Neurosci., 8(109), https://doi.org/10.3389/fnbeh.2014.00109, 18 pages.
National Institute for Health and Care Excellence (NICE) (Jan. 28, 2019) Antisocial Personality Disorder: Prevention and Management. Clinical guidance CG77 [online]. Available from www.nice.org.uk/guidance/cg77, 35 pages.
National Institute of Mental Health (NIMH) (Nov. 2017) Eating Disorders. Mental Health Information—Statistics (online). Retrieved Mar. 5, 2020, from https://www.nimh.nih.gov/health/statistics/eating-disorders.shtml#part_155063, 14 pages.
Nau, F. et al. (Jan. 2015). Serotonin 5-HT2 receptor activation prevents allergic asthma in a mouse model. American Journal of Physiology. Lung Cellular and Molecular Physiology, 308(2), L191-8. https://doi.org/10.1152/ajplung.00138.2013.
Nau, F., Yu, B., Martin, D., & Nichols, C. D. (2013). Serotonin $5\text{-}HT_{2a}$ Receptor Activation Blocks TNF-α Mediated Inflammation In Vivo. PLoS One, 8(10):2-9. https://doi.org/10.1371/journal.pone.0075426.
Naviaux, J.C. et al. (Jun. 2014). Reversal of autism-like behaviors and metabolism in adult mice with single-dose antipurinergic therapy. Translational Psychiatry, 4:e400, 11 pages. https://doi.org/10.1038/tp.2014.33.
Nechita, D. et al. (2018). A review of the influence the anxiety exerts on human life. Rom. J. Morphol. Embryol., 59(4): 1045-1051.
Nelis, S.M. et al. (May 2019). The impact of co-morbidity on the quality of life of people with dementia: findings from the IDEAL study. Age and Ageing, 48(3):361-367. https://doi.org/10.1093/ageing/afy155.
Nelson, R. J. et al. (Apr. 2005). Pleiotropic contributions of nitric oxide to aggressive behavior. Neuroscience and Biobehavioral Reviews, 30(3):346-355. https://doi.org/10.1016/j.neubiorev.2005.02.002.
Newman-Tancredi, A. et al. (Mar. 2018). Effects of the Serotonin 5-HT1A Receptor Biased Agonists, F13714 and F15599, on Striatal Neurotransmitter Levels Following L-DOPA Administration in Hemi-Parkinsonian Rats. Neurochemical Research, 43(5):1035-1046. https://doi.org/10.1007/s11064-018-2514-y.
Ngugi, A.K. et al. (May 2010). Estimation of the burden of active and life-time epilepsy: A meta-analytic approach. Epilepsia, 51(5): 883-890. https://doi.org/10.1111/j.1528-1167.2009.02481.x.
Ni, H.C. et al. (Oct. 2013) A head-To-head randomized clinical trial of methylphenidate and atomoxetine treatment for executive function in adults with attention-deficit hyperactivity disorder. Int J Neuropsychopharmacol, 16(9):1959-1973.
Nichols, D.E. (Apr. 2016) Psychedelics. Pharmacol Reviews, 68:264-355.
Nichols, D.E. (Feb. 2004) Hallucinogens. Pharmacology & Therapeutics, 101:131-181.
Nichols et al., "Improvements to the Synthesis of Psilocybin and a Facile Method for Preparing the 0-Acetyl Prodrug of Psilocin," Synthesis. 1999; 6:935-938.

(56) References Cited

OTHER PUBLICATIONS

Nicholson, B. & Verma S. (Mar. 2004). Comorbidities in chronic neuropathic pain. Pain Medicine. 5(S1):S9-25. Retrieved from: https://academic.oup.com/painmedicine/article-abstract/5/suppl_1/S9/1884243, on Jul. 30, 2020.
Nicolini, C. et al. (Jan. 2015). Decreased mTOR signaling pathway in human idiopathic autism and in rats exposed to valproic acid. Acta Neuropathologica Communications, 3:3, 13 pages, https://doi.org/10.1186/s40478-015-0184-4.
Niederhofer, H. (Sep. 2005). Atomoxetine Also Effective in Patients Suffering From Narcolepsy? Sleep, 28(9):1189, 1 page. https://www.researchgate.net/publication/7500498_Atomoxetine_Also_Effective_in_Patients_Suffering_From_Narcolepsy (accessed 3.26.20).
Nielsen, S. (2017). Benzodiazepines. Curr. Top. Behav. Neurosci. 34:141-159. https://doi.org/10.1007/7854_2015_425.
Nimmo-Smith, V. et al. (Jan. 2020). Anxiety Disorders in Adults with Autism Spectrum Disorder: A Population-Based Study. Journal of Autism and Developmental Disorders, 50:308-318. https://doi.org/10.1007/s10803-019-04234-3.
Nisbet, E. et al. (Sep. 2009) The nature relatedness scale. Linking individuals' connection with nature to environmental concern and behavior. Environment and Behavior 41(5):715-740.
Norris, M.L. et al. (Jun. 2011). Olanzapine Use for the Adjunctive Treatment of Adolescents with Anorexia Nervosa. Journal of Child and Adolescent Psychopharmacology, 21(3):213-220. https://doi.org/10.1089/cap.2010.0131.
Nour, M.M. et al. (Jun. 2016) Ego-Dissolution and Psychedelics: Validation of the Ego-Dissolution Inventory (EDI) Frontiers in Human Neuroscience, 10:269, doi: 10.3389/fnhum.2016.00269, 13 pages.
Nour, M.M. et al. (Apr. 2017) Psychedelics, Personality and Political Perspectives. Journal of Psychoactive Drugs, 49(3):182-191.
Nowacka, A. & Borczyk, M. (Oct. 2019). Ketamine applications beyond anesthesia—A literature review. European Journal of Pharmacology, 860, 172547, 14 pages. https://doi.org/10.1016/j.ejphar.2019.172547.
Nutt, D. et al. (Apr. 2, 2020) "Psychedelic Psychiatry's Brave New World", Cell, 181(1,2):24-28.
Oerbeck, B. et al. (Jan. 2017) ADHD, comorbid disorders and psychosocial functioning: How representative is a child cohort study? Findings from a national patient registry. BMC Psychiatry, 17:23, 9 pages. Available from: http://dx.doi.org/10.1186/s12888-017-1204-7.
Olguin, P. et al. (Mar. 2017). Medical comorbidity of binge eating disorder. Eat Weight Disord 22, 13-26.
Onakpoya, I.J. et al. (Jan. 2019). Benefits and harms of pregabalin in the management of neuropathic pain: A rapid review and meta-analysis of randomised clinical trials. BMJ Open 9, e023600, 19 pages. https://doi.org/10.1136/bmjopen-2018-023600.
Opbroek, A. et al. (Jun. 2002) Emotional blunting associated with SSRI-induced sexual dysfunction. Do SSRIs inhibit emotional responses? International Journal of Neuropsychopharmacology, 5:147-151.
Orekhova, E.V. et al. (Mar. 2008). Sensory gating in young children with autism: Relation to age, IQ, and EEG gamma oscillations. Neurosci. Lett., 434:218-223. https://doi.org/10.1016/j.neulet.2008.01.066.
Osland, S. et al. (Oct. 2018). The prevalence of diagnosed obsessive compulsive disorder and associated comorbidities: A population-based Canadian study. Psychiatry Research, 268:137-142. https://doi.org/10.1016/j.psychres.2018.07.018.
Ottman, R. et al. (Feb. 2011). Comorbidities of epilepsy: results from the Epilepsy Comorbidities and Health (EPIC) survey. Epilepsia, 52(2):308-315. https://doi.org/10.1111/j.1528-1167.2010.02927.x.
Otto, M.W. et al. (Dec. 2001). An effect-size analysis of the relative efficacy and tolerability of serotonin selective reuptake inhibitors for panic disorder. Am. J. Psychiatry 158:1989-1992. https://doi.org/10.1176/appi.ajp.158.12.1989.
Page, J. & Henry, D. (Mar. 2000). Consumption of NSAIDs and the Development of Congestive Heart Failure in Elderly Patients. Archives of Internal Medicine, 160(6):777-784. https://doi.org/10.1001/archinte.160.6.777.
Pahwa, R. et al. (2020). Chronic Inflammation. Statpearls [Internet]. NCBI Bookshelf. Retrieved from: https://www.ncbi.nlm.nih.gov/books/NBK493173/, 9 printed pages.
Palsson-McDermott, E. M. & O'Neill, L. A. J. (Oct. 2004). Signal transduction by the lipopolysaccharide receptor, Toll-like receptor-4. Immunology, 113(2):153-162. https://doi.org/10.1111/j.1365-2567.2004.01976.x.
Papakostas, G.I. et al. (2006) "The combination of duloxetine and bupropion for treatment-resistant major depressive disorder" Depression and Anxiety, 23:178-181.
Parameswaran, N. & Patial, S. (2010). Tumor necrosis factor-a signaling in macrophages. Critical Reviews in Eukaryotic Gene Expression, 20(2):87-103. https://doi.org/10.1615/critreveukargeneexpr.v20.i2.10.
Park, A. (Dec. 2021) Characterization of Psilocybin. Freedom to Operate, LLC. Triclinic Labs Report No. R2021638.01, 11 pages.
Park, J.H. & Park, H.J. (Aug. 2017) Botulinum toxin for the treatment of neuropathic pain. Toxins. 9:290, doi: 10.3390/toxins9090260, 15 pages.
Parkinson's Foundation (2020). Prescription Medications for Parkinson Disease. Retrieved from https://www.parkinson.org/Understanding-Parkinsons/Treatment/Prescription-Medications; retrieved on Jul. 30, 2020; 6 pages.
Parkinson's Foundation, P. (2020). Stages of Parkinson's disease. Retrieved from https://www.parkinson.org/Understanding-Parkinsons/What-is-Parkinsons/Stages-of-Parkinsons, 8 pages.
Parnas, J. et al. (Sep. 2005) EASE: Examination of Anomalous Self-Experience. Psychopathology. 38:236-258.
Passie, T. et al. (Oct. 2002) The pharmacology of psilocybin. Addiction Biology, 7:357-364.
Patra, S. (Dec. 2016) "Return of the psychedelics: Psilocybin for treatment resistant depression," Asian Journal of Psychiatry, vol. 24, p. 51-52.
Patton, J.H. (Nov. 1995) Factor structure of the Barratt Impulsiveness Scale. Journal of Clinical Psychology. 51:768-774.
Pauli, D. et al. (Apr. 2017). Motivation to change, coping, and self-esteem in adolescent anorexia nervosa: A validation study of the Anorexia Nervosa Stages of Change Questionnaire (ANSOCQ). Journal of Eating Disorders, 5(1):11, 11 pages. https://doi.org/10.1186/s40337-016-0125-z.
Pecina, S., & Berridge, K.C. (Dec. 2005). Hedonic hot spot in nucleus accumbens shell: Where do μ opioids cause increased hedonic impact of sweetness? The Journal of Neuroscience, 25(50):11777-11786.
Pelletier, M. & Siegel, R. M. (Dec. 2009). Wishing away inflammation? New links between serotonin and TNF signaling. Molecular Interventions, 9(6):299-301. https://doi.org/10.1124/mi.9.6.5.
Pennington, S. et al. (Aug. 2010). The cause of death in idiopathic Parkinson's disease. Parkinsonism & Related Disorders, 16(7): 434-437. https://doi.org/10.1016/j.parkreldis.2010.04.010.
Perez-Carbonell, L. et al. (Jun. 2020). Adherence to wakefulness promoting medication in patients with narcolepsy. Sleep Med. 70:50-54. https://doi.org/10.1016/j.sleep.2020.02.013.
Perini, G. I. et al. (Dec. 1996). Interictal mood and personality disorders in temporal lobe epilepsy and juvenile myoclonic epilepsy. Journal of Neurology, Neurosurgery & Psychiatry, 61(6):601-605. https://doi.org/10.1136/jnnp.61.6.601.
Perlis, M.L. et al. (Feb. 2001). Beta/Gamma EEG Activity in Patients with Primary and Secondary Insomnia and Good Sleeper Controls. Sleep, 24(1):110-117.
Persson, S. A. (Aug. 1978). LSD and related drugs as DA antagonists: receptor-mediated effects on the synthesis and turnover of DA. Life Sciences, 23(5):523-526. https://doi.org/10.1016/0024-3205(78)90165-0.
Peters, E. et al. (2004) Measuring Delusional Ideation: the 21-item Peters et al. Delusions Inventory (PDI). Schizophrenia Bulletin, 30(4):1005-1022.

(56) References Cited

OTHER PUBLICATIONS

Piedmont, R.L. (1999) Does spirituality represent the sixth factor of personality? Spiritual transcendence and the five-factor model. Journal of Personality. 67:985-1013.
Piton A. et al. (2011). Systematic resequencing of X-chromosome synaptic genes in autism spectrum disorder and schizophrenia. Molecular Psychiatry, 16(8):867-880. https://doi.org/10.1038/mp.2010.54.
Pittenger, C. et al. (Sep. 2014). Pharmacological treatment of obsessive- compulsive disorder. In Psychiatric Clinics of North America, 37(3):375-391. https://doi.org/10.1016/j.psc.2014.05.006.
Polat, G. et al. (Feb. 2017). Sepsis and Septic Shock: Current Treatment Strategies and New Approaches. Eurasian Journal of Medicine, 49(1):53-58. https://doi.org/10.5152/eurasianjmed.2017.17062.
Polito, V. & Stevenson, R.J. (2019) A systematic study of microdosing psychedelics. PLoS One. 14(2):e0211023, https://doi.org/10.1371/journal.pone.0211023, 26 pages.
Postal, M. et al. (Jan. 2016). Depressive symptoms are associated with tumor necrosis factor alpha in systemic lupus erythematosus. Journal of Neuroinflammation, 13(1):5. https://doi.org/10.1186/s12974-015-0471-9, 7 pages.
Price, J. et al. (2012) The Oxford Questionnaire on the Emotional Side-effects of Antidepressants (OQuESA): Development, validity, reliability and sensitivity to change. Journal of Affective Disorders. 140:66-74.
Prince J. (2008) Catecholamine dysfunction in attention-deficit/hyperactivity disorder. An update. Journal of Clinical Psychopharmacology. 28(3 Suppl 2):39-45.
Prochazkova, L. et al. (Dec. 2018). Exploring the effect of microdosing psychedelics on creativity in an open-label natural setting. Psychopharmacology, 235(12):3401-3413. https://doi.org/10.1007/s00213-018-5049-7.
PROSOLV® SMCC. Retrieved from Web Archive, Reset https://web.archive.org/web/20160318071326/http://www.jrspharma.com/pharmaen/productsservices/excipients/hfe/prosolvs-mcc.php Retrieved Mar. 18, 2016, 3 pages.
Pryor, T. et al. (May 1996). Clinical correlates of anorexia nervosa subtypes. The International Journal of Eating Disorders, 19(4):371-379. http://www.ncbi.nlm.nih.gov/pubmed/9156690.
Psilocybin for the Treatment of Cluster Headache. ClinicalTrials.gov [Internet]. Identifier: NCT02981173. Retreived from: https://clinicaltrials.gov/ct2/show/NCT02981173, 8 pages.
Psilocybin Patent Tracker. Psilocybin Alpha, 2020 [online]. Retrieved from: https://psilocybinalpha.com/data/psilocybin-patent-tracker; retrieved on Oct. 1, 2020, 2 printed pages.
Pugazhenthi, S. et al. (Jul. 2013). Induction of an Inflammatory Loop by Interleukin-1β and Tumor Necrosis Factor-a Involves NF-κB and STAT-1 in Differentiated Human Neuroprogenitor Cells. PLOS ONE, 8(7):1-12. https://doi.org/10.1371/journal.pone.0069585.
Pulikkan, J. et al. (2019). Role of the Gut Microbiome in Autism Spectrum Disorders. In Advances in Experimental Medicine and Biology, 1118:253-269. https://doi.org/10.1007/978-3-030-05542-4_13.
Quadri, S. et al. (Apr. 2009). Improvement of idiopathic central sleep apnea with zolpidem. J. Clin. Sleep Med. 5:122-129. https://doi.org/10.5664/jcsm.27439.
Quan, Q. et al. (2019). CDK5 Participates in Amyloid-β Production by Regulating PPARγ Phosphorylation in Primary Rat Hippocampal Neurons. Journal of Alzheimer's Disease : JAD, 71(2):443-460. https://doi.org/10.3233/JAD-190026.
Quan, X. et al. (2020). Related Network and Differential Expression Analyses Identify Nuclear Genes and Pathways in the Hippocampus of Alzheimer Disease. Medical Science Monitor : International Medical Journal of Experimental and Clinical Research, 26:e919311, 11 pages. https://doi.org/10.12659/MSM.919311.
Quintero J. et al. (2010). Reboxetine for ADHD in children non-responders or with poor tolerance to methylphenidate: A prospective long-term open-label study. ADHD Atten Deficit Hyperact Disord., 2(3):107-113.
Raffaeli, W. & Arnaudo, E. (Aug. 2017). Pain as a disease: An overview. J Pain Res., 10:2003-2008.
Rai, D. et al. (Jan. 2012). Epilepsy and psychiatric comorbidity: A nationally representative population-based study. Epilepsia 53:1095-1103. https://doi.org/10.1111/j.1528-1167.2012.03500.x.
Ramachandran, V. et al. (2018). Relief from intractable phantom pain by combining psilocybin and mirror visual-feedback (MVF). Neurocase, 24(2):105-110. Available from: https://doi.org/10.1080/13554794.2018.1468469 RAMACHANDRAN.
Ramadan, M.I. et al. (2006). Protect against drug-drug interactions with anxiolytics. Current Psychiatry, 5(5):16-28.
Ramos, A.A. et al. (2019). A meta-analysis on verbal working memory in children and adolescents with ADHD. Clinical Neuropsychologist, 34(5):873-898.
Rastam, M., et al. (2003). Outcome of teenage-onset anorexia nervosa in a Swedish community-based sample. European Child and Adolescent Psychiatry, 12(Suppl. 1):78-90. https://doi.org/10.1007/s00787-003-1111-y.
Rautiainen, M-R et al. (2016) Genome-wide association study of antisocial personality disorder. Transl Psychiatry. 6:e883, doi: 10.1038/tp.2016.155, 10 pages.
Raval et al., "Silicified Microcrystalline Cellulose as a Multifunctional Pharmaceutical Excipient," Drug Delivery Technology, 2009;9(4):28 and 30-32. Supplied by the British Library Oct. 12, 2019, 6 pages.
Ravindran, L.N. & Stein, M.B. (2010). The pharmacologic treatment of anxiety disorders: A review of progress. J. Clin. Psychiatry. 71(7): 839-854. https://doi.org/10.4088/JCP.10r06218blu.
Reas, D. and Grilo, C. (Mar. 2014). Current and emerging drug treatments for binge eating disorder. Expert Opinion on Emerging Drugs, 19(1), pp. 99-142.
Reimherr, F.W. et al. (2017). ADHD and Anxiety: Clinical Significance and Treatment Implications. Curr. Psychiatry Rep., 19:109, 10 pages. https://doi.org/10.1007/s11920-017-0859-6.
Reitz, C. & Mayeux, R. (Apr. 2014). Alzheimer disease: Epidemiology, diagnostic criteria, risk factors and biomarkers. Biochemical Pharmacology, 88(4):640-651. https://doi.org/10.1016/j.bcp.2013.12.024.
Remes, O. et al. (2016). A systematic review of reviews on the prevalence of anxiety disorders in adult populations. Brain Behav. https://doi.org/10.1002/brb3.497, 33 pages.
Repke et al., Psilocin Analogs. 1. Synthesis of 3-[2-(Dialkylamino)ethyl]- and 3-[2-(Cycloalkylamino)ethyl] indol-4-ols, J. Heterocyclic Chem., 14, 71 (Feb. 1977), 4 pages.
Rickels, K. et al. (Sep. 2005). Pregabalin for treatment of generalized anxiety disorder: A 4-week, multicenter, double-blind, placebo-controlled trial of pregabalin and alprazolam. Arch. Gen. Psychiatry 62, 1022-1030. https://doi.org/10.1001/archpsyc.62.9.1022.
Riediger C. et al. (2017). Adverse effects of antidepressants for chronic pain: A systematic review and meta-analysis. Front. Neurol. 8:307, 23 pages. doi: 10.3389/fneur.2017.00307.
Rintala, H. et al. (2017). Register-based study of the incidence, comorbidities and demographics of obsessive-compulsive disorder in specialist healthcare. BMC Psychiatry, 17(1):64, 8 pages. https://doi.org/10.1186/s12888-017-1224-3.
Ripoll, L.H. et al. (2011) Evidence-based pharmacotherapy for personality disorders. 14:1257-1288.
Robbins, M.S. (2013) The psychiatric comorbidities of cluster headache. Curr Pain Headache Rep, 17(2):313, DOI: 10.1007/s11916-012-0313-8, 8 pages.
Robner, A. et al. (Sep. 2017). Cognitive Flexibility in Juvenile Anorexia Nervosain Relation to Comorbid Symptoms of Depression, Obsessive Compulsive Symptoms and Duration of Illness. Zeitschrift für Kinder- und Jugendpsychiatrie und Psychotherapie, 45 (5):371-380. https://doi.org/10.1024/1422-4917/a000493.
Rodriguez, C. et al. (2016). Attention deficit/hyperactivity disorder (ADHD) diagnosis: An activation-executive model. Front. Psychol. 7:1406, 13 pages. doi: 10.3389/fpsyg.2016.01406.

(56) References Cited

OTHER PUBLICATIONS

Rojas, D.C. & Wilson, L.B. (2014). γ-band abnormalities as markers of autism spectrum disorders. Biomark Med. Mar. 2014; 8(3):353-368. doi: 10.2217/bmm.14.15.
Rosen, E. et al. (2017). Hepatic Complications of Anorexia Nervosa. Dig Dis Sci, 62:2977-2981. doi:10.1007/s10620-017-4766-9.
Rosenberg, M. (1965) Society and the adolescent self-image. Science, 148(3671):804, DOI:10.1126/science.148.3671.804, 2 pages.
Rosenblat, J.D. et al. (Aug. 2014). Inflamed moods: A review of the interactions between inflammation and mood disorders. Progress in Neuro-Psychopharmacology and Biological Psychiatry, 53:23-34. https://doi.org/10.1016/j.pnpbp.2014.01.013.
Ross, S. et al. (Dec. 2016). Rapid and sustained symptom reduction following psilocybin treatment for anxiety and depression in patients with life-threatening cancer: A randomized controlled trial. J. Psychopharmacol. 30:1165-1180. https://doi.org/10.1177/0269881116675512.
Rossi, P. and Whelan, J. (2016) What is cluster headache? Fact sheet for patients and their families. A publication to mark Cluster Headache Day 2016. Functional Neurology. 31(3):181-183.
Roth, T. et al. (2007). Insomnia: Definition, prevalence, etiology, and consequences. J. Clin. Sleep Med. Supplement to vol. 3, No. 5, https://doi.org/10.5664/jcsm.26929, 4 pages.
Roth, T. et al. (Nov. 2007). Efficacy and safety of doxepin 1 mg, 3 mg, and 6 mg in adults with primary insomnia. Sleep 30, 1555-61. https://doi.org/10.1093/sleep/30.11.1555.
Rucker, J. et al. (Dec. 2, 20175) "Psychiatry & the psychedelic drugs. Past, present & future," Neuropharmacol, 142:200-218.
Rucker, J. et al. (Dec. 2019) Psilocybin administration to healthy participants: safety and feasibility in a placebo-controlled study. Poster # W111, presented at the 58th Annual Meeting of The American College of Neuropsychopharmacology, Orlando, FL, USA, Dec. 8-11, 2019.
Ruffolo, S. et al. (Jan. 2006). Comorbidity of body dysmorphic disorder and eating disorders: Severity of psychopathology and body image disturbance. International Journal of Eating Disorders, 39(1), pp. 11-19.
Rupprecht, R. et al. (2009). Translocator protein (18 κD) as target for anxiolytics without benzodiazepine-like side effects. Science, New Series, vol. 325, No. 5939, pp. 490-493. https://doi.org/10.1126/science.1175055.
Ruscio, A. M. et al. (2010). The epidemiology of obsessive-compulsive disorder in the National Comorbidity Survey Replication. Molecular Psychiatry, 15(1), 53-63. https://doi.org/10.1038/mp.2008.94.
Rush, A.J. et al. (2003) The 16-Item Quick Inventory of Depressive Symptomatology (QIDS), Clinician Rating (QIDS-C), and Self-Report (QIDS-SR): A Psychometric Evaluation in Patients with Chronic Major Depression. Biol Psy, 54(5):573-583.
Russell, E.J. et al. (Apr. 2013). Risk of obsessive-compulsive disorder in pregnant and postpartum women: A meta-analysis. Journal of Clinical Psychiatry, 74(4), 377-385. https://doi.org/10.4088/JCP.12r07917.
Russo, A.J. (2014). Increased Epidermal Growth Factor Receptor (EGFR) Associated with Hepatocyte Growth Factor (HGF) and Symptom Severity in Children with Autism Spectrum Disorders (ASDs). Journal of Central Nervous System Disease. 6:79-83. https://doi.org/10.4137/jcnsd.s13767.
Ryder, S. & A, Stannard C.F. (2005). Treatment of chronic pain: Antidepressant, antiepileptic and antiarrhythmic drugs. Contin Educ Anaesthesia, Crit Care Pain. 5(1):18-21.
Rylander, M. et al. (2017). A comparison of the metabolic complications and hospital course of severe anorexia nervosa by binge-purge and restricting subtypes. Eating Disorders, 25(4), 345-357. https://doi.org/10.1080/10640266.2016.1269555.
Sagata, N. et al. (Oct. 2017). Dysregulated gene expressions of MEX3D, FOS and BCL2 in human induced-neuronal (iN) cells from NF1 patients: A pilot study. Scientific Reports. https://doi.org/10.1038/s41598-017-14440-7, 8 pages.
Sahu, A. & Gupta, R. (Dec. 2017). A study of psychiatric comorbidity after traumatic limb amputation: A neglected entity. Ind Psychiatry J. 26(6):228-32.
Sakashita, Y. et al. (2015). Effect of Psilocin on Extracellular Dopamine and Serotonin Levels in the Mesoaccumbens and Mesocortical Pathway in Awake Rats. Biol. Pharm. Bull. 38, 134-138 (2015).
Salama, R. M. et al. (2020). Neuroprotective effect of crocin against rotenone- induced Parkinson's disease in rats: Interplay between PI3K/Akt/mTOR signaling pathway and enhanced expression of miRNA-7 and miRNA-221. Neuropharmacology, 164, 107900., 12 pages. https://doi.org/10.1016/j.neuropharm.2019.107900.
Salisbury-Afshar, E. (2018). Management of Insomnia Disorder in Adults—Implementing AHRQ Effective Health Care Reviews. Am Fam Physician. 98(5), 5 pages. https://www.aafp.org/afp/2018/0901/p319.html#afp20180901p319-b4.
Sandbank, M. et al. (2020). Project AIM: Autism intervention meta-analysis for studies of young children. Psychological Bulletin. 146(1):1-29. https://doi.org/10.1037/bul0000215.
Sandiego, C.M. et al. (Oct. 2015). Imaging robust microglial activation after lipopolysaccharide administration in humans with PET. Proceedings of the National Academy of Sciences, 112(40), 12468-12473. https://doi.org/10.1073/pnas.1511003112.
Santiago, J.A. et al. (2017). Biological and Clinical Implications of Comorbidities in Parkinson's Disease. Frontiers in Aging Neuroscience, 9, 16 pages. https://doi.org/10.3389/fnagi.2017.00394.
Santini, E. et al. (2013). Exaggerated translation causes synaptic and behavioural aberrations associated with autism. Nature, 493, https://doi.org/10.1038/nature11782, 6 pages.
Saraf, G. et al. (Mar. 2017). Bipolar disorder comorbidity in patients with a primary diagnosis of OCD, International Journal of Psychiatry in Clinical Practice, 21:1, 70-74, doi: 10.1080/13651501.2016.1233344.
Saraiva, M., & O'garra, A. (Mar. 2010). The regulation of IL-10 production by immune cells. Nature Reviews Immunology, 10(3), 170-181. https://doi.org/10.1038/nri2711.
Sard, H. et al. (Oct. 2005). SAR of psilocybin analogs: Discovery of a selective 5-HT2C agonist. Bioorganic and Medicinal Chemistry Letters, 15(20), 4555-4559. https://doi.org/10.1016/j.bmcl.2005.06.104.
Saunders, A.M. et al. (Aug. 1993). Association of apolipoprotein E allele €4 with late-onset familial and sporadic Alzheimer's disease. Neurology, 43(8):1467-1467. https://doi.org/10.1212/WNL.43.8.1467.
Savage, C. (Jun. 1952) Lysergic Acid Diethylamide (LSD-25). A Clinical-Psychological Study. The American Journal of Psychiatry, 108:896-900.
Savioz, A., Leuba, G., & Vallet, P. G. (Sep. 2014). A framework to understand the variations of PSD-95 expression in brain aging and in Alzheimer's disease. Ageing Research Reviews, 18, 86-94. https://doi.org/10.1016/j.arr.2014.09.004.
Saxton, R. A. & Sabatini, D.M. (Mar. 2017). mTOR Signaling in Growth, Metabolism, and Disease. Cell, 168(6):960-976. https://doi.org/10.1016/j.cell.2017.02.004.
Sayal, K. et al. (Feb. 2018) ADHD in children and young people: prevalence, care pathways, and service provision. The Lancet Psychiatry, 5(2): 175-186. Available from: http://dx.doi.org/10.1016/S2215-0366(17)30167-0cdc.gov.
Scammell, T.E. (2015) Narcolepsy. N. Engl. J. Med., 373:4654-2662. https://doi.org/10.1056/NEJMra1500587.
Schachter, M. & Parkes, J.D. (Feb. 1980). Fluvoxamine and clomipramine in the treatment of cataplexy. Journal of Neurology, Neurosurgery, and Psychiatry, 43:171-174.
Scheller, J. et al. (May 2011). The pro- and anti-inflammatory properties of the cytokine interleukin-6. Biochimica et Biophysica Acta, 1813(5):878-888. https://doi.org/10.1016/j.bbamcr.2011.01.034.
Schneider, T. et al. (Jul. 2008). Gender-specific behavioral and immunological alterations in an animal model of autism induced by prenatal exposure to valproic acid. Psychoneuroendocrinology, 33:728-740. https://doi.org/10.1016/j.psyneuen.2008.02.011.

(56) References Cited

OTHER PUBLICATIONS

Schulke, S. (Mar. 2018). Induction of Interleukin-10 Producing Dendritic Cells As a Tool to Suppress Allergen-Specific T Helper 2 Responses. Frontiers in Immunology, 9:455, https://doi.org/10.3389/fimmu.2018.00455, 18 pages.
Schwalberg, M.D. et al. (Nov. 1992). Comparison of Bulimics, Obese Binge Eaters, Social Phobics, and Individuals With Panic Disorder on Comorbidity Across DSM-III-R Anxiety Disorders. J. Abnorm. Psychol., 101:675-681. https://doi.org/10.1037/0021-843X.101.4.675.
Sedgwick, O. et al. (2017) Neuropsychology and emotion processing in violent individuals with antisocial personality disorder or schizophrenia: The same or different? A systematic review and meta-analysis. Australian and New Zealand Journal of Psychiatry, 51(12):1178-1197.
Sedley, W. & Cunningham, M.O. (2013). Do cortical gamma oscillations promote or suppress perception? An under-asked question with an over-assumed answer. Front. Hum. Neurosci., 7:595, https://doi.org/10.3389/fnhum.2013.00595, 17 pages.
Serrano-Pozo, A. et al. (2011). Neuropathological Alterations in Alzheimer Disease. Cold Spring Harbor Perspectives in Medicine, 1(1):a006189, https://doi.org/10.1101/cshperspect.a006189, 23 pages.
Sewell, R.A. et al. (Jun. 2006) "Response of cluster headache to psilocybin and LSD" Neurology, 66(12):1920-1922.
Shah, K., & Lahiri, D.K. (Jun. 2014). Cdk5 activity in the brain - multiple paths of regulation. Journal of Cell Science, 127(11):2391-2400. https://doi.org/10.1242/jcs.147553.
Shannon, P. et al. (Nov. 2003). Cytoscape: a software environment for integrated models of biomolecular interaction networks. Genome Research, 13(11):2498-2504. https://doi.org/10.1101/gr.1239303.
Sharma, S.R. et al. (2018). Autism Spectrum Disorder: Classification, diagnosis and therapy. Pharmacology and Therapeutics, 190:91-104. https://doi.org/10.1016/j.pharmthera.2018.05.007.
Sherman, E.M.S. et al. (Mar. 2011). Neuropsychological outcomes after epilepsy surgery: Systematic review and pooled estimates. Epilepsia, 52(5):857-869. https://doi.org/10.1111/j.1528-1167.2011.03022.x.
Sherwood, A.M. et al. (2021) Psilocybin: crystal structure solutions enable phase analysis of prior art and recently patented examples. Acta Crystallographica, 78(1): 1-20.
Shier, A.C. et al. (2013) Pharmacological Treatment of Attention Deficit Hyperactivity Disorder in Children and Adolescents: Clinical Strategies. J Cent Nerv Syst Dis, 5, doi: 10.4137/JCNSD.S6691, 17 pages.
Shirota, O., et al., (Jun. 2003) "Concise large-scale synthesis of psilocin and psilocybin, principal hallucinogenic constituents of 'magic mushroom' " J Nat Prod, 66(6):885-887.
Shofty, B. et al. (Apr. 26, 2019). Loss of function in the autism and learning disabilities associated gene Nf1 disrupts corticocortical and corticostriatal functional connectivity in human and mouse. BioRxiv, preprint, https://doi.org/10.1101/618223, 35 pages.
Shoja Shafti, S., & Kaviani, H. (Feb. 2015). Aripiprazole versus quetiapine in treatment-resistant obsessive-compulsive disorder: A double-blind clinical trial. Therapeutic Advances in Psychopharmacology, 5(1):32-37. https://doi.org/10.1177/2045125314560739.
Shulgin et al., "TIHKAL: The Continuation," Transform Press, 1997, pp. 468-473.
Sid-Otmane, L. et al. (Apr. 2020). Selective metabotropic glutamate receptor 2 positive allosteric modulation alleviates L-DOPA-induced psychosis-like behaviours and dyskinesia in the MPTP-lesioned marmoset. European Journal of Pharmacology, 873:172957, https://doi.org/10.1016/j.ejphar.2020.172957, 6 pages.
Siervo, M. et al. (Jun. 2005). Application of the SCOFF, Eating Attitude Test 26 (EAT 26) and Eating Inventory (TFEQ) questionnaires in young women seeking diet- therapy. Eating and Weight Disorders, 10(2):76-82. https://doi.org/10.1007/BF03327528.
Sifferlin A., "What You Need to Know About Magic Mushrooms and Depression," Time, 4 pages. (Dec. 1, 2016.).
Silber, M.H. et al. (2002) The epidemiology of narcolepsy in Olmsted County, Minnesota: A population-based study. Sleep, 25(2):197-202. https://doi.org/10.1093/sleep/25.2.197.
Silva, N. et al. (Feb. 2014) Searching for a neurobiological basis for self- medication theory in ADHD comorbid with substance use disorders: An in vivo study of dopamine transporters using $^{99m}$Tc-TRODAT-1 SPECT. Clin Nucl Med, 39(2):e129-e134.
Simon, N.M. (2009) Generalized Anxiety Disorder and Psychiatric Comorbidities Such as Depression, Bipolar Disorder, and Substance Abuse. J Clin Psychiatry, 70(suppl 2): 10-14.
Singh, A., & Trevick, S. (Nov. 2016). The Epidemiology of Global Epilepsy. Neurologic Clinics, 34(4):837-847. https://doi.org/10.1016/j.ncl.2016.06.015.
Siniscalco, D. et al. (Jun. 2018). Inflammation and neuro-immune dysregulations in autism spectrum disorders. Pharmaceuticals, 11:56, https://doi.org/10.3390/ph11020056, 14 pages.
Skapinakis, P. et al. (Aug. 2016) "Pharmacological and psychotherapeutic interventions for management of obsessive-compulsive disorder in adults: a systematic review and network meta-analysis" The Lancet Psychiatry, 3(8):730-739. https://doi.org/10.1016/S2215-0366(16)30069-4.
Smith, B.W. et al. (2008) The Brief Resilience Scale: Assessing the Ability to Bounce Back. International Journal of Behavioral Medicine. 15:194-200.
Smith, K.N. et al. (2019). Changes in meal-related anxiety predict treatment outcomes in an intensive family-based treatment program for adolescents with anorexia nervosa. Eating Disorders, DOI: 10.1080/10640266.2019.1688008, 13 pages.
Snaith, R.P. et al. (1995) A scale for the assessment of hedonic tone. The Snaith- Hamilton Pleasure Scale. The British Journal of Psychiatry, 167:99-103.
Soler, J. et al. (2018). Genetic variability in scaffolding proteins and risk for schizophrenia and autism-spectrum disorders: A systematic review. Journal of Psychiatry and Neuroscience, 43(4):223-244. https://doi.org/10.1503/jpn.170066.
Souery, D. et al. (Jul. 2007). Clinical Factors Associated With Treatment Resistance in Major Depressive Disorder: Results From a European Multicenter Study. The Journal of Clinical Psychiatry, 68(07):1062-1070. https://doi.org/10.4088/JCP.v68n0713.
Spangler, E.L., Rigby, P., & Ingram, D.K. (1986). Scopolamine impairs learning performance of rats in a 14-unit T-maze. Pharmacology, Biochemistry and Behavior, 25:673-679. https://doi.org/10.1016/0091-3057(86)90158-9.
Spielberger, C.D. (2020) State-Trait Anxiety Inventory for AdultsTM. STAI—Adult Manual. Mind Garden Inc., www.mindgarden.com, 87 pages.
Spowart-Manning L. et al. (May 2004) The T-maze continuous alternation task for assessing the effects of putative cognition enhancers in the mouse. Behav Brain Res, 151(1-2):37-46.
Srinivas, H.V. & Shah, U. (2017). Comorbidities of epilepsy. Neurology India, 65(Supplement):S18-S24. https://doi.org/10.4103/neuroindia.NI_922_16, 15 pages.
Srivastava, R.K. et al. (2011). Role of Donepezil in Autism: Its Conduciveness in Psychopharmacotherapy. Case Reports in Psychiatry, 2011:563204, https://doi.org/10.1155/2011/563204, 2 pages.
Stahl, S.M. (Dec. 1998) Mechanism of action of serotonin selective reuptake inhibitors. Serotonin receptors and pathways mediate therapeutic effects and side effects. J. Affect. Disord., 51:215-235. https://doi.org/10.1016/S0165-0327(98)00221-3.
Stancil, S. et al. (Nov. 2019). Naltrexone Reduces Binge Eating and Purging in Adolescents in an Eating Disorder Program. Journal of Child and Adolescent Psychopharmacology, 29(9):721-724.
Stancu, C., & Sima, A. (Dec. 2001). Statins: mechanism of action and effects. Journal of Cellular and Molecular Medicine, 5(4), 378-387. https://doi.org/10.1111/j.1582-4934.2001.tb00172.x.
Starr, M.S. (1996). The role of dopamine in epilepsy. Synapse. 22:159-194.
Stefano, S. et al. (Apr. 2008). Antidepressants in short-term treatment of binge eating disorder: Systematic review and meta-analysis. Eating Behaviors, 9(2), pp. 129-136.
Steger, M.F. et al. (2008) Understanding the serach for meaning in life: Personality, cognitive style, and the dynamic between seeking and experiencing meaning. Journal of Personality, 76:199-228.

(56) References Cited

OTHER PUBLICATIONS

Stein, D.J. et al. (Aug. 2019) “Obsessive-compulsive disorder” Nature Reviews Disease Primers, 5(1):52; doi: 10.1038/s41572-019-0102-3, 21 pages.
Stein, D.J. et al. (Jun. 2017). Epidemiology of anxiety disorders: From surveys to nosology and back. Dialogues Clin Neurosci, 19:127-135.
Stein, M.B. & Sareen, J. (2015). Generalized anxiety disorder. N. Engl. J. Med., 373:2059-2068. https://doi.org/10.1056/NEJMcp1502514.
Steinhausen, H-C. (Jan. 2009). Outcome of Eating Disorders. Child and Adolescent Psychiatric Clinics of North America, 18(Issue 1):225-242. https://doi.org/10.1016/j.chc.2008.07.013.
Stevenson, R.A. et al. (2019). Conjunctive visual processing appears abnormal in Autism. Frontiers in Psychology, 9:2668, https://doi.org/10.3389/fpsyg.2018.02668, 7 pages.
Stice, L. V., & Lavner, J. A. (Mar. 2019). Social Connectedness and Loneliness Mediate the Association Between Autistic Traits and Internalizing Symptoms Among Young Adults. Journal of Autism and Developmental Disorders, 49(3), 1096-1110. https://doi.org/10.1007/s10803-018-3812-6.
Sticht, G., & Kaferstein, H. (Sep. 2000). Detection of psilocin in body fluids. Forensic Science International, 113(1-3):403-407. https://doi.org/10.1016/S0379-0738(00)00213-9.
Stojanovic, A. et al. (Mar. 2014). Increased serum interleukin-6 levels in early stages of psychosis: Associations with at-risk mental states and the severity of psychotic symptoms. Psychoneuroendocrinology, 41, 23-32. https://doi.org/10.1016/j.psyneuen.2013.12.005.
Strawbridge, R. et al. (Mar. 2019). Inflammatory profiles of severe treatment-resistant depression. Journal of Affective Disorders, 246:42-51. https://doi.org/10.1016/j.jad.2018.12.037.
Strunk, D.R. et al. (Jun. 2006) Depressive symptoms are associated with unrealistic negative predictions of future life events. Behavior Research and Therapy, 44:861-882.
Studerus, E. et al. (2010) Psychometric evaluation of the altered states of consciousness rating scale (OAV). PLoS One, 5:e12412, 19 pages.
Studerus, E. et al. (2011) “Acute, subacute and long-term subjective effects of psilocybin in healthy humans: a pooled analysis of experimental studies” J Psychopharmacol, 25(11):1434-1452.
Su, H., Lei, C.-T., & Zhang, C. (Apr. 2017). Interleukin-6 Signaling Pathway and Its Role in Kidney Disease: An Update. Frontiers in Immunology, 8:405, https://doi.org/10.3389/fimmu.2017.00405, 10 pages.
Subedi, B. & Grossberg, G.T. (2011) Phantom limb pain: Mechanisms and treatment approaches. Pain Res Treat, 2011:864605, doi: 10.155/2011/864605, 8 pages.
Substance Abuse and Mental Health Services Administration. (Jun. 2016) Table 3.35, DSM-IV to DSM-5 Hypersomnolence Disorder Comparison. In: Impact of the DSM-IV to DSM-5 Changes on the National Survey on Drug Use and Health [Internet]. Rockville (MD): Substance Abuse and Mental Health Services Administration (US). Retrieved from NCBI Bookshelf, https://www.ncbi.nlm.nih.gov/books/NBK519704/table/ch3.t35/, on Jul. 30, 2020, 3 printed pages.
Suda, S. et al. (2011). Decreased expression of axon-guidance receptors in the anterior cingulate cortex in autism. Molecular Autism, 2:14, https://doi.org/10.1186/2040-2392-2-14, 5 pages.
Suto, F. et al. (2005). Plexin-A4 mediates axon-repulsive activities of both secreted and transmembrane semaphorins and plays roles in nerve fiber guidance. Journal of Neuroscience, 25(14):3628-3637. https://doi.org/10.1523/JNEUROSCI.4480-04.2005.
Swieboda, P. et al. (2013) Assessment of pain: types, mechanism and treatment. Ann Agric Environ Med, 1(1):2-7.
Sztainberg, Y. & Zoghbi, H. Y. (2016). Lessons learned from studying syndromic autism spectrum disorders. Nature Neuroscience, 19(11):1408-1418. https://doi.org/10.1038/nn.4420.
Tai, J. et al. (Jan. 2018). Neuroprotective effects of a triple GLP-1/GIP/glucagon receptor agonist in the APP/PS1 transgenic mouse model of Alzheimer’s disease. Brain Research, 1678:64-74. https://doi.org/10.1016/j.brainres.2017.10.012.
Takamori, S. (Feb. 2016). Presynaptic Molecular Determinants of Quantal Size. Frontiers in Synaptic Neuroscience, 8:2, https://doi.org/10.3389/fnsyn.2016.00002, 9 pages.
Tan, L.L. et al. (2019). Gamma oscillations in somatosensory cortex recruit prefrontal and descending serotonergic pathways in aversion and nociception. Nat. Commun. 10:983, https://doi.org/10.1038/s41467-019-08873-z, 17 pages.
Tan, T. et al. (2018). Low-frequency r TMS ameliorates autistic-like behaviors in rats induced by neonatal isolation through regulating the synaptic gaba transmission. Frontiers in Cellular Neuroscience, 12:Article 46, https://doi.org/10.3389/fncel.2018.00046, 12 pages.
Tanaka, T. et al. (Sep. 2014). IL-6 in Inflammation, Immunity, and Disease. Cold Spring Harbor Perspectives in Biology, 6(10):a016295, https://doi.org/10.1101/cshperspect.a016295, 16 pages.
Tarpey, P. et al. (2004). Mutations in the DLG3 gene cause nonsyndromic X-linked mental retardation. American Journal of Human Genetics, 75:318-324. https://doi.org/10.1086/422703.
Tatsumi, M. et al. (Dec. 1997). Pharmacological profile of antidepressants and related compounds at human monoamine transporters. Eur. J. Pharmacol., 340, 249-258. https://doi.org/10.1016/S0014-2999(97)01393-9.
Taylor, J.F. et al. (1994) Self-Report Assessment of Female Sexual Function: Psychometrie Evaluation of the Brief Index of Sexual Functioning for Women. Archives of Sexual Behavior. 23(6):627-643.
Tecott, L. et al. (1995). Eating disorder and epilepsy in mice lacking 5-HT2C serotonin receptors. Nature, 374(6522), pp. 542-546.
Tellegen, A. and Atkinson, G. (1974) Openness To Absorbing and Self-Altering Experiences (“Absorption”), a Trait Related to Hypnotic Susceptibility. Journal of Abnormal Psychology, 83:268-277.
Tennant, R. et al. (2007) The Warrwick-Edinburgh Mental Well-being Scale (WEMWBS): development and the UK validation. Health and Quality of Life Outcomes, 5:63 doi:10.1186/1477-7525-5-63, 14 pages.
Terrando, N. et al. (Nov. 2010). Tumor necrosis factor-a triggers a cytokine cascade yielding postoperative cognitive decline. Proceedings of the National Academy of Sciences, 107(47):20518-20522. https://doi.org/10.1073/pnas.1014557107.
Thamby, A., & Jaisoorya, T. S. (Jan. 2019) “Antipsychotic augmentation in the treatment of obsessive-compulsive disorder” Indian Journal of Psychiatry, 61(7):S51-S57. https://doi.org/10.4103/psychiatry.IndianJPsychiatry_519_18.
Thapar, A. et al. (Nov. 2005). Do depression symptoms predict seizure frequency—or vice versa? Journal of Psychosomatic Research, 59(5):269-274. https://doi.org/10.1016/j.jpsychores.2005.04.001.
Thase, M.E. (1999). Antidepressant treatment of the depressed patient with insomnia. Journal of Clinical Psychiatry, 60(suppl. 17):28-31.
Thomas, A. et al. (2009) “Marble burying reflects a repetitive and perseverative behavior more than novelty-induced anxiety” Psychopharmacology, 204(2):361-373. NIH Public Access Author Manuscript, available in PMC Jul. 8, 2010, 22 pages.
Tokudome, K. et al. (Jun. 2016). Synaptic vesicle glycoprotein 2A (SV2A) regulates kindling epileptogenesis via GABAergic neurotransmission. Scientific Reports, 6(1):27420. https://doi.org/10.1038/srep27420, 12 pages.
Tolba, R. et al. (2018) The opioid epidemic and pain medicine specialists: Where to begin and what is next? Ochsner J, 18(1):20-22.
Toronto Research Chemicals; Certificate of Analysis; Product available for sale (Catalog No. P839650); Test Date: Apr. 5, 2013, 1 page.
Torres, A.R. et al. (Nov. 2006) “Obsessive-compulsive disorder: Prevalence, Comorbidity, impact, and help-seeking in the British National Psychiatric Morbidity Survey of 2000” American Journal of Psychiatry, 163(11):1978-1985. https://doi.org/10.1176/ajp.2006.163.11.1978.
Tramutola, A. et al. (Jun. 2015). Alteration of mTOR signaling occurs early in the progression of Alzheimer disease (AD): analysis of brain from subjects with pre-clinical AD, amnestic mild cognitive impairment and late-stage AD. Journal of Neurochemistry, 133(5), 739-749. https://doi.org/10.1111/jnc.13037.

(56) References Cited

OTHER PUBLICATIONS

Treynor, W. et al. (Jun. 2003) Rumination Reconsidered: A Psychometric Analysis. Cognitive Therapy and Research, 27:247-259.
Trulson, M. E., Stark, A. D., & Jacobs, B. L. (Jul. 1977). Comparative effects of hallucinogenic drugs on rotational behavior in rats with unilateral 6-hydroxydopamine lesions. European Journal of Pharmacology, 44(2), 113-119. https://doi.org/10.1016/0014-2999(77)90097-8.
Trunko, M.E. et al. (Apr. 2011). Aripiprazole in anorexia nervosa and low-weight bulimia nervosa: Case reports. International Journal of Eating Disorders, 44(3):269-275. https://doi.org/10.1002/eat.20807.
Tsai, S.-J. (Oct. 2017). Effects of interleukin-1beta polymorphisms on brain function and behavior in healthy and psychiatric disease conditions. Cytokine & Growth Factor Reviews, 37:89-97. https://doi.org/10.1016/j.cytogfr.2017.06.001.
Tucha, L. et al. (Feb. 2017) Sustained attention in adult ADHD: time-on-task effects of various measures of attention. J Neural Transm, 124(Suppl. 1):S39-S53.
Tully, P.J. et al. (2016). Anxiety and Cardiovascular Disease Risk: a Review. Curr. Cardiol. Rep., 18:120, https://doi.org/10.1007/s11886-016-0800-3, 8 pages.
Tully, P.J. et al. (Dec. 2014). The anxious heart in whose mind? A systematic review and meta-regression of factors associated with anxiety disorder diagnosis, treatment and morbidity risk in coronary heart disease. J. Psychosom. Res., 77:439-448. https://doi.org/10.1016/j.jpsychores.2014.10.001.
Tumolo, J. (Sep. 2018) "Uncovering the Therapeutic Potential of Psychedelics" Retrieved from Psychiatry & Behavioral Health Learning Network [online]. Retrieved from: https://www.hmpgloballearningnetwork.com/site/pcn/article/uncovering-therapeutic-potential-psychedelics, 8 pages.
Tyrer, P. and Baldwin, D. (2006). Generalised anxiety disorder. Lancet, 368:2156-2166. https://doi.org/10.1016/S0140-6736(06)69865-6.
Ulfvebrand, S. et al. (Sep. 2015). Psychiatric comorbidity in women and men with eating disorders results from a large clinical database. Psychiatry Research, 230(2), 294-299. https://doi.org/10.1016/j.psychres.2015.09.008.
Unruh, K. E., Bodfish, J. W., & Gotham, K. O. (2018). Adults with Autism and Adults with Depression Show Similar Attentional Biases to Social-Affective Images. Journal of Autism and Developmental Disorders, 50:2336-2347. https://doi.org/10.1007/s10803-018-3627-5.
U.S. Appl. No. 16/155,386: Third Party Observations with Concise Description of Relevance, filed Jul. 26, 2019, 22 pages.
U.S. Appl. No. 16/155,386: Third Party Observations with Concise Description of Relevance, filed May 23, 2019, 27 pages.
U.S. Appl. No. 16/155,386: Third Party Observations with Concise Description of Relevance, filed May 28, 2019, 31 pages.
U.S. Appl. No. 17/604,610: Third Party Pre-Issuance Submission Under 37 C.F.R. 1.290 with Concise Description of Relevance, filed Mar. 9, 2022, 128 pages.
Uyeno, E.T. (Mar. 1967). Effects of mescaline and psilocybin on dominance behavior of the rat. Archives Internationales de Pharmacodynamie et de Therapie, 166(1), 60-64. http://www.ncbi.nlm.nih.gov/pubmed/6034329.
Valbrun, L. and Zvonarev, V. (Dec. 2020). The Opioid System and Food Intake: Use of Opiate Antagonists in Treatment of Binge Eating Disorder and Abnormal Eating Behavior. Journal of Clinical Medicine Research, 12(2), pp. 41-63.
Van Ameringen, M. et al. (Mar. 2014) "DSM-5 obsessive-compulsive and related disorders: Clinical implications of new criteria" Depression and Anxiety, 31(6):487-493. https://doi.org/10.1002/da.22259.
Van Den Beuken-Van Everdingen, M.H.J. et al. (Jun. 2006) Update on Prevalence of Pain in Patients with Cancer: Systematic Review and Meta-Analysis. Journal of Pain and Symptom Management. 51(6):1070-1090, with Appendix I, 1090:e1-e9.
Van Hecke, A.V. et al. (2013). Measuring the Plasticity of Social Approach: A Randomized Controlled Trial of the Effects of the PEERS Intervention on EEG Asymmetry in Adolescents with Autism Spectrum Disorders. J. Autism Dev. Disord., 45(2):316-335. https://doi.org/10.1007/s10803-013-1883-y.
Van Spijker, B.A.J et al. (2014) The Suicidal Ideation Attributes Scale (SIDAS): Community-Based Validation Study of a New Scale for the Measurement of Suicidal Ideation. Suicide and Life-Threatening Behavior, 44(4):408-419.
Varga, Z. et al. (2017). Cardiovascular Risk of Nonsteroidal Anti-Inflammatory Drugs: An Under-Recognized Public Health Issue. Cureus, 9(4): e1144, https://doi.org/10.7759/cureus.1144, 12 pages.
Vaupel, D. et al. (Jun. 1979). The inhibition of food intake in the dog by LSD, mescaline, psilocin, -amphetamine and phenylisopropylamine derivatives. Life Sciences, 24(26), pp. 2427-2431.
Veale, D. et al. (Nov. 2014) "Atypical antipsychotic augmentation in SSRI treatment refractory obsessive-compulsive disorder: A systematic review and meta-analysis" BMC Psychiatry, 14(1):317, https://doi.org/10.1186/s12888-014-0317-5, 13 pages.
Velikonja, T., Fett , A. K., & Velthorst, E. (2019). Patterns of Nonsocial and Social Cognitive Functioning in Adults with Autism Spectrum Disorder: A Systematic Review and Meta-analysis. JAMA Psychiatry, 76(2):135-151. https://doi.org/10.1001/jamapsychiatry.2018.3645.
Venlafaxine Hydrochloride (Sep. 2, 20203). Drugs.com (online). Retrieved from: https://www.drugs.com/monograph/venlafaxine-hydrochloride.html, 19 printed pages.
Verbeeck, W. et al. (Oct. 2017). Bupropion for attention deficit hyperactivity disorder (ADHD) in adults. Cochrane Database of Systematic Reviews, 2017, Issue 10, Art. No. CD009504, DOI: 10.1002/14651858.CD009504.pub2, 58 pages.
Vinik, A. et al. Diabetic Neuropathies. Table 7, Drugs Approved by the FDA for Treatment of Neuropathic Pain Syndromes. [Updated Feb. 5, 2018]. In: Feingold, K.R., Anawalt, B., Boyce, A. et al., editors. Endotext [Internet]. South Dartmouth (MA): MDText.com, Inc.; 2000-. Retrieved from: https://www.ncbi.nlm.nih.gov/books/NBK279175/table/diab-neuropathies.medication/, retrieved on Jul. 30, 2020, 2 printed pages.
Volkow, N.D. et al. (Aug. 2007) Depressed dopamine activity in caudate and preliminary evidence of limbic involvement in adults with attention-deficit/hyperactivity disorder. Arch Gen Psychiatry, 64(8):932-940.
Volkow, N.D. et al. (Feb. 1, 2007) Brain dopamine transporter levels in treatment and drug naïve adults with ADHD. Neuroimage [Internet]. 34(3):1182-90. Available from: http://www.ncbi.nlm.nih.gov/pubmed/17126039.
Vollenweider, F. (Jul. 1998) Advances and Pathophysiological Models of Hallucinogenic Drug Actions in Humans: A Preamble to Schizophrenia Research. Pharmacopsychiatry, 31(Suppl):92-103. https://doi.org/10.1055/s-2007-979353.
Vollenweider, F.X. et al. (Sep. 2007) The effects of the preferential 5-HT2A agonist psilocybin on prepulse inhibition of startle in healthy human volunteers depend on interstimulus interval. Neuropsychopharmacology, 32(9):1876-1887.
Vollenweider, F.X. et al. (May 1999). 5-HT modulation of dopamine release in basal ganglia in psilocybin-induced psychosis in man—a PET study with [$^{11}$C]raclopride. Neuropsychopharmacology, 20(5):424-433. https://doi.org/10.1016/S0893-133X(98)00108-0.
Von Bernhardi, R. et al. (Oct. 2, 20158). Role of TGFβ signaling in the pathogenesis of Alzheimer's disease. Frontiers in Cellular Neuroscience, 9:426, https://doi.org/10.3389/fncel.2015.00426, 21 pages.
Voon, P. et al. (2017). Chronic pain and opioid misuse: a review of reviews. Substance Abuse Treatment, Prevention and Policy, 12:36, DOI 10.1186/s13011-017-0120-7, 9 pages.
Vossler, D.G. (Oct. 2016). Antiepileptic drugs. Are generics as effective as brand name? Neurology, 87(17):e211-e214. https://doi.org/10.1212/WNL.0000000000003323.
Wade, A.G. et al. (Jan. 2011). Prolonged release melatonin in the treatment of primary insomnia: Evaluation of the age cut-off for short- and long-term response. Curr. Med. Res. Opin., 27:87-98. https://doi.org/10.1185/03007995.2010.537317.

(56) References Cited

OTHER PUBLICATIONS

Wagner, J. and Wagner, M.L. (2000). Non-benzodiazepines for the treatment of insomnia. Sleep Med. Rev., 4(6):551-581. https://doi.org/10.1053/smrv.2000.0126.
Wahlberg (2015) "UW-Madison tunes in to 'magic mushroom' medicine" Oct. 11, 2015; retrieved from Web Archive, https://web.archive.org/web/20181214181711/https://madison.com/wsi/news/local/health-med-fit/uw-madison-tunes-in-to-magic-mushroom-medicine/article5c229322-I 132-5328-90cl-017e917f0696.html, retrieved Dec. 14, 2018, 1 page.
Walia, K.S et al. (Sep. 2004) Side Effects of Antiepileptics—A Review. Pain Pract, (3):194-203.
Walsh, B.T. et al. (Jun. 2006). Fluoxetine after weight restoration in anorexia nervosa: A randomized controlled trial. Journal of the American Medical Association, 295(22):2605-2612. https://doi.org/10.1001/jama.295.22.2605.
Wang, G. et al. (2017). Resveratrol mitigates lipopolysaccharide-mediated acute inflammation in rats by inhibiting the TLR4/NF-κBp65/MAPKs signaling cascade. Scientific Reports, 7:45006, https://doi.org/10.1038/srep45006, 13 pages.
Wang, J. et al. (2016). Enhanced Gamma oscillatory activity in rats with chronic inflammatory pain. Front. Neurosci. 10:489, https://doi.org/10.3389/fnins.2016.00489, 8 pages.
Wang, L. et al. (Sep. 2003). IL-6 Induces NF-κB Activation in the Intestinal Epithelia. The Journal of Immunology, 171(6):3194-3201. https://doi.org/10.4049/jimmunol.171.6.3194.
Wang, Q. et al. (May 2018). CDK5-Mediated Phosphorylation-Dependent Ubiquitination and Degradation of E3 Ubiquitin Ligases GP78 Accelerates Neuronal Death in Parkinson's Disease. Molecular Neurobiology, 55(5):3709-3717. https://doi.org/10.1007/s12035-017-0579-2.
Wang, X. et al. (2018). Gastrodin Rescues Autistic-Like Phenotypes in Valproic Acid- Induced Animal Model. Frontiers in Neurology, 9:1052, https://doi.org/10.3389/fneur.2018.01052, 10 pages.
Wang, Z.-J. et al. (Feb. 2020). A dual GLP-1 and Gcg receptor agonist rescues spatial memory and synaptic plasticity in APP/PS1 transgenic mice. Hormones and Behavior, 118:104640. https://doi.org/10.1016/j.yhbeh.2019.104640, 9 pages.
Washburn, J.J. et al. (Apr. 2007) Development of Antisocial Personality Disorder in Detained Youth: The Predictive Value of Mental Disorders. J Consult Clin Psychol, 75(2):221-231. NIH Public Access Author Manuscript, 20 pages.
Watson, J. et al. (Jul. 2019). Use of multiple inflammatory marker tests in primary care: using Clinical Practice Research Datalink to evaluate accuracy. British Journal of General Practice, 69(684), e462-e469. https://doi.org/10.3399/bjgp19X704309.
Weber, A. et al. (2010). Interleukin-1 (IL-1) Pathway. Science Signaling, 3(105):cm1, https://doi.org/10.1126/scisignal.3105cm1, 7 pages.
Weber, H.P., et al. (1974) "Crystal structures of the teonanacatl hallucinogens. Part 1. Psilocybin C12HI7N204P" J Chem Soc, Perkin Trans, 2:942-946.
Wegner, D.M. and Zanakos, S. (1994) Chronic Thought Suppression. Journal of Personality, 62:615-640.
Wei, D. Y-T. et al. (2018) Cluster headache: Epidemiology, pathophysiology, clinical features, and diagnosis. Annals of Indian Academy of Neurology, 21(5):3-8.
Weissman, A.N. (1979) The Dysfunctional Attitude Scale: A validation study. [Dissertation in Education, Doctor of Philosophy]. University of Pennsylvania. Publicly Accessible Penn Dissertations. 1182. https://repository.upenn.edu/edissertations/1185, 209 pages.
Welch, E. et al. (2016). Treatment-seeking patients with binge-eating disorder in the Swedish national registers: clinical course and psychiatric comorbidity. BMC Psychiatry, 16:163, doi: 10.1186/s12888-016-0840-7, 8 pages.
Werner, K.B. et al. (Apr. 2015) Epidemiology, comorbidity, and behavioral genetics of antisocial personality disorder and psychopathy. Psychiatr Ann. 45(4):195-199. HHS Public Access Author Manuscript, 8 pages.
Westmoreland, P. et al. (Jul. 2016). Medical Complications of Anorexia Nervosa and Bulimia. The American Journal of Medicine, 129:30-37.
White, H. K., & Levin, E. D. (Apr. 1999). Four-week nicotine skin patch treatment effects on cognitive performance in Alzheimer's disease. Psychopharmacology, 143(2):158-165. https://doi.org/10.1007/s002130050931.
Whitfield, D.R. et al. (Dec. 2014). Assessment of ZnT3 and PSD95 protein levels in Lewy body dementias and Alzheimer's disease: association with cognitive impairment. Neurobiology of Aging, 35(12):2836-2844. https://doi.org/10.1016/j.neurobiolaging.2014.06.015.
Whyatt, C., & Craig, C. (Jul. 1, 20138). Sensory-motor problems in autism. Frontiers in Integrative Neuroscience. 7:51, https://doi.org/10.3389/fnint.2013.00051, 12 pages.
Wiedemann, K. et al. (2001). Anxiolyticlike effects of atrial natriuretic peptide on cholecystokinin tetrapeptide-induced panic attacks. Preliminary findings. Archives of General Psychiatry, 58:371-377. https://doi.org/10.1001/archpsyc.58.4.371.
Wilcox, J.A. (Nov. 2014) "Psilocybin and obsessive compulsive disorder" Journal of Psychoactive Drugs, 46(5):393-395: DOI: 10.1080/02791072.2014.963754.
Wilens, T.E. et al. (Oct. 2011) An update on the pharmacotherapy of attention-deficit/hyperactivity disorder in adults. Expert Rev Neurother, 11(10):1443-1465. NIH Public Access Author Manuscript; available in PMC Aug. 1, 2012, 34 pages.
Williams, J.M.G. et al. (1986) Autobiographical Memory in Suicide Attempters. Journal of Abnormal Psychology, 95:144-149.
Williams, K. et al. (2013). Selective serotonin reuptake inhibitors (SSRIs) for autism spectrum disorders (ASD). Cochrane Database of Systematic Reviews, 8:CD004677, https://doi.org/10.1002/14651858.CD004677.pub3, 46 pages.
Willoughby, J.O. et al. (2003). Persistent abnormality detected in the non-ictal electroencephalogram in primary generalised epilepsy. J. Neurol. Neurosurg. Psychiatry, 74:51-55. https://doi.org/10.1136/jnnp.74.1.51.
Wilson, S. et al. (Jul. 2017) Interpersonal dysfunction in personality disorders: A meta-analytic review. Psychol Bull, 143(7):677-734. HHS Public Access Author Manuscript, 120 pages.
Wingo A, Ghaemi S. (Nov. 2007) A systematic review of rates and diagnostic validity of comorbid adult attention-deficit/hyperactivity disorder and bipolar disorder. J Clin Psychiatry, 68(11):1775-1784.
Winkelman, J.W. et al. (Sep. 2011). Randomized polysomnography study of gabapentin enacarbil in subjects with restless legs syndrome. Mov. Disord., 26:2065-2072. https://doi.org/10.1002/mds.23771.
Winter, J.C. et al. (2007). Psilocybin-induced stimulus control in the rat. Pharmacology Biochemistry and Behavior, 87(4):472-480. NIH Public Access Author Manuscript; available in PMC Oct. 3, 2007, 18 pages.
Witkin, J.M. (Oct. 2008) "Animal models of obsessive-compulsive disorder" Current Protocols in Neuroscience. 45:9.30.1-9.30.9. DOI: 10.1002/0471142301.ns0930s45.
Wong, M. et al. (Feb. 2008). TNFα blockade in human diseases: Mechanisms and future directions. Clinical Immunology, 126(2):121-136. https://doi.org/10.1016/j.clim.2007.08.013.
World Health Organization (WHO) (2015). International statistical classification of diseases and related health problems (ICD-10), 10th revision, Fifth edition. vol. 1, Tabular List. Geneva, Switzerland: WHO Press, www.who.int; 1076 pages.
World Health Organization (WHO) (2019). Risk reduction of cognitive decline and dementia—WHO Guidelines. Foreward and Executive Summary, pp. 3-11.
World Health Organization (WHO) (Sep. 19, 2019). Dementia. Retrieved from https://www.who.int/news-room/fact-sheets/detail/dementia, 5 pages.
Worrell, G.A. et al. (Jul. 2004). High-frequency oscillations and seizure generation in neocortical epilepsy. Brain 127, 1496-1506. https://doi.org/10.1093/brain/awh149.
Wu, H. et al. (Sep. 2016). Field potential oscillations in the bed nucleus of the Stria terminalis correlate with compulsion in a rat model of obsessive-compulsive disorder. J. Neurosci. 36, 10050-10059.

(56) References Cited

OTHER PUBLICATIONS

Wultsch, T. et al. (2007) "Behavioural and expressional phenotyping of nitric oxide synthase-I knockdown animals" Journal of Neural Transmission, (Suppl 72):69-85. https://doi.org/10.1007/978-3-211-73574-9_10.
Xie, Z. et al. (May 2017). A review of sleep disorders and melatonin. Neurol. Res., 39:559-565. https://doi.org/10.1080/01616412.2017.1315864.
Xu, C. et al. ( Mar. 2019). Integrative analysis of shared genetic pathogenesis by obsessive-compulsive and eating disorders. Molecular Medicine Reports, 19(3):1761-1766. https://doi.org/10.3892/mmr.2018.9772.
Xu, P. et al. (Jun. 2016). Activation of serotonin 2C receptors in dopamine neurons inhibits binge-like eating in mice. Biological Psychiatry, 81, 737-747.
Yang, S. et al. (Apr. 19, 2018). Role of TNF-TNF Receptor 2 Signal in Regulatory T Cells and Its Therapeutic Implications. Frontiers in Immunology, 9:784, https://doi.org/10.3389/fimmu.2018.00784, 11 pages.
Yilmaz, Z. et al. (Mar. 2015). Genetics and epigenetics of eating disorders. Advances in Genomics and Genetics, 5:131-150. HHS Public Access Author Manuscript, 36 pages.
Ypsilantis, E. and Tang, T.Y. (2010) Pre-emptive analgesia for chronic limb pain after amputation for peripheral vascular disease: A systematic review. Annals of Vascular Surgery, 24:1139-1146.
Yu, B. et al. (Nov. 2008). Serotonin 5-hydroxytryptamineza receptor activation suppresses tumor necrosis factor-alpha-induced inflammation with extraordinary potency. The Journal of Pharmacology and Experimental Therapeutics, 327(2):316-323.
Zammit, G. et al. (2007). Evaluation of the efficacy and safety of ramelteon in subjects with chronic insomnia. J. Clin. Sleep Med., 3:495-504. https://doi.org/10.5664/jcsm.26914.
Zetner, M. et al. (2008) Emotions evoked by the sound of music: Characterization, classification, and measurement. Emotion. 8:494-521.
Zhai, H. et al. (Dec. 2019). Baicalin attenuated substantia nigra neuronal apoptosis in Parkinson's disease rats via the mTOR/AKT/GSK-3β pathway. Journal of Integrative Neuroscience, 18(4), 423-429. https://doi.org/10.31083/j.jin.2019.04.192.
Zhang, J.-M., & An, J. (2007). Cytokines, Inflammation and Pain. Int Anesthesiol Clin., 69(2):482-489. NIH Public Access Author Manuscript, available in PMC Nov. 30, 2009, 10 pages.
Zhou, R. et al. (2018). Elevated Resting State Gamma Oscillatory Activities in Electroencephalogram of Patients With Post-herpetic Neuralgia. Front. Neurosci. 12, 750, 10 pages. https://doi.org/10.3389/fnins.2018.00750.
Zhou, Y. et al. (2017). Comorbid generalized anxiety disorder and its association with quality of life in patients with major depressive disorder. Sci. Rep. 7:40511, https://doi.org/10.1038/srep40511, 8 pages.
Zipfel, S. et al. (Dec. 2015). Anorexia nervosa: Aetiology, assessment, and treatment. The Lancet Psychiatry, vol. 2, Issue 12, pp. 1099-1111. https://doi.org/10.1016/S2215-0366(15)00356-9.
Zulauf, C.A. et al. (Mar. 2014). The complicated relationship between attention deficit/hyperactivity disorder and substance use disorders. Curr Psychiatry Rep, 16(3):436; doi:10.1007/s11920-013-0436-6. HHS Public Access Author Manuscript; available in PMC Apr. 29, 2015, 17 pages.
Jendrzejewska I. et al., "Application of X-ray powder diffraction and differential scanning calorimetry for identification of counterfeit drugs," Monatsh Chem. vol. 149(5): 977-985. (2018).
Registry No. 1026609-93-7, File REGISTRY on STN, entered STN Jun. 8, 2008, 3 pages.
US Third Party submission by Sisi Li for U.S. Appl. No. 18/285,109, filed Oct. 31, 2024, 89 pages.
Cleveland Clinic: "Bipolar Disorder" [Online]. Published on Apr. 12, 2022. Retrieved from Internet on Jun. 13, 2025. URL: https://my.clevelandclinic.org/health/diseases/9294-bipolar-disorder, 16 pages on (Year: 2022).
Davis et al., "Effects of psilocybin-assisted therapy on major depressive disorder: a randomized clinical trial," JAMA Psychiatry 78(5):481-489 (2021). doi: 10.1001/jamapsychiatry.2020.3285. Erratum in: JAMA Psychiatry. Feb. 10, 2021:569. doi: 10.1001/jamapsychiatry.2020.4714. (52 total pages).
Lyons, "More Realistic Forecasting of Future Life Events After Psilocybin for Treatment-Resistant Depression" Frontiers in Psychology, vol. 9(1721):1-11 (2018).
Naulls, S. and Bunn, S., "Psychedelic drugs to treat post-traumatic stress disorder (PTSD)," UK Parliament [online], Published Monday Apr. 22, 2024, 11 pages. Available from: https://post.parliament.uk/psychedelic-drugs-to-treat-post-traumatic-stress-disorder-ptsd/ [Accessed Jun. 18, 2025 ).
Wikberg, "Comparison Between the Montgomery-Asberg Depression Rating Scale- Self (MADRS-S) and the Beck Depression Inventory II (BDI-11) in Primary Care" The Primary Care Companion for CNS Disorders, 17(3):1-6 (2015).
Ziani et al., "Drug repurposing and personalized treatment strategies for bipolar disorder using transcriptomics: an exploratory study". Braz J Psychiatry, 2024. vol. 46, 9 pages (2024).
Co-pending U.S. Appl. No. 18/703,950, inventor Mill; Trevor Anthony, filed Apr. 23, 2024.
Co-pending U.S. Appl. No. 18/718,103, inventors Londesbrough; Derek John et al., filed Jun. 10, 2024.
Hilfiker, Polymorhism: In the Pharmaceutical Industry. WILEY-VCH Vrlag GmbH & Co. KGaA, Weinheim. (2.7 Crystallization of Polymorphs; 8.3 Statistical Aspects and Frequency of Solvates, 18 pages (2016). retrieved at https://onlinelibrary.wiley.com/doi/epdf/10.1002/3527607889.fmatter.
Saigal N., et al., "Microcrystalline Cellulose as a Versatile Excipient in Drug Research," Journal of Young Pharmacists, 2009, vol. 1, pp. 6-12.
Author Unknown, "Advanced Certificate in Powder Diffraction on the Web—'Bragg's Law,'" [web.archive.org] (Mar. 6, 2016), [Retrieved from Internet on Oct. 22, 2025 at URL: https://web.archive.org/web/20160306112519/ http:/pd.chem.ucl.ac.uk/pdnn/powintro/braggs.htm], 2 pages.
Author Unknown, "Bragg's Law," [web.archive.org] (Jan. 22, 2016), [Retrieved from Internet on Oct. 22, 2025 at URL: https://web.archive.org/web/20160122192959/https:/en.wikipedia.org/wiki/Bragg's_law] , 7 pages.
Author Unknown, Wikipedia, "Excipient." [web.archive.org] (Web capture date: Dec. 16, 2016). [Retrieved from Internet on Nov. 5, 2025 at URL: https://web.archive.org/web/20161216043440/https://en.wikipedia.org/ wiki/Excipient]; 6 pages.
Berger K.J., et al., "Mycotoxins Revisited: Part II," The Journal of Emergency Medicine, vol. 28, No. 2, pp. 175-183, (Feb. 2005).
Collett J.H., et al., "Dosage Regimens," Aultons Pharmaceutics The Design and Manufacture of Medicines, [basicmedicalkey.com] (Jun. 2, 2016) [Retrieved online at URL: https://basicmedicalkey.com/dosage-regimens/#S0080 (Retrieval Date Unknown]; 7 pages.
Higuchi, T. , "Practice guideline for the treatment of mood disorders," The Japanese journal of clinical medicine 65(9):1627-1632 (Year: 2007) (includes English machine translation, 12 pages total).
Jha M.K., et al., "When Discontinuing SSRI Antidepressants Is a Challenge: Management Tips," American Jn of Psychiatry, Dec. 2018, vol. 175 (12), pp. 1176-1184.
Johnson, M.W. et al., "The abuse potential of medical psilocybin according to the 8 factors of the Controlled Substances Act," Neuropharmacology 142: 143-166 (May 9, 2018). Epub Jun. 5, 2018.
Keks et al. "Switching and stopping antidepressants." Australian Prescriber. Jun. 2016;39(3):76-83. doi: 10.18773/austprescr.2016.039.
Li, Nan-Xi et al., "Dose effect of psilocybin on primary and secondary depression: a preliminary systematic review and meta-analysis," Journal of Affective Disorders 296:26-34 (Jan. 2022).
Mayoclinic., "Selective Serotonin Reuptake Inhibitors (SSRIs)," The Wayback Machine (Oct. 18, 2020); [Retrieved online at URL: [https://web.archive.org/web/20201018173546/https://www.mayoclinic.org/diseases-conditions/depression/in-depth/ssris/art-20044825 (Retreival Date Unknown]; 4 pages.

(56) References Cited

OTHER PUBLICATIONS

Muttoni et al. "Classical psychedelics for the treatment of depression and anxiety: A systematic review." Journal of Affective Disorders. Nov. 2019;258:11-24. doi: 10.1016/j.jad.2019.07.076.
Nutt D., "Psychedelic Drugs a New Era In Psychiatry?," Dialogues in Clinical Neuroscience, 2019, vol. 21 (2), 10 Pages (Jun. 2019).
Okajima, Yuka and Kunitoshl Kamijima, "Starting and stopping pharmacotherapy of depression," Journal of clinical and experimental medicine 219(13):949-953 (month unknown) (2006). (includes English machine translation, 10 total pages).
O'Neil, Maryadele J. et al., Eds., The Merck Index—An Encyclopedia of Chemicals, Drugs, and Biologicals. 13th Edition, Whitehouse Station, NJ: Merck and Co., Inc., p. 1419, 2 p. total (month unknown) (2001).
Gotvaldova, Stability of psilocybin and its four analogs in the biomass of the psychotropic mushroom Psilocybe cubensis, vol. 13, issue 2, pp. 439-446, 2021, Drug Testing and Analysis.†

* cited by examiner
† cited by third party

Psilocybin

$C_{12}H_{17}N_2O_4P$

Exact Mass: 284.09

Mol. Wt.: 284.25

CB646 -TOP- MIXED PHASE; JCCA2160-F- MIDDLE PATTERN A'; JCCA2160-F-TM2- BOTTOM PATTERN B

PSILOCYBIN COMPOSITIONS, METHODS OF MAKING AND METHODS OF USING THE SAME

CROSS-REFERENCE TO RELATED APPLICATIONS

The present application is a National Stage Entry of International Patent Application No. PCT/EP2022/058483, filed Mar. 30, 2022, titled "Psilocybin Compositions, Methods of Making and Methods of Using the Same," which claims the benefit of priority to and benefit of U.S. Provisional Application Ser. No. 63/168,055, filed Mar. 30, 2021, the contents of which each are hereby incorporated by reference in their entirety.

BACKGROUND

Psilocybin belongs to a class of drugs referred to psychedelics ("mind-manifesting" drugs). Specifically, psilocybin is considered a 5-hydroxytryptaminergic (serotonergic) psychedelic, as distinguished from other tryptamines such as dimethyltryptamine (DMT), ergolines such as lysergic acid diethylamide (LSD), and phenethylamines such as mescaline. Psilocybin was first isolated from psilocybe mushrooms and later synthesized in a laboratory.

Provided the potential therapeutic applications, there is a need in the art for pharmaceutical compositions of psilocybin that meet regulatory criteria for approved drug products (e.g., stable during product storage and acceptable content uniformity).

SUMMARY

Psilocybin is a challenging active pharmaceutical ingredient (API) to formulate because of its physical characteristics and potential chemical instability (e.g., facile hydrolysis to psilocin). Crystalline psilocybin is an acicular, rod-like crystal with a high aspect ratio and, as such, has poor flow properties (particularly hydrate forms), which are undesirable for direct mixing formulation scale-up and commercial manufacturing. Also, during pharmaceutical development (see Example 1), Applicant discovered that solid dosage forms containing certain, commonly-used silica-containing excipients provided non-ideal results upon storage of the drug product under ICH stability testing conditions (e.g., drug product discolouration and a loss of potency without a commensurate increase psilocybin related substance impurities). Finally, given the psychedelic properties of psilocybin, it should be administered as a low dose drug (e.g., 1 mg of psilocybin may be used for some indications). Accordingly, a suitable formulation must allow accommodation of low API loadings, but provide pharmaceutically acceptable content uniformity (as measured by European Pharmacopeia 2.96. or USP <905>).

The present disclosure relates to pharmaceutical compositions containing psilocybin and methods of preparing the same.

In one aspect, the present disclosure provides a pharmaceutical composition comprising: a therapeutically effective amount of psilocybin; and one or more pharmaceutically acceptable excipients, wherein potency of the psilocybin in the composition and the mass balance of psilocybin and related substances in the composition remains at industry and pharmaceutically acceptable levels (e.g., European Pharmacopeia, USP) under industry and pharmaceutically acceptable storage conditions (e.g., European Pharmacopeia, USP) and the psilocybin is provided in pharmaceutically acceptable content uniformity (as measured by European Pharmacopeia 2.96. or USP <905>).

In one aspect, the present disclosure provides a pharmaceutical composition comprising: a therapeutically effective amount of psilocybin; and one or more pharmaceutically acceptable excipients, wherein, after storage of the composition at 40° C. and 75% relative humidity for one month, the potency of the psilocybin in the composition decreases by less than 5% and the mass balance of psilocybin and related substances is greater than 97%.

In one aspect, the present disclosure provides a method of making a pharmaceutical composition comprising: (a) direct mixing psilocybin and one or more pharmaceutically acceptable excipients to provide a blend and (b) filling a capsule with the blend to provide the pharmaceutical composition, wherein the content uniformity of the composition complies with the European Pharmacopeia 2.96. or USP <905>.

DETAILED DESCRIPTION

Definitions

Figure 1:
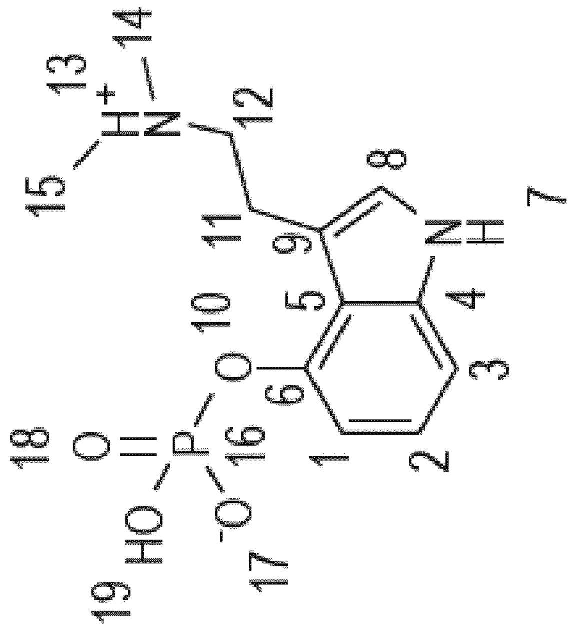
FIG. 1 is a numbered structural formula of psilocybin.

Throughout this disclosure, various patents, patent applications and publications (including non-patent publications) are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "mass balance of psilocybin and related substances" as used herein means the sum of psilocybin and its related substances (i.e., psilocin and unidentified impurities defined by their relative retention times (RRT)) as determined by HPLC analysis. In some embodiments, the mass balance is determined on a weight % basis. In some embodiments, the unidentified impurities defined by their relative retention times are selected from the group consisting of about RRT 0.85, about RRT 1.25, about RRT 1.38, about RRT 1.44, and about RRT 1.51 as determined using the Related Substance HPLC Method. The following HPLC conditions ("Related Substance HPLC Method") may be used to determine the mass balance of psilocybin and related substances of the composition of the present disclosure:

| | | | |
|---|---|---|---|
| Column | Waters Xbridge C18, 3.5 μm, 4.6 × 150 mm | | |
| Column Temperature | 30° C. | | |
| Flow Rate | 1.0 mL/min | | |
| Wavelength (UV) | 267 nm | | |
| Injection Volume | 20 μL | | |
| Run Time | 27 minutes | | |
| Mobile Phase A | Water:Methanol:TFA - 95:5:0.1 | | |
| Mobile Phase B | Methanol:Water:TFA - 95:5:0.1 | | |
| Preparation of diluent | Water:Methanol - 95:5 | | |
| Gradient (% v/v) | Time (mins) | % A | % B |
| | 0 | 100 | 0 |
| | 2 | 100 | 0 |
| | 15 | 0 | 100 |
| | 20 | 0 | 100 |
| | 20.1 | 100 | 0 |
| | 27 | 100 | 0 |

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of psilocybin is that amount that is required to reduce at least one symptom of depression in a patient. The actual amount that comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

As used herein, "substantially absent" with reference to XRPD diffractogram peak means the peak has a relative intensity compared to a reference peak present in the diffractogram of less than about 5%, less than about 4%, less than about 3%, less than about 2%, or less than about 1% of the intensity of the reference peak, or that the peak is not detectable.

As used herein the term "subject" and "patient" are used interchangeably.

The term "treating" as used herein with regard to a patient, refers to improving at least one symptom of the patient's disorder. Treating can be improving, or at least partially ameliorating a disorder.

The term "therapeutic effect" as used herein refers to a desired or beneficial effect provided by the method and/or the composition. For example, the method for treating depression provides a therapeutic effect when the method reduces at least one symptom of depression in a patient.

XRPD diffractograms and XRPD peak positions may be acquired using Cu Kα radiation.

DSC thermograms and TGA thermograms may be acquired using a heating rate of 20° C./min.

All disease and disorders listed herein are defined as described in the Diagnostic and Statistical Manual of Mental Disorders (DSM-5), published by the American Psychiatric Association, or in International Classification of Diseases (ICD), published by the World Health Organization.

As used herein, the following Medical Dictionary for Regulatory Activities (MedDRA) terms are considered to be adverse events that are psychedelic in nature: altered mood, altered state of consciousness, autoscopy, delusional perception, disinhibition, dissociation, dissociative identity disorder, dreamy state, emotional disorder, euphoric mood, feeling abnormal, hallucination, hyperacusis, hyperaesthesia, hypoaesthesia, illusion, paranoia, parosmia, photophobia, sensory disturbance, time perception altered, thinking abnormal, synaesthesia, substance-induced psychotic distress, and somatic hallucination.

The following abbreviations have been used herein:

DSC—Differential Scanning Calorimetry
RT—room temperature
TBME—methyl tert-butyl ether
TGA—Thermogravimetric Analysis
THF—tetrahydrofuran
RRT—relative retention time
wrt—with respect to
XRPD—X-Ray Powder Diffraction

Crystalline Forms of Psilocybin

The pharmaceutical compositions of the present disclosure can include one or more of the crystalline psilocybins disclosed in U.S. Pat. No. 10,519,175, which is herein incorporated by reference in its entirety for all purposes.

Polymorph A

In some embodiments, the present disclosure provides pharmaceutical compositions wherein the psilocybin is crystalline Polymorph A (or "Polymorph A").

According to the present disclosure, the psilocybin used is of a pharmaceutically acceptable chemical purity. In some embodiments, the psilocybin used is of a pharmaceutically acceptable chemical purity and is amorphous. In some embodiments, the psilocybin used is of a pharmaceutically acceptable chemical purity and is crystalline. In some embodiments, the psilocybin used is of a pharmaceutically acceptable chemical purity and is crystalline Polymorph A.

In some embodiments, the crystalline psilocybin is characterized by one or more of:

(a) peaks in an XRPD diffractogram at 11.5, 12.0 and 14.5°2θ±0.1°2θ; and/or (b) an endothermic event in a DSC thermogram having a first onset temperature of between 145° C. and 165° C. and a second onset temperature of between 205° C. and 220° C.

In some embodiments, the crystalline psilocybin is further characterized by at least one further peak at 19.7, 20.4, 22.2, 24.3 or 25.7°2θ±0.1°2θ.

In some embodiments, the crystalline psilocybin is characterized by having either: (a) a water content of <0.5% w/w; or (b) <0.5% w/w loss in the TGA thermogram between 25° C. and 200° C.

In some embodiments, the psilocybin has a chemical purity of greater than 97% and no single impurity greater than 1% as determined by HPLC analysis. In some embodiments, the psilocybin has a chemical purity of greater than 97% by HPLC, and no single impurity of greater than 1% including phosphoric acid as measured by $^{31}P$ NMR, and psilocin as determined by HPLC.

In some embodiments, the phosphoric acid impurity, and any other impurity that might be present are present in an amount of less than 0.5%, through less than 0.4%, 0.3%, to 0.2% or less.

In some embodiments, the psilocybin is Polymorph A and is characterized by at least one further peak in an XRPD diffractogram at 17.5, °2θ±0.1°2θ which peak has a relative intensity compared to the peak at 14.5°2θ±0.1°2θ of at least 5%.

In some embodiments, the psilocybin is Polymorph A and is characterized by at least one further peak in an XRPD diffractogram at 17.5°2θ±0.1°2θ which peak has a relative intensity compared to the peak at 14.5°2θ±0.1°2θ of at least 5%, at least 6%, at least 7%, through 8%, and 9% to at least 10%.

In some embodiments, the psilocybin is Polymorph A and is characterized by XRPD peaks at 11.5±0.1, 12.0±0.1, 14.5±0.1, 17.5±0.1, and 19.7±0.1°2θ. In some embodiments, the psilocybin is Polymorph A and is characterized by XRPD peaks at 11.5±0.1, 12.0±0.1, 14.5±0.1, 17.5±0.1, and 19.7±0.1°2θ and the psilocybin has a chemical purity of greater than 97% and no single impurity greater than 1% as determined by HPLC analysis.

Figure 2A:
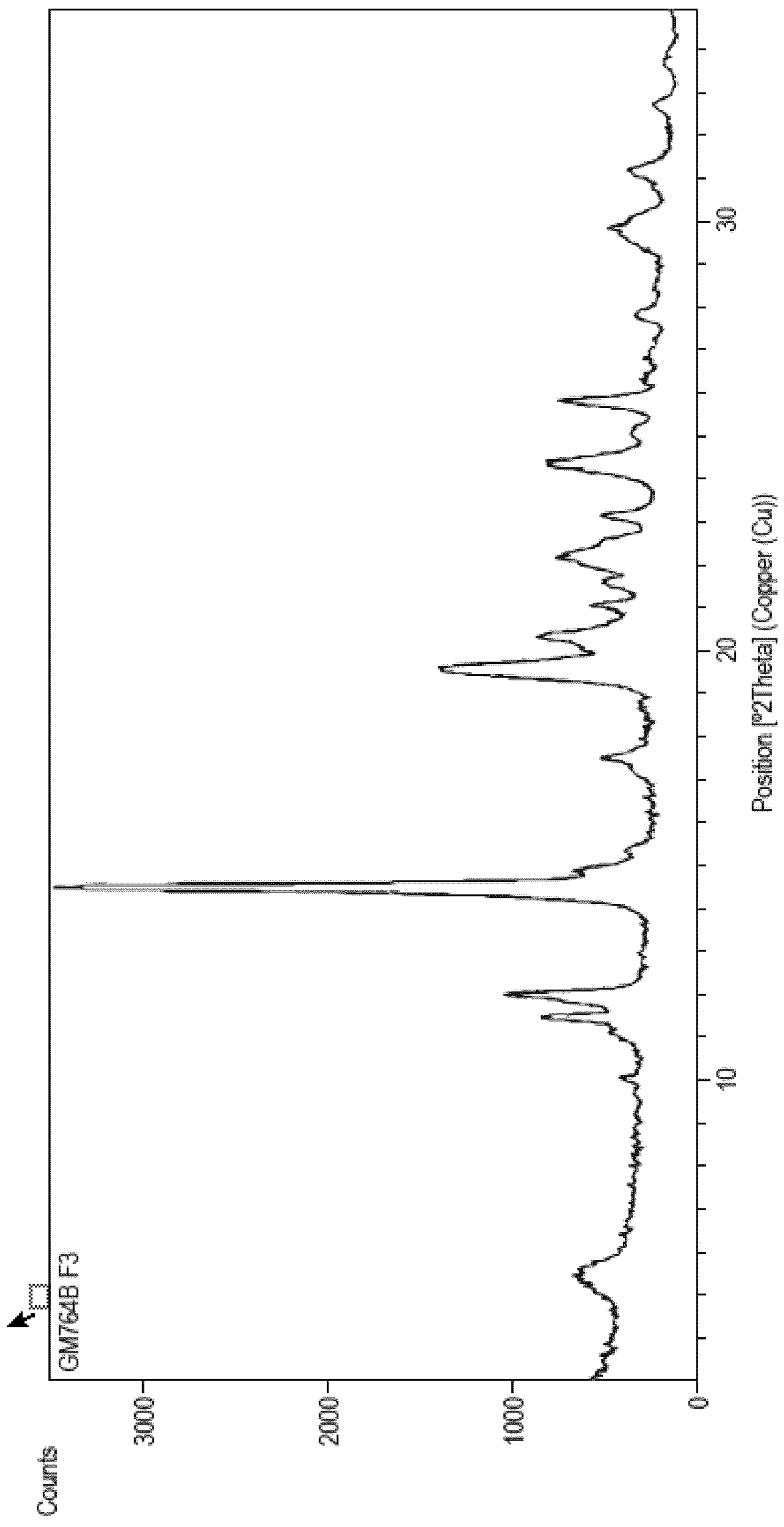
FIG. 2A is a XRPD diffractogram of Polymorph A
Figure 3A:
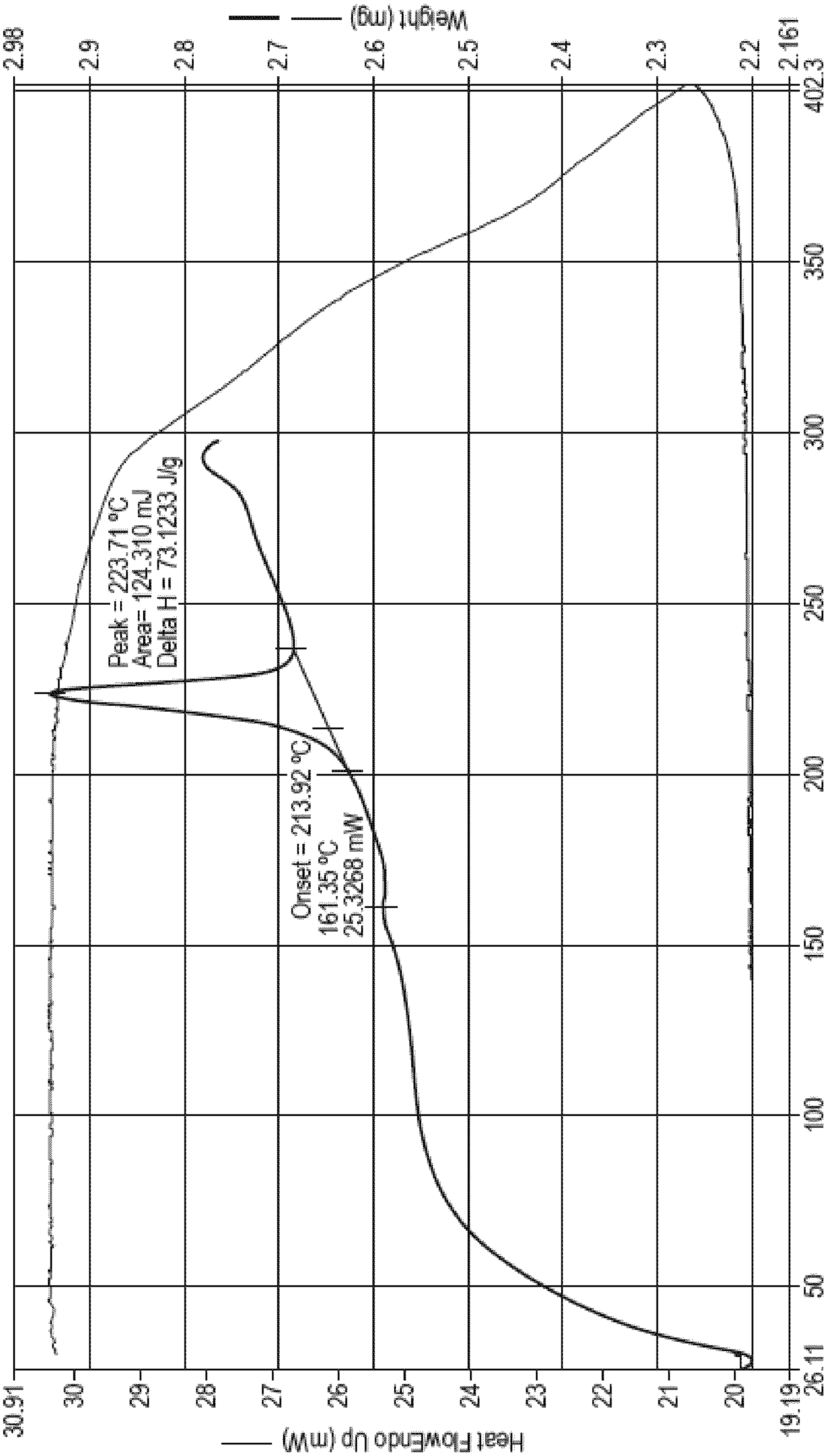
FIG. 3A is a DSC and TGA thermograph of Polymorph A

In some embodiments, the psilocybin is Polymorph A and has: (a) an XRPD diffractogram substantially as illustrated in FIG. 2A; and/or (b) a DSC thermogram substantially as illustrated in FIG. 3A.

In some embodiments, psilocybin Polymorph A has relatively large, uniform, rod shaped crystals with a size range of 50 to 200 microns.

In some embodiments disclosed herein, psilocybin Polymorph A exhibits an XRPD diffractogram characterized by the diffractogram summarized in Table 1. In some embodiments, described herein, the crystalline psilocybin Polymorph A comprises at least 3 peaks of (±0.1°2θ) of Table 1. In some embodiments, the crystalline psilocybin Polymorph A comprises at least 4 peaks of (±0.1°2θ) of Table 1. In some embodiments, the crystalline psilocybin Polymorph A comprises at least 5 peaks of (±0.1°2θ) of Table 1. In some embodiments, the crystalline psilocybin Polymorph A comprises at least 6 peaks of (+0.1°2θ) of Table 1. In some embodiments, the crystalline psilocybin Polymorph A comprises at least 8 peaks of (±0.1°2θ) of Table 1. In some embodiments, the crystalline psilocybin Polymorph A comprises at least 10 peaks of ('0.1°2θ) of Table 1. In some embodiments, the crystalline psilocybin Polymorph A comprising at least 15 peaks of (±0.1°2θ) of Table 1. A peak at about 17.5, °2θ±0.1°2θ distinguishes psilocybin Polymorph A from Polymorph A', in which the peak is absent or substantially absent (i.e. has a relative intensity compared to the peak at 14.5°2θ±0.1°2θ of less than 2%, or less than 1%).

TABLE 1

XRPD peak positions for Polymorph A

| Position [°2Θ] | Relative Intensity [%] |
|---|---|
| 5.6 | 8.42 |
| 11.5 | 13.05 |
| 12.0 | 26.45 |
| 14.5 | 100 |
| 17.5 | 10.71 |
| 19.7 | 37.29 |
| 20.4 | 20.06 |
| 22.2 | 17.83 |
| 23.2 | 6.99 |
| 24.3 | 17.93 |
| 25.7 | 16.4 |
| 26.8 | 3.15 |
| 27.8 | 4.54 |
| 29.7 | 9.53 |
| 31.2 | 6.51 |
| 32.6 | 2.45 |
| 33.7 | 1.75 |

In some embodiments, crystalline psilocybin Polymorph A is characterized by XRPD diffractogram peaks at 11.5, 12.0, 14.5, and 17.5°2θ±0.1°2θ. In some embodiments, crystalline psilocybin Polymorph A is further characterized by at least one additional peak appearing at 19.7, 20.4, 22.2, 24.3 or 25.7°2θ±0.1°2θ. In some embodiments, crystalline psilocybin Polymorph A is further characterized by at least two additional peaks appearing at 19.7, 20.4, 22.2, 24.3 or 25.7°2θ±0.1°2θ. In some embodiments, crystalline psilocybin Polymorph A is further characterized by at least three additional peaks appearing at 19.7, 20.4, 22.2, 24.3 or 25.7°2θ±0.1°2θ. In yet a further embodiment, crystalline psilocybin Polymorph A exhibits an XRPD diffractogram substantially the same as the XRPD diffractogram shown in FIG. 2A.

In some embodiments, crystalline psilocybin Polymorph A is characterized by XRPD diffractogram peaks at 14.5 and 17.5°2θ±0.1°2θ with the peak at 17.5°2θ having an intensity which is at least 5% of the intensity of the peak at 14.5°2θ, or at least 6%, through at least 7%, at least 8%, at least 9%, to at least 10%.

In some embodiments, crystalline psilocybin Polymorph A is absent or substantially absent of an XRPD diffractogram peaks at 10.1. By "substantially absent" it is meant that any XRPD diffractogram peaks at 10.1 is less than 2% of the intensity of the peak at 14.5°2θ, such as less than 1%, or is not detectable in the XRPD diffractogram, In some embodiments, crystalline psilocybin Polymorph A is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C.

In some embodiments, crystalline psilocybin Polymorph A exhibits a DSC thermogram substantially the same as the DSC thermogram in FIG. 3A.

In some embodiments, crystalline psilocybin Polymorph A is characterized by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In some embodiments, crystalline psilocybin Polymorph A is characterized by having <0.5% w/w loss, such as <0.4% w/w, such as <0.3% w/w, such as <0.2% w/w, such as <0.1% w/w, in the TGA thermogram between ambient temperature, such as about 25° C., and 200° C. In some embodiments, crystalline psilocybin Polymorph A loses less than 2% by weight in a loss on drying test, such as less than 1% by weight, such as less than 0.5% by weight. The loss on drying test is performed at 70° C.

In some embodiments, crystalline psilocybin Polymorph A is a white to off white solid.

In some embodiments, crystalline psilocybin Polymorph A is of a pharmaceutically acceptable chemical purity, for example, the crystalline psilocybin Polymorph A has a chemical purity of greater than 97%, such as greater than 98%, or such as greater than 99% as determined by HPLC. In some embodiments, crystalline psilocybin Polymorph A has no single impurity of greater than 1%, greater than 0.5%, greater than 0.4%, though 0.3% to 0.2% or less including phosphoric acid as measured by $^{31}P$ NMR, and psilocin as determined by HPLC. In some embodiments, crystalline psilocybin Polymorph A has a chemical purity of greater than 97 area %, greater than 98 area %, or greater than 99 area % as determined by HPLC. In some embodiments, crystalline psilocybin Polymorph A has no single impurity greater than 1 area %, greater than 0.5 area %, greater than 0.4 area %, though 0.3 area % to 0.2 area % or less, as determined by HPLC. In some embodiments, crystalline psilocybin Polymorph A has no single impurity greater than 2 area %, greater than 1.75 area %, greater than 1.5 area %, greater than 1.25 area %, greater than 1 area %, greater than 0.5 area %, greater than 0.4 area %, greater than 0.3 area %, greater than 0.2 area % or less, as determined by HPLC. In some embodiments, crystalline psilocybin Polymorph A does not contain psilocin at a level greater than 2 area %, greater than 1.75 area %, greater than 1.5 area %, greater than 1.25%, greater than 1 area %, greater than 0.5 area %, greater than 0.4 area %, greater than 0.3 area %, greater than 0.2 area % or less, as measured by HPLC. In some embodiments, crystalline psilocybin Polymorph A does not contain psilocin at a level greater than 1 area %, greater than 0.5 area %, greater than 0.4 area %, though 0.3 area % to 0.2 area % or less, as determined by HPLC. In some embodiments, crystalline psilocybin Polymorph A does not contain phosphoric acid at a level greater than 1 weight %, greater than 0.5 weight %, greater than 0.4 area %, though 0.3 area % to 0.2 area % or less, as determined by $^{31}P$ NMR. In some embodiments, crystalline psilocybin Polymorph A has a chemical assay of at least 95 weight %, such as at least 96 weight %, or such as at least 98 weight %.

In some embodiments, crystalline psilocybin Polymorph A has no single impurity of greater than 2%, greater than 1.75%, greater than 1.5%, greater than 1.25%, greater than 1%, greater than 0.5%, greater than 0.4%, greater than 0.3%, or greater than 0.2% including phosphoric acid as determined by $^{31}P$ NMR, and psilocin as determined by HPLC. In some embodiments, crystalline psilocybin Polymorph A does not contain psilocin at a level greater than 2%, greater than 1.75%, greater than 1.5%, greater than 1.25%, greater than 1%, greater than 0.5%, greater than 0.4%, greater than 0.3%, greater than 0.2% or less, as determined by HPLC. In some embodiments, crystalline psilocybin Polymorph A does not contain phosphoric acid at a level greater than 2 weight %, greater than 1.75 weight %, greater than 1.5 weight %, greater than 1.25 weight %, greater than 1 weight %, greater than 0.5 weight %, greater than 0.4 weight %, greater than 0.3 weight %, greater than 0.2 weight % or less, as determined by $^{31}P$ NMR.

Polymorph A'

Alternatively, the crystalline psilocybin may be in the form of Polymorph A' characterized by one or more of:

(a) peaks in an XRPD diffractogram at 11.5, 12.0 and 14.5°2θ±0.1°2θ, but absent or substantially absent of a peak at 17.5°2θ±0.1°2θ;

(b) having a first onset temperature of between 145° C. and 165° C. and a second onset temperature of between 205° C. and 220° C.

By substantial absence of a peak at 17.5°2θ±0.1°2θ is meant that the peak at 17.5°2θ±0.1°2θ (if present) has a relative intensity, compared to a peak at 14.5°2θ±0.1°2θ, of less than 5%, in some embodiments, less than 4%, through less than 3%, to 2%, 1% or less.

In some embodiments, crystalline psilocybin Polymorph A' exhibits an XRPD diffractogram characterized by the diffractogram summarized in Table 2. In some embodiments, described herein the crystalline psilocybin Polymorph A' comprises at least 3 peaks of (±0.1°2θ) of Table 2 but absent or substantially absent of a peak at 17.5°2θ±0.1°2θ. In some embodiments, the crystalline psilocybin Polymorph A' comprising at least 4 peaks of (±0.1°2θ) of Table 2 but absent or substantially absent of a peak at 17.5°2θ±0.1°2θ. In some embodiments, the crystalline psilocybin Polymorph A' comprises at least 5 peaks of (±0.1°2θ) of Table 2 but absent or substantially absent of a peak at 17.5°2θ±0.1°2θ. In some embodiments, the crystalline psilocybin Polymorph A' comprises at least 6 peaks of (±0.1°2θ) of Table 2 but absent or substantially absent of a peak at 17.5°2θ±0.1°2θ. In some embodiments, the crystalline psilocybin Polymorph A' comprises at least 8 peaks of (±0.1°2θ) of Table 2 but absent or substantially absent of a peak at 17.5°2θ±0.1°2θ. In some embodiments, the crystalline psilocybin Polymorph A' comprises at least 10 peaks of (±0.1°2θ) of Table 2 but absent or substantially absent of a peak at 17.5°2θ±0.1°2θ. In some embodiments, the crystalline psilocybin Polymorph A' comprises at least 15 peaks of (±0.1°2θ) of Table 2 but absent or substantially absent of a peak at 17.5°2θ±0.1°2θ. In some embodiments, the crystalline psilocybin Polymorph A' comprises at least 20 peaks of (±0.1°2θ) of Table 2 but the absence or substantial absence of a peak at 17.5°2θ±0.1°2θ. In some embodiments, the crystalline psilocybin Polymorph A' comprises at least 25 peaks of (±0.1°2θ) of Table 2 but the peak at 17.5°2θ±0.1°2θ is absent or substantially absent.

TABLE 2

XRPD peak positions for Polymorph A'

| Position [°2Θ] | Relative Intensity [%] |
|---|---|
| 5.5 | 4.89 |
| 10.1 | 4.09 |
| 11.5 | 22.05 |

TABLE 2-continued

| XRPD peak positions for Polymorph A' | |
|---|---|
| Position [°2Θ] | Relative Intensity [%] |
| 12.0 | 22.77 |
| 14.5 | 100 |
| 14.9 | 11.29 |
| 17.5 | 1.08 |
| 18.7 | 2.44 |
| 19.4 | 23.02 |
| 19.6 | 33.7 |
| 20.3 | 17.01 |
| 21.1 | 12.08 |
| 21.6 | 8.51 |
| 22.2 | 15.54 |
| 22.6 | 8.78 |
| 23.1 | 10.11 |
| 24.3 | 21.83 |
| 25.1 | 4.36 |
| 25.8 | 15.4 |
| 26.3 | 4.28 |
| 26.8 | 2.86 |
| 27.8 | 5.96 |
| 28.6 | 1.91 |
| 29.7 | 10.56 |
| 31.1 | 7.35 |
| 32.6 | 3.72 |
| 33.8 | 1.54 |

In some embodiments, crystalline psilocybin Polymorph A' is characterized by XRPD diffractogram peaks at 11.5, 12.0, and 14.5°2θ±0.1°2θ but the substantial absence of a peak at 17.5°2θ±0.1°2θ. In some embodiments, crystalline psilocybin Polymorph A' is further characterized by at least one additional peak appearing at 19.7, 20.4, 22.2, 24.3, or 25.7°2θ±0.1°2θ. In some embodiments, crystalline psilocybin Polymorph A' is further characterized by at least two additional peaks appearing at 19.7, 20.4, 22.2, 24.3, or 25.7°2θ±0.1°2θ. In some embodiments, crystalline psilocybin Polymorph A' is further characterized, and distinguished from Polymorph A by the presence of a peak appearing at 10.1°2θ±0.1°2θ. In yet a further embodiment, crystalline psilocybin Polymorph A' exhibits an XRPD diffractogram substantially the same as the XRPD diffractogram shown in FIG. 2B.

In some embodiments, crystalline psilocybin Polymorph A' is characterized by XRPD diffractogram peaks at 14.5 and 17.5°2θ±0.1°2θ wherein the intensity of the peak at 17.5°2θ is less than 5% of the intensity of the peak at 14.5°2θ, such as less than 4%, such as less than 3%, such as at less than 2%, such as less than 1%, or such as about 1%.

In some embodiments, crystalline psilocybin Polymorph A' is characterized by XRPD diffractogram peaks at 10.1 and 14.5°2θ±0.1°2θ wherein the intensity of the peak at 10.1°2θ is at least 1% of the intensity of the peak at 14.5°2θ, such as at least than 2%, such as at least than 3%, or such as about 4%.

In some embodiments, crystalline psilocybin Polymorph A' is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C. In some embodiments, crystalline psilocybin Polymorph A' exhibits a DSC thermogram substantially the same as the DSC thermogram in FIG. 3B.

In some embodiments, crystalline psilocybin Polymorph A' is characterized by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In some embodiments, crystalline psilocybin Polymorph A' is characterized by having <0.5% w/w loss, such as <0.4% w/w, such as <0.3% w/w, such as <0.2% w/w, such as <0.1% w/w, in the TGA thermogram between ambient temperature, such as 25° C., and 200° C. In some embodiments, crystalline psilocybin Polymorph A' loses less than 2% by weight in a loss on drying test, such as less than 1% by weight, such as less than 0.5% by weight. The loss on drying test is performed at 70° C.

In some embodiments, crystalline psilocybin Polymorph A' is a white to off white solid.

XRPD diffractograms and XRPD peak positions are acquired using Cu Kα radiation.

DSC and TGA thermograms are acquired using a heating rate of 20° C./min.

Figure 2B:
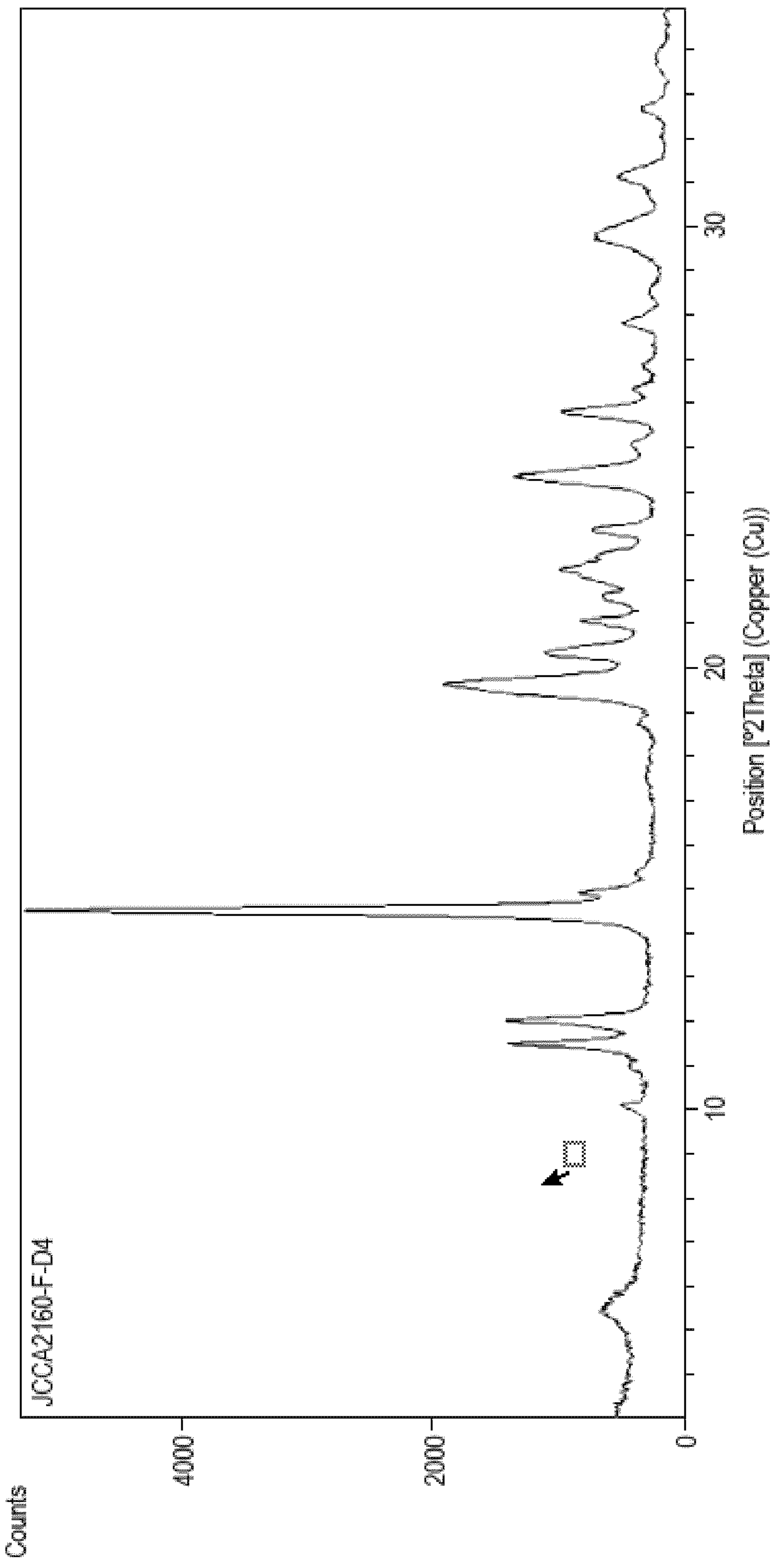
FIG. 2B is a XRPD diffractogram of Polymorph A'
Figure 3B:
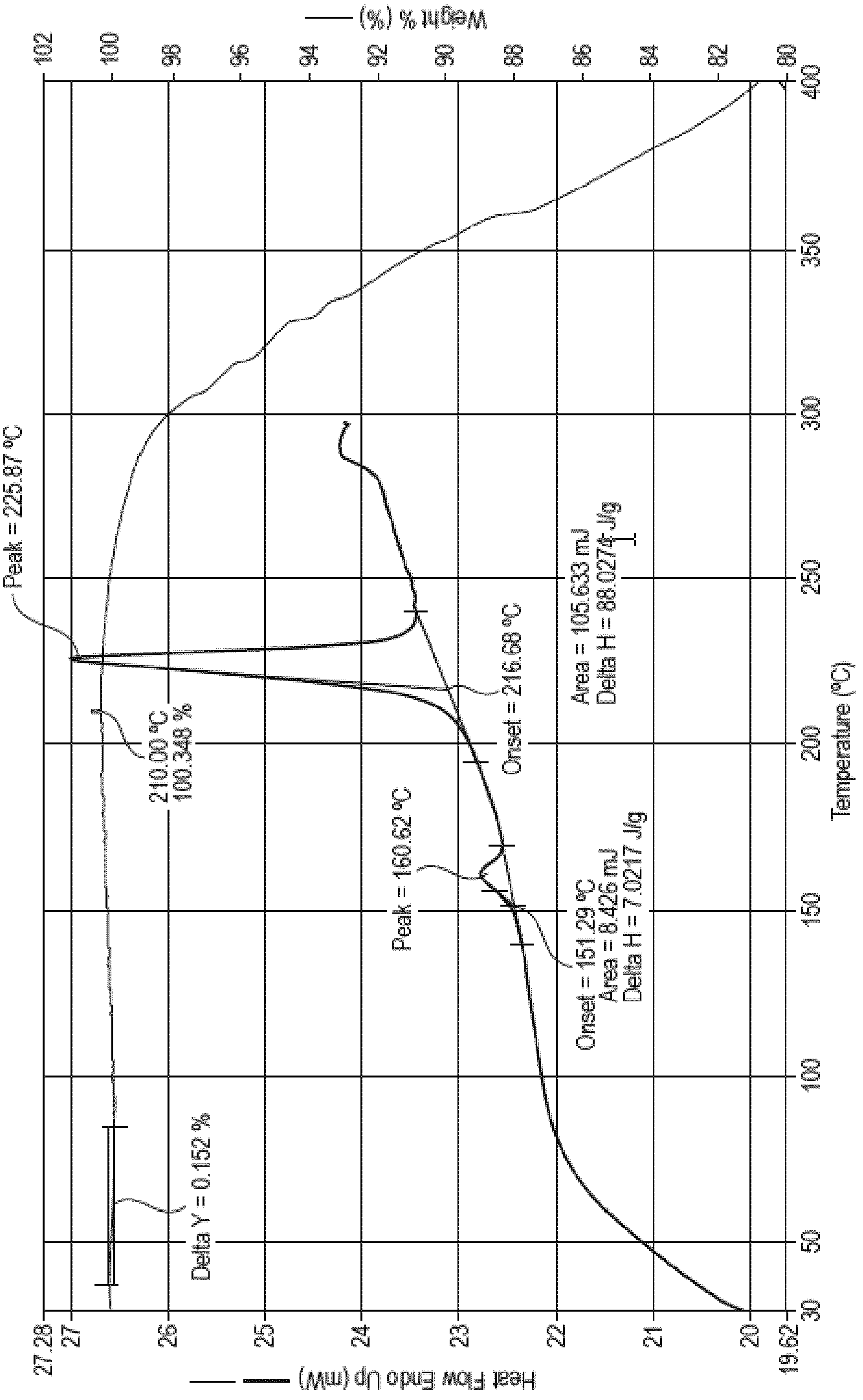
FIG. 3B is a DSC and TGA thermograph of Polymorph A'

In some embodiments, there is provided high purity crystalline psilocybin, Polymorph A or Polymorph A', exhibiting an XRPD diffractogram as substantially illustrated in FIG. 2A or 2B and a DSC thermograph as substantially illustrated in FIG. 3A or 3B or a mixture thereof.

In some embodiments, the crystalline psilocybin Polymorph A exhibits an XRPD diffractogram as illustrated in FIG. 2A and a DSC thermograph as illustrated in FIG. 3A.

In some embodiments, the crystalline psilocybin Polymorph A' exhibits an XRPD diffractogram as substantially illustrated in FIG. 2B and a DSC thermograph as substantially illustrated in FIG. 3B.

In some embodiments, the high purity crystalline psilocybin Polymorph A is characterized by a XRPD diffractogram as substantially illustrated in FIG. 2A and a DSC thermograph as substantially illustrated in FIG. 3A.

In some embodiments, the high purity crystalline psilocybin Polymorph A' is characterized by a XRPD diffractogram as illustrated in FIG. 2B and a DSC thermograph as illustrated in FIG. 3B.

Figure 2C:
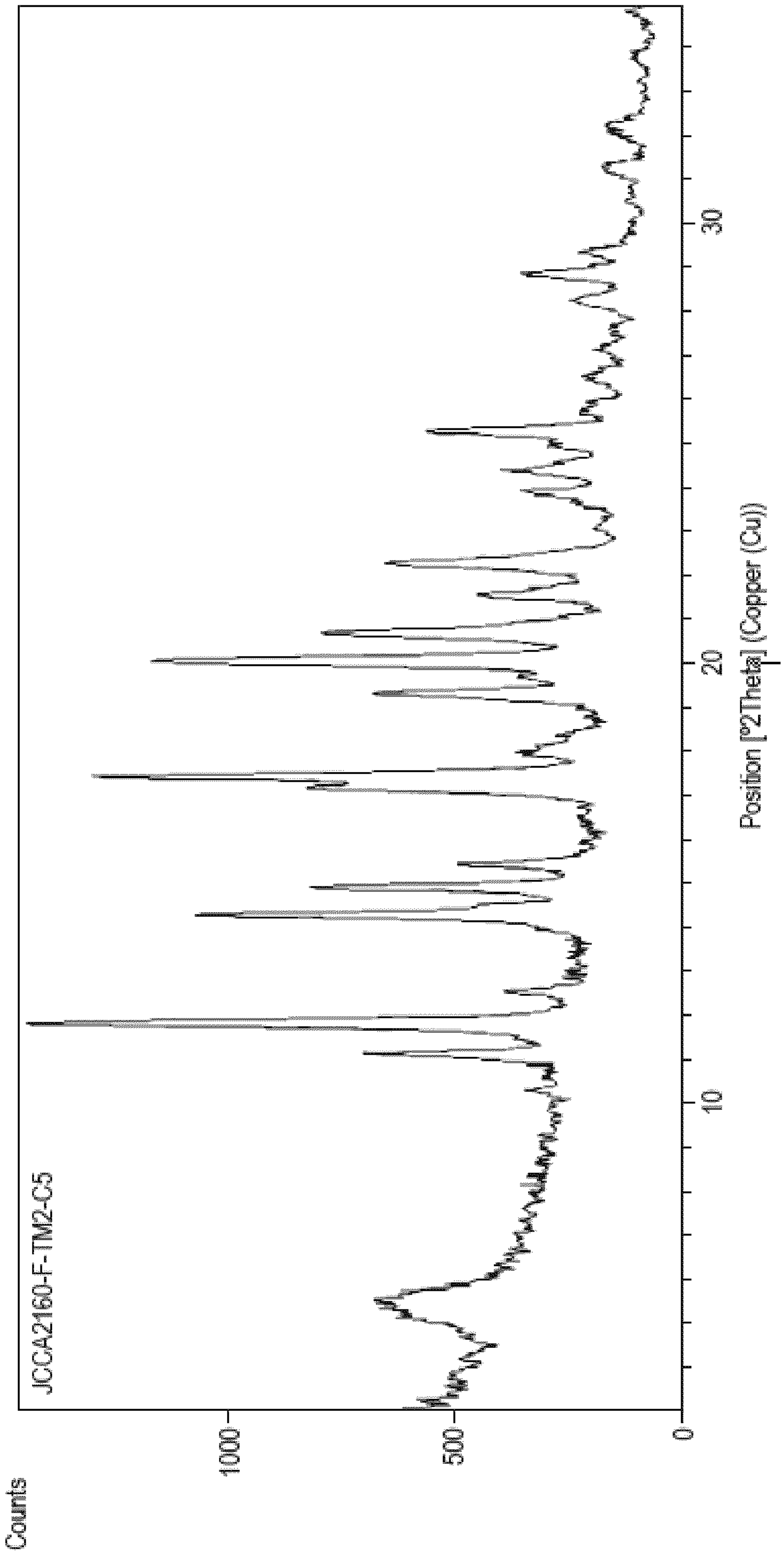
FIG. 2C is a XRPD diffractogram of Polymorph B
Figure 2D:
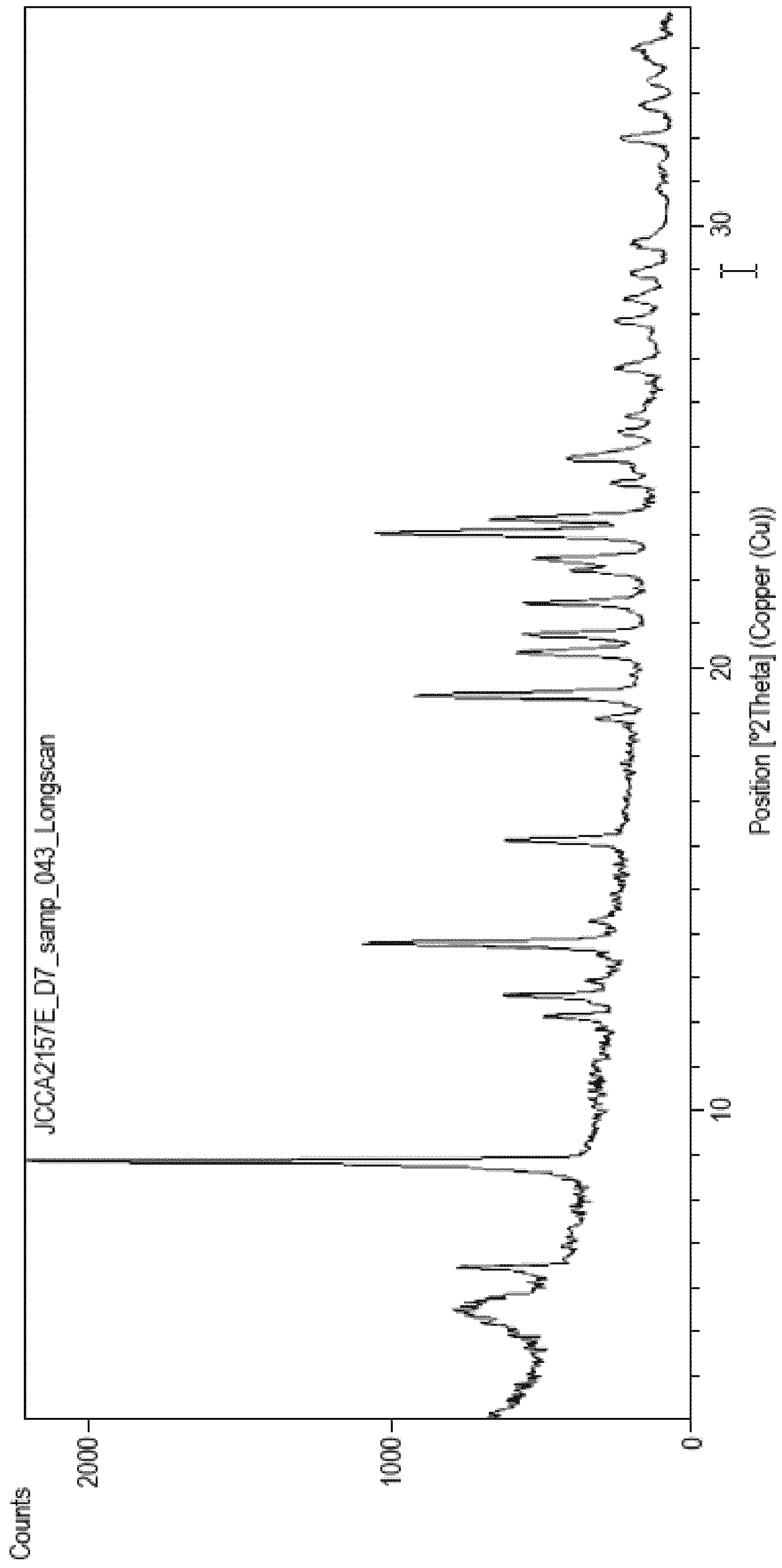
FIG. 2D is a XRPD diffractogram of a Hydrate A
Figure 2E:
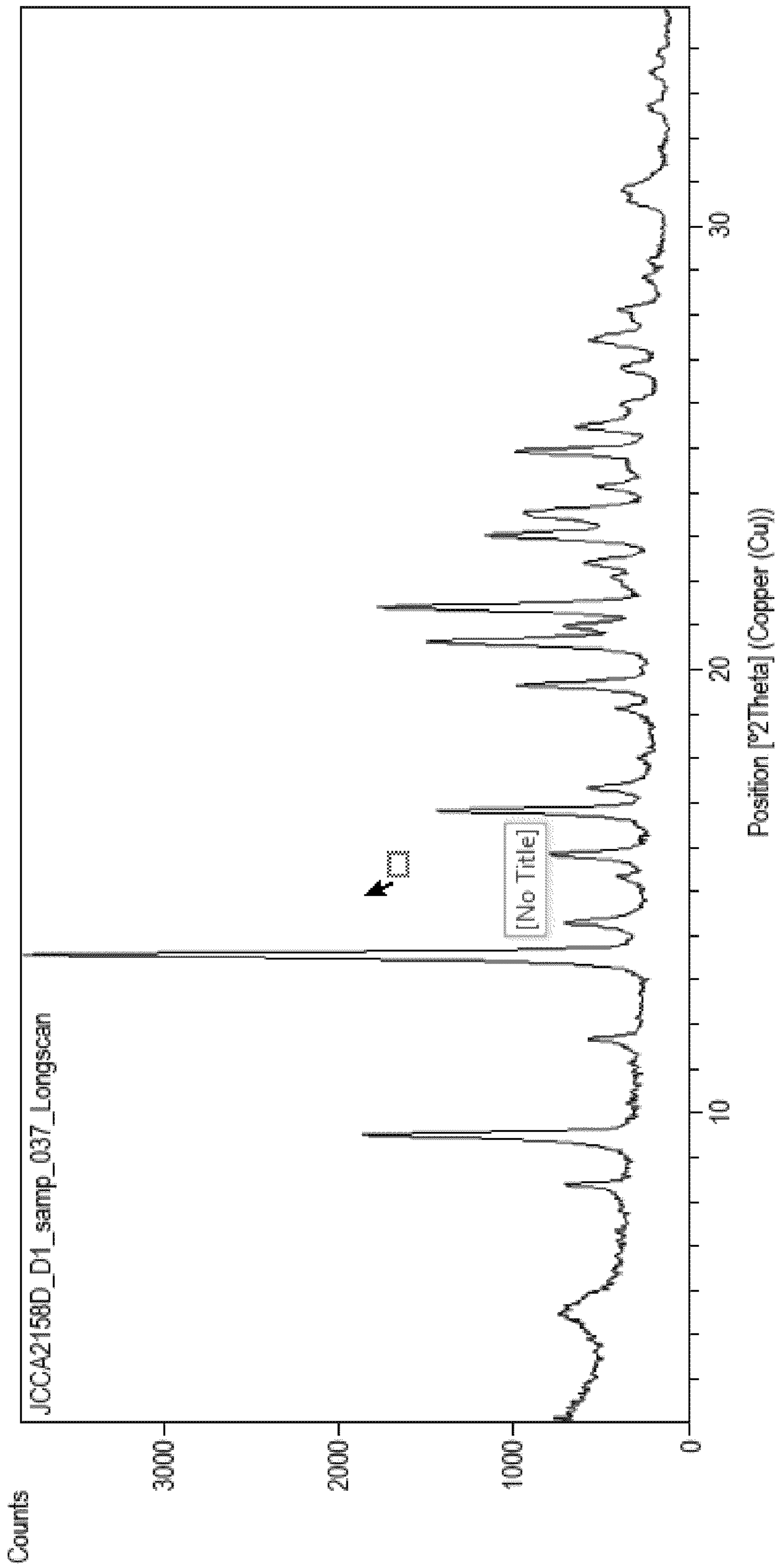
FIG. 2E is a XRPD diffractogram of an ethanol solvate
Figure 2F:
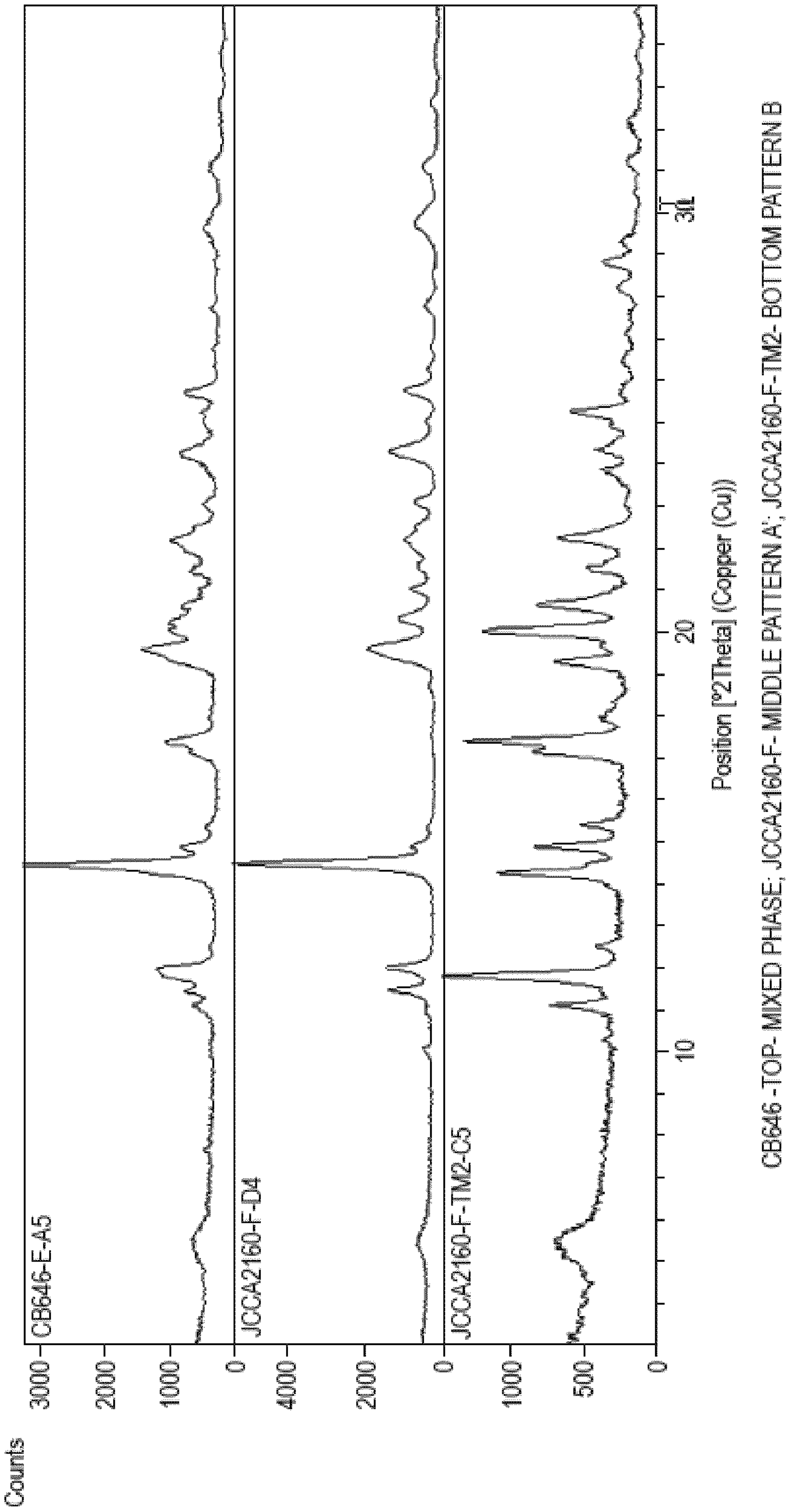
FIG. 2F is a XRPD diffractogram of product obtained during development of the process (top)—compared to the diffractograms Polymorph A' (middle) and Polymorph B (bottom).
Figure 4:
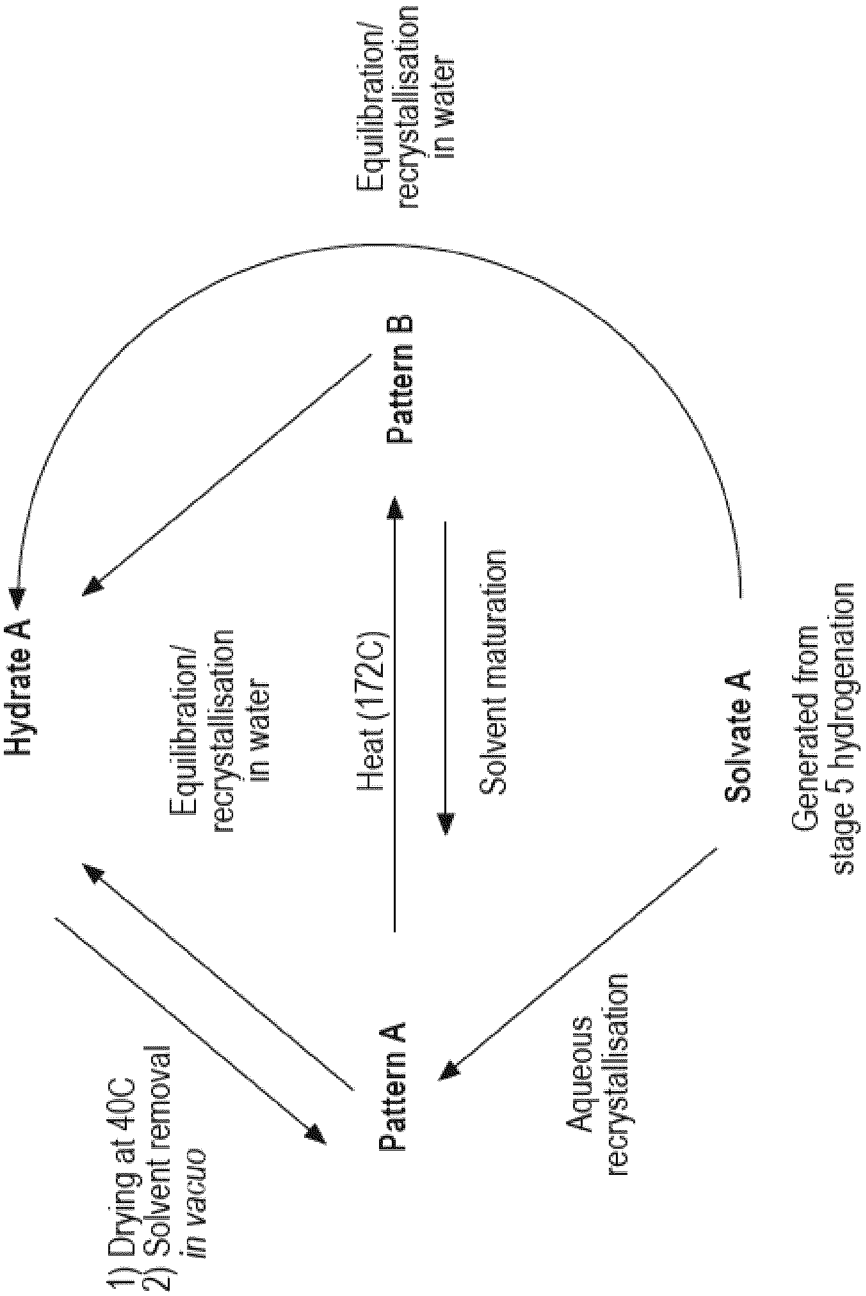
FIG. 4 is a form phase diagram showing the interrelationship of form in water-based systems.
Figure 5:
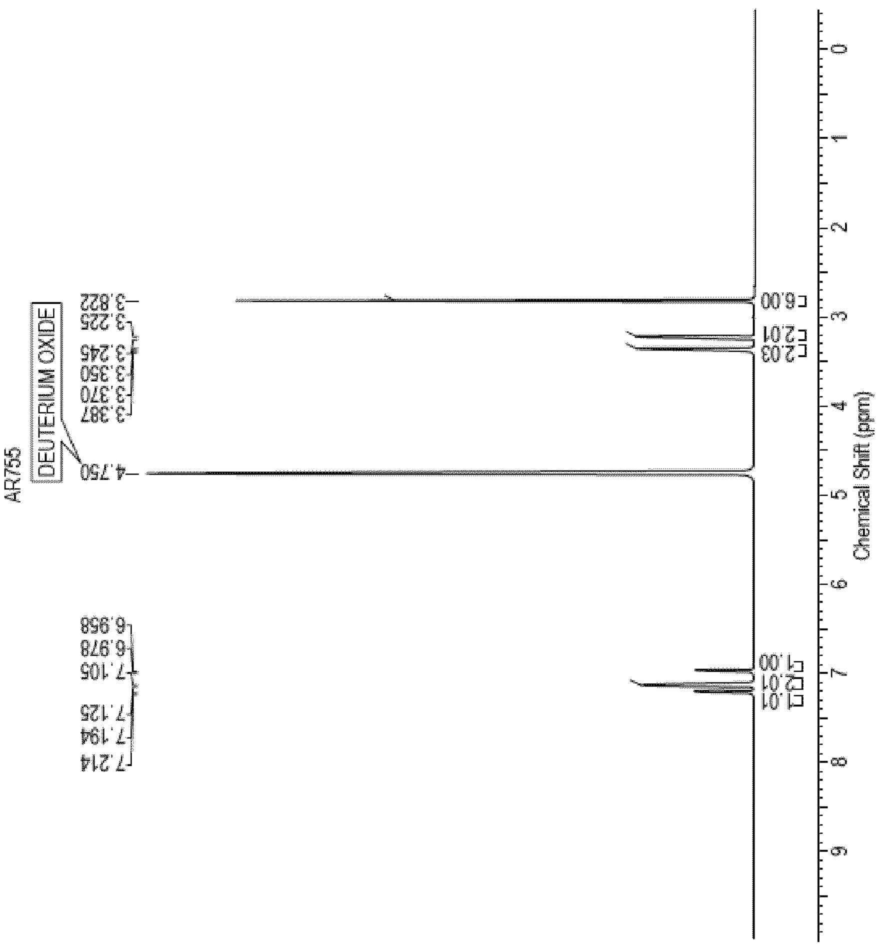
FIG. 5 is a $^{1}H$ NMR spectrum of psilocybin.
Figure 6:
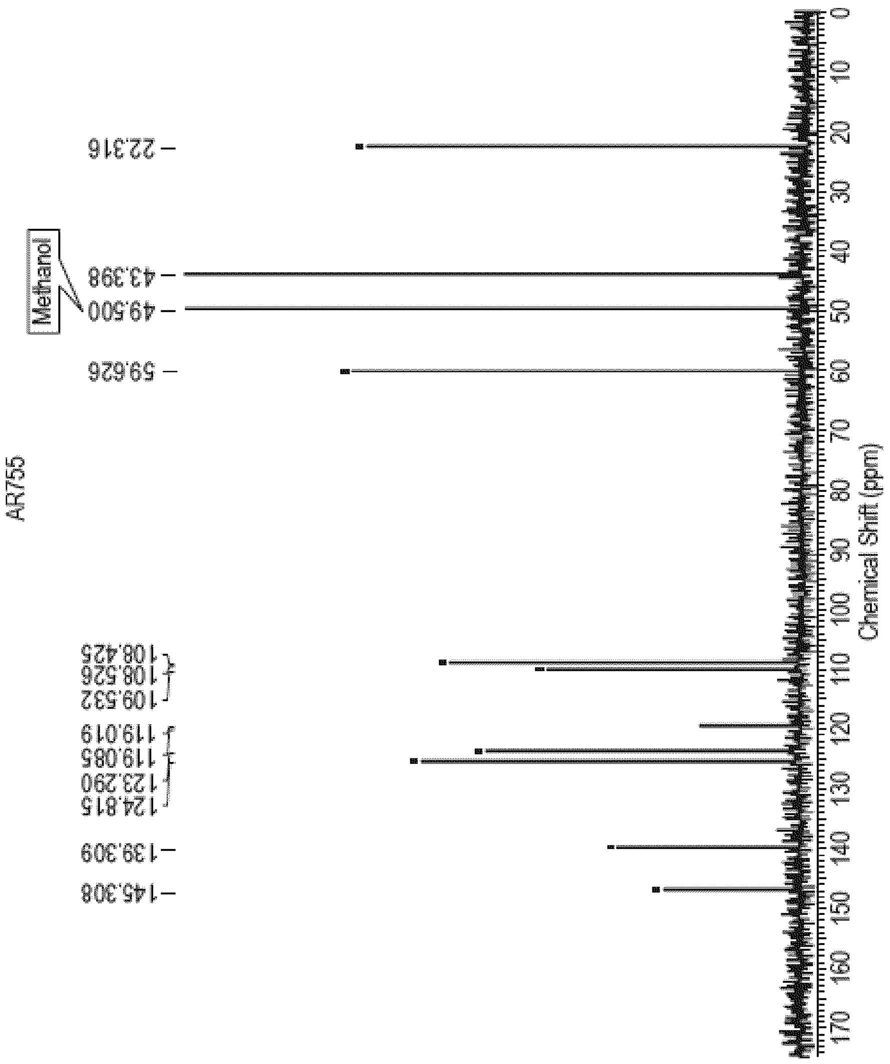
FIG. 6 is a $^{13}C$ NMR spectrum of psilocybin.
Figure 7:
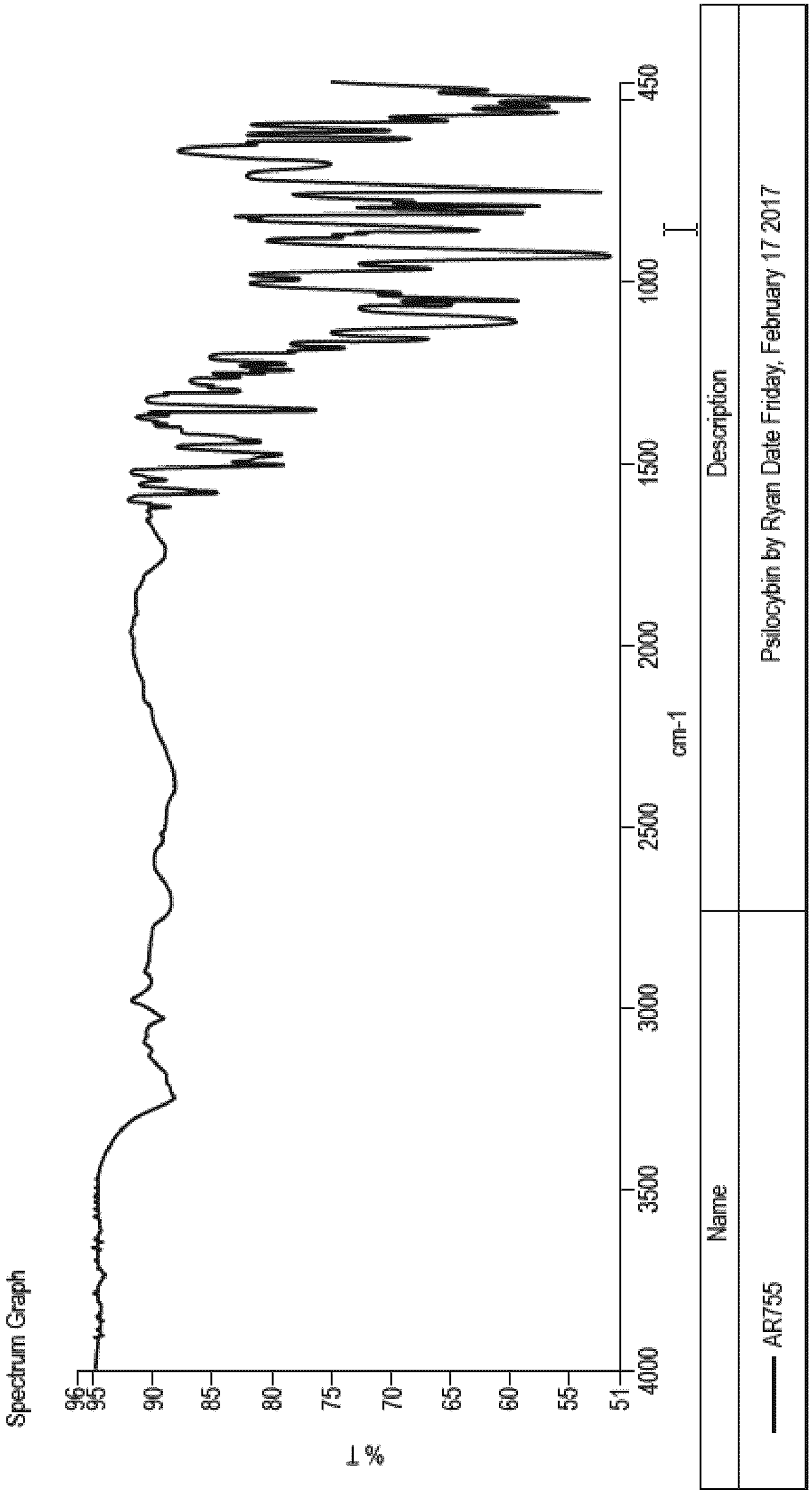
FIG. 7 is a FT-IR Spectrum of psilocybin.
Figure 8:
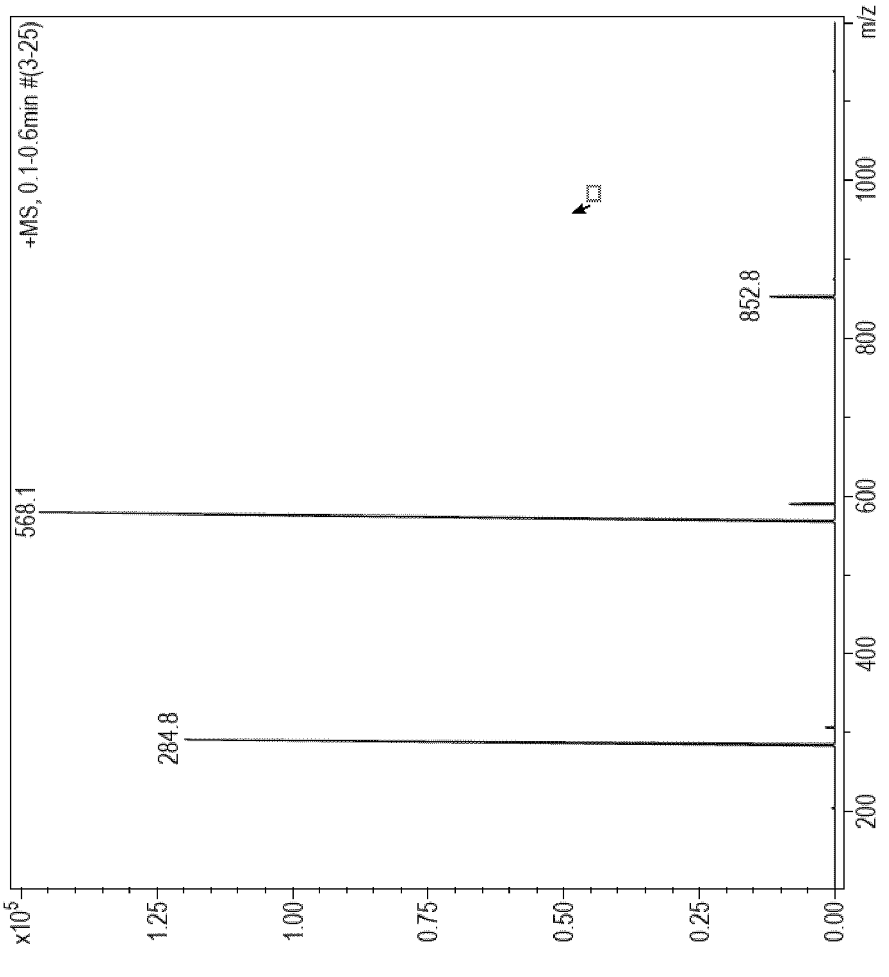
FIG. 8 is a Mass Spectrum of psilocybin.

Polymorph A (including its isostructural variant Polymorph A') (FIGS. 2A and 2B) differs from Polymorph B (FIG. 2C), the Hydrate A (FIG. 2D) and the ethanol solvate (FIG. 2E: Solvate A), and the relationship between some of the different forms is illustrated in FIG. 4.

The crystalline psilocybin Polymorph A' is a white to off white solid, and/or has a chemical purity of greater than 97%, in some embodiments greater than 98%, and in some embodiments greater than 99% by HPLC, and has no single impurity of greater than 2%, greater than 1.75%, greater than 1.5%, greater than 1.25%, greater than 1%, greater than 0.75%, greater than 0.5%, greater than 0.4%, through 0.3% to 0.2% or less including phosphoric acid as determined by $^{31}P$ NMR, and psilocin as determined by HPLC. In some embodiments, crystalline psilocybin Polymorph A', has a chemical assay of at least 95 weight %, such as at least 96 weight %, or such as at least 98 weight %.

In some embodiments, crystalline psilocybin Polymorph A' is of a pharmaceutically acceptable chemical purity, for example, the crystalline psilocybin Polymorph A' has a chemical purity of greater than 97%, such as greater than 98%, or such as greater than 99%, as measured by HPLC. In some embodiments, crystalline psilocybin Polymorph A' has no single impurity of greater than 2%, greater than 1.75%, greater than 1.5%, greater than 1.25%, greater than 1%, greater than 0.5%, greater than 0.4%, greater than 0.3%, greater than 0.2% or less including phosphoric acid as determined by $^{31}P$ NMR, and psilocin as determined by HPLC. In some embodiments, crystalline psilocybin Polymorph A' has no single impurity greater than 2 area %, greater than 1.75 area %, greater than 1.5 area %, greater than 1.25 area %, greater than 1 area %, greater than 0.5 area %, greater than 0.4 area %, greater than 0.3 area %, greater than 0.2 area % or less, as determined by HPLC. In some embodiments, crystalline psilocybin Polymorph A' does not contain psilocin at a level greater than 2%, greater than 1.75%, greater than 1.5%, greater than 1.25%, greater than 1%, greater than 0.5%, greater than 0.4%, greater than 0.3%, greater than 0.2% or less, as determined by HPLC. In some embodiments, crystalline psilocybin Polymorph A' does not contain psilocin at a level greater than 2 area %, greater than 1.75 area %, greater than 1.5 area %, greater than 1.25%, greater than 1 area %, greater than 0.5 area %, greater than 0.4 area %, greater than 0.3 area %, greater than 0.2 area % or less, as determined by HPLC. In some embodiments, crystalline psilocybin Polymorph A' does not contain phosphoric acid at a level greater than 2 weight %, greater than 1.75 weight %, greater than 1.5 weight %, greater than 1.25 weight %, greater than 1 weight %, greater than 0.5 weight %, greater than 0.4 weight %, greater than 0.3 weight %, greater than 0.2 weight % or less, as measured by $^{31}P$ NMR.

The heating of Polymorph A or A' results in an endothermic event having an onset temperature of circa 150° C. corresponding to solid-solid transition of Polymorph A or Polymorph A' to Polymorph B. Continued heating of the resulting solid, i.e., Polymorph B, results in a second endothermic event corresponding to a melting point having an onset temperature of between 205 and 220° C. (see FIGS. 3A and 3B).

Hydrate A

In some embodiments there is provided a crystalline form of psilocybin, Hydrate A, characterized by one or more of:

(a) peaks in an XRPD diffractogram at 8.9, 12.6 and 13.8°2θ±0.1°2θ; and/ or (b) an endothermic event in a DSC thermogram having a first onset temperature of between 90° C. and 100° C., a second onset temperature of between 100° C. and 120° C. and a third onset temperature of between 210° C. and 220° C.

The XPRD diffractogram may exhibit at least one further peak at 6.5, 12.2, 19.4, 20.4 or 20.8°2θ±0.1°2θ.

In some embodiments, psilocybin Hydrate A exhibits an XRPD diffractogram characterized by the diffractogram summarized in Table 3. In some embodiments, described herein the crystalline psilocybin Hydrate A comprises at least 3 peaks of (±0.1°2θ) of Table 3. In some embodiments, the crystalline psilocybin Hydrate A comprises at least 4 peaks of (±0.1°2θ) of Table 3. In some embodiments, the crystalline psilocybin Hydrate A comprises at least 5 peaks of (±0.1°2θ) of Table 3. In some embodiments, the crystalline psilocybin Hydrate A comprises at least 8 peaks of (±0.1°2θ) of Table 3. In some embodiments, the crystalline psilocybin Hydrate A comprises at least 10 peaks of (±0.1°2θ) of Table 3.

TABLE 3

XRPD peak positions for Hydrate A

| Position [°2Θ] | Relative Intensity [%] |
|---|---|
| 5.6 | 14.4 |
| 6.5 | 18.84 |
| 8.9 | 100 |
| 12.2 | 11.51 |
| 12.6 | 18.65 |
| 13.8 | 44.22 |
| 16.2 | 21.22 |
| 18.9 | 6.62 |
| 19.4 | 38.68 |
| 20.4 | 21.32 |
| 20.8 | 19.73 |
| 21.5 | 20.75 |
| 22.3 | 12.8 |
| 22.5 | 19.38 |
| 23.1 | 47.53 |
| 23.5 | 25.79 |
| 24.3 | 5.62 |
| 24.8 | 14.62 |
| 25.4 | 5.27 |
| 26.9 | 6.53 |
| 27.9 | 7.82 |
| 28.4 | 5.78 |
| 29.0 | 5.09 |
| 29.7 | 4.83 |
| 32.1 | 8.27 |
| 32.8 | 4.81 |
| 33.4 | 3.74 |
| 34.2 | 5.96 |

In some embodiments, crystalline psilocybin Hydrate A is characterized by XRPD diffractogram peaks at 8.9, 12.6 and 13.8°2θ±0.1°2θ. In some embodiments, crystalline psilocybin Hydrate A is further characterized by at least one peak appearing at 6.5, 12.2, 19.4, 20.4 or 20.8°2θ±0.1°2θ. In some embodiments, crystalline psilocybin Hydrate A is further characterized by at least two peaks appearing at 6.5, 12.2, 19.4, 20.4 or 20.8°2θ±0.1°2θ. In yet a further embodiment, crystalline psilocybin Hydrate A exhibits an XRPD diffractogram substantially the same as the XRPD diffractogram shown in FIG. 2D.

In some embodiments, crystalline psilocybin Hydrate A is characterized by an endothermic event in a DSC thermogram having a first onset temperature of between 85° C. and 105° C., such as between 90° C. and 100° C., such as at about 96° C.; a second onset temperature of between 100° C. and 120° C.such as between 105° C. and 115° C., such as at about 109° C.; and a third onset temperature of between 205 and 220° C., such as between 210 and 220° C., such as between 210 and 218° C., or such as between 210 and 216° C., such as about 216° C. In some embodiments, crystalline psilocybin Hydrate A exhibits a DSC thermogram substantially the same as the DSC thermogram in FIG. 3D.

In some embodiments, crystalline psilocybin Hydrate A is characterized by having a water content of between 10% and 18%, such as between 12% and 16%, or such as about 13%. The skilled person would know of methods to determine the water content of a compound, for example Karl Fischer Titration. In some embodiments, crystalline psilocybin Hydrate A is characterized by having a weight loss in the TGA thermogram of between 10% and 18%, such as between 12% and 16%, or such as about 13%, between ambient temperature, such as about 25° C., to 120° C.

In some embodiments, crystalline psilocybin Hydrate A is of a pharmaceutically acceptable chemical purity, for example, the crystalline psilocybin Hydrate A has a chemical purity of greater than 97%, such as greater than 98%, or such as greater than 99% as determined by HPLC. In some embodiments, crystalline psilocybin Hydrate A has no single impurity of greater than 1%, greater than 0.5%, greater than 0.4%, though 0.3% to 0.2% or less including phosphoric acid as measured by $^{31}P$ NMR, and psilocin as determined by HPLC. In some embodiments, crystalline psilocybin Hydrate A has a chemical purity of greater than 97 area %, greater than 98 area %, or greater than 99 area % as determined by HPLC. In some embodiments, crystalline psilocybin Hydrate A has no single impurity greater than 1 area %, greater than 0.5 area %, greater than 0.4 area %, though 0.3 area % to 0.2 area % or less, as determined by HPLC. In some embodiments, crystalline psilocybin Hydrate A has no single impurity greater than 2 area %, greater than 1.75 area %, greater than 1.5 area %, greater than 1.25 area %, greater than 1 area %, greater than 0.5 area %, greater than 0.4 area %, greater than 0.3 area %, greater than 0.2 area % or less, as determined by HPLC. In some embodiments, crystalline psilocybin Hydrate A does not contain psilocin at a level greater than 2 area %, greater than 1.75 area %, greater than 1.5 area %, greater than 1.25%, greater than 1 area %, greater than 0.5 area %, greater than 0.4 area %, greater than 0.3 area %, greater than 0.2 area % or less, as measured by HPLC. In some embodiments, crystalline psilocybin Hydrate A does not contain psilocin at a level greater than 1 area %, greater than 0.5 area %, greater than 0.4 area %, though 0.3 area % to 0.2 area % or less, as determined by HPLC. In some embodiments, crystalline psilocybin Hydrate A does not contain phosphoric acid at a level greater than 1 weight %, greater than 0.5 weight %, greater than 0.4 area %, though 0.3 area % to 0.2 area % or less, as determined by $^{31}P$ NMR. In some embodiments, crystalline psilocybin Hydrate A has a chemical assay of at least 95 weight %, such as at least 96 weight %, or such as at least 98 weight %.

In some embodiments, crystalline psilocybin Hydrate A has no single impurity of greater than 2%, greater than 1.75%, greater than 1.5%, greater than 1.25%, greater than 1%, greater than 0.5%, greater than 0.4%, greater than 0.3%, or greater than 0.2% including phosphoric acid as determined by $^{31}P$ NMR, and psilocin as determined by HPLC. In some embodiments, crystalline psilocybin Hydrate A does not contain psilocin at a level greater than 2%, greater than 1.75%, greater than 1.5%, greater than 1.25%, greater than 1%, greater than 0.5%, greater than 0.4%, greater than 0.3%, greater than 0.2% or less, as determined by HPLC. In some embodiments, crystalline psilocybin Hydrate A does not contain phosphoric acid at a level greater than 2 weight %, greater than 1.75 weight %, greater than 1.5 weight %, greater than 1.25 weight %, greater than 1 weight %, greater than 0.5 weight %, greater than 0.4 weight %, greater than 0.3 weight %, greater than 0.2 weight % or less, as determined by $^{31}P$ NMR.

Polymorph B

In some embodiments, there is provided a crystalline form of psilocybin, Polymorph B, characterized by one or more of:

(a) peaks in an XRPD diffractogram at 11.1, 11.8 and 14.3°2θ±0.1°2θ; and/or (b) a single endothermic event in a DSC thermogram having an onset temperature of between 205 and 220° C.

The XPRD diffractogram may exhibit at least one further peak at 14.9, 15.4, 19.3, 20.0 or 20.6°2θ±0.1°2θ.

In some embodiments, the XRPD diffractogram is as substantially illustrated in FIG. 2C.

Figure 3C:
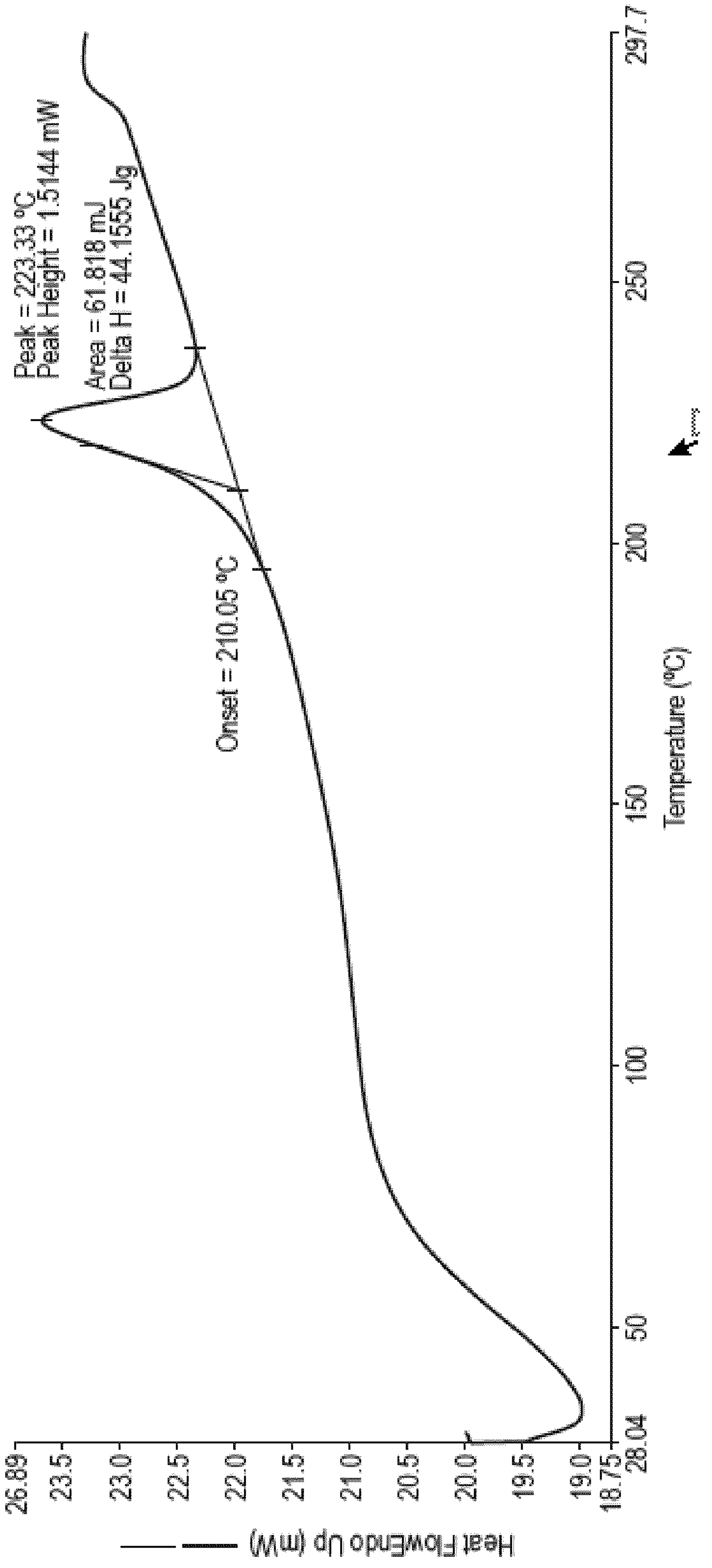
FIG. 3C is a DSC thermograph of Polymorph B
Figure 3D:
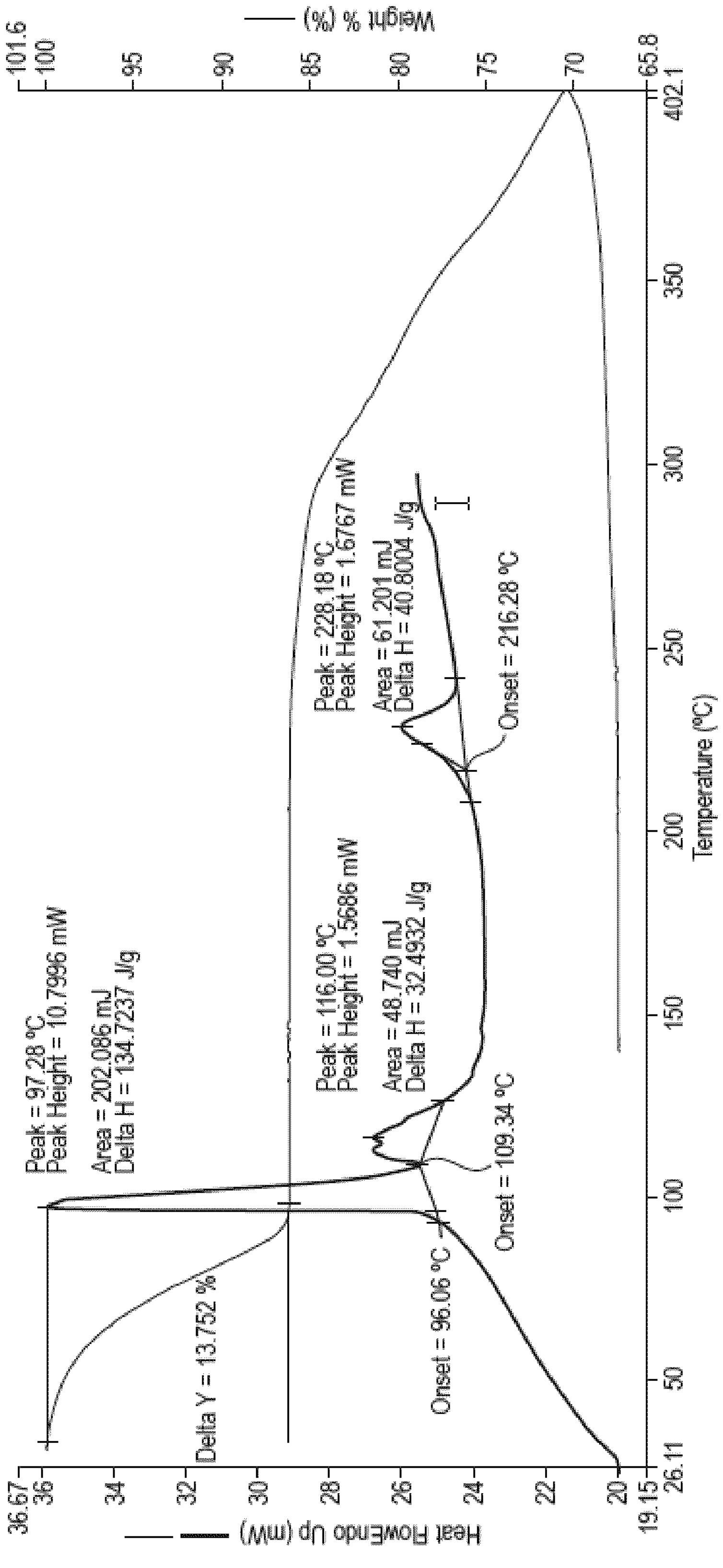
FIG. 3D is a DSC and TGA thermograph of Hydrate A
Figure 3E:
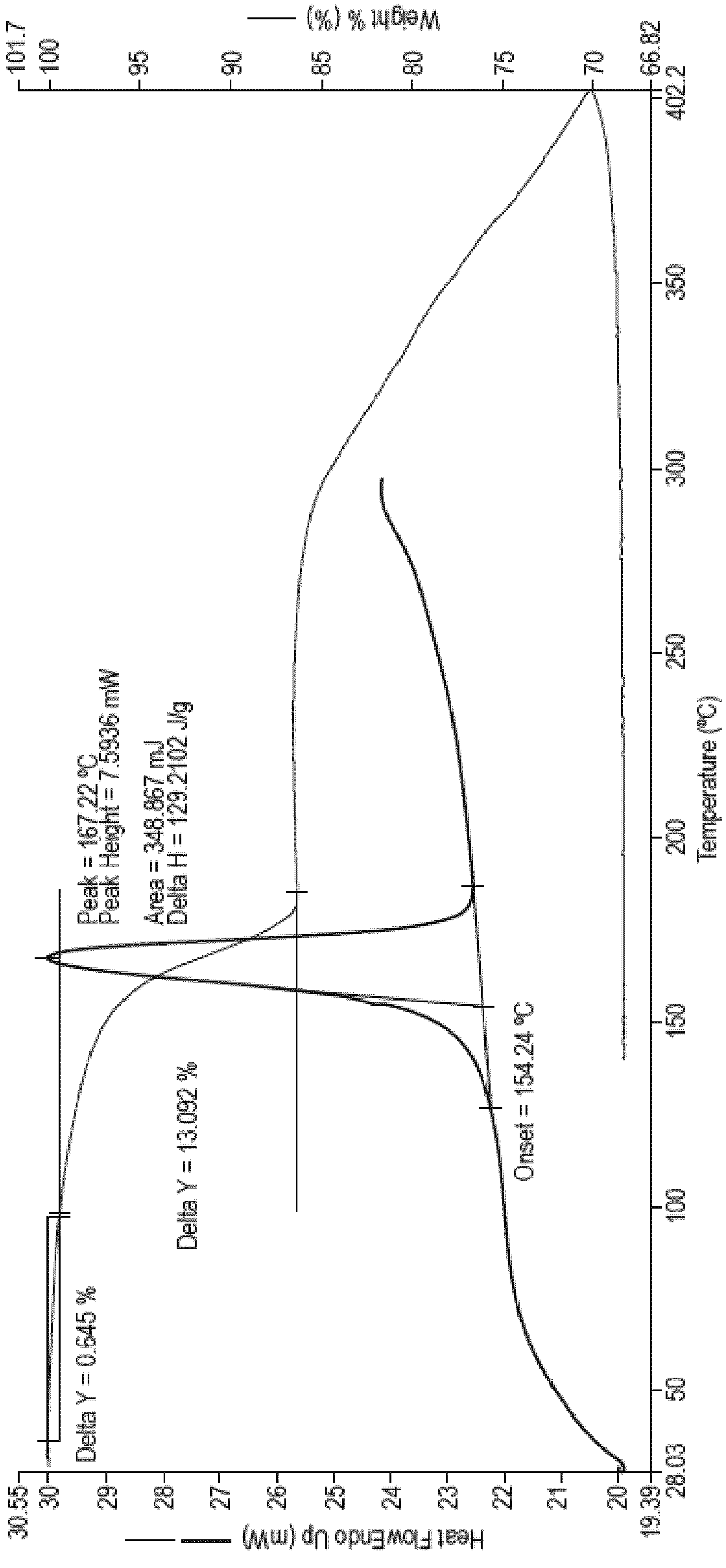
FIG. 3E is a DSC and TGA thermograph of ethanol solvate

In some embodiments, the DSC thermogram is substantially as illustrated in FIG. 3C.

In some embodiments, psilocybin Polymorph B exhibits an XRPD diffractogram characterized by the diffractogram summarized in Table 4. In some embodiments, described herein the crystalline psilocybin Polymorph B comprises at least 3 peaks of (±0.1°2θ) of Table 4. In some embodiments, the crystalline psilocybin Polymorph B comprises at least 4 peaks of (±0.1°2θ) of Table 4. In some embodiments, the crystalline psilocybin Polymorph B comprises at least 5 peaks of (±0.1°2θ) of Table 4. In some embodiments, the crystalline psilocybin Polymorph B comprising at least 8 peaks of (±0.1°2θ) of Table 4. In some embodiments, the crystalline psilocybin Polymorph B comprises at least 10 peaks of (±0.1°2θ) of Table 4.

TABLE 4

XRPD peak positions for Polymorph B

| Position [°2Θ] | Relative Intensity [%] |
|---|---|
| 5.5 | 21.33 |
| 11.1 | 36.91 |
| 11.8 | 100.00 |
| 12.5 | 12.73 |
| 14.3 | 70.23 |
| 14.9 | 50.01 |
| 15.4 | 23.67 |
| 17.1 | 51.58 |
| 17.4 | 91.25 |
| 18.0 | 12.61 |
| 19.3 | 39.33 |
| 20.0 | 76.61 |
| 20.6 | 50.26 |
| 21.5 | 20.77 |
| 22.3 | 40.19 |
| 23.9 | 13.32 |
| 24.3 | 16.03 |
| 25.3 | 32.94 |
| 28.3 | 7.60 |
| 28.9 | 17.89 |
| 29.3 | 8.96 |
| 31.3 | 6.57 |
| 32.2 | 6.90 |
| 33.8 | 2.37 |

In some embodiments, crystalline psilocybin Polymorph B is characterized by XRPD diffractogram peaks at 11.1, 11.8 and 14.3°2θ±0.1°2θ. In some embodiments, crystalline psilocybin Polymorph B is further characterized by at least one peak appearing at 14.9, 15.4, 19.3, 20.0 or 20.6°2θ±0.1°2θ. In some embodiments, crystalline psilocybin Polymorph B is further characterized by at least two peaks appearing at 14.9, 15.4, 19.3, 20.0 or 20.6°2θ±0.1°2θ. In yet a further embodiment, crystalline psilocybin Polymorph B exhibits an XRPD diffractogram substantially the same as the XRPD diffractogram shown in FIG. 2C.

In some embodiments, crystalline psilocybin Polymorph B is characterized by a single endothermic event in a DSC thermogram having an onset temperature of between 205 and 220° C., such as between 210 and 220° C., such as between 210 and 218° C., or such as between 210 and 216° C. In some embodiments, crystalline psilocybin Polymorph B exhibits a DSC thermogram substantially the same as the DSC thermogram in FIG. 3C.

In some embodiments, crystalline psilocybin Polymorph B is characterized by having a water content of <0.5% w/w, such as <0.4% w/w, such as <0.3% w/w, such as <0.2% w/w, or such as <0.1% w/w. The skilled person would know of methods to determine the water content of a compound, for example Karl Fischer Titration. In some embodiments, crystalline psilocybin Polymorph B is characterized by having <0.5% w/w loss, such as <0.4% w/w, such as <0.3% w/w, such as <0.2% w/w, such as <0.1% w/w, in the TGA thermogram between ambient temperature, such as about 25° C., and 200° C. In some embodiments, crystalline psilocybin Polymorph B loses less than 2% by weight in a loss on drying test, such as less than 1% by weight, such as less than 0.5% by weight. The loss on drying test is performed at 70° C.

In some embodiments, crystalline psilocybin Polymorph B is of a pharmaceutically acceptable chemical purity, for example, the crystalline psilocybin Polymorph B has a chemical purity of greater than 97%, such as greater than 98%, or such as greater than 99% as determined by HPLC. In some embodiments, crystalline psilocybin Polymorph B has no single impurity of greater than 1%, greater than 0.5%, greater than 0.4%, though 0.3% to 0.2% or less including phosphoric acid as measured by $^{31}P$ NMR, and psilocin as determined by HPLC. In some embodiments, crystalline psilocybin Polymorph B has a chemical purity of greater than 97 area %, greater than 98 area %, or greater than 99 area % as determined by HPLC. In some embodiments, crystalline psilocybin Polymorph B has no single impurity greater than 1 area %, greater than 0.5 area %, greater than 0.4 area %, though 0.3 area % to 0.2 area % or less, as determined by HPLC. In some embodiments, crystalline psilocybin Polymorph B has no single impurity greater than 2 area %, greater than 1.75 area %, greater than 1.5 area %, greater than 1.25 area %, greater than 1 area %, greater than 0.5 area %, greater than 0.4 area %, greater than 0.3 area %, greater than 0.2 area % or less, as determined by HPLC. In some embodiments, crystalline psilocybin Polymorph B does not contain psilocin at a level greater than 2 area %, greater than 1.75 area %, greater than 1.5 area %, greater than 1.25%, greater than 1 area %, greater than 0.5 area %, greater than 0.4 area %, greater than 0.3 area %, greater than 0.2 area % or less, as measured by HPLC. In some embodiments, crystalline psilocybin Polymorph B does not contain psilocin at a level greater than 1 area %, greater than 0.5 area %, greater than 0.4 area %, though 0.3 area % to 0.2 area % or less, as determined by HPLC. In some embodiments, crystalline psilocybin Polymorph B does not contain phosphoric acid at a level greater than 1 weight %, greater than 0.5 weight %, greater than 0.4 area %, though 0.3 area % to 0.2 area % or less, as determined by $^{31}P$ NMR. In some embodiments, crystalline psilocybin Polymorph B has a chemical assay of at least 95 weight %, such as at least 96 weight %, or such as at least 98 weight %.

In some embodiments, crystalline psilocybin Polymorph B has no single impurity of greater than 2%, greater than 1.75%, greater than 1.5%, greater than 1.25%, greater than 1%, greater than 0.5%, greater than 0.4%, greater than 0.3%, or greater than 0.2% including phosphoric acid as determined by $^{31}P$ NMR, and psilocin as determined by HPLC. In some embodiments, crystalline psilocybin Polymorph B does not contain psilocin at a level greater than 2%, greater than 1.75%, greater than 1.5%, greater than 1.25%, greater than 1%, greater than 0.5%, greater than 0.4%, greater than 0.3%, greater than 0.2% or less, as determined by HPLC. In some embodiments, crystalline psilocybin Polymorph B does not contain phosphoric acid at a level greater than 2 weight %, greater than 1.75 weight %, greater than 1.5 weight %, greater than 1.25 weight %, greater than 1 weight %, greater than 0.5 weight %, greater than 0.4 weight %, greater than 0.3 weight %, greater than 0.2 weight % or less, as determined by $^{31}P$ NMR.

The psilocybin in the form Polymorph A or A' has the general properties illustrated in Table 5 below:

TABLE 5

| | |
|---|---|
| Appearance: | White to off white solid |
| Major endothermic event in DSC (onset temperature) (corresponding to a melt): | 210-215° C. |
| Hygroscopicity: | Psilocybin forms Hydrate A at high humidity and when added to water but the water of hydration is lost rapidly on drying. The anhydrous form is therefore being developed. |
| Crystalline form: | Anhydrous Polymorph A and/ or A' |
| pKa (calculated): | 1.74, 6.71, 9.75 |
| Solubility | approx. 15 mg/ml in Water |

The psilocybin conforms to the spectra as set out in Table 6 below and illustrated in the spectra of FIGS. 5-8.

TABLE 6

| Technique | Conclusions |
|---|---|
| Proton ($^{1}H$) and Carbon ($^{13}C$) NMR | Assignment of the proton (FIG. 5) and carbon spectra (FIG. 6) are concordant with Psilocybin. |
| FT-Infrared Spectroscopy (FT-IR) | Assignment of the FT-IR spectrum (FIG. 7) is concordant with Psilocybin. |
| Mass Spectroscopy (MS) | Assignment of the mass spectrum (FIG. 8) is concordant with Psilocybin. |

The high purity is attained by careful control of reaction conditions to ensure that potential organic impurities are significantly reduced.

Known and potential impurities in Psilocybin are shown in Table 7 below:

TABLE 7

| Impurity | Relative Retention Time (RRT) | Structure | Origin |
|---|---|---|---|
| Psilocin | 1.65 | 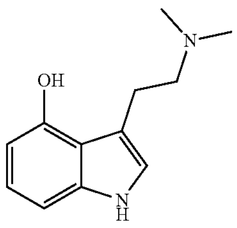 | Starting material (stage 3). Also generated by hydrolysis of Psilocybin. Only significant impurity observed in psilocybin batches. |

TABLE 7-continued

| Impurity | Relative Retention Time (RRT) | Structure | Origin |
|---|---|---|---|
| Stage 4A | | 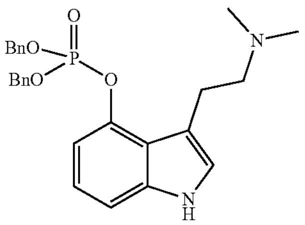 [SMILES: CN(C)CCc1c[nH]c2cccc(OP(=O)(OCc3ccccc3)OCc3ccccc3)c12] | Initial product formed in the stage 4 reaction. Converts to stage 4 on stirring in THF. Converts to Psilocybin in stage 5. |
| Stage 4 | 2.74 | 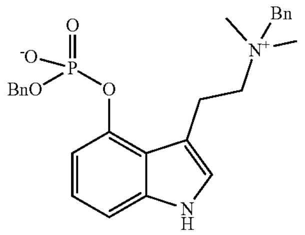 | Intermediate |
| N-Benzylated stage 4 | | 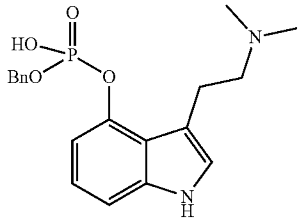 [SMILES: CN(C)CCc1c[nH]c2cccc(OP(=O)(O)OCc3ccccc3)c12] | Identified by MS in Stage 4. Converts to Psilocybin in stage 5. |
| Stage 4 Anhydride Impurity | | 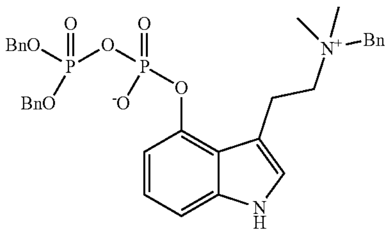 | Identified by MS in Stage 4. Converts to Stage 5 Pyrophosphoric acid impurity in stage 5. |
| Stage 5 Pyrophosphoric acid impurity | | 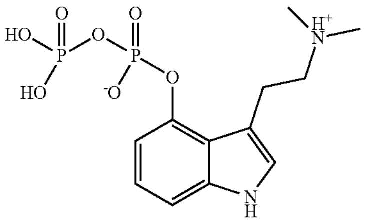 | Identified by MS Formed from the stage 4 anhydride. Removed in the stage 6 re-crystallisation by a combination of hydrolysis to Psilocybin and increased solubility due to the extra phosphate group. |
| Stage 5 (intermediates) | 1.89 and 2.45 | 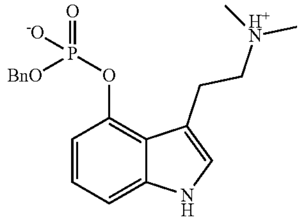 | 2 Intermediates are formed during the hydrogenation. These subsequently convert to product (structures based on chemistry). Monitored and controlled in stage 5 reaction. |

TABLE 7-continued

| Impurity | Relative Retention Time (RRT) | Structure | Origin |
|---|---|---|---|
| | | 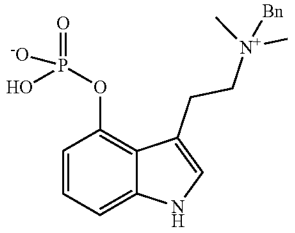 | |

Pharmaceutical Compositions of the Present Disclosure

The present disclosure provides pharmaceutical compositions containing psilocybin that are stable when stored for prolonged periods of time.

In some embodiments, the present disclosure provides a pharmaceutical composition comprising: a therapeutically effective amount of psilocybin; and one or more pharmaceutically acceptable excipients, wherein potency of the psilocybin in the composition and the mass balance of psilocybin and related substances in the composition remains at industry and pharmaceutically acceptable levels (e.g., European Pharmacopeia, USP) under industry and pharmaceutically acceptable storage conditions (e.g., European Pharmacopeia, USP) and the psilocybin is provided in pharmaceutically acceptable content uniformity (as measured by European Pharmacopeia 2.96. or USP <905>).

In some embodiments, the present disclosure provides a pharmaceutical composition comprising: a therapeutically effective amount of psilocybin; and one or more pharmaceutically acceptable excipients, wherein, after storage of the composition at 40° C. and 75% relative humidity for one month, the potency of the psilocybin in the composition decreases by less than 5% and the mass balance of psilocybin and related substances is greater than 97%.

In some embodiments, after storage of the composition at 40° C. and 75% relative humidity for two months, three months, four months, five months, or six months the potency of the psilocybin in the composition decreases by less than 5% and the mass balance of psilocybin and related substances is greater than 97%. In some embodiments, after storage of the composition at 40° C. and 75% relative humidity for two months, the potency of the psilocybin in the composition decreases by less than 5% and the mass balance of psilocybin and related substances is greater than 97%. In some embodiments, after storage of the composition at 40° C. and 75% relative humidity for the disclosed period of time, the potency of the psilocybin in the composition decreases by less than 5%, less than 4%, less than 2%, or less than 1% and the mass balance of the psilocybin and related substances in the composition is greater than 97%. In some embodiments, after storage of the composition at 40° C. and 75% relative humidity for the disclosed period of time, the potency of the psilocybin in the composition decreases by less than 5%, less than 4%, less than 2%, or less than 1% and the mass balance of the psilocybin and related substances in the composition is greater than 98% or 99%.

In some embodiments, the composition comprises about 1% to 10% by weight of psilocybin, e.g., about 1%, about 2%, about 3%, about 4%, about 5%, about 6%, about 7%, about 8%, about 9%, or about 10%, including all ranges and values therebetween. In some embodiments, the composition comprises about 1% to 15% by weight of psilocybin, e.g., about 1%, about 2%, about 3%, about 4%, about 5%, about 6%, about 7%, about 8%, about 9%, about 10%, about 11%, about 12%, about 13%, about 14% or about 15%, including all ranges and values therebetween. In some embodiments, the composition comprises about 1 mg to 40 mg of psilocybin, e.g., 1 mg, 2 mg, 3 mg, 4 mg, 5 mg, 6 mg, 7 mg, 8 mg, 9 mg, 10 mg, 12 mg, 14 mg, 16 mg, 18 mg, 20 mg, 22 mg, 24 mg, 26 mg, 28 mg, 30 mg, 32 mg, 34 mg, 36 mg, 38 mg, or 40 mg, including all ranges and values therebetween. In some embodiments, the composition comprises about 1 mg to 25 mg of psilocybin, e.g., 1 mg, 2 mg, 3 mg, 4 mg, 5 mg, 6 mg, 7 mg, 8 mg, 9 mg, 10 mg, 12 mg, 14 mg, 16 mg, 18 mg, 20 mg, 22 mg, 24 mg, or 25 mg, including all ranges and values therebetween. In some embodiments, the composition comprises about 1 mg to 10 mg of psilocybin, e.g., 1 mg, 2 mg, 3 mg, 4 mg, 5 mg, 6 mg, 7 mg, 8 mg, 9 mg, or 10 mg, including all ranges and values therebetween. In some embodiments, the composition comprises about 1 mg to 5 mg of psilocybin, e.g., 1 mg, 2 mg, 3 mg, 4 mg, or 5 mg, including all ranges and values therebetween. In some embodiments, the composition comprises about 1 mg of psilocybin. In some embodiments, the composition comprises about 5 mg of psilocybin. In some embodiments, the composition comprises 10 mg of psilocybin. In some embodiments, the composition comprises 15 mg of psilocybin. In some embodiments, the composition comprises about 20 mg of psilocybin. In some embodiments, the composition comprises about 25 mg of psilocybin.

In some embodiments, the chemical purity of the psilocybin in the composition is not less than 97%, not less than 98%, or not less than 99%, as determined by HPLC analysis. In some embodiments, the chemical purity of the psilocybin in the composition is not less than 97%, as determined by HPLC analysis.

In some embodiments, the chemical purity of the psilocybin in the composition is greater than 97%, greater than 98%, or greater than 99%, as determined by HPLC analysis. In some embodiments, the chemical purity of the psilocybin in the composition is greater than 97%, as determined by HPLC analysis. In some embodiments, the chemical purity of the psilocybin in the composition is greater than 97% and no single impurity of greater than 2% as determined by HPLC analysis. In some embodiments, the chemical purity of the psilocybin in the composition is greater than 97% and no single impurity of greater than 1% as determined by HPLC analysis.

In some embodiments, the psilocybin comprises a crystalline psilocybin. In some embodiments, the crystalline psilocybin is a crystalline psilocybin disclosed in U.S. Pat. No. 10,519,175, which is herein incorporated by reference in its entirety for all purposes. In some embodiments, the crystalline psilocybin is crystalline psilocybin Polymorph A. In some embodiments, the crystalline psilocybin is crystalline psilocybin Hydrate A. In some embodiments, the crystalline psilocybin is crystalline psilocybin Polymorph A'. In some embodiments, the crystalline psilocybin is crystalline psilocybin Polymorph B.

In some embodiments, the psilocybin comprises amorphous psilocybin.

Pharmaceutically Acceptable Excipients:

In some embodiments, the composition comprises at least one pharmaceutically acceptable excipient.

In some embodiments, the composition comprises at least one pharmaceutically acceptable excipient that does not substantially chemically or physically interact with a functional group of psilocybin. In some embodiments, the composition comprises at least one pharmaceutically acceptable excipient that does not substantially chemically or physically interact with the phosphonate ester of psilocybin. In some embodiments, the composition comprises at least one pharmaceutically acceptable excipient that does not form a covalent bond and/or hydrogen bond with the phosphonate ester of psilocybin.

In some embodiments, the composition does not contain a pharmaceutically acceptable excipient that substantially chemically or physically interacts with a functional group of psilocybin. In some embodiments, the composition does not contain a pharmaceutically acceptable excipient that substantially chemically or physically interacts with the phosphonate ester of psilocybin. In some embodiments, the composition does not contain a pharmaceutically acceptable excipient that substantially forms a covalent bond and/or hydrogen bond with the phosphonate ester of psilocybin. In some embodiments, the composition does not contain an inorganic silicate, silicon dioxide, or silicified excipient. In some embodiments, the composition does not contain aluminum calcium silicate, calcium silicate, diatomaceous earth, magnesium silicate, Perlite, potassium silicate, silica aerogel, silicon dioxide, sodium aluminosilicate, sodium calcium aluminosilicate, sodium silicate, talc (basic magnesium silicate) or tricalcium silicate. In some embodiments, the composition does not contain silicified microcrystalline cellulose.

In some embodiments, the composition does not contain a poly-hydroxylated excipient, for example a sugar alcohol or saccharide. In some embodiments, the composition does not contain polyols, mannitol, xylitol, sucrose, sorbitol or fructose.

In some embodiments, the composition does not contain a calcium base. In some embodiments, the composition does not contain calcium carbonate or calcium phosphate.

As noted above, the compositions of the present disclosure comprise one or more pharmaceutically acceptable excipients.

Diluents:

In some embodiments, the composition comprises a diluent. In some embodiments, the diluent is a starch-based material.

In some embodiments, the diluent is pregelatinized starch. As referred to herein, the term “pregelatinized starch” refers to starch that that is fully pregelatinized or partially pregelatinized. In some embodiments, the pregelatinized starch is partially pregelatinized.

In some embodiments, the pregelatinized starch comprises native starch and pre-compacted starch powder. In some embodiments, the pregelatinized starch is produced by the process comprising the steps of fluidizing a mixture comprising native starch and pre-compacted starch powder; and spraying a slurry comprising pre-compacted starch powder onto the fluidized mixture. Pre-compacted starch powder is also characterized as a partially pre-gelatinized starch. However, this is distinguished from fully or completely pre-gelatinized starch, since a significant amount of intact native starch remains in the pre-compacted starch powder.

The term “native starch” refers to the starch that is derived directly from any one of a number of plant sources. Native starch is extracted from plant sources (e.g., maize), with its granule structure remaining substantially intact. The term “pre-compacted starch powder” refers to the product obtained by subjecting a non-gelatinized, granular, native starch to physical compaction with the possible input of thermal energy. After the compaction, the starch is ground and sieved to yield a free-flowing powder.

In some embodiments, the pregelatinized starch is derived from maize starch, potato starch, wheat starch or combinations thereof. In some embodiments, the pregelatinized starch is derived from maize starch. In some embodiments, the pregelatinized starch is derived from potato starch. In some embodiments, the pregelatinized starch is derived from wheat starch.

In some embodiments, the diluent is Colorcon Starcap®, Roquette Lycatab® C, Roquette Lycatab® PGS, Grain Processing Corporation (GPC) Spress® B820, Cargil C☆PharmGel™, Insta-starch, Seppic Sepistab™ ST 200, or DFE Pharma Prejel PAH P5. Starcap® is a partially pregelatinized maize starch with engineered physical properties. StarcapR may be described on the basis of its physical characteristics, such as a Carr's Index of about 21, a flow rate of about 5.6 g/sec and an average mean particle size of about 90 microns. In some embodiments, the compositions of the present disclosure comprise Starcap®. Starcap® is described in U.S. Pat. No. 7,186,293 and E.P. Patent No. 1,861,427, which are hereby incorporated by reference in their entireties for all purposes.

In some embodiments, the compositions of the present disclosure comprise a diluent characterized by its average mean particle size. In some embodiments, the average mean particle size of the diluent is about 40 to about 200 microns, e.g., about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 105 microns, about 110 microns, about 115 microns, about 120 microns, about 125 microns, about 130 microns, about 135 microns, about 140 microns, about 145 microns, about 150 microns, about 155 microns, about 160 microns, about 165 microns, about 170 microns, about 175 microns, about 180 microns, about 185 microns, about 190 microns, about 195 microns, or about 200 microns, including all ranges and values in between. In some embodiments, the average mean particle size of the diluent is about 50 to about 120 microns. In some embodiments, the average mean particle size of the diluent is about 60 to about 120 microns. In some embodiments, the average mean particle size of the diluent is about 90 microns. In embodiments, the average mean particle size of the diluent is about 100 microns. In embodiments, the average mean particle size of the diluent is about 150 microns.

In some embodiments, the compositions of the present disclosure comprise a diluent characterized by its flow properties, such as Carr's index, Hausner ratio or flow rate.

In some embodiments, the Carr's index of the diluent is about 12 to about 25, e.g., about 12, about 13, about 14, about 15, about 16, about 17, about 18, about 19, about 20, about 21, about 22, about 23, or about 24, including all ranges and values in between. In some embodiments, the Carr's index of the diluent is less than about 11. In some embodiments, the Carr's index of the diluent is about 12 to about 16. In some embodiments, the Carr's index of the diluent is about 18 to about 21. In some embodiments, the Carr's index of the diluent is less than about 24. In some embodiments, the Carr's index of the diluent is about 16. In some embodiments, the Carr's index of the diluent is about 17. In some embodiments, the Carr's index of the diluent is about 20. In some embodiments, the Carr's index of the diluent is about 21.

In some embodiments, the Hausner ratio of the diluent is about 1.0 to about 1.6, e.g., about 1.0, about 1.05, about 1.10, about 1.15, about 1.20, about 1.25, about 1.30, about 1.35, about 1.40, about 1.45, about 1.50, about 1.55, or about 1.60, including all ranges and values in between. In some embodiments, the Hausner ratio of the diluent is less than about 1.6. In some embodiments, the Hausner ratio of the diluent is less than about 1.2. In some embodiments, the Hausner ratio of the diluent is 1.29.

In some embodiments, the flow rate of the diluent is about 2 g/sec to about 10 g/sec, as measured using a Sotax FT300 Flowability Tester (vibration setting at 1.7 g), e.g. about 2.00 g/sec, about 2.25 g/sec, about 2.50 g/sec, about 2.75 g/sec, about 3.00 g/sec, about 3.25 g/sec, about 3.50 g/sec, about 3.75 g/sec, about 4.00 g/sec, about 4.25 g/sec, about 4.50 g/sec, about 4.75 g/sec, about 5.00 g/sec, about 5.25 g/sec, about 5.50 g/sec, about 5.75 g/sec, about 6.00 g/sec, about 6.25 g/sec, about 6.50 g/sec, about 6.75 g/sec, about 7.00 g/sec, about 7.25 g/sec, about 7.50 g/sec, about 7.75 g/sec, about 8.00 g/sec, about 8.25 g/sec, about 8.50 g/sec, about 8.75 g/sec, about 9.00 g/sec, about 9.25 g/sec, about 9.50 g/sec, about 9.75 g/sec, or about 10.00 g/sec, including all ranges and values in between. In some embodiments, the flow rate of the diluent is about 3.6 g/sec. In some embodiments, the flow rate of the diluent is about 5.6 g/sec. In some embodiments, the flow rate of the diluent is about 8.5 g/sec.

In some embodiments, the compositions of the present disclosure comprise a diluent characterized by its bulk density. In some embodiments, the bulk density of the diluent is about 0.40 g/mL to about 0.70 g/mL, e.g. about 0.40 g/mL, about 0.41 g/mL, about 0.42 g/mL, about 0.43 g/mL, about 0.44 g/mL, about 0.45 g/mL, about 0.46 g/mL, about 0.47 g/mL, about 0.48 g/mL, about 0.49 g/mL, about 0.50 g/mL, about 0.51 g/mL, about 0.52 g/mL, about 0.53 g/mL, about 0.54 g/mL, about 0.55 g/mL, about 0.56 g/mL, about 0.57 g/mL, about 0.58 g/mL, about 0.59 g/mL, about 0.60 g/mL, about 0.61 g/mL, about 0.62 g/mL, about 0.63 g/mL, about 0.64 g/mL, about 0.65 g/mL, about 0.66 g/mL, about 0.67 g/mL, about 0.68 g/mL, about 0.69 g/mL, or about 0.70 g/mL, including all ranges and values in between. In some embodiments, the bulk density of the diluent is about 0.47 g/mL. In some embodiments, the bulk density of the diluent is about 0.63 g/mL.

In some embodiments, the compositions of the present disclosure comprise a diluent characterized by its moisture content. In some embodiments, the moisture content of the diluent is about 1% to about 20%, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%, including all ranges and values in between. In some embodiments, the moisture content of the diluent is about 6%. In some embodiments, the moisture content of the diluent is less than about 15%.

In some embodiments, the composition comprises about 85-99% by weight of a diluent, e.g., about 85%, about 86%, about 87%, about 88%, about 89%, about 90%, about 91%, about 92%, about 93%, about 94%, about 95%, about 96%, about 97%, about 98%, or about 99%, including all ranges and values therebetween.

In some embodiments, the diluent is pregelatinized starch. In some embodiments, the composition comprises about 85% to about 99% pregelatinized starch, e.g., about 85%, about 86%, about 87%, about 88%, about 89%, about 90%, about 91%, about 92%, about 93%, about 94%, about 95%, about 96%, about 97%, about 98%, or about 99%, including all ranges and values in between. In some embodiments, the composition comprises about 98% pregelatinized starch. In some embodiments, the composition comprises about 94% pregelatinized starch. In some embodiments, the composition comprises about 89% pregelatinized starch.

Lubricants:

In some embodiments, the composition comprises a lubricant. In some embodiments, the lubricant is selected from the group consisting of sodium stearyl fumarate, magnesium stearate, calcium stearate, zinc stearate, glyceryl monostearate, glyceryl behenate, glyceryl palmostearate, magnesium lauryl stearate, stearic acid, talc, and hydrogenated castor oil. In some embodiments, the lubricant is sodium stearyl fumarate.

In some embodiments, the composition comprises about 0.5-2.0% by weight of a lubricant, e.g., about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%, including all ranges and values in between.

In some embodiments, the lubricant is sodium stearyl fumarate. In some embodiments, the composition comprises about 0.5% to about 2.0% sodium stearyl fumarate, e.g., about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%, including all ranges and values in between. In some embodiments, the composition comprises about 1% sodium stearyl fumarate.

In some embodiments, the composition comprises about 0.5-2% by weight of the lubricant, e.g., about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, including all ranges and values therebetween.

Glidants:

In some embodiments, the composition comprises a glidant. In some embodiments, the glidant is selected from the group consisting of calcium phosphate trihydrate, calcium silicate, cellulose, powdered, colloidal silicon dioxide, magnesium silicate, silicon dioxide, starch, talc, and combinations thereof.

In some embodiments, the glidant is calcium silicate. In some embodiments, the composition comprises about 0.5% to about 2% calcium silicate, e.g., about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%, including all ranges and values in between. In some embodiments, the composition comprises about 1% calcium silicate.

In some embodiments, the glidant is silicon dioxide. In some embodiments, the glidant is colloidal silicon dioxide. In some embodiments, the composition comprises about 0.1% to about 0.5% silicon dioxide, e.g., about 0.1%, about 0.15%, about 0.2%, about 0.25%, about 0.3%, about 0.35%, about 0.4%, about 0.45%, or about 0.5%, including all ranges and values in between.

In some embodiments, the glidant is magnesium silicate. In some embodiments, the composition comprises about 0.5% to about 2% magnesium silicate, e.g., about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%, including all ranges and values in between. In some embodiments, the composition comprises about 1% magnesium silicate.

In some embodiments, the glidant is talc. In some embodiments, the composition comprises about 1% to about 10% talc, e.g., about 1.0%, about 2.0%, about 3.0%, about 4.0%, about 5.0%, about 6.0%, about 7.0%, about 8.0%, about 9.0%, or about 10.0%, including all ranges and values in between.

Disintegrants:

In some embodiments, the composition comprises a disintegrant. In some embodiments, the disintegrant is selected from the group consisting of starch (e.g., pregelatinized starch), sodium starch glycolate, povidone, crospovidone, croscarmellose sodium, polcarin, methylcellulose, hydroxypropyl cellulose (HPC), microcrystalline cellulose, carboxymethyl cellulose, sodium alginate, calcium alginate, magnesium aluminium silicate, cellulose, chitosan, colloidal silicon dioxide (SiO2), docusate sodium, guar gum and combinations thereof. In some embodiments, the composition comprises about 0.1% to about 98% disintegrant, e.g. about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.4%, about 2.6%, about 2.8%, about 3.0%, about 3.2%, about 3.4%, about 3.6%, about 3.8%, about 4.0%, about 4.2%, about 4.4%, about 4.6%, about 4.8%, about 5.0%, about 5.5%, about 6.0%, about 6.5%, about 7.0%, about 7.5%, about 8.0%, about 8.5%, about 9.0%, about 9.5%, about 10.0%, about 11.0%, about 12.0%, about 13.0%, about 14.0%, about 15.0%, about 16.0%, about 17.0%, about 18.0%, about 19.0%, about 20.0%, about 22.0%, about 24.0%, about 26.0%, about 28.0%, about 30.0%, about 33.0%, about 36.0%, about 39.0%, about 42.0%, about 46.0%, about 50.0%, about 54.0%, about 58.0%, about 62.0%, about 68.0%, about 74.0%, about 80.0%, about 86.0%, about 92.0%, or about 98.0%, including all ranges and values in between.

In some embodiments, the disintegrant is starch. In some embodiments, the starch is pregelatinized starch. In some embodiments, the composition comprises about 50% to about 98% starch, e.g., about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, or about 98%, including all ranges and values in between.

In some embodiments, the disintegrant is sodium starch glycolate. In some embodiments, the composition comprises about 2% to about 8% sodium starch glycolate, e.g., about 2.0%, about 2.5%, about 3.0%, about 3.5%, about 4.0%, about 4.5%, about 5.0%, about 5.5%, about 6.0%, about 6.5%, about 7.0%, about 7.5%, or about 8.0%, including all ranges and values in between. In some embodiments, the composition comprises about 4% sodium starch glycolate.

In some embodiments, the disintegrant is povidone. In some embodiments, the composition comprises about 0.5% to about 5% povidone, about 0.5%, about 1.0%, about 1.5%, about 2.0%, about 2.5%, about 3.0%, about 3.5%, about 4.0%, about 4.5%, or about 5.0%, including all ranges and values in between.

In some embodiments, the disintegrant is crospovidone. In some embodiments, the composition comprises about 2% to about 5% crospovidone, e.g., about 2.0%, about 2.5%, about 3.0%, about 3.5%, about 4.0%, about 4.5%, or about 5.0%, including all ranges and values in between.

In some embodiments, the disintegrant is croscarmellose sodium. In some embodiments, the composition comprises about 10% to about 25% croscarmellose sodium, e.g., about 10%, about 11%, about 12%, about 13%, about 14%, about 15%, about 16%, about 17%, about 18%, about 19%, about 20%, about 21%, about 22%, about 23%, about 24%, or about 25%, including all ranges and values in between. In some embodiments, the composition comprises about 17.5% croscarmellose sodium.

In some embodiments, the disintegrant is polcarin potassium. In some embodiments, the composition comprises about 2% to about 10% polcarin potassium, e.g., about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0%, including all ranges and values in between. In some embodiments, the composition comprises about 2% to about 3% polcarin potassium.

In some embodiments, the disintegrant is methylcellulose. In some embodiments, the composition comprises about 2% to about 10% methylcellulose, e.g., about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0%, including all ranges and values in between. In some embodiments, the composition comprises about 5% methylcellulose.

In some embodiments, the disintegrant is hydroxypropyl cellulose. In some embodiments, the composition comprises about 2% to about 5% hydroxypropyl cellulose, e.g., about 2.0%, about 2.5%, about 3.0%, about 3.5%, about 4.0%, about 4.5%, or about 5.0%, including all ranges and values in between. In some embodiments, the composition comprises about 2% to about 3% hydroxypropyl cellulose.

In some embodiments, the disintegrant is microcrystalline cellulose. In some embodiments, the composition comprises about 5% to about 15% microcrystalline cellulose, e.g., about 5%, about 6%, about 7%, about 8%, about 9%, about 10%, about 11%, about 12%, about 13%, about 14%, or about 15%, including all ranges and values in between. In some embodiments, the composition comprises about 10% microcrystalline cellulose.

In some embodiments, the disintegrant is carboxymethyl cellulose. In some embodiments, the composition comprises about 1% to about 6% carboxymethyl cellulose, e.g., about 1.0%, about 1.5%, about 2.0%, about 2.5%, about 3.0%, about 3.5%, about 4.0%, about 4.5%, about 5.0%, about 5.5%, or about 6.0%, including all ranges and values in between. In some embodiments, the composition comprises about 2% to about 3% carboxymethyl cellulose.

In some embodiments, the disintegrant is sodium alginate. In some embodiments, the composition comprises about 2.5% to about 10% sodium alginate, e.g., about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0%, including all ranges and values in between. In some embodiments, the composition comprises about 4% to about 5% sodium alginate.

In some embodiments, the disintegrant is calcium alginate. In some embodiments, the composition comprises about 2.5% to about 10% calcium alginate, e.g., about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0%, including all ranges and values in between. In some embodiments, the composition comprises about 4% to about 5% calcium alginate.

In some embodiments, the disintegrant is magnesium aluminum silicate

In some embodiments, the disintegrant is chitosan.

In some embodiments, the disintegrant is colloidal silicon dioxide. In some embodiments, the composition comprises about 0.1% to about 0.55% colloidal silicon dioxide, e.g., about 0.1%, about 0.15%, about 0.2%, about 0.25%, about 0.3%, about 0.35%, about 0.4%, about 0.45%, about 0.5%, or about 0.55%, including all ranges and values in between.

In some embodiments, the disintegrant is cellulose. In some embodiments, the composition comprises about 5% to about 15% cellulose, e.g., about 5%, about 6%, about 7%, about 8%, about 9%, about 10%, about 11%, about 12%, about 13%, about 14%, or about 15%, including all ranges and values in between.

In some embodiments, the disintegrant is docusate sodium. In some embodiments, the composition comprises about 0.1% to about 1.0% docusate sodium, e.g., about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, In some embodiments, the composition comprises about 0.5% docusate sodium.

Dosage Forms:

According to the present disclosure, the pharmaceutical composition may be in any pharmaceutically acceptable form that maintains the integrity and potency of the psilocybin contained therein and provides pharmaceutically acceptable psilocybin content uniformity (as measured by European Pharmacopeia 2.96. or USP <905>). In some embodiments, the pharmaceutical composition is in solid form. In some embodiments, the pharmaceutical composition is an oral dosage form. In some embodiments, the pharmaceutical composition is solution (for example, an aqueous solution). In some embodiments, the pharmaceutical composition is a tablet. In some embodiments, the pharmaceutical composition is a capsule. In some embodiments, the pharmaceutical composition is a powder.

In some embodiments, the pharmaceutical composition comprises psilocybin; about 85-99% by weight of a diluent and about 0.5-2% by weight of the lubricant.

In some embodiments, the composition comprises: psilocybin; about 85-99% by weight of a diluent, e.g., about 85%, about 86%, about 87%, about 88%, about 89%, about 90%, about 91%, about 92%, about 93%, about 94%, about 95%, about 96%, about 97%, about 98%, or about 99%, including all ranges and values therebetween; and about 0.5-2% by weight of the lubricant, e.g., about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, including all ranges and values therebetween.

In some embodiments, the composition comprises: psilocybin; about 85-99% by weight of Pregelatinized starch (Starcap), e.g., about 85%, about 86%, about 87%, about 88%, about 89%, about 90%, about 91%, about 92%, about 93%, about 94%, about 95%, about 96%, about 97%, about 98%, or about 99%, including all ranges and values therebetween; and about 0.5-2% by weight of Sodium Stearyl Fumarate, e.g., about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, including all ranges and values therebetween.

In some embodiments, the composition comprises about 1% by weight of psilocybin, about 98% by weight of a diluent, and about 1% by weight of a lubricant. In some embodiments, the composition comprises about 1% by weight of psilocybin, about 98% by weight of Pregelatinized starch (Starcap), and about 1% by weight of Sodium Stearyl Fumarate.

In some embodiments, the composition comprises about 5% by weight of psilocybin, about 94% by weight of a diluent, and about 1% by weight of a lubricant. In some embodiments, the composition comprises about 5% by weight of psilocybin, about 94% by weight of Pregelatinized starch (Starcap), and about 1% by weight of Sodium Stearyl Fumarate.

In some embodiments, the composition comprises about 10% by weight of psilocybin, about 89% by weight of a diluent, and about 1% by weight of a lubricant. In some embodiments, the composition comprises about 10% by weight of psilocybin, about 89% by weight of Pregelatinized starch (Starcap), and about 1% by weight of Sodium Stearyl Fumarate.

In some embodiments, the pharmaceutical composition is a capsule. In some embodiments, the capsule material comprises methylcellulose, gellan gum, carrageenan, pectin, glycerin, hydroxypropyl (HP) starch, plasticizer, buffer (e.g., phosphate buffer), amorphous starch (e.g., amylopectin), a softener or combinations thereof. In some embodiments, the capsule material comprises hydroxypropyl methylcellulose. In some embodiments, the capsule material comprises starch (e.g., hydroxypropyl starch or amylopectin). In some embodiments, the capsule material is VcapsPlus®, Vcaps®, Quali-V®, EMBROCaps®-VG, VegiCaps®, SeaGel™, or VegaGels®.

In some embodiments, the capsule material comprises about 1% to about 7% moisture content, e.g., about 1%, about 2%, about 3%, about 4%, about 5%, about 6% or about 7%, including all ranges and values in between. In some embodiments, the capsule material comprises less than about 6% moisture content. In some embodiments, the capsule material comprises about 3% to about 7% moisture content. In some embodiments, the capsule material comprises about 4% to about 6% moisture content.

In some embodiments, the content uniformity of the compositions of the present disclosure comply with the European Pharmacopeia 2.96. or USP <905>.

Powder Blends:

In some embodiments, the compositions of the present disclosure comprise a powder blend (i.e., a mixture of psilocybin and one or more pharmaceutically acceptable excipients) that is suitable for use in a capsule. In some embodiments, the compositions of the present disclosure comprise a powder blend that is suitable for direct compression to provide a tablet.

In some embodiments, the powder blends of the present disclosure are characterized by their flow properties, such as the Carr's index or the Hausner ratio.

In some embodiments, the Carr's index of the powder blend is about 12 to about 25, e.g., about 12, about 13, about 14, about 15, about 16, about 17, about 18, about 19, about 20, about 21, about 22, about 23, or about 24 including all ranges and values in between. In some embodiments, the Carr's index of the powder blend is less than about 11. In some embodiments, the Carr's index of the powder blend is about 12 to about 16. In some embodiments, the Carr's index of the powder blend is about 18 to about 21. In some embodiments, the Carr's index of the powder blend is less than about 24. In some embodiments, the Carr's index of the powder blend is about 16. In some embodiments, the Carr's index of the powder blend is about 17. In some embodiments, the Carr's index of the powder blend is about 20. In some embodiments, the Carr's index of the powder blend is about 21.

In some embodiments, the Hausner ratio of the powder blend is about 1.0 to about 1.6, e.g., about 1.00, about 1.05, about 1.10, about 1.15, about 1.20, about 1.25, about 1.30, about 1.35, about 1.40, about 1.45, about 1.50, about 1.55, or about 1.6, including all ranges and values in between. In some embodiments, the Hausner ratio of the powder blend is less than about 1.6. In some embodiments, the Hausner ratio of the powder blend is less than about 1.2. In some embodiments, the Hausner ratio of the powder blend is 1.29.

In some embodiments, the powder blends of the present disclosure are characterized by their bulk density In some embodiments, the bulk density of the powder blend is about 0.40 g/mL to about 0.70 g/mL, e.g. about 0.40 g/mL, about 0.41 g/mL, about 0.42 g/mL, about 0.43 g/mL, about 0.44 g/mL, about 0.45 g/mL, about 0.46 g/mL, about 0.47 g/mL, about 0.48 g/mL, about 0.49 g/mL, about 0.50 g/mL, about 0.51 g/mL, about 0.52 g/mL, about 0.53 g/mL, about 0.54 g/mL, about 0.55 g/mL, about 0.56 g/mL, about 0.57 g/mL, about 0.58 g/mL, about 0.59 g/mL, about 0.60 g/mL, about 0.61 g/mL, about 0.62 g/mL, about 0.63 g/mL, about 0.64 g/mL, about 0.65 g/mL, about 0.66 g/mL, about 0.67 g/mL, about 0.68 g/mL, about 0.69 g/mL, or about 0.70 g/mL, including all ranges and values in between. In some embodiments, the bulk density of the powder blend is about 0.44 g/mL to 0.52 g/mL. In some embodiments, the bulk density of the powder blend is about 0.45 g/mL to 0.55 g/mL. In some embodiments, the bulk density of the powder blend is about 0.47 g/mL. In some embodiments, the bulk density of the composition is about 0.63 g/mL.

In some embodiments, the powder blends of the present disclosure are characterized by their ratio of native starch to pre-compacted starch. In some embodiments, the ratio of native starch to pre-compacted starch is about 70:30 to about 99:1, e.g., about 70:30, about 71:29, about 72:28, about 73:27, about 74:26, about 75:25, about 76:24, about 77:23, about 78:22, about 79:21, about 80:20, about 81: 19, about 82:18, about 83: 17, about 84: 16, about 85:15, about 86:14, about 87:13, about 88: 12, about 89: 11, about 90: 10, about 91:9, about 92:8, about 93:7, about 94:6, about 95:5, about 96:4, about 97:3, about 98:2, or about 99: 1, including all ranges and values in between. In some embodiments, ratio of native starch to pre-compacted starch is about 85:15 to about 95:5.

In some embodiments, the powder blend comprises: psilocybin; about 85-99% by weight of a diluent and about 0.5-2% by weight of the lubricant.

In some embodiments, the powder blend comprises: psilocybin about 85-99% by weight of a diluent, e.g., about 85%, about 86%, about 87%, about 88%, about 89%, about 90%, about 91%, about 92%, about 93%, about 94%, about 95%, about 96%, about 97%, about 98%, or about 99%, including all ranges and values therebetween; and about 0.5-2% by weight of the lubricant, e.g., about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, including all ranges and values therebetween.

In some embodiments, the powder blend comprises: psilocybin; about 85-99% by weight of Pregelatinized starch (Starcap), e.g., about 85%, about 86%, about 87%, about 88%, about 89%, about 90%, about 91%, about 92%, about 93%, about 94%, about 95%, about 96%, about 97%, about 98%, or about 99%, including all ranges and values therebetween; and about 0.5-2% by weight of Sodium Stearyl Fumarate, e.g., about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, including all ranges and values therebetween.

In some embodiments of the present method, the powder blend comprises about 1% to 10% by weight of psilocybin, e.g., about 1%, about 2%, about 3%, about 4%, about 5%, about 6%, about 7%, about 8%, about 9%, or about 10%, including all ranges and values therebetween. In some embodiments, the powder blend comprises about 1% to 15% by weight of psilocybin, e.g., about 1%, about 2%, about 3%, about 4%, about 5%, about 6%, about 7%, about 8%, about 9%, about 10%, about 11%, about 12%, about 13%, about 14% or about 15%, including all ranges and values therebetween.

In some embodiments, the powder blend comprises about 1% by weight of psilocybin, about 98% by weight of a diluent, and about 1% by weight of a lubricant. In some embodiments, the powder blend comprises about 1% by weight of psilocybin, about 98% by weight of Pregelatinized starch (Starcap), and about 1% by weight of Sodium Stearyl Fumarate.

In some embodiments, the powder blend comprises about 5% by weight of psilocybin, about 94% by weight of a diluent, and about 1% by weight of a lubricant. In some embodiments, the powder blend comprises about 5% by weight of psilocybin, about 94% by weight of Pregelatinized starch (Starcap), and about 1% by weight of Sodium Stearyl Fumarate.

In some embodiments, the composition comprises about 10% by weight of psilocybin, about 89% by weight of a diluent, and about 1% by weight of a lubricant. In some embodiments, the powder blend comprises about 10% by weight of psilocybin, about 89% by weight of Pregelatinized starch (Starcap), and about 1% by weight of Sodium Stearyl Fumarate.

In some embodiments, the content uniformity of the powder blends of the present disclosure comply with the European Pharmacopeia 2.96. or USP <905>.

Methods of Making the Pharmaceutical Compositions of the Present Disclosure

In some embodiments, the present disclosure provides a method of making a pharmaceutical composition comprising: (a) direct mixing psilocybin and one or more pharmaceutically acceptable excipients to provide a blend and (b) filling a capsule with the blend to provide the pharmaceutical composition, wherein the content uniformity of the composition complies with the European Pharmacopeia 2.96. or USP <905>.

In some embodiments, the blend is prepared by blending psilocybin and the one or more pharmaceutically acceptable excipients for about 15 to about 60 minutes, e.g., about 15 minutes, about 20 minutes, about 25 minutes, about 30 minutes, about 35 minutes, about 40 minutes, about 45 minutes, about 50 minutes, about 55 minutes or about 60 minutes. In some embodiments, the blending is carried out in one or more stages. In some embodiments, the blending is carried out in 2 stages. In some embodiments, the blending is carried out in 3 stages.

In some embodiments of the present method, the mass balance of psilocybin and related substances in the composition decreases by less than 3% after storage of the composition at 40° C. and 75% relative humidity for one month. In some embodiments, the mass balance of psilocybin and related substances in the composition decreases by less than 3% after storage of the composition at 40° C. and 75% relative humidity for two months.

In some embodiments of the present method, the blend comprises about 1% to 10% by weight of psilocybin, e.g., about 1%, about 2%, about 3%, about 4%, about 5%, about 6%, about 7%, about 8%, about 9%, or about 10%, including all ranges and values therebetween. In some embodiments, the blend comprises about 1% to 15% by weight of psilocybin, e.g., about 1%, about 2%, about 3%, about 4%, about 5%, about 6%, about 7%, about 8%, about 9%, about 10%, about 11%, about 12%, about 13%, about 14% or about 15%, including all ranges and values therebetween. In some embodiments, the capsule contains 1 mg to 40 mg of psilocybin, e.g., 1 mg, 2 mg, 3 mg, 4 mg, 5 mg, 6 mg, 7 mg, 8 mg, 9 mg, 10 mg, 12 mg, 14 mg, 16 mg, 18 mg, 20 mg, 22 mg, 24 mg, 26 mg, 28 mg, 30 mg, 32 mg, 34 mg, 36 mg, 38 mg, or 40 mg, including all ranges and values therebetween. In some embodiments, the capsule comprises about 1 mg to 25 mg of psilocybin, e.g., 1 mg, 2 mg, 3 mg, 4 mg, 5 mg, 6 mg, 7 mg, 8 mg, 9 mg, 10 mg, 12 mg, 14 mg, 16 mg, 18 mg, 20 mg, 22 mg, 24 mg, or 25 mg, including all ranges and values therebetween. In some embodiments, the capsule comprises about 1 mg to 10 mg of psilocybin, e.g., 1 mg, 2 mg, 3 mg, 4 mg, 5 mg, 6 mg, 7 mg, 8 mg, 9 mg, or 10 mg, including all ranges and values therebetween. In some embodiments, the capsule comprises about 1 mg to 5 mg of psilocybin, e.g., 1 mg, 2 mg, 3 mg, 4 mg, or 5 mg, including all ranges and values therebetween. In some embodiments, the capsule contains 1 mg, 5 mg, 10 mg, or 25 mg of psilocybin. In some embodiments, the capsule contains 1 mg of psilocybin. In some embodiments, the capsule contains 5 mg of psilocybin. In some embodiments, the capsule contains 10 mg of psilocybin. In some embodiments, the capsule contains 15 mg of psilocybin. In some embodiments, the capsule contains 20 mg of psilocybin. In some embodiments, the capsule contains 25 mg of psilocybin.

In some embodiments of the present method, the blend comprises one or more pharmaceutically acceptable excipients. In some embodiments, the one or more pharmaceutically acceptable excipients comprises a diluent. In some embodiments, the diluent is pregelatinized starch.

In some embodiments of the present method, the blend further comprises a lubricant. In some embodiments, the lubricant is selected from the group consisting of sodium stearyl fumarate, magnesium stearate, calcium stearate, zinc stearate, glyceryl monostearate, glyceryl behenate, glyceryl palmostearate, magnesium lauryl stearate, stearic acid, talc, and hydrogenated castor oil. In some embodiments, the lubricant is sodium stearyl fumarate.

In some embodiments, the blend does not contain a glidant.

Figure 9:
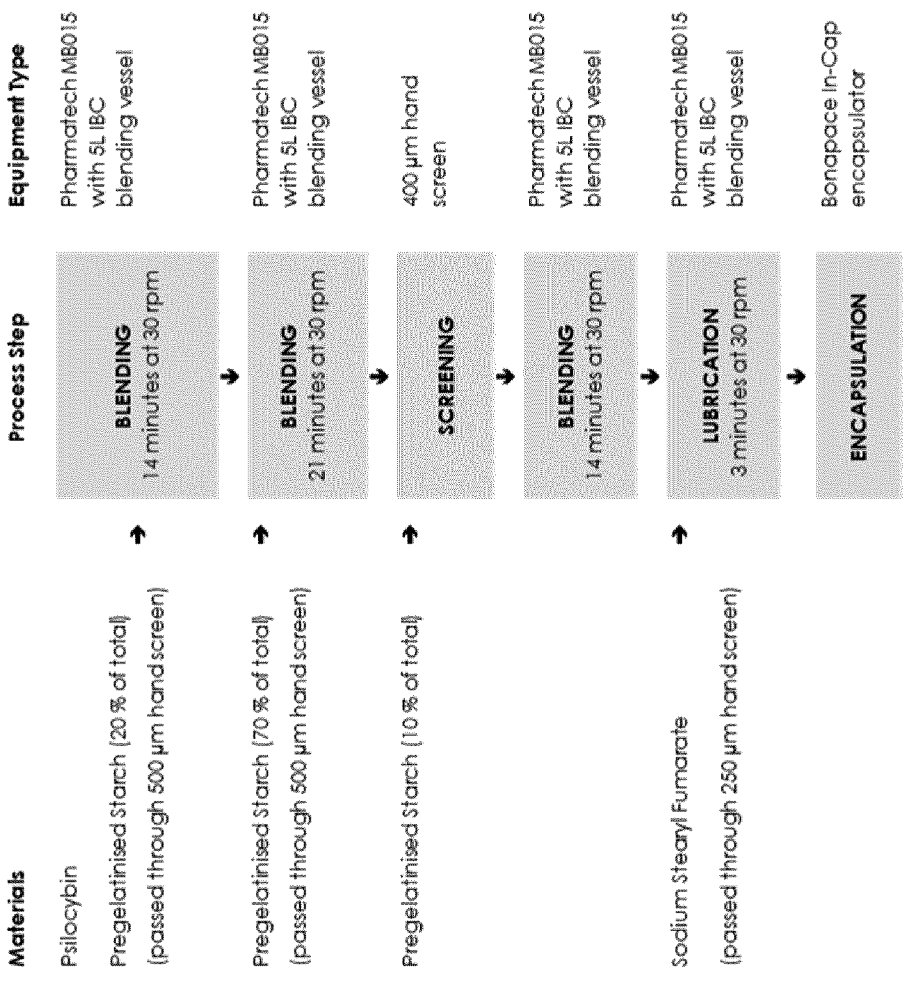
FIG. 9 shows a non-limiting example of a process flow diagram for preparing psilocybin capsules of the present disclosure.

In some embodiments, the method of making a pharmaceutical composition of the present disclosure is the method described in FIG. 9.

Without being bound by any particular theory, it was surprisingly found that the disclosed methods of making pharmaceutical compositions by direct mixing psilocybin and one or more pharmaceutically acceptable excipients provide compositions with pharmaceutically acceptable content uniformity (as measured by European Pharmacopeia 2.96. or USP <905>) even at low levels of drug loading.

Methods of Treating Depressive Disorders

In some embodiments, the methods provided herein are used to treat a subject with a depressive disorder, comprising administering a therapeutically effect of a composition disclosed herein. In some embodiments, the methods provided herein are used to treat a subject with a mood disorder, comprising administering a therapeutically effect of a composition disclosed herein. The compositions of the present disclosure may be used to treat any condition or disorder that is treatable by administration of psilocybin. Methods of the present disclosure may be used to treat disorders described in PCT Publication No. WO2020/212951, WO2020/212948 and WO2020/212952, which are hereby incorporated by reference in their entireties for all purposes.

In some embodiments, the depressive disorder is major depressive disorder, atypical depression, bipolar disorder, catatonic depression, depressive disorder due to a medical condition, postpartum depression, premenstrual dysphoric disorder, or seasonal affective disorder.

In some embodiments, a depressive disorder comprises a medical diagnosis based on the criteria and classification from Diagnostic and Statistical Manual of Medical Disorders, 5th Ed. In some embodiments, a depressive disorder comprises a medical diagnosis based on an independent medical evaluation.

In some embodiments, the methods described herein are provided to a subject with depression that is resistant to treatment. In some embodiments, the subject has been diagnosed with "treatment-resistant depression". The term "treatment-resistant depression" refers to a kind of depression that does not respond or is resistant to at least one or more treatment attempts of adequate dose and duration. In some embodiments, the subject with treatment-resistant depression has failed to respond to 1 treatment attempt, 2 treatment attempts, 3 treatment attempts, 4 treatment attempts, or 5 treatment attempts. In some embodiments, the subject with treatment-resistant depression has been diagnosed with major depressive disorder and has failed to respond to 3 or more treatment attempts. In some embodiments, the subject with treatment-resistant depression has been diagnosed with bipolar disorder and has failed to respond to 1 treatment attempt.

In some embodiments, the methods provided herein reduce at least one sign or symptom of a depressive disorder. In some embodiments, the methods provided herein reduce at least one sign or symptom of a depressive disorder by between about 5% and about 100%, for example, about 5%, about 10%, about 15%, about 20%, about 25%, about 30%, about 35%, about 40% , about 45%, about 50%, about 55%, about 60%, about 65%, about 70%, about 75%, about 80%, about 85%, about 90%, about 95%, or about 100%, or more, compared to prior to treatment.

In some embodiments, no other treatment is administered to the subject to reduce the sign or symptom of depression after administration of the psilocybin.

In some embodiments, the method of the present disclosure further comprises administering to the subject at least one additional therapeutic to reduce the sign or symptom of depression. In some embodiments, at least one additional therapeutic is a selective serotonin reuptake inhibitor, a serotonin and norepinephrine reuptake inhibitor, a tricyclic antidepressant, a tetracyclic antidepressant, a dopamine reuptake inhibitor, a 5-HT1A receptor antagonist, a 5-HT2 receptor antagonist, a 5-HT3 receptor antagonist, a monoamine oxidase inhibitor, or a noradrenergic antagonist. In some embodiments, at least one additional therapeutic is administered prior to administration of psilocybin, on the same day as the administration of psilocybin, or after administration of psilocybin.

In some embodiments, the subject with the depressive disorder has an additional comorbidity or disorder. In some embodiments, the additional comorbidity or disorder is an anxiety disorder, an obsessive-compulsive disorder, alcoholism, a personality disorder, a cardiovascular disease, a neurological disease, or cancer. In some embodiments, the subject has dementia, Alzheimer's Disease, or Parkinson's Disease. In some embodiments, reducing at least one sign or symptom of depression in the subject using the methods of the present disclosure prevents one or more comorbidities or disorders in the subject.

EXAMPLES

The following examples, which are included herein for illustration purposes only, are not intended to be limiting.

Example 1: Composition AND Stability OF Psilocybin Tablets Containing Silicified Microcrystalline Starch Following formulation optimization, 1 mg and 5 mg psilocybin-containing tablets having the shown in Table 8 were prepared and subjected to 6-month drug product stability studies.

TABLE 8

Unit Formula for 1 mg and 5 mg Psilocybin Tablets

| Excipient | 1 mg (%) | 1 mg (g) | 5 mg (%) | 5 mg (g) |
|---|---|---|---|---|
| Psilocybin (COM 360) | 1.0 | 7.0 | 5.0 | 35.0 |
| Silicified Microcrystalline Cellulose (SMCC 50) | 20.5 | 143.5 | 12.5 | 87.5 |
| Silicified Microcrystalline Cellulose (SMCC 90) | 75.5 | 528.5 | 79.5 | 556.5 |
| Sodium Starch Glycolate | 1.0 | 7.0 | 1.0 | 7.0 |

TABLE 8-continued

Unit Formula for 1 mg and 5 mg Psilocybin Tablets

| Excipient | 1 mg (%) | 1 mg (g) | 5 mg (%) | 5 mg (g) |
|---|---|---|---|---|
| Colloidal silicon Dioxide (Aerosil) | 1.0 | 7.0 | 1.0 | 7.0 |
| Sodium Stearyl Fumarate (Pruv) | 1.0 | 7.0 | 1.0 | 7.0 |
| TOTAL | 100.0 | 700.0 | 100.0 | 700.0 |

Results: The stability study storage conditions and results are shown in Table 9 and Table 10, below. Upon storage, the tablets became discolored and lost API potency. However, there was no obvious, commensurate increase in psilocybin-related impurities, for example, psilocin (i.e., there was an apparent loss of mass balance). Thus, even when the tablets were stored in the presence of a desiccant, the drug product stability was determined to be unsuitable for a pharmaceutical product.

TABLE 9

Stability of 1 mg Psilocybin Tablet

| Storage condition | Initials | T = 1 m | T = 3 m | T = 6 m | Comments |
|---|---|---|---|---|---|
| 25'C./60% RH (with desiccant) | 96.0% | 93.0% | 95.0% | 92.0% | No mass balance and no obvious linear increases in psilocin |
| 40'C./75% RH (with desiccant) | 96.0% | 92.0% | 93.0% | 93.0% | No mass balance and no obvious linear increases in psilocin |
| 40'C./75% RH (without desiccant) | 96.0% | 93.0% | 91.0% | 81.0% | No mass balance and no obvious linear increases in psilocin. |

TABLE 10

Stability of Psilocybin 5 mg Tablets

| Storage condition | Initials | T = 1 m | T = 3 m | T = 6 m | Comments |
|---|---|---|---|---|---|
| 25'C./60% RH (with desiccant) | 100.0% | 98.0% | 97.0%[1] | 94.0% | No mass balance and no obvious linear increases in psilocin |
| 40'C./75% RH (with desiccant) | 100.0% | 98.0% | 98.0%[1] | 96.0% | No mass balance and no obvious linear increases in psilocin |
| 40'C./75% RH (without desiccant) | 100.0% | 98.0% | 96.0%[1] | 93.0% | No mass balance and no obvious linear increases in psilocin |

[1]browning first observed

Discussion: To determine the role that water may play in the loss of mass balance, a moisture barrier aqueous film coating was applied to the tablet to reduce moisture penetration. However, the coated tablets had even lower stability. Another possibility is that the amorphous form could have been formed during compression of the tablet. Amorphous forms are less stable than their crystalline counterparts, and in certain circumstances degrade via different mechanisms, which could potentially explain the lack of obvious API degradation. This too was ruled out after it became clear that low recoveries were being seen when blends were manufactured by other methods, again without accompanying degradation. Furthermore, similarly instability was observed in capsules that were prepared by filling empty capsules with the tablet formulation blend (i.e., the excipient blend of Table 8).

Example 2: Composition and Stability of Psilocybin Capsules in the Absence of Silicon Dioxide-Based Excipients Experiments were conducted to explore whether the observed loss of mass balance upon product storage resulted from the interaction of silanized microcrystalline cellulose and/or colloidal silica (both added to enhance flow of the API) with the psilocybin (e.g., irreversible binding of the psilocybin to the excipient surface).

Without being bound by any theory, it was hypothesized that psilocybin (via its phosphonate ester group) could form a strong interaction (e.g., H-bond) with the silanized surface resulting in a loss of potency without a commensurate increase in psilocybin-related impurities.

Two capsule formulations using starch-based excipients starch 1500 and Starcap were evaluated. Blends containing 1% (1 mg) and 10% (25 mg) of psilocybin were prepared with each excipient. Table 11 shows the physical properties of each blend. Starcap showed superior filling and content uniformity as shown in.

TABLE 11

Comparison of Starch 1500 and Starcap Formulations

| Batch Details | Starch 1500 | | Starcap | |
|---|---|---|---|---|
| Batch size (g) | 700 | 700 | 700 | 100 |
| Blend Strength | 1% | 10% | 1% | 10% |
| Capsule Strength (mg) | 1 | 25 | 25 | 1 |
| Bulk Density (g/ml) | 0.66 | 0.56 | 0.50 | 048 |
| Carr's Index (%) | 17 | 21 | 16 | 20 |
| Mean Blend Assay | 101 | 101 | 98 | 98 |
| Blend RSD (%) | 1.9 | 0.7 | 3.8 | 1.1 |
| Mean capsule fill weight (mg) | 112 | 243 | 100 | 259 |
| range | 109-117 | 219-269 | 94-105 | 252-269 |
| Fill Weight RSD (%) | 2.1 | 6.1* | 2.7 | 1.6 |
| Mean Capsule Assay 9%) | 99 | 96 | 97 | 98 |
| Mean content uniformity (%) | 99 | 97 | 98 | 96 |
| Content Uniformity, AV | 4.3 | 19.8* | 5.5 | 9.0 |

*Fail

The Starcap formulation was selected for further development. Table 12 shows the capsule composition and FIG. 9 shows the method of preparing the composition using a direct mixing method. These capsules were tested for their stability, below.

TABLE 12

Unit Formula for Psilocybin Capsules

| Excipient | 1 mg (%) | 1 mg (g) | 5 mg (%) | 5 mg (g) | 25 mg (%) | 25 mg (g) |
|---|---|---|---|---|---|---|
| Psilocybin (COM 360) | 1.0 | 7.0 | 5.0 | 35.0 | 10.0 | 70.0 |
| Pregelatinized starch (Starcap) | 98.0 | 686 | 94.0 | 658 | 89.0 | 623.0 |
| Sodium Stearyl Fumarate (Pruv) | 1.0 | 7.0 | 1.0 | 7.0 | 1.0 | 7.0 |
| Capsule, HPMC, white opaque | 1 unit | Size 2* | 1 unit | Size 2* | 1 unit | Size 0** |
| TOTAL | 100.0 | 700.0 | 100.0 | 700.0 | 100.0 | 700.0 |

*fill weight 100 mg,
**fill weight 250mg

Table 13 shows the results from storage of the 1 mg capsules (with desiccant) at 25° C./60% RH for one and two months. The data shows that the capsules were within specification and complied with all measured parameters at both timepoints.

TABLE 13

Stability Data for Psilocybin 1 mg Capsules (with Desiccant) - Stored at 25° C./60% RH

| Attribute | Method | Specification | Initial | 1 M | 2 M |
|---|---|---|---|---|---|
| Appearance | Visual | Off-white powder in a white size 2 capsule | Complies | Complies | Complies |
| Assay | HPLC | 90.0%-110.0% LC (0.90-1.10 mg) | 100.5% | 100.6% | 98.8% |
| Related Substances | HPLC | Psilocin NMT 1.0% Ind. impurities NMT 0.5% | 0.5% | 0.4% | 0.4% |
| | | RRT 1.24 | 0.1% | 0.1% | 0.1% |
| | | RRT 1.35 | ND | ND | 0.1% |
| | | RRT 1.51 | ND | 0.1% | ND |
| | | Total Impurities NMT 3.0% | 0.5% | 0.6% | 0.6% |

TABLE 13-continued

| Stability Data for Psilocybin 1 mg Capsules (with Desiccant) - Stored at 25° C./60% RH | | | | | |
|---|---|---|---|---|---|
| Attribute | Method | Specification | Initial | 1 M | 2 M |
| Moisture content | Ph. Eur. 2.2.32 | Record Results | 7.66% | 3.05% | 4.80% |
| Dissolution | Ph. Eur. 2.9.3 Paddle/HPLC | Q = 80% at 45 mins | 98% | 102% | 105% |

Table 14 shows the results from storage of the 1 mg capsules (with desiccant) at 40° C./75% RH for one and two months. The data shows that the capsules were within specification and complied with all measured parameters at both timepoints.

TABLE 14

| Stability Data for Psilocybin 1 mg Capsules (with Desiccant) - Stored at 40° C./75% RH | | | | | |
|---|---|---|---|---|---|
| Attribute | Method | Specification | Initial | 1 M | 2 M |
| Appearance | Visual | Off-white powder in a white size 2 capsule | Complies | Complies | Complies |
| Assay | HPLC | 90.0%-110.0% of label claim (0.90-1.10 mg) | 100.5% | 101.8% | 100.1% |
| Related substances | HPLC | Psilocin NMT 1.0% | 0.5% | 0.4% | 0.4% |
| | | Individual imps NMT 0.5% | | | |
| | | RRT 0.85 | ND | 0.1% | ND |
| | | RRT 1.25 | 0.1% | 0.1% | 0.1% |
| | | RRT 1.38 | ND | 0.1% | 0.1% |
| | | RRT 1.44 | ND | 0.1% | ND |
| | | RRT 1.51 | ND | 0.1% | ND |
| | | Total impurities NMT 3.0% | 0.5% | 0.8% | 0.5% |
| Moisture content | Ph. Eur. 2.2.32 | Record Results | 7.66% | 4.07% | 5.60% |
| Dissolution | Ph. Eur. 2.9.3 Paddle/HPLC | Q = 80% at 45 mins | 98% | 102% | 104% |

Table 15 shows the results from storage of the 5 mg capsules (with desiccant) at 25° C./60% RH for one and two months. The data shows that the capsules were within specification and complied with all measured parameters at both timepoints.

TABLE 15

| Stability Data for Psilocybin 5 mg Capsules (with Desiccant) - Stored at 25° C./60% RH | | | | | |
|---|---|---|---|---|---|
| Attribute | Method | Specification | Initial | 1 M | 2 M |
| Appearance | Visual | Off-white powder in a white size 2 capsule | Complies | Complies | Complies |
| Assay | HPLC | 90.0%-110.0% of LC (4.50-5.50 mg) | 99.7% | 99.5% | 99.2% |
| Related substances | HPLC | Psilocin NMT 1.0% | 0.5% | 0.5% | 0.4% |
| | | Individual imps NMT 0.5% | | | |
| | | RRT 1.26 | 0.1% | 0.1% | 0.1% |
| | | RRT 1.39 | ND | ND | 0.1% |
| | | Total impurities NMT 3.0% | 0.5% | 0.6% | 0.5% |
| Moisture content | Ph Eur 2.2.32 | Record Results | 10.71% | 6.31% | 6.26% |
| Dissolution | Ph. Eur. 2.9.3 Paddle/HPLC | Q = 80% at 45 mins | 99% | 99% | 102% |

Table 16 shows the results from storage of the 5 mg capsules (with desiccant) at 40° C./75% RH for one and two months. The data shows that the capsules were within specification and complied with all measured parameters at both timepoints.

TABLE 16

Stability Data for Psilocybin 5 mg Capsules (with Desiccant) - Stored at 40° C./75% RH

| Attribute | Method | Specification | Initial | 1 M | 2 M |
|---|---|---|---|---|---|
| Appearance | Visual | Off-white powder in a white size 2 capsule | Complies | Complies | Complies |
| Assay | HPLC | 90.0%-110.0% of LC (4.50-5.50 mg) | 99.7% | 100.0% | 98.4% |
| Related substances | HPLC | Psilocin NMT 1.0% | 0.5% | 0.5% | 0.4% |
| | | Individual imps NMT 0.5% | | | |
| | | RRT 1.24 | 0.1% | 0.1% | 0.1% |
| | | RRT 1.37 | ND | 0.1% | 0.1% |
| | | Total Impurities NMT 3.0% | 0.5% | 0.7% | 0.5% |
| Moisture Content | Ph. Eur. 2.2.32 | Record Results | 10.71% | 5.94% | 6.58% |
| Dissolution | Ph. Eur. 2.9.3 Paddle/HPLC | Q = 80% at 45 mins | 99% | 98% | 101% |

Table 17 shows the results from storage of the 25 mg capsules (with desiccant) at 25° C./60% RH for one and two months. The data shows that the capsules were within specification and complied with all measured parameters at both timepoints.

TABLE 17

Stability Data for Psilocybin 25 mg Capsules (with Desiccant) - Stored at 25° C./60% RH

| Attribute | Method | Specification | Initial | 1 M | 2 M |
|---|---|---|---|---|---|
| Appearance | Visual | Off-white powder in a white size 0 capsule | Complies | Complies | Complies |
| Assay | HPLC | 90.0%-110.0% of LC (22.5-27.50 mg) | 101.0% | 99.8% | 99.4% |
| Related substances | HPLC | Psilocin NMT 1.0% | 0.5% | 0.4% | 0.4% |
| | | Individual imps NMT 0.5% | | | |
| | | RRT 1.26 | 0.1% | 0.1% | 0.1% |
| | | RRT 1.37 | ND | 0.1% | 0.1% |
| | | Total Impurities NMT 3.0% | 0.5% | 0.6% | 0.5% |
| Moisture Content | Ph. Eur. 2.2.32 | Record Results | 8.29% | 7.64% | 7.39% |
| Dissolution | Ph. Eur. 2.9.3 Paddle/ HPLC | Q = 80% at 45 mins | 100% | 101% | 102% |

Table 18 shows the results from storage of the 25 mg capsules (with desiccant) at 40° C./75% RH for one and two months. The data shows that the capsules were within specification and complied with all measured parameters at both timepoints.

The HPLC data referred to in this Example were obtained using the Related Substance HPLC Method described herein.

TABLE 18

| Stability Data for Psilocybin 25 mg Capsules (with Desiccant) - Stored at 40° C./75% RH | | | | | |
|---|---|---|---|---|---|
| Attribute | Method | Specification | Initial | 1 M | 2 M |
| Appearance | Visual | Off-white powder in a white size 0 capsule | Complies | Complies | Complies |
| Assay | HPLC | 90.0%-110.0% of LC (22.5-27.50 mg) | 101.3% | 99.2% | 100.4% |
| Related substances | HPLC | Psilocin NMT 1.0% | 0.5% | 0.5% | 0.4% |
| | | Individual imps NMT 0.5% | | | |
| | | RRT 1.25 | 0.1% | 0.1% | 0.1% |
| | | RRT 1.37 | ND | 0.1% | 0.1% |
| | | Total Impurities NMT 3.0% | 0.6% | 0.6% | 0.5% |
| Moisture Content | Ph. Eur. 2.2.32 | Record Results | 8.29% | 7.39% | 6.64% |
| Dissolution | Ph. Eur. 2.9.3 Paddle/ HPLC | Q = 80% at 45 mins | 100% | 102% | |

Example 3: Composition and Stability of Psilocybin Capsules Formulated With Silicon Dioxide-Based and Other Excipients Compositions of psilocybin with the silicon dioxide-containing excipients in Table 19 will be studied under stability conditions that are similar to those used in Example 2 and stability parameters recorded for each psilocybin composition.

TABLE 19

| Silicon dioxide-based excipients for use in stability testing. Name |
|---|
| Aluminum calcium silicate |
| Calcium silicate |
| Diatomaceous earth (filter aid) |
| Magnesium silicate |
| Perlite (filter aid) |
| Potassium silicate |
| Silica aerogel |
| Silicon dioxides |
| Sodium aluminosilicate |
| Sodium calcium aluminosilicate |
| Sodium silicate |
| Talc (basic magnesium silicate) |
| Tricalcium silicate |

Compositions of psilocybin with the hydrogen-bond-forming sugars or polyols in Table 20 will be studied under stability conditions that are similar to those used in Example 2 and stability parameters recorded for each psilocybin composition.

TABLE 20

| Polyol and sugar alcohol excipients for use in stability testing. | |
|---|---|
| Index | Name |
| 1 | Polyols |
| 2 | Mannitol |
| 3 | Xylitol |
| 4 | Sucrose |
| 5 | Sorbitol |
| 6 | Fructose |

Compositions of psilocybin with the basic excipients in Table 21 will be studied under stability conditions that are similar to those used in Example 2 and stability parameters recorded for each psilocybin composition.

TABLE 21

| Basic excipients for use in stability testing. | |
|---|---|
| Index | Name |
| 1 | Calcium Carbonate |
| 2 | Calcium Phosphate |

Example 4: Composition AND Stability of Psilocybin Capsules Formulated with Silicon Dioxide-Based Excipients, Pregelatinized Starch, or Combinations THEREOF A loss of potency was observed in tablet and capsules prepared from the same blend composition, as described in Examples 1 and 2. The blend contained silicified microcrystalline cellulose (SMCC) and Colloidal Silicon Dioxide (Aerosil).

Compositions of psilocybin with the silicon dioxide-containing excipients and pregelatinized starch in Table 22 were studied under stability conditions like those used in Example 2. The stability results were recorded for each psilocybin composition.

Table 22 shows the composition prepared that contains 10% by weight of silicified microcrystalline cellulose (SMCC), 1% by weight of colloidal silicon dioxide (Aerosil) and 1% by weight of psilocybin.

TABLE 22

| Unit Formula for Low Level SMCC Composition. | | |
|---|---|---|
| Excipient | Amount (%) | Mass (g) |
| Psilocybin | 1.0 | 0.7 |
| Silicified Microcrystalline Cellulose (SMCC 50) | 2.5 | 1.8 |
| Silicified Microcrystalline Cellulose (SMCC 90) | 7.5 | 5.2 |
| Sodium Starch Glycolate | 1.0 | 0.7 |
| Pregelatinized Starch (StarCap) | 86.0 | 60.2 |

TABLE 22-continued

| Unit Formula for Low Level SMCC Composition. | | |
|---|---|---|
| Excipient | Amount (%) | Mass (g) |
| Colloidal silicon Dioxide (Aerosil) | 1.0 | 0.7 |
| Sodium Stearyl Fumarate (Pruv) | 1.0 | 0.7 |
| TOTAL | 100.0 | 70.0 |

The composition described in Table 23 was used as a control composition which contains no silicon dioxide and 1% by weight of psilocybin.

TABLE 23

| Unit Formula for Starcap Control Composition (1% Psilocybin). | | |
|---|---|---|
| Excipient | Amount (%) | Mass (g) |
| Psilocybin | 1.0 | 0.7 |
| Pregelatinised Starch (StarCap) | 98.0 | 68.6 |
| Sodium Stearyl Fumarate (Pruv) | 1.0 | 0.7 |
| TOTAL | 100.0 | 70.0 |

The composition described in Table 24 was used to replicate the development formulation used in the previous 1% by weight of psilocybin tablet.

TABLE 24

| Unit Formula for 1% psilocybin tablet composition. | | |
|---|---|---|
| Excipient | Amount (%) | Mass (g) |
| Psilocybin | 1.0 | 0.7 |
| Silicified microcrystalline cellulose (SMCC 50) | 20.5 | 14.4 |
| Silicified microcrystalline cellulose (SMCC 90) | 75.5 | 52.8 |
| Sodium starch glycolate | 1.0 | 0.7 |
| Colloidal silicon dioxide (Aerosil) | 1.0 | 0.7 |
| Sodium stearyl fumarate (Pruv) | 1.0 | 0.7 |
| TOTAL | 100.0 | 70.0 |

The composition in Table 25 was used to replicate the development formulation used in the previous 5% by weight of psilocybin tablet.

TABLE 25

| Unit Formula for 5% psilocybin tablet composition. | | |
|---|---|---|
| Excipient | Amount (%) | Mass (g) |
| Psilocybin | 5.0 | 3.5 |
| Silicified Microcrystalline Cellulose (SMCC 50) | 12.5 | 8.7 |
| Silicified Microcrystalline Cellulose (SMCC 90) | 79.5 | 55.7 |
| Sodium Starch Glycolate | 1.0 | 0.7 |
| Colloidal silicon Dioxide (Aerosil) | 1.0 | 0.7 |
| Sodium Stearyl Fumarate (Pruv) | 1.0 | 0.7 |
| TOTAL | 100.0 | 70.0 |

Method: Each of the compositions described above were split equally into 6 separate HDPE sample bottles. Three of these bottles contained a 1 g desiccant sachet. All bottles were sealed shut with lids and parafilm. The bottles were subjected to the conditions as described in Table 26.

TABLE 26

| Stability Storage Conditions | | | | | | |
|---|---|---|---|---|---|---|
| y Conditions | Desiccant | T = 0* | T = 2 weeks | T = 1 month | T = 3 months | T = 6 months |
| 25° C./60% RH | yes | Y Assay/RS | Y Assay/RS | Y Assay/RS | Y Assay/RS | Y Assay/RS |
| 40° C./75% RH | yes | Y Assay/RS | Y Assay/RS | Y Assay/RS | Y Assay/RS | Y Assay/RS |
| 60° C. | yes | Y Assay/RS | Y Assay/RS | Y Assay/RS | Y Assay/RS | Y Assay/RS |
| 25° C./60% RH | No | Y Assay/RS | Y Assay/RS | Y Assay/RS | Y Assay/RS | Y Assay/RS |
| 40° C./75% RH | No | Y Assay/RS | Y Assay/RS | Y Assay/RS | Y Assay/RS | Y Assay/RS |
| 60° C. | No | Y Assay/RS | Y Assay/RS | Y Assay/RS | Y Assay/RS | Y Assay/RS |

*T = 2 weeks and T = 1 month analysis was grouped together

The compositions were tested at for moisture content by Karl Fischer KF analysis and analysed by high performance liquid chromatography (HPLC) using the conditions described in Table 27. Analysis was performed at the start of the study (initial), 2 weeks, 1 month, 2 months and 6 months.

TABLE 27

| HPLC parameters for testing compositions | |
|---|---|
| Column: | Waters XBridge C18, 3.5 μm, 150 × 4.6 mm |
| Column Oven: | 30° C. |
| Injection Volume | 20 μL |
| Autosampler Temperature: | Ambient or 20° C. |
| Flow Rate: | 1.0 mL/min |
| Detection: | UV 267 nm |
| Mobile Phase A | 95:5:0.1 Water:MeOH:TFA |
| Mobile Phase B | 95:5:0.1 MeOH:Water:TFA |

TABLE 27-continued

| HPLC parameters for testing compositions | | | |
|---|---|---|---|
| Gradient Program | Time (mins) | % A | % B |
| | 0 | 100 | 0 |
| | 2 | 100 | 0 |
| | 15 | 0 | 100 |
| | 20 | 0 | 100 |
| | 20.1 | 100 | 0 |
| | 27 | 100 | 0 |
| Needle Wash: | 90:10 Water:MeOH | | |
| Run Time: | 27 minutes | | |

Figure 10:
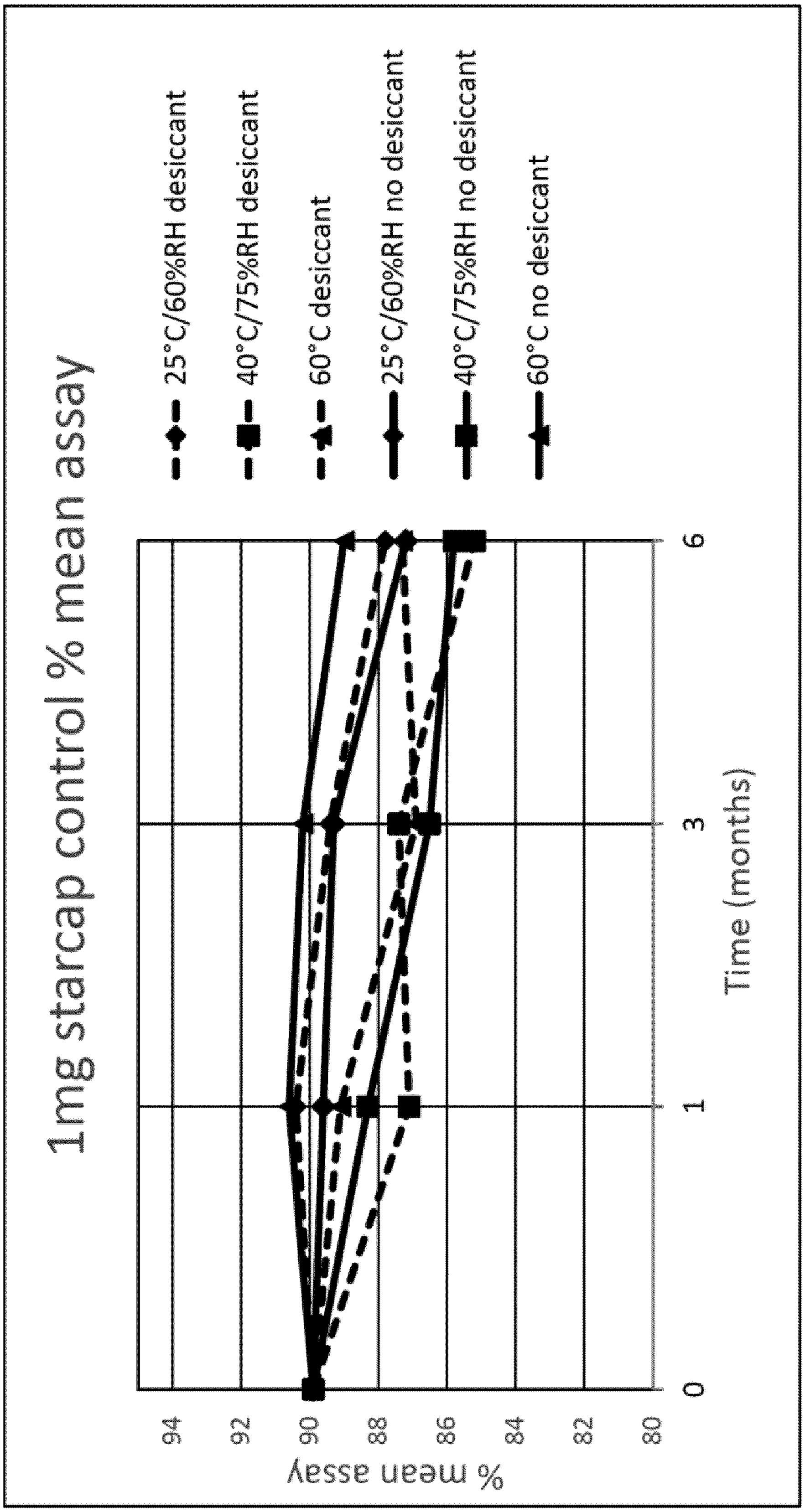
FIG. 10 shows the mean assay plot for the control composition from the stability study of Example 4.

Table 28 and FIG. 10 show the results from storage of the Starcap control composition with and without desiccant at 25° C./60% relative humidity (RH), 40° C./75%RH, and 60° C. for two weeks, one month, three months and six months. The moisture content at T=0 of the composition was 7.11%, as determined by Karl Fisher analysis.

TABLE 28

| Starcap Control Composition Analytical Testing Results | | | | | |
|---|---|---|---|---|---|
| Time | Storage | Samples with desiccant | | Samples without desiccant | |
| Point | Conditions | Assay | Related Substances | Assay | Related Substances |
| Initial | N/A | Prep. 1 = 89.3% | Psilocin RRT 1.52-0.5% | Prep. 1 = 89.3% | Psilocin RRT 1.52-0.5% |
| | | Prep. 2 = 90.5% | RRT 1.36-0.1% | Prep. 2 = 90.5% | RRT 1.36-0.1% |
| | | Average = 89.9% | Total = 0.6% | Average = 89.9% | Total = 0.6% |
| 2 week | 25° C./60% RH | Prep. 1 = 87.1% | Psilocin RRT 1.58-0.5% | Prep. 1 = 88.1% | Psilocin RRT 1.59-0.5% |
| | | Prep. 2 = 87.2% | RRT 1.41-0.1% | Prep. 2 = 88.1% | RRT 1.42-0.1% |
| | | Average = 87.2% | Total = 0.6% | Average = 88.1% | Total = 0.5% |
| | 40° C./75% RH | Prep. 1 = 87.5% | Psilocin RRT 1.59-0.5% | Prep. 1 = 89.2% | Psilocin RRT 1.59-0.5% |
| | | Prep. 2 = 87.1% | RRT 1.42-0.1% | Prep. 2 = 88.7% | RRT 1.42-0.1% |
| | | Average = 87.3% | Total = 0.6% | Average = 88.9% | Total = 0.6% |
| | 60° C. | Prep. 1 = 86.0% | Psilocin RRT 1.60-0.5% | Prep. 1 = 89.6% | Psilocin RRT 1.59-0.5% |
| | | Prep. 2 = 84.2% | RRT 1.42-0.1% | Prep. 2 = 88.5% | RRT 1.42-0.1% |
| | | Average = 85.1% | Total = 0.6% | Average = 89.0% | Total = 0.6% |
| 1 month | 25° C./60% RH | Prep. 1 = 90.0% | Psilocin RRT 1.58-0.5% | Prep. 1 = 89.9% | Psilocin RRT 1.58-0.5% |
| | | Prep. 2 = 90.9% | RRT 1.41-0.1% | Prep. 2 = 89.3% | RRT 1.41-0.1% |
| | | Average = 90.4% | Total = 0.6% | Average = 89.6% | Total = 0.6% |
| | 40° C./75% RH | Prep. 1 = 86.7% | Psilocin RRT 1.58-0.5% | Prep. 1 = 88.1% | Psilocin RRT 1.58-0.5% |
| | | Prep. 2 = 87.6% | RRT 1.41-0.1% | Prep. 2 = 88.4% | RRT 1.41-0.1% |
| | | Average = 87.1% | Total = 0.6% | Average = 88.3% | Total = 0.6% |
| | 60° C. | Prep. 1 = 89.1% | Psilocin RRT 1.58-0.6% | Prep. 1 = 90.8% | Psilocin RRT 1.58-0.5% |
| | | Prep. 2 = 89.0% | RRT 1.42-0.1% | Prep. 2 = 90.4% | RRT 1.41-0.1% |
| | | Average = 89.1% | Total = 0.6% | Average = 90.6% | Total = 0.6% |
| 3 months | 25° C./60% RH | Prep. 1 = 89.4% | Psilocin RRT 1.51-0.5% | Prep. 1 = 89.3% | Psilocin RRT 1.51-0.5% |
| | | Prep. 2 = 89.5% | RRT 1.36-0.1% | Prep. 2 = 89.2% | RRT 1.36-0.1% |
| | | Average = 89.4% | Total = 0.6% | Average = 89.3% | Total = 0.6% |
| | 40° C./75% RH | Prep. 1 = 87.3% | Psilocin RRT 1.51-0.5% | Prep. 1 = 86.5% | Psilocin RRT 1.51-0.4% |
| | | Prep. 2 = 87.4% | RRT 1.36-0.1% | Prep. 2 = 86.6% | RRT 1.36-0.1% |
| | | Average = 87.4% | Total = 0.6% | Average = 86.5% | Total = 0.5% |
| | 60° C. | Prep. 1 = 86.3% | Psilocin RRT 1.65-0.6% | Prep. 1 = 90.7% | Psilocin RRT 1.65-0.5% |
| | | Prep. 2 = 87.5% | RRT 1.50-0.1% | Prep. 2 = 89.7% | RRT 1.51-0.1% |
| | | Average = 86.9% | Total = 0.7% | Average = 90.2% | Total = 0.6% |
| 6 months | 25° C./60% RH | Prep. 1 = 87.8% | Psilocin RRT 1.57-0.55% | Prep. 1 = 86.9% | Psilocin RRT 1.57-0.56% |
| | | Prep. 2 = 87.8% | RRT 1.41-0.06% | Prep. 2 = 87.6% | RRT 1.41-0.06% |
| | | Average = 87.8% | Total = 0.6% | Average = 87.2% | Total = 0.6% |
| | 40° C./75% RH | Prep. 1 = 85.4% | Psilocin RRT 1.56-0.40% | Prep. 1 = 86.2% | Psilocin RRT 1.56-0.40% |
| | | Prep. 2 = 85.1% | RRT 1.40-0.07% | Prep. 2 = 85.4% | RRT 1.40-0.06% |
| | | Average = 85.2% | Total = 0.5% | Average = 85.8% | Total = 0.5% |
| | 60° C. | Prep. 1 = 87.2% | Psilocin RRT 1.57-0.66% | Prep. 1 = 90.3% | Psilocin RRT 1.57-0.58% |
| | | Prep. 2 = 87.4% | RRT 1.41-0.09% | Prep. 2 = 87.6% | RRT 1.40-0.10% |
| | | Average = 87.3% | Total = 0.8% | Average = 89.0% | Total = 0.7% |

Figure 11:
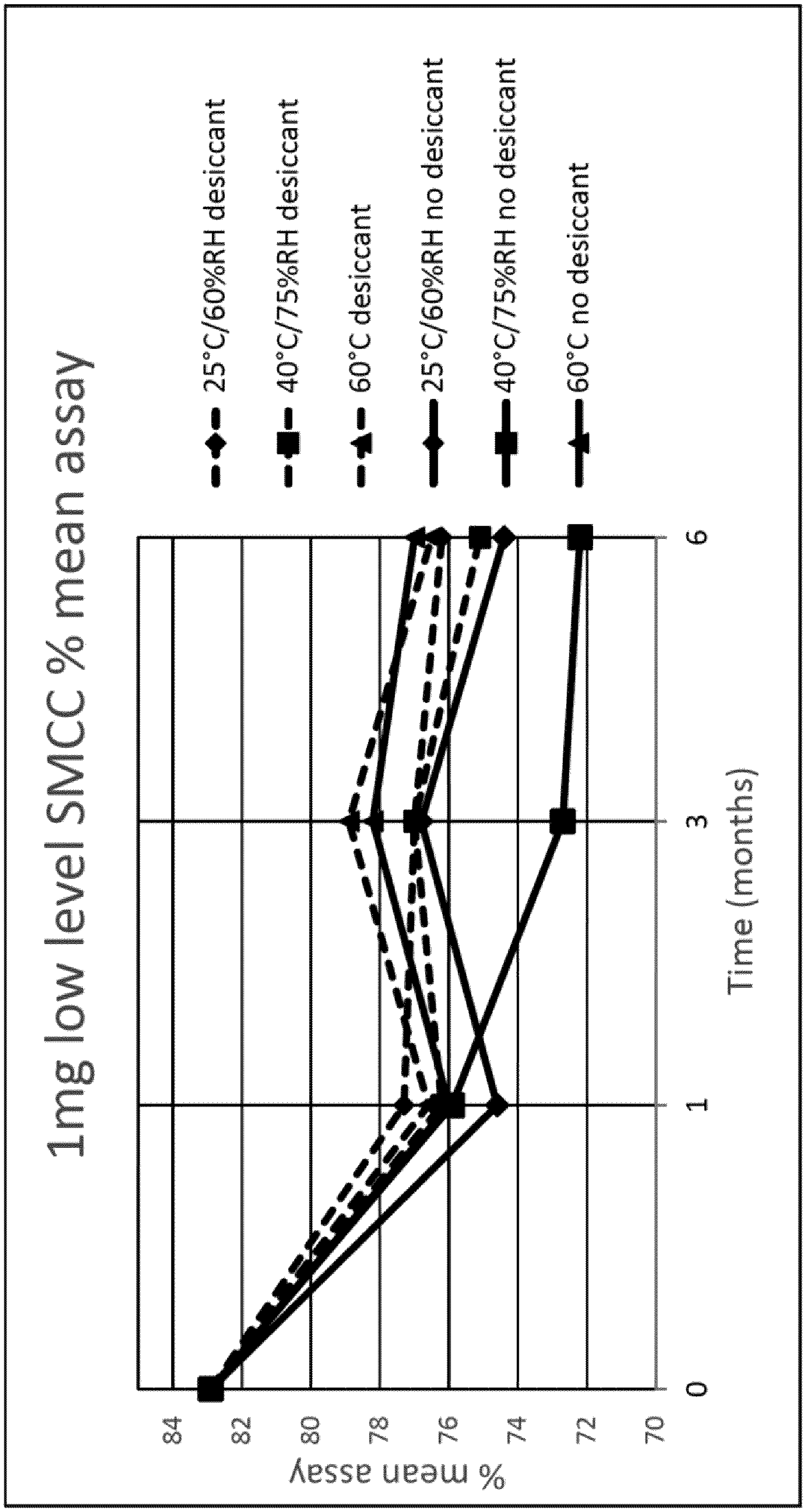
FIG. 11 shows the mean assay plot for the low level SMCC composition from the stability study of Example 4.

Table 29 and FIG. 11 show the results from storage of the 1 mg psilocybin low level SMCC composition with and without desiccant at 25° C./60% RH, 40° C./75%RH, and 60° C.for two weeks, one month, three months and six months. The moisture content at T=0 of the composition was 6.77%, as determined by Karl Fisher analysis.

TABLE 29

1 mg Low Level SMCC Composition Analytical Testing Results

| Time Point | Storage Conditions | Samples with desiccant: Assay | Samples with desiccant: Related Substances | Samples without desiccant: Assay | Samples without desiccant: Related Substances |
|---|---|---|---|---|---|
| Initial | N/A | Prep. 1 = 84.0% | Psilocin RRT 1.51-0.4% | Prep. 1 = 84.0% | Psilocin RRT 1.51-0.4% |
| | | Prep. 2 = 81.9% | RRT 1.36-0.1% | Prep. 2 = 81.9% | RRT 1.36-0.1% |
| | | Average = 82.9% | Total = 0.5% | Average = 82.9% | Total = 0.5% |
| 2 week | 25° C./60% RH | Prep. 1 = 66.6% | Psilocin RRT 1.60-0.4% | Prep. 1 = 67.4% | Psilocin RRT 1.59-0.4% |
| | | Prep. 2 = 67.6% | RRT 1.42-0.1% | Prep. 2 = 69.5% | RRT 1.42-0.1% |
| | | Average = 67.1% | Total = 0.4% | Average = 68.5% | Total = 0.5% |
| | 40° C./75% RH | Prep. 1 = 66.8% | Psilocin RRT 1.60-0.4% | Prep. 1 = 69.8% | Psilocin RRT 1.59-0.4% |
| | | Prep. 2 = 68.4% | RRT 1.42-0.1% | Prep. 2 = 68.6% | RRT 1.42-0.1% |
| | | Average = 67.6% | Total = 0.4% | Average = 69.2% | Total = 0.4% |
| | 60° C. | Prep. 1 = 70.1% | Psilocin RRT 1.59-0.4% | Prep. 1 = 68.8% | Psilocin RRT 1.59-0.4% |
| | | Prep. 2 = 70.6% | RRT 1.42-0.1% | Prep. 2 = 71.2% | RRT 1.42-0.1% |
| | | Average = 70.3% | Total = 0.5% | Average = 70.0% | Total = 0.4% |
| 1 month | 25° C./60% RH | Prep. 1 = 77.7% | Psilocin RRT 1.59-0.4% | Prep. 1 = 76.6% | Psilocin RRT 1.59-0.4% |
| | | Prep. 2 = 77.0% | RRT 1.42-0.1% | Prep. 2 = 72.6% | RRT 1.42-0.1% |
| | | Average = 77.3% | Total = 0.5% | Average = 74.6% | Total = 0.4% |
| | 40° C./75% RH | Prep. 1 = 76.8% | Psilocin RRT 1.59-0.4% | Prep. 1 = 76.2% | Psilocin RRT 1.59-0.3% |
| | | Prep. 2 = 75.6% | RRT 1.42-0.1% | Prep. 2 = 75.6% | RRT 1.42-0.1% |
| | | Average = 76.2% | Total = 0.4% | Average = 75.9% | Total = 0.4% |
| | 60° C. | Prep. 1 = 77.6% | Psilocin RRT 1.59-0.4% | Prep. 1 = 75.8% | Psilocin RRT 1.59-0.4% |
| | | Prep. 2 = 75.5% | RRT 1.42-0.1% | Prep. 2 = 76.2% | RRT 1.42-0.1% |
| | | Average = 76.6% | Total = 0.5% | Average = 76.0% | Total = 0.4% |
| 3 months | 25° C./60% RH | Prep. 1 = 76.1% | Psilocin RRT 1.51-0.4% | Prep. 1 = 75.7% | Psilocin RRT 1.51-0.4% |
| | | Prep. 2 = 77.8% | RRT 1.36-0.1% | Prep. 2 = 77.9% | RRT 1.36-0.1% |
| | | Average = 77.0% | Total = 0.5% | Average = 76.8% | Total = 0.5% |
| | 40° C./75% RH | Prep. 1 = 76.8% | Psilocin RRT 1.51-0.3% | Prep. 1 = 73.1% | Psilocin RRT 1.51-0.2% |
| | | Prep. 2 = 77.2% | RRT 1.35-0.1% | Prep. 2 = 72.3% | RRT 1.35-0.1% |
| | | Average = 77.0% | Total = 0.4% | Average = 72.7% | Total = 0.3% |
| | 60° C. | Prep. 1 = 79.6% | Psilocin RRT 1.65-0.4% | Prep. 1 = 80.7% | Psilocin RRT 1.65-0.3% |
| | | Prep. 2 = 78.2% | RRT 1.50-0.1% | Prep. 2 = 75.7% | RRT 1.50-0.1% |
| | | Average = 78.9% | RRT 1.62-0.1% | Average = 78.2% | RRT 1.62-0.1% |
| | | | Total = 0.5% | | Total = 0.5% |
| 6 months | 25° C./60% RH | Prep. 1 = 78.1% | Psilocin RRT 1.56-0.45% | Prep. 1 = 72.6% | Psilocin RRT 1.56-0.44% |
| | | Prep. 2 = 74.4% | RRT 1.41-0.06% | Prep. 2 = 76.2% | RRT 1.41-0.06% |
| | | Average = 76.2% | Total = 0.5% | Average = 74.4% | Total = 0.5% |
| | 40° C./75% RH | Prep. 1 = 74.2% | Psilocin RRT 1.56-0.23% | Prep. 1 = 75.2% | Psilocin RRT 1.56-0.19% |
| | | Prep. 2 = 76.0% | RRT 1.40-0.07% | Prep. 2 = 69.3% | RRT 1.40-0.06% |
| | | Average = 75.1% | Total = 0.3% | Average = 72.2% | Total = 0.3% |
| | 60° C. | Prep. 1 = 75.7% | Psilocin RRT 1.56-0.48% | Prep. 1 = 76.3% | Psilocin RRT 1.57-0.40% |
| | | Prep. 2 = 77.3% | RRT 1.41-0.10% | Prep. 2 = 77.7% | RRT 1.41-0.10% |
| | | Average = 76.5% | Total = 0.6% | Average = 77.0% | Total = 0.5% |

Figure 12:
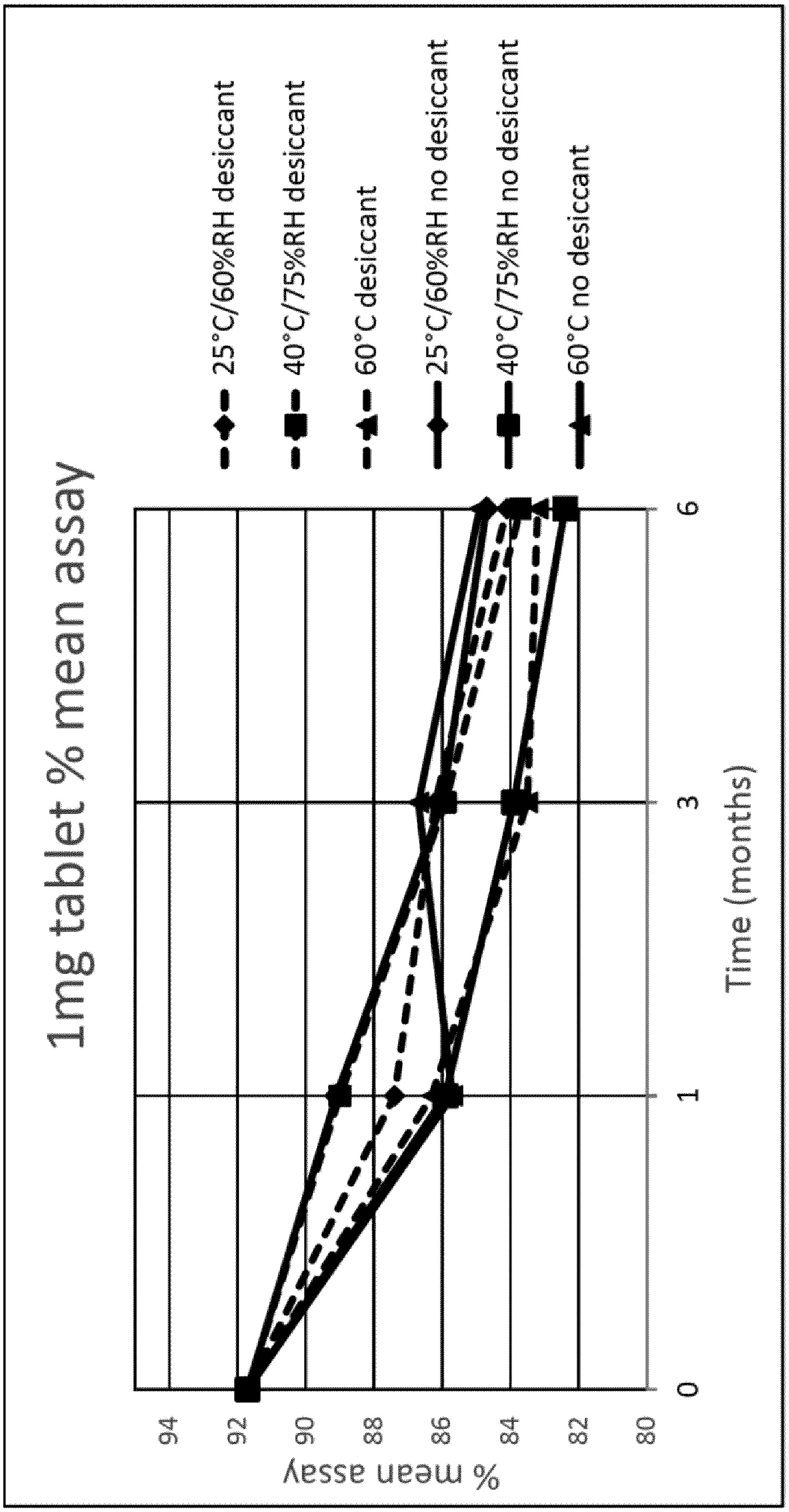
FIG. 12 shows the mean assay plot for the 1 mg capsule composition from the stability study of Example 4.

Table 30 and FIG. 12 show the results from storage of the 1 mg psilocybin tablet composition with and without desiccant at 25° C./60% RH, 40° C./75%RH, and 60° C. for two weeks, one month, three months and six months. The moisture content at T=0 of the composition was 3.05%, as determined by Karl Fisher analysis.

TABLE 30

1 mg Psilocybin Tablet Composition Analytical Testing Results

| Time Point | Storage Conditions | Samples With desiccant: Assay | Samples With desiccant: Related Substances | Samples Without desiccant: Assay | Samples Without desiccant: Related Substances |
|---|---|---|---|---|---|
| Initial | N/A | Prep. 1 = 93.0% | Psilocin RRT 1.51-0.3% | Prep. 1 = 93.0% | Psilocin RRT 1.51-0.3% |
| | | Prep. 2 = 90.4% | RRT 1.36-0.1% | Prep. 2 = 90.4% | RRT 1.36-0.1% |
| | | Average = 91.7% | Total = 0.3% | Average = 91.7% | Total = 0.3% |
| 2 week | 25° C./60% RH | Prep. 1 = 77.9% | Psilocin RRT 1.59-0.3% | Prep. 1 = 83.2% | Psilocin RRT 1.59-0.3% |
| | | Prep. 2 = 77.0% | RRT 1.42-0.1% | Prep. 2 = 84.3% | RRT 1.42-0.1% |
| | | Average = 77.4% | Total = 0.3% | Average = 83.7% | Total = 0.3% |
| | 40° C./75% RH | Prep. 1 = 80.4% | Psilocin RRT 1.59-0.3% | Prep. 1 = 84.6% | Psilocin RRT 1.59-0.3% |
| | | Prep. 2 = 81.1% | RRT 1.42-0.1% | Prep. 2 = 85.3% | RRT 1.42-0.1% |
| | | Average = 80.7% | Total = 0.4% | Average = 84.9% | Total = 0.3% |
| | 60° C. | Prep. 1 = 78.4% | Psilocin RRT 1.59-0.3% | Prep. 1 = 83.5% | Psilocin RRT 1.59-0.3% |
| | | Prep. 2 = 81.1% | RRT 1.42-0.1% | Prep. 2 = 83.2% | RRT 1.42-0.1% |
| | | Average = 79.7% | Total = 0.4% | Average = 83.4% | Total = 0.4% |
| 1 month | 25° C./60% RH | Prep. 1 = 87.6% | Psilocin RRT 1.59-0.3% | Prep. 1 = 89.7% | Psilocin RRT 1.59-0.3% |
| | | Prep. 2 = 87.1% | RRT 1.42-0.1% | Prep. 2 = 88.5% | RRT 1.42-0.1% |
| | | Average = 87.4% | Total = 0.4% | Average = 89.1% | Total = 0.3% |
| | 40° C./75% RH | Prep. 1 = 89.3% | Psilocin RRT 1.59-0.3% | Prep. 1 = 88.1% | Psilocin RRT 1.59-0.2% |
| | | Prep. 2 = 88.7% | RRT 1.42-0.1% | Prep. 2 = 83.6% | RRT 1.42-0.1% |
| | | Average = 89.0% | Total = 0.3% | Average = 85.9% | Total = 0.3% |

TABLE 30-continued 1 mg Psilocybin Tablet Composition Analytical Testing Results

| Time Point | Storage Conditions | Samples With desiccant Assay | Samples With desiccant Related Substances | Samples Without desiccant Assay | Samples Without desiccant Related Substances |
|---|---|---|---|---|---|
| | 60° C. | Prep. 1 = 86.1%<br>Prep. 2 = 86.4%<br>Average = 86.3% | Psilocin RRT 1.59-0.3%<br>RRT 1.42-0.1%<br>Total = 0.4% | Prep. 1 = 85.0%<br>Prep. 2 = 86.4%<br>Average = 85.7% | Psilocin RRT 1.59-0.3%<br>RRT 1.42-0.1%<br>Total = 0.4% |
| 3 months | 25° C./60% RH | Prep. 1 = 85.6%<br>Prep. 2 = 86.7%<br>Average = 86.2% | Psilocin RRT 1.51-0.3%<br>RRT 1.36-0.1%<br>Total = 0.3% | Prep. 1 = 85.0%<br>Prep. 2 = 86.9%<br>Average = 86.0% | Psilocin RRT 1.51-0.3%<br>RRT 1.36-0.1%<br>Total = 0.3% |
| | 40° C./75% RH | Prep. 1 = 85.9%<br>Prep. 2 = 85.8%<br>Average = 85.9% | Psilocin RRT 1.51-0.2%<br>RRT 0.70-0.1%<br>RRT 1.35-0.1%<br>Total = 0.4% | Prep. 1 = 83.2%<br>Prep. 2 = 84.6%<br>Average = 83.9% | Psilocin RRT 1.51-0.2%<br>RRT 0.70-0.2%<br>RRT 1.35-0.1%<br>Total = 0.4% |
| | 60° C. | Prep. 1 = 83.8%<br>Prep. 2 = 83.3%<br>Average = 83.5% | Psilocin RRT 1.64-0.3%<br>RRT 1.50-0.1%<br>Total = 0.4% | Prep. 1 = 86.1%<br>Prep. 2 = 87.4%<br>Average = 86.7% | Psilocin RRT 1.64-0.3%<br>RRT 1.44-0.1%<br>RRT 1.50-0.1%<br>Total = 0.5% |
| 6 months | 25° C./60% RH | Prep. 1 =84.3%<br>Prep. 2 = 83.9%<br>Average =84.1% | Psilocin RRT 1.56-0.29%<br>RRT 1.40-0.07%<br>Total = 0.4% | Prep. 1 =85.3%<br>Prep. 2 = 84.1%<br>Average =84.7% | Psilocin RRT 1.56-0.29%<br>RRT 1.41-0.1%<br>Total = 0.5% |
| | 40° C./75% RH | Prep. 1 =83.6%<br>Prep. 2 = 83.8%<br>Average =83.7% | Psilocin RRT 1.56-0.12%<br>RRT 1.40-0.09%<br>Total = 0.2% | Prep. 1 = 82.7%<br>Prep. 2 = 82.1%<br>Average = 82.4% | Psilocin RRT 1.56-0.13%<br>RRT 1.40-0.08%<br>Total = 0.2% |
| | 60° C. | Prep. 1 = 82.6%<br>Prep. 2 = 83.8%<br>Average = 83.2% | Psilocin RRT 1.57-0.34%<br>RRT 1.40-0.11%<br>Total = 0.5% | Prep. 1 = 84.6%<br>Prep. 2 = 85.2%<br>Average = 84.9% | Psilocin RRT 1.56-0.36%<br>RRT 1.40-0.13%<br>Total = 0.5% |

Figure 13:
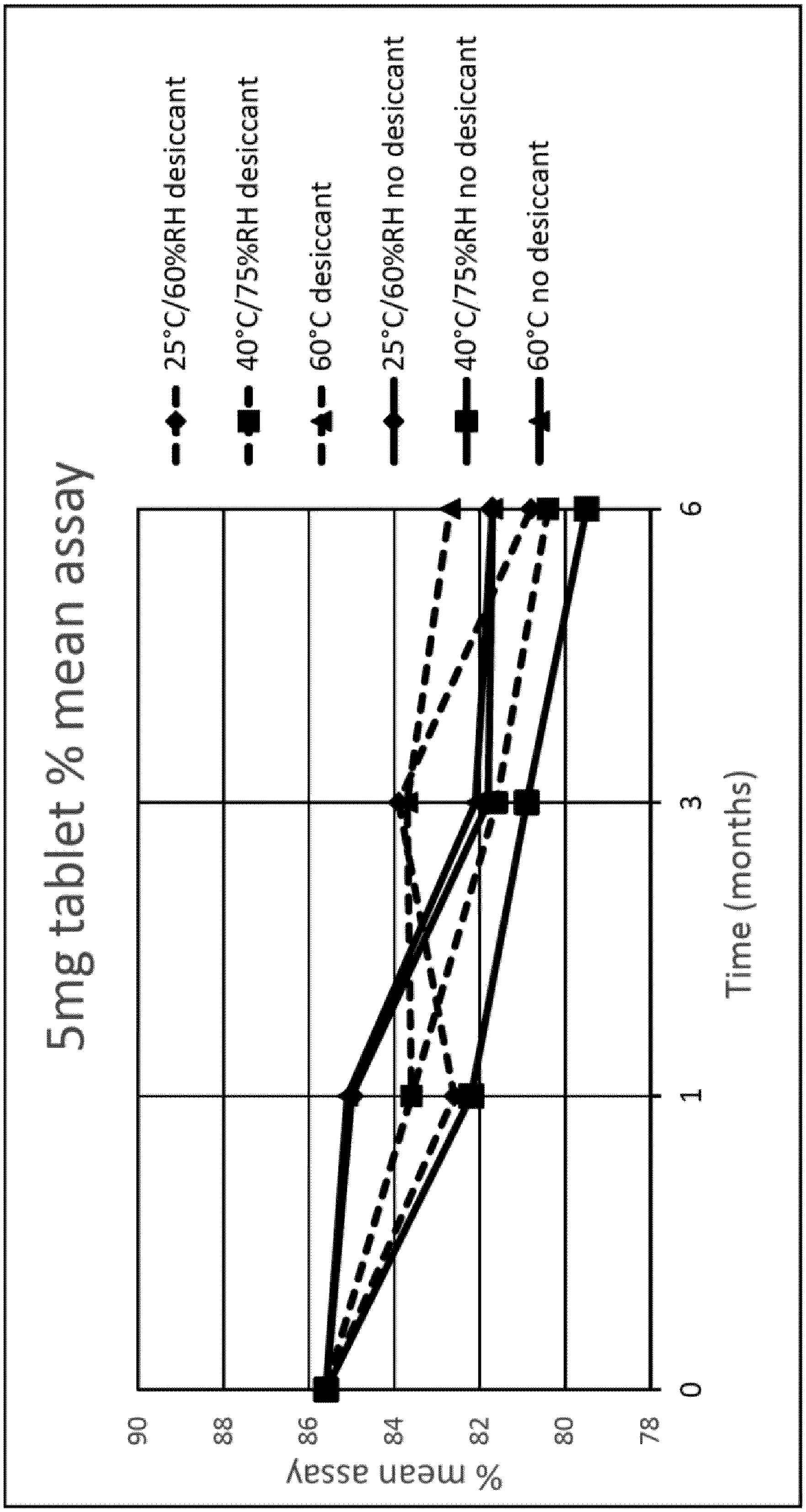
FIG. 13 shows the mean assay plot for the 5 mg capsule composition from the stability study of Example 4.

Table 31 and FIG. 13 show the results from storage of the 5% psilocybin tablet composition with and without desiccant at 25° C./60% RH, 40° C./75% RH, and 60° C.for two weeks, one month, three months and six months. The moisture content at T=0 of the composition was 2.72%, as determined by Karl Fisher analysis.

TABLE 31

5 mg Psilocybin Tablet Composition Analytical Testing Results

| Time Point | Storage Conditions | Samples With desiccant Assay | Samples With desiccant Related Substances | Samples Without desiccant Assay | Samples Without desiccant Related Substances |
|---|---|---|---|---|---|
| Initial | N/A | Prep. 1 = 86.5%<br>Prep. 2 = 84.7%<br>Average = 85.6% | Psilocin RRT 1.51-0.4%<br>RRT 1.36-0.1%<br>Total = 0.5% | Prep. 1 = 86.5%<br>Prep. 2 = 84.7%<br>Average = 85.6% | Psilocin RRT 1.51-0.4%<br>RRT 1.36-0.1%<br>Total = 0.5% |
| 2 week | 25° C./60% RH | Prep. 1 = 78.4%<br>Prep. 2 = 77.8%<br>Average = 78.1% | Psilocin RRT 1.59-0.4%<br>RRT 1.42-0.1%<br>Total = 0.4% | Prep. 1 = 81.2%<br>Prep. 2 = 81.0%<br>Average = 81.1% | Psilocin RRT 1.59-0.4%<br>RRT 1.42-0.1%<br>Total = 0.5% |
| | 40° C./75% RH | Prep. 1 = 76.8%<br>Prep. 2 = 75.1%<br>Average = 76.0% | Psilocin RRT 1.59-0.4%<br>RRT 1.42-0.1%<br>Total = 0.5% | Prep. 1 = 76.9%<br>Prep. 2 = 79.8%<br>Average = 78.4% | Psilocin RRT 1.59-0.4%<br>RRT 1.42-0.1%<br>Total = 0.5% |
| | 60° C. | Prep. 1 = 80.6%<br>Prep. 2 = 81.0%<br>Average = 80.8% | Psilocin RRT 1.59-0.4%<br>RRT 1.42-0.1%<br>Total = 0.5% | Prep. 1 = 83.6%<br>Prep. 2 = 79.9%<br>Average = 81.7% | Psilocin RRT 1.59-0.4%<br>RRT 1.42-0.1%<br>Total = 0.5% |
| 1 month | 25° C./60% RH | Prep. 1 = 82.9%<br>Prep. 2 = 82.3%<br>Average = 82.6% | Psilocin RRT 1.59-0.4%<br>RRT 1.42-0.1%<br>Total = 0.5% | Prep. 1 = 86.0%<br>Prep. 2 = 84.0%<br>Average = 85.0% | Psilocin RRT 1.59-0.4%<br>RRT 1.42-0.1%<br>Total = 0.5% |
| | 40° C./75% RH | Prep. 1 = 83.9%<br>Prep. 2 = 83.4%<br>Average = 83.6% | Psilocin RRT 1.59-0.4%<br>RRT 1.42-0.1%<br>Total = 0.5% | Prep. 1 = 82.8%<br>Prep. 2 = 81.6%<br>Average = 82.2% | Psilocin RRT 1.59-0.4%<br>RRT 1.42-0.1%<br>Total = 0.4% |
| | 60° C. | Prep. 1 = 83.4%<br>Prep. 2 = 83.9%<br>Average = 83.6% | Psilocin RRT 1.59-0.4%<br>RRT 1.42-0.1%<br>Total = 0.5% | Prep. 1 = 83.8%<br>Prep. 2 = 86.4%<br>Average = 85.1% | Psilocin RRT 1.59-0.4%<br>RRT 1.42-0.1%<br>Total = 0.5% |
| 3 months | 25° C./60% RH | Prep. 1 = 84.2%<br>Prep. 2 = 83.6%<br>Average = 83.9% | Psilocin RRT 1.51-0.4%<br>RRT 1.36-0.1%<br>Total = 0.5% | Prep. 1 = 82.3%<br>Prep. 2 = 81.3%<br>Average = 81.8% | Psilocin RRT 1.51-0.4%<br>RRT 1.36-0.1%<br>Total = 0.5% |
| | 40° C./75% RH | Prep. 1 = 81.7%<br>Prep. 2 = 81.6%<br>Average = 81.6% | Psilocin RRT 1.50-0.4%<br>RRT 1.35-0.1%<br>Total = 0.4% | Prep. 1 = 80.3%<br>Prep. 2 = 81.5%<br>Average = 80.9% | Psilocin RRT 1.51-0.3%<br>RRT 1.35-0.1%<br>Total = 0.4% |
| | 60° C. | Prep. 1 = 83.4%<br>Prep. 2 = 83.9%<br>Average = 83.7% | Psilocin RRT 1.64-0.5%<br>RRT 1.49-0.1%<br>Total = 0.6% | Prep. 1 = 82.1%<br>Prep. 2 = 82.1%<br>Average = 82.1% | Psilocin RRT 1.64-0.5%<br>RRT 1.49-0.1%<br>Total = 0.6% |

TABLE 31-continued

| 5 mg Psilocybin Tablet Composition Analytical Testing Results | | | | | |
|---|---|---|---|---|---|
| Time | Storage | Samples With desiccant | | Samples Without desiccant | |
| Point | Conditions | Assay | Related Substances | Assay | Related Substances |
| 6 months | 25° C./60% RH | Prep. 1 = 81.3%<br>Prep. 2 =80.2%<br>Average = 80.8% | Psilocin RRT 1.56-0.47%<br>RRT 1.40-0.06%<br>Total = 0.5% | Prep. 1 = 82.1%<br>Prep. 2 = 81.3%<br>Average = 81.7% | Psilocin RRT 1.56- 0.46%<br>RRT 1.40-0.07%<br>Total = 0.5% |
| | 40° C./75% RH | Prep. 1 =80.2%<br>Prep. 2 = 80.5%<br>Average = 80.4% | Psilocin RRT 1.56-0.31%<br>RRT 1.40-0.08%<br>Total = 0.4% | Prep. 1 = 79.9%<br>Prep. 2 = 79.2%<br>Average = 79.5% | Psilocin RRT 1.56-0.29%<br>RRT 1.40-0.08%<br>Total = 0.4% |
| | 60° C. | Prep. 1 = 83.0%<br>Prep. 2 = 82.4%<br>Average =82.7% | Psilocin RRT 1.57-0.60%<br>RRT 1.41-0.10%<br>Total = 0.7% | Prep. 1 = 81.5%<br>Prep. 2 = 81.9%<br>Average = 81.7% | Psilocin RRT 1.57-0.57%<br>RRT 1.41-0.11%<br>Total = 0.7% |

Table 32 shows the assay results for the Img psilocybin capsule control sample stability study.

TABLE 32

| 1 mg Psilocybin Capsule Control Sample Assay Results | |
|---|---|
| Timepoint | Mean % Assay |
| T = 2 weeks & 1 month | 101.5 |
| T = 3 months | 97.1 |
| T = 6 months | 100.6 |

Results: For all studies the level of Psilocin impurity remained unchanged throughout the time of the study.

The compositions containing silicon dioxide excipients showed an increasing downward trend in the assay when compared to the control composition (see Table 33). In addition, Table 33 indicates that the use of a desiccant has a limited effect on composition stability.

TABLE 33

| Differences in % Assay from T-0 months to T = 6 months | | | | | | | | |
|---|---|---|---|---|---|---|---|---|
| | 1% psilocybin Starcap control | | 1% low level SMCC | | 1% psilocybin tablet | | 5% psilocybin tablet | |
| Storage Condition | desiccant | no desiccant | desiccant | no desiccant | desiccant | no desiccant | desiccant | no desiccant |
| 25° C./60% RH | −2.1 | −2.7 | −6.7 | −8.5 | −7.6 | −7.0 | −4.8 | −3.9 |
| 40° C./75% RH | −4.7 | −4.1 | −7.8 | −10.7 | −8.0 | −7.3 | −5.2 | −6.1 |
| 60° C. | −2.6 | −0.9 | −6.4 | −5.9 | −8.5 | −6.8 | −2.9 | −3.9 |

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

EMBODIMENTS

1. A pharmaceutical composition comprising:

a therapeutically effective amount of psilocybin; and one or more pharmaceutically acceptable excipients, wherein, after storage of the composition at 40° C. and 75% relative humidity for one month, the potency of the psilocybin in the composition decreases by less than 5% and the mass balance of psilocybin and related substances is greater than 97%.

2. The pharmaceutical composition of embodiment 1, wherein the composition comprises at least one pharmaceutically acceptable excipient that does not substantially chemically or physically interact with the phosphonate ester of psilocybin.

3. The pharmaceutical composition of any one of embodiments 1-2, wherein the composition does not contain a pharmaceutically acceptable excipient that substantially chemically or physically interacts with the phosphonate ester of psilocybin.

4. The pharmaceutical composition of any one of embodiments 1-3, wherein the composition does not contain an inorganic silicate, silicon dioxide or a silicified excipient.

5. The pharmaceutical composition of any one of embodiments 1-4, wherein the composition does not contain aluminum calcium silicate, calcium silicate, diatomaceous earth, magnesium silicate, Perlite, potassium silicate, silica aerogel, silicon dioxide, sodium aluminosilicate, sodium calcium aluminosilicate, sodium silicate, talc (basic magnesium silicate) or tricalcium silicate.

6. The pharmaceutical composition of any one of embodiments 1-5, wherein the composition does not contain silicified microcrystalline cellulose.

7. The pharmaceutical composition of any one of embodiments 1-6, wherein the composition does not contain polyols, mannitol, xylitol, sucrose, sorbitol or fructose.

8. The pharmaceutical composition of any one of embodiments 1-7, wherein the composition does not contain calcium carbonate or calcium phosphate.

9. The pharmaceutical composition of any one of embodiments 1-8, wherein the composition does not contain a glidant.

10. The pharmaceutical composition of any one of embodiments 1-9, wherein the one or more pharmaceutically acceptable excipients comprises a diluent.
11. The pharmaceutical composition of any one of embodiments 1-10, wherein the one or more pharmaceutically acceptable excipients comprises a lubricant.
12. The pharmaceutical composition of any one of embodiments 1-11, wherein the composition comprises:
a) about 85-99% by weight of a diluent; and
b) about 0.5-2.0% by weight of a lubricant.
13. The pharmaceutical composition of any one of embodiments 1-12, wherein the composition comprises about 1%-10% by weight of psilocybin.
14. The pharmaceutical composition of any one of embodiments 10-13, wherein the diluent is pregelatinized starch.
15. The pharmaceutical composition of any one of embodiments 11-14, wherein the lubricant is selected from the group consisting of sodium stearyl fumarate, magnesium stearate, calcium stearate, zinc stearate, glyceryl monostearate, glyceryl behenate, glyceryl palmostearate, magnesium lauryl stearate, stearic acid, talc, and hydrogenated castor oil.
16. The pharmaceutical composition of embodiment 15, wherein the lubricant is sodium stearyl fumarate.
17. The pharmaceutical composition of any one of embodiments 1-16, wherein the chemical purity of psilocybin in the composition is not less than 97% as determined by HPLC analysis.
18. The pharmaceutical composition of any one of embodiments 1-17, wherein the composition comprises 1 mg to 40 mg of psilocybin.
19. The pharmaceutical composition of any one of embodiments 1-17, wherein the composition comprises 1 mg of psilocybin
20. The pharmaceutical composition of any one of embodiments 1-17, wherein the composition comprises 5 mg of psilocybin.
21. The pharmaceutical composition of any one of embodiments 1-17, wherein the composition comprises 10 mg of psilocybin.
22. The pharmaceutical composition of any one of embodiments 1-17, wherein the composition comprises 25 mg of psilocybin.
23. The pharmaceutical composition of any one of embodiments 1-22, wherein the psilocybin comprises a crystalline psilocybin.
24. The pharmaceutical composition of embodiment 23, wherein the crystalline psilocybin is crystalline Polymorph A.
25. The pharmaceutical composition of embodiment 23, wherein the crystalline psilocybin is crystalline Hydrate A.
26. The pharmaceutical composition of embodiment 23, wherein the crystalline psilocybin is crystalline Polymorph A'.
27. The pharmaceutical composition of embodiment 23, wherein the crystalline psilocybin is crystalline Polymorph B.
28. The pharmaceutical composition of any one of embodiments 1-22, wherein the psilocybin is amorphous.
29. The pharmaceutical composition of any one of embodiments 1-28, wherein the composition is a capsule.
30. The pharmaceutical composition of any one of embodiments 1-28, wherein the composition is a tablet.
31. The pharmaceutical composition of any one of embodiments 1-22, wherein the composition is a solution.
32. The pharmaceutical composition of any one of embodiments 1-30, wherein the content uniformity of the composition complies with the European Pharmacopeia 2.96. or USP <905>.
33. A method of making a pharmaceutical composition comprising:
a) direct mixing psilocybin and one or more pharmaceutically acceptable excipients to provide a blend, and
b) filling a capsule with the blend to provide the pharmaceutical composition, wherein the content uniformity of the composition complies with the European Pharmacopeia 2.96. or USP <905>
34. The method of embodiment 33, wherein the mass balance of psilocybin and related substances in the composition decreases by less than 3% after storage of the composition at 40° C. and 75% relative humidity for one month.
35. The method of any one of embodiments 33-34, wherein the blend comprises about 1% to about 10% by weight of psilocybin.
36. The method of any one of embodiments 33-35, wherein the capsule contains 1 mg, 5 mg, 10 mg or 25 mg of psilocybin.
37. The method of any one of embodiments 33-36, wherein the one or more pharmaceutically acceptable excipients comprises a diluent.
38. The method of any one of embodiments 33-37, wherein the blend further comprises a lubricant.
39. The method of any one of embodiments 33-38, wherein the blend does not contain a glidant.
40. A pharmaceutical composition prepared by the process of any one of embodiments 33-39.
41. A method of treating a mood disorder, comprising administering a therapeutically effective amount of the composition of any one of embodiments 1-32 and 40.

The invention claimed is:

1. A pharmaceutical composition comprising:
a therapeutically effective amount of psilocybin; and
about 85% to about 99%, by weight, partially pregelatinized starch, wherein the potency of the psilocybin in the composition decreases by less than 5%.

2. The pharmaceutical composition of claim 1, further comprising a lubricant.

3. The pharmaceutical composition of claim 2, wherein the composition comprises about 0.5% to about 2.0%, by weight, the lubricant.

4. The pharmaceutical composition of claim 3, wherein the lubricant is sodium stearyl fumarate.

5. The pharmaceutical composition of claim 1, wherein the composition is a capsule.

6. The pharmaceutical composition of claim 1, wherein the composition comprises about 1% to about 10%, by weight, psilocybin.

7. The pharmaceutical composition of claim 1, wherein the composition does not contain silicified microcrystalline cellulose.

8. The pharmaceutical composition of claim 1, wherein the composition comprises 1 mg of psilocybin.

9. The pharmaceutical composition of claim 1, wherein the composition comprises 5 mg of psilocybin.

10. The pharmaceutical composition of claim 1, wherein the composition comprises 10 mg of psilocybin.

11. The pharmaceutical composition of claim 1, wherein the composition comprises 25 mg of psilocybin.

12. The pharmaceutical composition of claim 1, wherein the composition comprises 40 mg of psilocybin.

13. A pharmaceutical composition comprising:
about 1% to about 10%, by weight, psilocybin;
about 85% to about 99%, by weight, partially pregelatinized starch; and
about 0.5% to about 2.0%, by weight, sodium stearyl fumarate, wherein the potency of the psilocybin in the composition decreases by less than 5%.

14. The pharmaceutical composition of claim 13, wherein the composition does not contain silicified microcrystalline cellulose.

15. The pharmaceutical composition of claim 13, wherein the composition is a capsule.

16. The pharmaceutical composition of claim 13, wherein the composition comprises 1 mg of psilocybin.

17. The pharmaceutical composition of claim 13, wherein the composition comprises 5 mg of psilocybin.

18. The pharmaceutical composition of claim 13, wherein the composition comprises 10 mg of psilocybin.

19. The pharmaceutical composition of claim 13, wherein the composition comprises 25 mg of psilocybin.

20. The pharmaceutical composition of claim 13, wherein the composition comprises 40 mg of psilocybin.

21. The pharmaceutical composition of claim 1, wherein the content uniformity of the composition complies with the European Pharmacopeia 2.96. or USP <905>.

22. The pharmaceutical composition of claim 13, wherein the content uniformity of the composition complies with the European Pharmacopeia 2.96. or USP <905>.

* * * * *